(12) United States Patent
Gerstenberger et al.

(10) Patent No.: US 11,254,668 B2
(45) Date of Patent: Feb. 22, 2022

(54) PYRAZOLO[1,5-A]PYRAZIN-4-YL AND RELATED DERIVATIVES

(71) Applicant: Pfizer Inc., New York, NY (US)

(72) Inventors: Brian Stephen Gerstenberger, Brookline, MA (US); Andrew Fensome, Harvard, MA (US); Dafydd Rhys Owen, Concord, MA (US); Matthew Frank Brown, Stonington, CT (US); Matthew Merrill Hayward, Old Lyme, CT (US); Felix Vajdos, Ledyard, CT (US); Li Huang Xing, Lexington, MA (US); Stephen Wayne Wright, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 105 days.

(21) Appl. No.: 16/638,271

(22) PCT Filed: Aug. 9, 2018

(86) PCT No.: PCT/IB2018/056007
§ 371 (c)(1),
(2) Date: Feb. 11, 2020

(87) PCT Pub. No.: WO2019/034973
PCT Pub. Date: Feb. 21, 2019

(65) Prior Publication Data
US 2020/0172537 A1  Jun. 4, 2020

Related U.S. Application Data

(60) Provisional application No. 62/545,142, filed on Aug. 14, 2017.

(51) Int. Cl.
C07D 471/04 (2006.01)
C07D 401/04 (2006.01)
C07D 401/14 (2006.01)
C07D 405/14 (2006.01)
C07D 519/00 (2006.01)

(52) U.S. Cl.
CPC ......... C07D 471/04 (2013.01); C07D 401/04 (2013.01); C07D 401/14 (2013.01); C07D 405/14 (2013.01); C07D 519/00 (2013.01)

(58) Field of Classification Search
CPC .. C07D 471/04; C07D 401/14; C07D 519/00; C07D 405/14; C07D 401/04
USPC .................................................. 514/210.21
See application file for complete search history.

(56) References Cited

U.S. PATENT DOCUMENTS 8,927,545 B2    1/2015  Qiao et al.
2013/0209400 A1  8/2013 Taña et al.

2014/0228349 A1  8/2014 Boys et al.
2015/0210708 A1  7/2015 Wishart et al.
2018/0179209 A1  6/2018 Wu et al.

FOREIGN PATENT DOCUMENTS

WO    2008/078091 A1    7/2008
WO    2010/016005 A1    2/2010
WO    2010/117787 A2   10/2010
(Continued)

OTHER PUBLICATIONS

Fradera et al., "Design of selective PI3Kδ inhibitors using an iterative scaffold-hopping workflow", Bioorganic & Medicinal Chemistry Letters 29(18):2575-2580 (2019).
Qiao et al., "Structure-activity relationship study of EphB3 receptor tyrosine kinase inhibitors", Bioorganic & Medicinal Chemistry Letters 19:6122-6126 (2009).
International Search Report and Written Opinion issued for PCT Application No. PCT/IB2018/056007 dated Jan. 4, 2019.
Kisseleva et al, "Signaling through the JAK/STAT pathway, recent advances and future challenges", Gene 285:1-24 (2002).
(Continued)

*Primary Examiner* — Kahsay Habte
(74) *Attorney, Agent, or Firm* — A. David Jordan

(57) ABSTRACT

A compound having the structure:

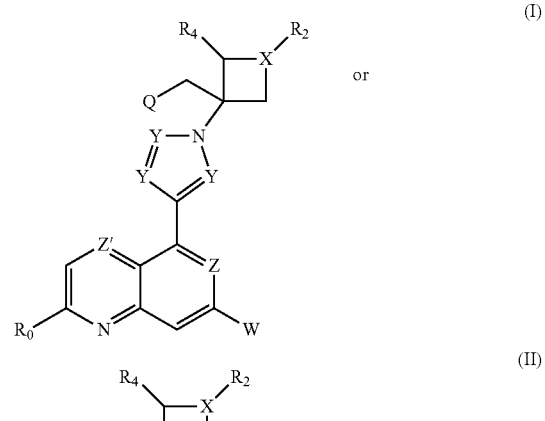

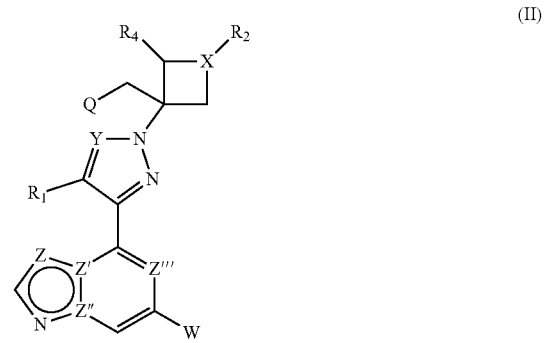

or a pharmaceutically acceptable salt thereof, or a pharmaceutically acceptable solvate of said compound or pharmaceutically acceptable salt, wherein variables are defined in the specification. Also provided are methods of treatment as Janus Kinase inhibitors and pharmaceutical compositions containing the compounds of the invention and combinations thereof with other therapeutic agents.

10 Claims, No Drawings

(56) References Cited

FOREIGN PATENT DOCUMENTS

| | | |
|---|---|---|
| WO | 2011/101161 A1 | 8/2011 |
| WO | 2011/130146 A1 | 10/2011 |
| WO | 2011/157397 A1 | 12/2011 |
| WO | 2013/055645 A1 | 4/2013 |
| WO | 2013/143663 A1 | 10/2013 |
| WO | 2015/017610 A1 | 2/2015 |
| WO | 2015/086693 A1 | 6/2015 |
| WO | 2016/090285 A1 | 6/2016 |
| WO | 2016/119707 A1 | 8/2016 |
| WO | 2016/130920 A2 | 8/2016 |
| WO | 2016/148306 A1 | 9/2016 |
| WO | 2016/173484 A1 | 11/2016 |
| WO | 2017/108723 A2 | 6/2017 |
| WO | 2018/136202 A2 | 7/2018 |
| WO | 2018/136661 A1 | 7/2018 |
| WO | 2018/234342 A1 | 12/2018 |

OTHER PUBLICATIONS

Liang et al, "Therapeutic potential of tyrosine kinase 2 in autoimmunity", Expert Opinion on Therapeutic Targets 18 (5):571-580 (2014).
Menet et al, "Advances in the Discovery of Selective JAK Inhibitors", Progress in Medicinal Chemistry 52:153-223 (2013).
Murray, "The JAK-STAT Signaling Pathway: Input and Output Integration", The Journal of Immunology 178:2623-2629 (2007).
Neubauer et al, "Jak2 Deficiency Defines an Essential Developmental Checkpoint in Definitive Hematopoiesis", Cell 93:397-409 (1998).
O'Shea et al, "JAK and STAT Signaling Molecules in Immunoregulation and Immune-Mediated Disease", Immunity 36:542-550 (2012).
Parganas et al, "Jak2 Is Essential for Signaling through a Variety of Cytokine Receptors", Cell 93:385-395 (1998).
Yamaoka et al, "The Janus kinases (Jaks)", Genome Biology 5:253 (2004).

PYRAZOLO[1,5-A]PYRAZIN-4-YL AND RELATED DERIVATIVES

FIELD OF THE INVENTION

The present invention provides pharmaceutically active pyrazolo[1,5-a]pyrazin-4-yl and related TYK2 ligands and analogues. Such compounds are useful for inhibiting Janus Kinases (JAKs). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, cell function, survival, apoptosis, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva et al., Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the interferon (IFN) family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gamma C family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes: TYK2 in particular. TYK2 is a JAK kinase family member, and is important in the signaling of the type I interferons (including IFNalpha, INFbeta), IL-6, IL-10, IL-12 and IL-23 (Liang, Y. et al., Expert Opinion on Therapeutic Targets, 18, 5, 571-580 (2014)). As such, TYK2 signals with other members of the JAK kinase family in the following combinations: TYK2/JAK1, TYK2/JAK2, TYK2/JAK1/JAK2. TYK2 has been shown to be important in the differentiation and function of multiple cell types important in inflammatory disease and autoimmune disease including natural killer cells, B cells, and T helper cell types. Aberrant TYK2 expression is associated with multiple autoimmune or inflammatory conditions. Modulation of immune activity through inhibition of TYK2 kinase activity can prove useful in the treatment of various immune disorders (O'Shea J J, Plenge R, Immunity, 36, 542-50 (2012); Murray, P. J., J. Immunol., 178, 2623-2629 (2007); Kisseleva, T., et al., Gene, 285, 1-24 (2002)) while avoiding JAK2 dependent erythropoietin (EPO) and thrombopoietin (TPO) signaling (Neubauer H., et al., Cell, 93(3), 397-409 (1998); Parganas E., et al., Cell, 93(3), 385-95 (1998)).

SUMMARY OF THE INVENTION

The present invention provides a compound having the structure:

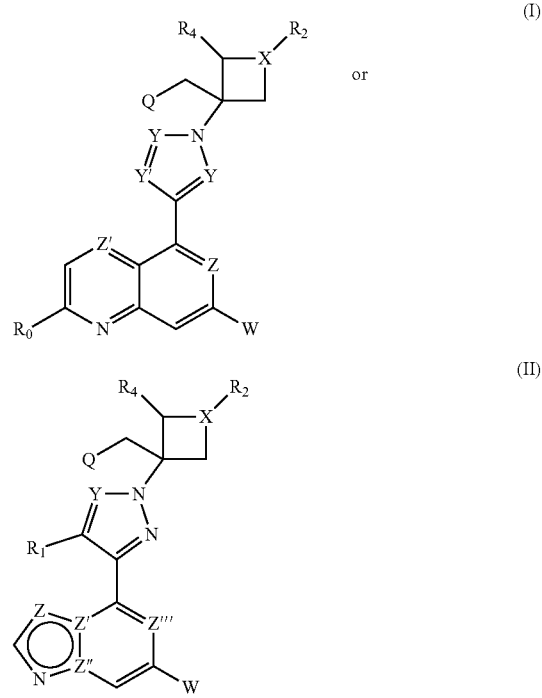

or a pharmaceutically acceptable salt thereof, or a pharmaceutically acceptable solvate of said compound or pharmaceutically acceptable salt, wherein:

W is H, halo, or is selected from the group consisting of:

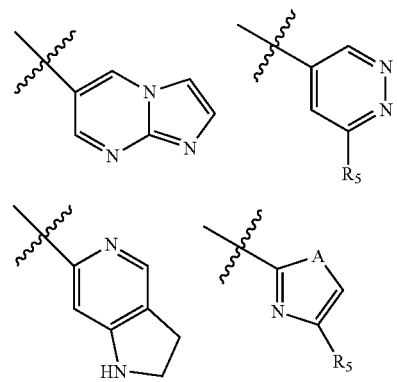

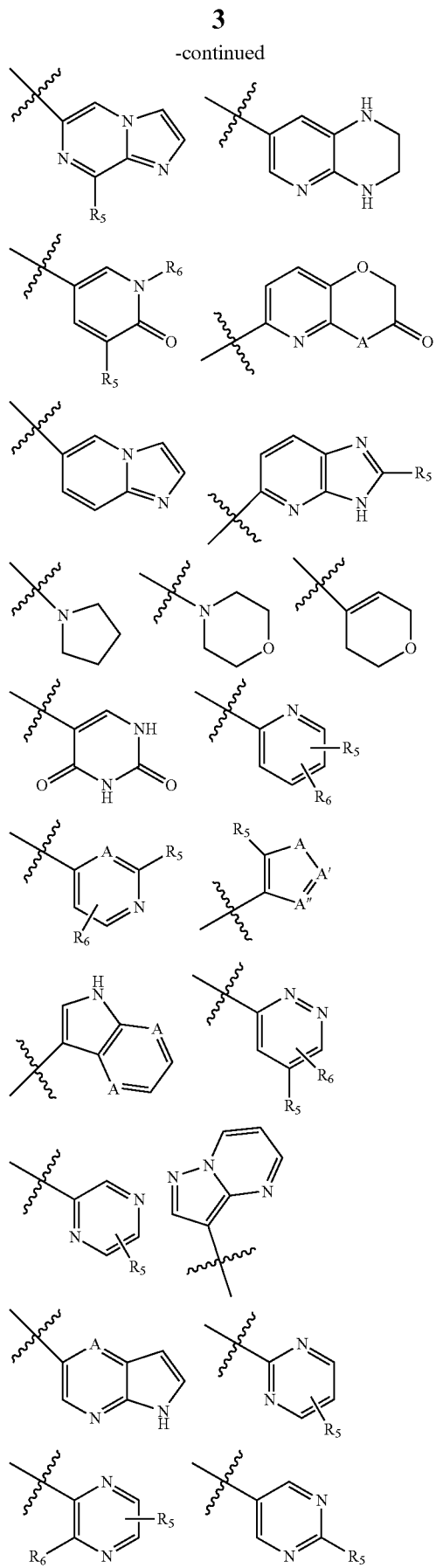
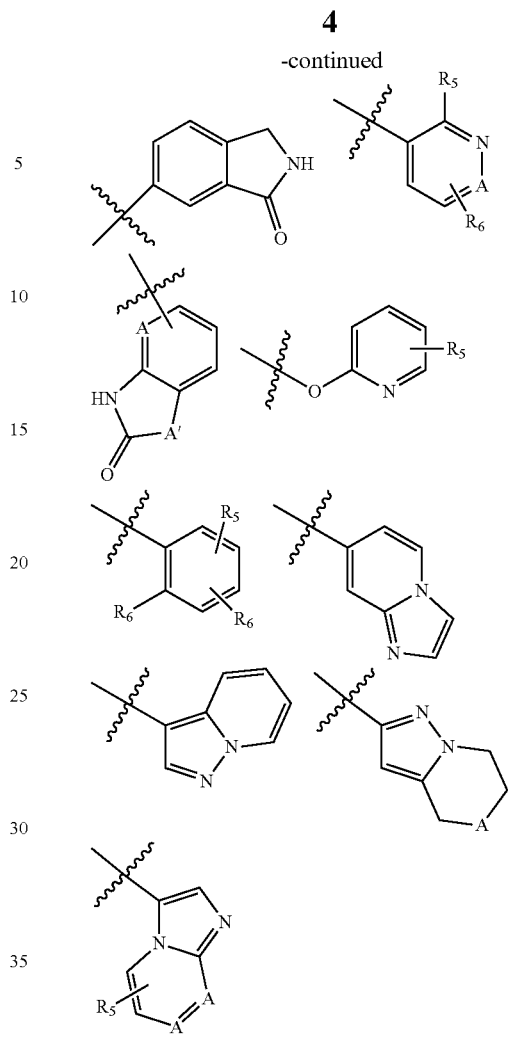

A, A' and A" are independently O, S, C=O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C=O; where C$_1$-C$_8$ alkyl is optionally substituted by OH, halo, N(C$_1$-C$_6$ alkyl) and heterocyclic;

Y, Z, and Z' are independently C—R$_1$ or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$C$_6$ alkyl)-; Z" and Z''' are independently C—R' or N—R";

R$_0$ is H, D or C$_1$-C$_6$ alkyl-;

Y' is O, C—R$_1$ or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-;

Q is CN or CONH$_2$;

R$_2$ is selected from the group consisting of H, C$_1$-C$_6$ alkyl-, C$_1$-C$_6$ alkoxy-, hydroxy(C$_1$-C$_6$ alkyl)-, phenyl(C$_1$-C$_6$ alkyl)-, C$_3$-C$_8$ cycloalkyl, halo(C$_3$-C$_8$ cycloalkyl), spirocyclic, formyl, heteroaryl, heterocyclic, —COR, —OCOR, —COOR, —NR$_7$COR, CONR$_7$R$_8$, and —(CH$_2$)$_n$—W', where W' is cyano, hydroxy, C$_3$-C$_8$ cycloalkyl, —SO$_2$NR$_7$R$_8$, and —SO$_2$-R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_8$ alkyl; or, R$_2$ and R$_3$ when taken together forms a C$_3$-C$_8$ cycloalkyl group or C$_4$-C$_8$ heterocyclic group; wherein heterocyclic or heteroaryl group may be substituted by C$_1$-C$_8$ alkyl, halo or hydroxy;

X is C—R$_3$ or N, where R$_3$ may be H or C$_1$-C$_8$ alkyl;

R$_4$, R$_5$ and R$_6$ are independently H, halo, amino, —OH, —CO$_2$H, —CONH$_2$, C$_1$-C$_6$ alkyl, C$_1$-C$_8$ alkoxy-, -hydroxy (C$_1$-C$_6$ alkoxy)-, hydroxy(C$_1$-C$_6$ alkoxy)-, heteroaryl-, heterocyclic-, —SO$_2$NH$_2$, —NHSO$_2$(C$_1$-C$_6$ alkyl), —NHCO (C$_1$-C$_6$ alkyl), —NHCO$_2$(C$_1$-C$_6$ alkyl), —SO$_2$(C$_1$-C$_6$ alkyl), amino(C$_1$-C$_6$ alkoxy), amino(C$_1$-C$_6$ alkyl)- or hydroxy(C$_1$-C$_6$ alkyl)-;

R, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 0, 1, 2 or 3.

In other aspects, the present invention also provides:

pharmaceutical compositions which comprise a pharmaceutically acceptable carrier and a compound of structure I or II;

methods for treating conditions or disorders including inflammation, autoimmune disease, systemic lupus erythematous, lupus nephritis, discoid lupus, cutaneous lupus, central nervous system lupus, rheumatoid arthritis, psoriatic arthritis, inflammatory bowel disease, Crohn's disease, ulcerative colitis, asthma, allergic asthma, Type I diabetes, polymyositis, dermatomyositis, type I interferonopathies including Aicardi-Goutières syndrome and other mendelian diseases of overexpression of type I interferon, multiple sclerosis, primary progressive multiple sclerosis, relapsing remitting multiple sclerosis, primary biliary cirrhosis also known as primary biliary cholangitis, primary sclerosing cholangitis, autoimmune hepatitis, non-alcoholic fatty liver disease, non-alcoholic steatohepatitis, psoriasis, dermatomyositis, scleroderma, atopic dermatitis, vitiligo, alopecia areata, spondylopathy, ankylosing spondylitis, Alzheimer's disease, neuro-inflammation myositis, vasculitis, pemphigus, Crohn's disease, lupus, nephritis, psoriasis, multiple sclerosis, major depression disorder, allergy, asthma, Sjogren's disease, dry eye syndrome, transplant rejection, cancer, inflammatory bowel disease, septic shock, cardiopulmonary dysfunction, vitiligo, alopecia, acute respiratory disease, ankylosing spondylitis, autoimmune hepatitis, primary sclerosing cholangitis, primary biliary cirrhosis, Alzheimer's disease, or cachexia by administering to a subject in need a therapeutically effective amount of a compound of structure I or II or a pharmaceutically acceptable salt thereof;

Methods for treating conditions or disorders including atopic dermatitis, eczema, psoriasis, scleroderma, lupus, pruritus, fatigue, other pruritic conditions, allergic reactions including allergic dermatitis in mammal, horse allergic diseases including bite hypersensitivity, summer eczema, sweet itch in horses, heaves, inflammatory airway disease, recurrent airway obstruction, airway hyper-responsiveness, and chronic obstruction pulmonary disease by administering to a mammal in need a therapeutically effective amount of a compound of structure I or II, or a pharmaceutically acceptable salt thereof; and, methods for the preparation of compounds of the present invention. p The present invention will be further understood from the following description given by way of example only. The present invention is directed to a class of pyrazolo[1,5-a]pyrazin-4-yl derivatives. In particular, the present invention is directed to pyrazolo[1,5-a]pyrazin-4-yl compounds useful as inhibitors of JAKs, and particularly TYK2. While the present invention is not so limited, an appreciation of various aspects of the invention will be gained through the following discussion and the examples.

The term "alkyl", alone or in combination, means an acyclic, saturated hydrocarbon group of the structure $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH group. The term "heterocyclic" refers to a saturated or partially saturated (i.e., non aromatic) heterocycle which contains three to ten ring atoms where one or more, preferably, one, two or three ring atoms, are heteroatom(s) selected from N, O and S, the remaining being carbon, and which may be attached via a ring nitrogen atom or a ring carbon atom. Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "aryl" refers to an aromatic monocyclic or bicyclic hydrocarbon containing six to ten ring carbon atoms which may be attached via one of the ring carbon atoms. Equally, when substituted, the substituent may be located on a ring carbon atom. Specific examples include, but are not limited to, phenyl, tolyl, xylyl, trimethylphenyl, and naphthyl. Examples of aryl substituents include, but are not limited to, alkyl, hydroxyl, halo, nitrile, alkoxy, trifluoromethyl, carboxamido, SO$_2$Me, benzyl, and substituted benzyl.

The term "heteroaryl" refers to a monovalent aromatic monocyclic or bicyclic heterocycle of five to ten ring atoms where one or more, preferably, one, two or three ring atoms, are heteroatom(s) selected from N, O, and S, the remaining being carbon, and which may be attached via a ring carbon atom or a ring nitrogen atom with an appropriate valency. Equally, when substituted, the substituent may be located on a ring carbon atom or a ring nitrogen atom with an appropriate valency. Specific examples include, but are not limited to, thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a monocyclic, saturated hydrocarbon group of the formula $C_nH_{2n-1}$. Examples include, but are not limited to, cyclopropyl, cyclobutyl, cyclopentyl, cyclohexyl, and cycloheptyl. Unless otherwise specified, a cycloalkyl group comprises from 3 to 8 carbon atoms. The terms "halo" and "halogen" refer to fluoride (F), chloride (Cl), bromide (Br) or iodide (I).

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder. The phrase "therapeutically-effective" is to be understood to be equivalent to the phrase "effective for the treatment, prevention, or amelioration", and both are intended to qualify the amount of an agent—which will achieve the goal of improvement in the severity of cancer, cardiovascular disease, or pain and inflammation and the frequency of incidence over treatment of each agent by itself.

"Pharmaceutically acceptable" means suitable for use in mammals, companion animals or livestock animals.

If substituents are described as being "independently selected" from a group, each substituent is selected independent of the other. Each substituent therefore may be identical to or different from the other substituent(s).

DETAILED DESCRIPTION OF THE INVENTION

The present invention is related to novel compounds which are TYK2 modulators useful for the treatment of diseases and conditions associated with dysregulation of TYK2. The present invention further provides pharmaceutical compositions comprising such JAK enzyme modulators as well as methods of treating and/or preventing such diseases and conditions. Accordingly, the present invention provides a compound of structure (I) and (II) as represented above having the structures:

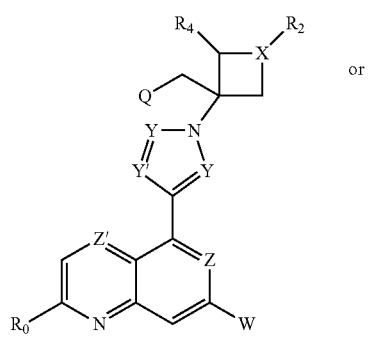

(I)

or

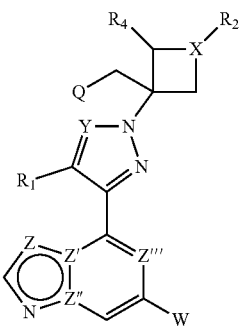

(II)

or a pharmaceutically acceptable salt thereof, or a pharmaceutically acceptable solvate of said compound or pharmaceutically acceptable salt, wherein:

W is H, halo, or is selected from the group consisting of:

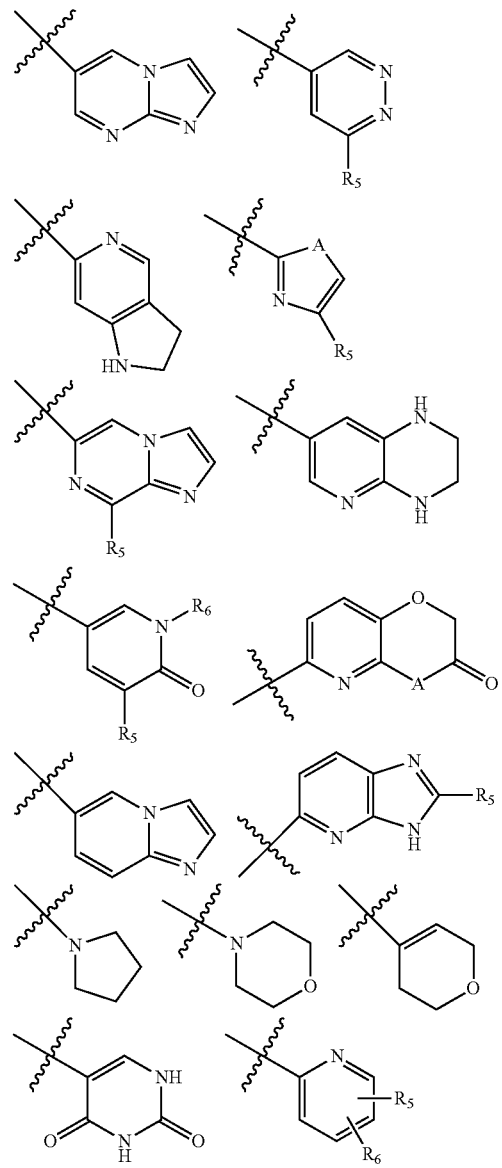

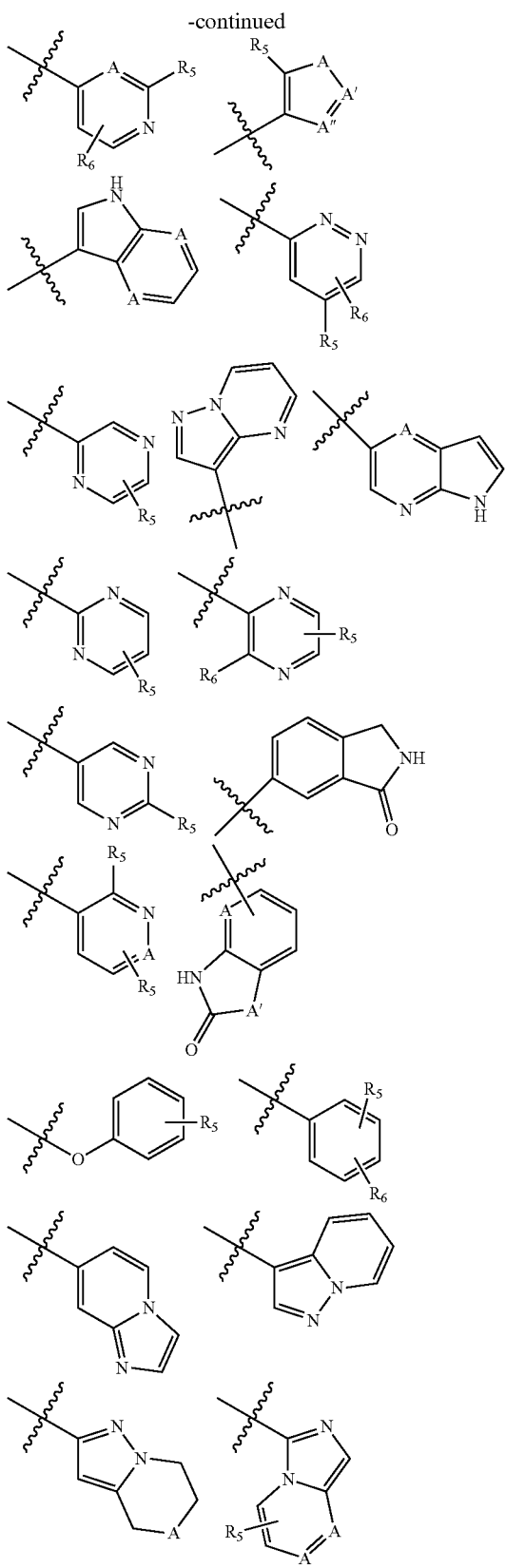

A, A' and A" are independently O, S, C=O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C=O; where C$_1$-C$_6$ alkyl is optionally substituted by OH, halo, N(C$_1$-C$_6$ alkyl) and heterocyclic;

Y, Z, and Z' are independently C—R$_1$ or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-; Z" and Z"' are independently C—R' or N—R";

R$_0$ is H, D or C$_1$-C$_6$ alkyl-;

Y' is O, C—R$_1$ or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-;

Q is CN or CONH$_2$;

R$_2$ is selected from the group consisting of H, C$_1$-C$_6$ alkyl-, C$_1$-C$_6$ alkoxy-, hydroxy(C$_1$-C$_6$ alkyl)-, phenyl(C$_1$-C$_6$ alkyl)-, C$_3$-C$_8$ cycloalkyl, halo(C$_3$-C$_8$ cycloalkyl), spirocyclic, formyl, heteroaryl, heterocyclic, —COR, —OCOR, —COOR, —NR$_7$COR, CONR$_7$R$_8$, and —(CH$_2$)$_n$—W', where W' is cyano, hydroxy, C$_3$-C$_8$ cycloalkyl, —SO$_2$NR$_7$R$_8$, and —SO$_2$—R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; or, R$_2$ and R$_3$ when taken together forms a C$_3$-C$_8$ cycloalkyl group or C$_4$-C$_8$ heterocyclic group; wherein heterocyclic or heteroaryl group may be substituted by C$_1$-C$_6$ alkyl, halo or hydroxy;

X is C—R$_3$ or N, where R$_3$ may be H or C$_1$-C$_6$ alkyl;

R$_4$, R$_5$ and R$_6$ are independently H, halo, amino, —OH, —CO$_2$H, —CONH$_2$, C$_1$-C$_6$ alkyl, C$_1$-C$_6$ alkoxy-, -hydroxy(C$_1$-C$_6$ alkoxy)-, hydroxy(C$_1$-C$_6$ alkoxy)-, heteroaryl-, heterocyclic-, —SO$_2$NH$_2$, —NHSO$_2$(C$_1$-C$_6$ alkyl), —NHCO(C$_1$-C$_6$ alkyl), —NHCO$_2$(C$_1$-C$_6$ alkyl), —SO$_2$(C$_1$-C$_6$ alkyl), amino(C$_1$-C$_6$ alkoxy), amino(C$_1$-C$_6$ alkyl)- or hydroxy(C$_1$-C$_6$ alkyl)-;

R, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 0, 1, 2 or 3.

In particular embodiments, the invention provides a compound having the structure I or II above wherein X is C. In other embodiments, the invention provides a compound having the structure I or II above wherein R$_2$ is CN and R$_4$ is H. The invention also provides a compound having the structure I or II above wherein Y is CH or N. The invention further provides a compound having the structure I or II above wherein Z is N and Z' is CH.

The invention additionally provides a compound having the structure (Ia):

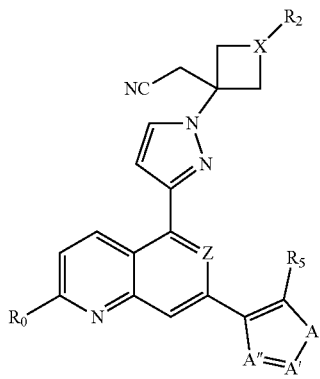

(Ia)

or a pharmaceutically acceptable salt thereof, or a pharmaceutically acceptable solvate of said compound or pharmaceutically acceptable salt, wherein:

A, A' and A" are independently O, S, C=O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alkyl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C=O; where C$_1$-C$_6$ alkyl is optionally substituted by OH, halo, N(C$_1$-C$_6$ alkyl) and heterocyclic;

Z is C—R$_1$ or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-; Z" and Z''' are independently C—R' or N—R";

R$_5$ and R$_6$ are independently H, halo, amino, —OH, —CO$_2$H, —CONH$_2$, C$_1$-C$_6$ alkyl, C$_1$-C$_6$ alkoxy-, -hydroxy (C$_1$-C$_6$ alkoxy)-, hydroxy(C$_1$-C$_6$ alkoxy)-, heteroaryl-, heterocyclic-, —SO$_2$NH$_2$, —NHSO$_2$(C$_1$-C$_6$ alkyl), —NHCO (C$_1$-C$_6$ alkyl), —NHCO$_2$(C$_1$-C$_6$ alkyl), —SO$_2$(C$_1$-C$_6$ alkyl), amino(C$_1$-C$_6$ alkoxy), amino(C$_1$-C$_6$ alkyl)- or hydroxy(C$_1$-C$_6$ alkyl)-; R$_0$ is H, D or C$_1$-C$_6$ alkyl-; and, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl.

The invention additionally provides a compound having the structure (Ib):

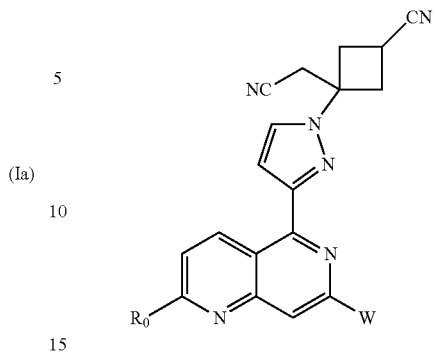

(Ib)

or a pharmaceutically acceptable salt thereof, or a pharmaceutically acceptable solvate of said compound or pharmaceutically acceptable salt, wherein:

W is H, halo, or is selected from the group consisting of:

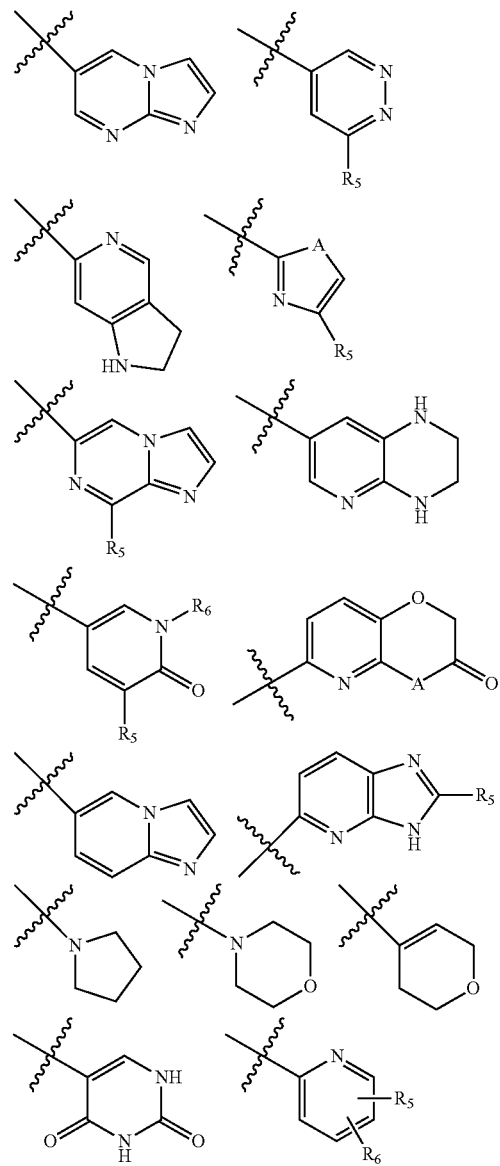

-continued

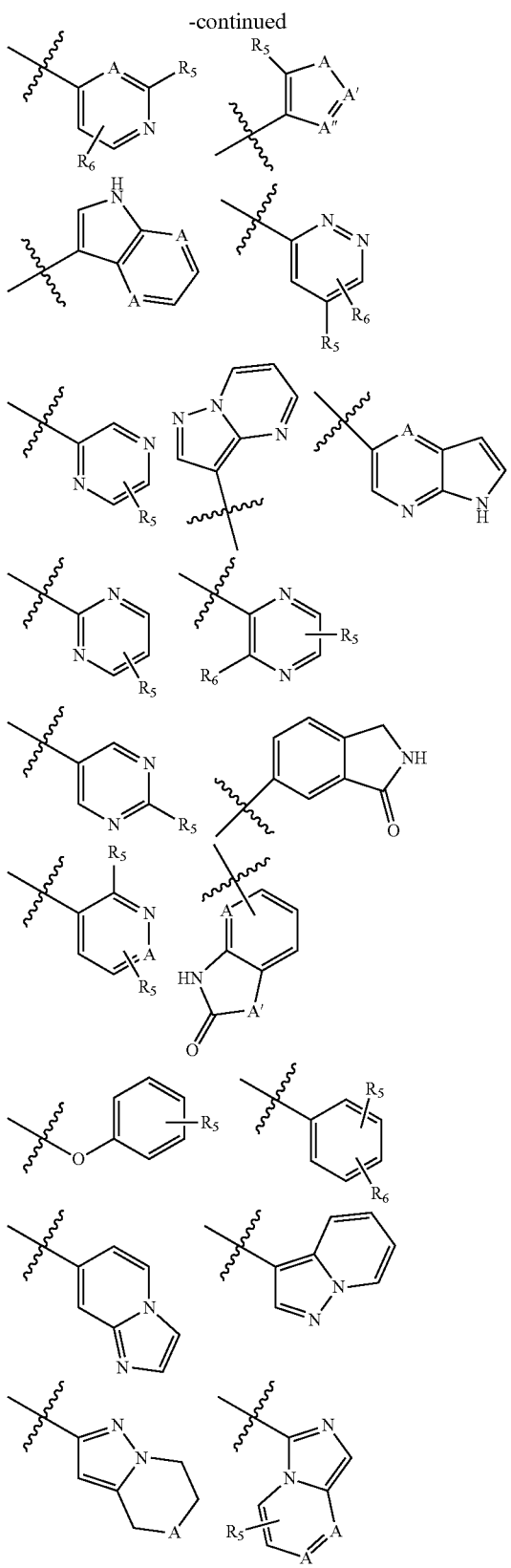

A, A' and A" are independently O, S, C=O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C=O; where C$_1$-C$_6$ alkyl is optionally substituted by OH, halo, N(C$_1$-C$_6$ alkyl) and heterocyclic;

R$_0$ is H, D or C$_1$-C$_6$ alkyl-;

R$_5$ and R$_6$ are independently H, halo, amino, —OH, —CO$_2$H, —CONH$_2$, C$_1$-C$_6$ alkyl, C$_1$-C$_6$ alkoxy-, -hydroxy(C$_1$-C$_6$ alkoxy)-, hydroxy(C$_1$-C$_6$ alkoxy)-, heteroaryl-, heterocyclic-, —SO$_2$NH$_2$, —NHSO$_2$(C$_1$-C$_6$ alkyl), —NHCO(C$_1$-C$_6$ alkyl), —NHCO$_2$(C$_1$-C$_6$ alkyl), —SO$_2$(C$_1$-C$_6$ alkyl), amino(C$_1$-C$_6$ alkoxy), amino(C$_1$-C$_6$ alkyl)- or hydroxy(C$_1$-C$_6$ alkyl)-; and, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl. In particular embodiments, the invention provides the compound of structure (Ib) wherein A is N—R", A' is N and A" is CH, where R" is H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-, R$_5$ and R$_6$ are independently H, halo, amino, —OH, —CONH$_2$, C$_1$-C$_6$ alkyl, C$_1$-C$_6$ alkoxy-, -hydroxy(C$_1$-C$_6$ alkoxy)-, —NHSO$_2$(C$_1$-C$_6$ alkyl), amino(C$_1$-C$_6$ alkyl)- or hydroxy(C$_1$-C$_6$ alkyl)-; and, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl. In other embodiments, R$_5$ is H and R" is methyl.

The invention additionally provides a compound having the structure (IIa):

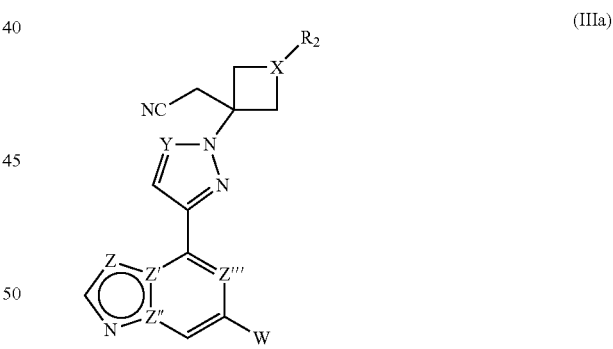

(IIIa)

or a pharmaceutically acceptable salt thereof, or a pharmaceutically acceptable solvate of said compound or pharmaceutically acceptable salt, wherein:

W is H, halo, or is selected from the group consisting of:

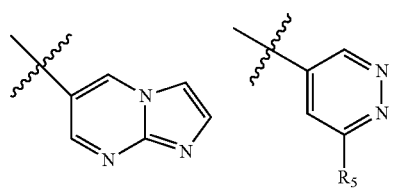

-continued

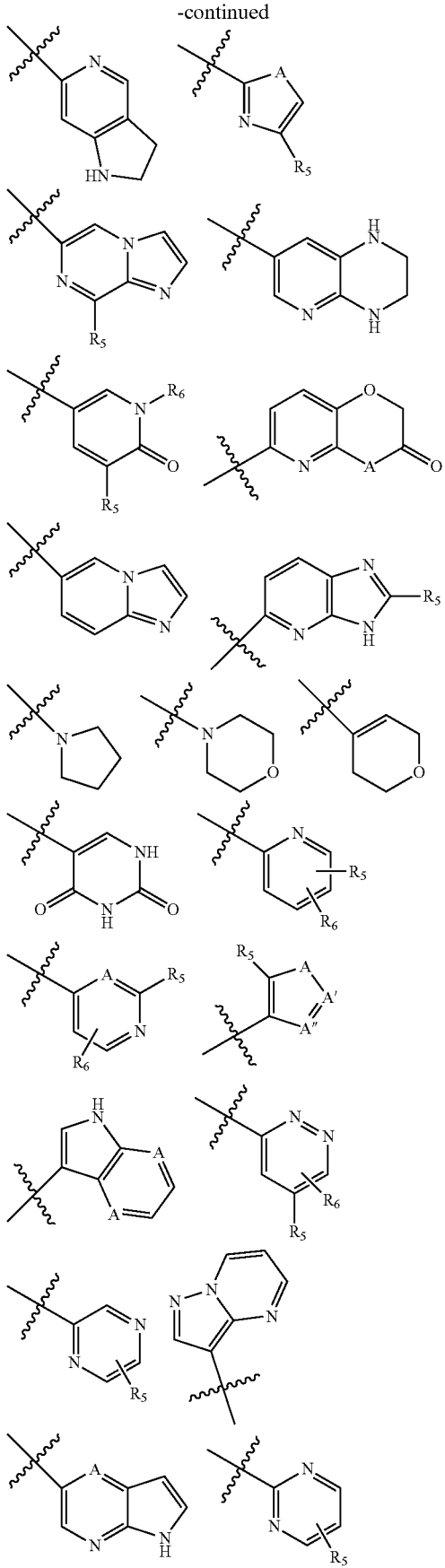

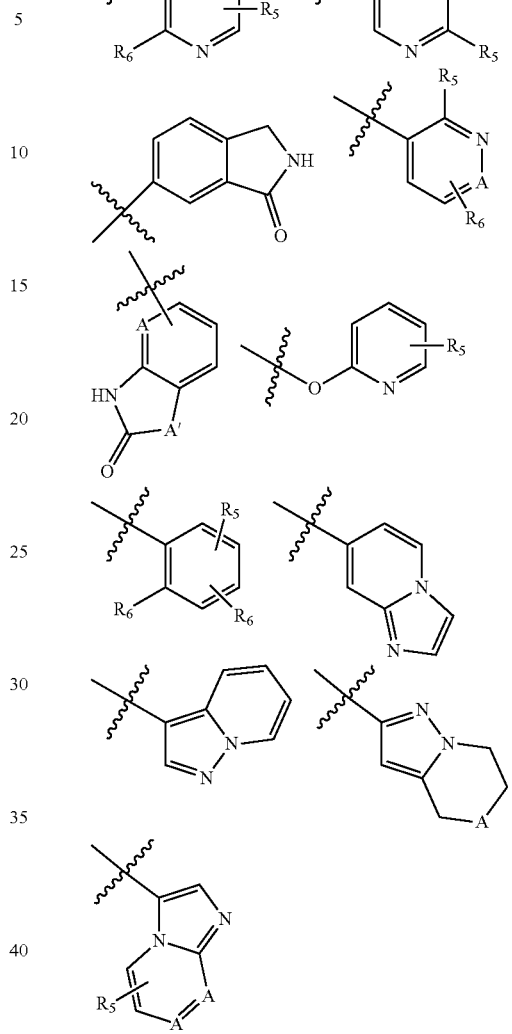

A, A' and A" are independently O, S, C═O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C═O; where C$_1$-C$_6$ alkyl is optionally substituted by OH, halo, N(C$_1$-C$_6$ alkyl) and heterocyclic;

Y, Z, and Z' are independently C—R, or N, where R$_1$ is H, halo, amino, —NR$_7$COR$_6$, COR$_6$, —CONR$_7$R$_8$, —NHSO$_2$ (C$_1$-C$_6$ alkyl), C$_1$-C$_6$ alkyl, halo, amino(C$_1$-C$_6$ alkyl)- or hydroxy(C$_1$-C$_6$ alkyl)-; Z" and Z"' are independently C—R' or N—R";

R$_2$ is selected from the group consisting of H, C$_1$-C$_6$ alkyl-, C$_1$-C$_6$ alkoxy-, hydroxy(C$_1$-C$_6$ alkyl)-, phenyl(C$_1$-C$_6$ alkyl)-, cycloalkyl, spirocyclic, formyl, heteroaryl, heterocyclic, —COR, —OCOR, —COOR, —NR$_7$COR, CONR$_7$R$_8$, and —(CH$_2$)$_n$—W', where W' is cyano, hydroxy, C$_3$-C$_8$ cycloalkyl, —SO$_2$NR$_7$R$_8$, and —SO$_2$—R$_9$, where R$_9$ is $C_1$-$C_6$ alkyl, $C_3$-$C_8$ cycloalkyl, heteroaryl, or heterocyclic; wherein each of said alkyl, cycloalkyl, heterocyclic, or heteroaryl may be unsubstituted or substituted by halo, cyano, hydroxy, or $C_1$-$C_6$ alkyl;

X is C—$R_3$ or N, where $R_3$ may be H or $C_1$-$C_6$ alkyl;

$R_5$ and $R_6$ are independently H, halo, amino, —OH, —$CO_2$H, —$CONH_2$, $C_1$-$C_6$ alkyl, $C_1$-$C_6$ alkoxy-, -hydroxy($C_1$-$C_6$ alkoxy)-, hydroxy($C_1$-$C_6$ alkoxy)-, heteroaryl-, heterocyclic-, —$SO_2NH_2$, —$NHSO_2$($C_1$-$C_6$ alkyl), —NHCO($C_1$-$C_6$ alkyl), —$NHCO_2$($C_1$-$C_6$ alkyl), —$SO_2$($C_1$-$C_6$ alkyl), amino($C_1$-$C_6$ alkoxy), amino($C_1$-$C_6$ alkyl)- or hydroxy($C_1$-$C_6$ alkyl)-;

R, $R_7$ and $R_8$ are each independently H, $C_1$-$C_6$ alkyl, $C_1$-$C_4$ alkoxy($C_1$-$C_6$ alkyl) or $C_3$-$C_8$ cycloalkyl, said $C_1$-$C_6$ alkyl is optionally substituted by halo, CN or hydroxy; or, $R_7$ and $R_8$ together with the atom bonded thereto form a 5- or 6-membered ring, said ring being optionally substituted by halo, hydroxy, CN, or $C_1$-$C_6$ alkyl;

and, n is 0, 1, 2 or 3. In particular embodiments, the invention provides the above compound wherein X is C. In other embodiments, $R_2$ is CN and $R_4$ is H. In yet other embodiments, Y is CH or N, and/or Z is N and Z' is CH.

The invention also provides a compound having the structure (IIIb):

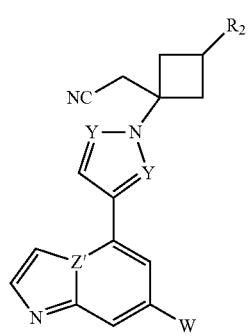

(IIIb)

or a pharmaceutically acceptable salt thereof, or a pharmaceutically acceptable solvate of said compound or pharmaceutically acceptable salt, wherein:

W is H, halo, or is selected from the group consisting of:

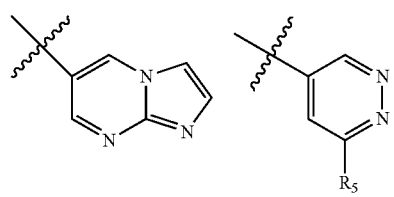

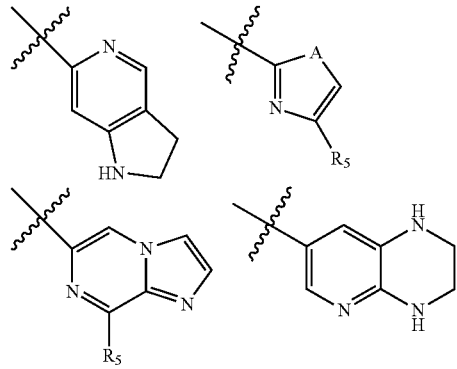

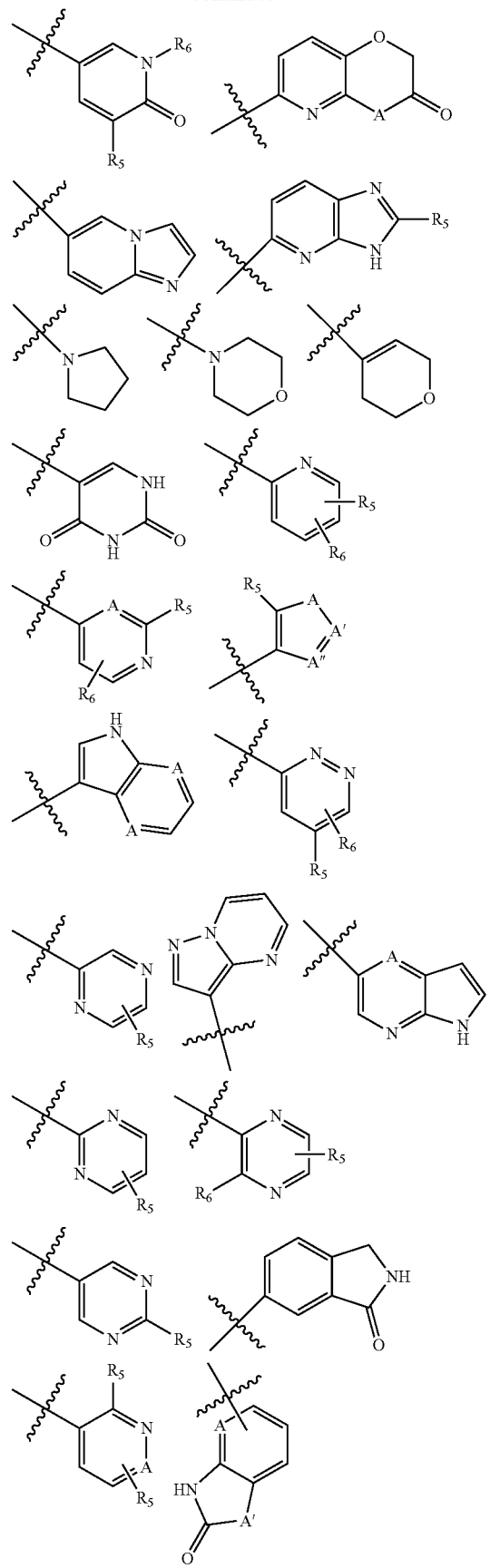

-continued

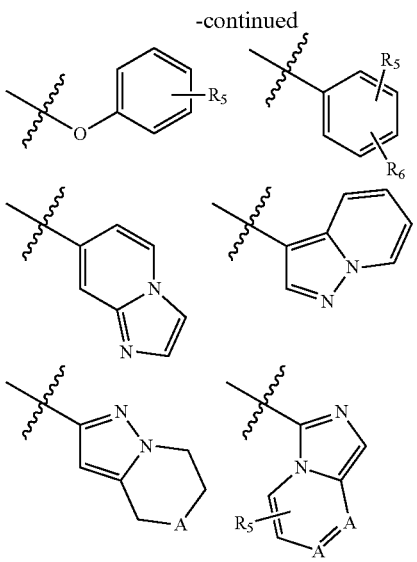

A, A' and A" are independently O, S, C=O, C—R', N or N—R", where R' and R" may independently be H, amino, —NR₇COR₆, COR₆, —CONR₇R₈, —NHSO₂(C₁-C₆ alkyl), C₁-C₆ alkyl, halo, amino(C₁-C₆ alkyl)-, C₃-C₈ cycloalkyl, heteroaryl, heterocyclic, heterocyclic(C₁-C₆ alk-yl)-, hydroxy(C₁-C₆ alkyl)-, or hydroxy(halo-C₁-C₆ alkyl)-, where each said moiety may be present or absent, and is present where the rules of valency permit, subject to the proviso that not more than one of A, A' and A" is O, S or C=O; where $C_1$-$C_8$ alkyl is optionally substituted by OH, halo, N($C_1$-$C_6$ alkyl) and heterocyclic;

Y and Z' are independently C—R, or N, where $R_1$ is H, halo, amino, —NR₇COR₆, COR₆, —CONR₇R₆, —NHSO₂(C₁-C₆ alkyl), C₁-C₆ alkyl, halo, amino(C₁-C₆ alkyl)- or hydroxy(C₁-C₆ alkyl)-;

$R_2$ is selected from the group consisting of H, $C_1$-$C_6$ alkyl-, $C_1$-$C_6$ alkoxy-, hydroxy($C_1$-$C_6$ alkyl)-, phenyl($C_1$-$C_6$ alkyl)-, cycloalkyl, spirocyclic, formyl, heteroaryl, heterocyclic, —COR, —OCOR, —COOR, —NR₇COR, CONR₇R₆, and —(CH₂)ₙ—W', where W' is cyano, hydroxy, $C_3$-$C_8$ cycloalkyl, —SO₂NR₇R₆, and —SO₂-R₉, where $R_9$ is $C_1$-$C_6$ alkyl, $C_3$-$C_8$ cycloalkyl, heteroaryl, or heterocyclic; wherein each of said alkyl, cycloalkyl, heterocyclic, or heteroaryl may be unsubstituted or substituted by halo, cyano, hydroxy, or $C_1$-$C_6$ alkyl;

$R_5$ and $R_6$ are independently H, halo, amino, —OH, —CO₂H, —CONH₂, C₁-C₆ alkyl, C₁-C₆ alkoxy-, -hydroxy (C₁-C₆ alkoxy)-, hydroxy(C₁-C₆ alkoxy)-, heteroaryl-, heterocyclic-, —SO₂NH₂, —NHSO₂(C₁-C₆ alkyl), —NHCO (C₁-C₆ alkyl), —NHCO₂(C₁-C₆ alkyl), —SO₂(C₁-C₆ alkyl), amino(C₁-C₆ alkoxy), amino(C₁-C₆ alkyl)- or hydroxy(C₁-C₆ alkyl)-;

R, $R_7$ and $R_8$ are each independently H, C₁-C₆ alkyl, C₁-C₄ alkoxy(C₁-C₆ alkyl) or C₃-C₈ cycloalkyl, said C₁-C₆ alkyl is optionally substituted by halo, CN or hydroxy; or, $R_7$ and $R_8$ together with the atom bonded thereto form a 5- or 6-membered ring, said ring being optionally substituted by halo, hydroxy, CN, or C₁-C₆ alkyl;

and, n is 0, 1, 2 or 3. In certain embodiments, the invention provides the compound wherein Z' is C.

The invention additionally provides a compound having the structure (IIIc):

$$\text{(IIIc)}$$

or a pharmaceutically acceptable salt thereof, or a pharmaceutically acceptable solvate of said compound or pharmaceutically acceptable salt, wherein:

A, A' and A" are independently O, S, C=O, C—R', N or N—R", where R' and R" may independently be H, amino, —NR₇COR₆, COR₆, —CONR₇R₈, —NHSO₂(C₁-C₆ alkyl), C₁-C₆ alkyl, halo, amino(C₁-C₆ alkyl)-, C₃-C₈ cycloalkyl, heteroaryl, heterocyclic, heterocyclic(C₁-C₆ alk-yl)-, hydroxy(C₁-C₆ alkyl)-, or hydroxy(halo-C₁-C₆ alkyl)-, where each said moiety may be present or absent, and is present where the rules of valency permit, subject to the proviso that not more than one of A, A' and A" is O, S or C=O; where $C_1$-$C_8$ alkyl is optionally substituted by OH, halo, N($C_1$-$C_6$ alkyl) and heterocyclic;

Y is C—$R_1$ or N, where $R_1$ is H, halo, amino, —NR₇COR₆, COR₆, —CONR₇R₆, —NHSO₂(C₁-C₆ alkyl), C₁-C₆ alkyl, halo, amino(C₁-C₆ alkyl)- or hydroxy(C₁-C₆ alkyl)-;

$R_5$ and $R_6$ are independently H, halo, amino, —OH, —CO₂H, —CONH₂, C₁-C₆ alkyl, C₁-C₆ alkoxy-, -hydroxy (C₁-C₆ alkoxy)-, hydroxy(C₁-C₆ alkoxy)-, heteroaryl-, heterocyclic-, —SO₂NH₂, —NHSO₂(C₁-C₆ alkyl), —NHCO (C₁-C₆ alkyl), —NHCO₂(C₁-C₆ alkyl), —SO₂(C₁-C₆ alkyl), amino(C₁-C₆ alkoxy), amino(C₁-C₆ alkyl)- or hydroxy(C₁-C₆ alkyl)-; and, $R_7$ and $R_8$ are each independently H, C₁-C₆ alkyl, C₁-C₄ alkoxy(C₁-C₆ alkyl) or C₃-C₈ cycloalkyl, said C₁-C₆ alkyl is optionally substituted by halo, CN or hydroxy; or, $R_7$ and $R_8$ together with the atom bonded thereto form a 5- or 6-membered ring, said ring being optionally substituted by halo, hydroxy, CN, or C₁-C₆ alkyl. In certain embodiments, the invention provides the above compound wherein A is N—R", A' is N and A" is CH, where R" is H, amino, —NR₇COR₆, COR₆, —CONR₇R₆, —NHSO₂(C₁-C₆ alkyl), C₁-C₆ alkyl, halo, amino(C₁-C₆ alkyl)- or hydroxy(C₁-C₆ alkyl)-, $R_5$ and $R_6$ are independently H, halo, amino, —OH, —CONH₂, C₁-C₆ alkyl, C₁-C₆ alkoxy-, -hydroxy(C₁-C₆ alkoxy)-, —NHSO₂(C₁-C₆ alkyl), amino(C₁-C₆ alkyl)- or hydroxy(C₁-C₆ alkyl)-; and, $R_7$ and $R_8$ are each independently H, C₁-C₆ alkyl, C₁-C₄ alkoxy(C₁-C₆ alkyl) or C₃-C₈ cycloalkyl, said C₁-C₆ alkyl is optionally substituted by halo, CN or hydroxy; or, $R_7$ and $R_8$ together with the atom bonded thereto form a 5- or 6-membered ring, said ring being optionally substituted by halo, hydroxy, CN, or C₁-C₆ alkyl. In other embodiments, the invention provides the above compound wherein A is N—CH₃, A' is N and A" is CH; $R_5$ is H and each Y is N.

In specific embodiments, the invention provides a compound selected from the group consisting of:

cis-3-{3-[7-(3-amino-1H-pyrazol-4-yl)-1,6-naphthyridin-5-yl]-1H-pyrazol-1-yl}-3-(cyanomethyl)cyclobutanecarbonitrile;

N-[4-(5-{1-[cis-3-cyano-1-(cyanomethyl)cyclobutyl]-1H-pyrazol-3-yl}-1,6-naphthyridin-7-yl)phenyl]methanesulfonamide;

trans-3-{3-[7-(5-amino-1H-pyrazol-3-yl)-1,6-naphthyridin-5-yl]-1H-pyrazol-1-yl}-3-(cyanomethyl)cyclobutanecarbonitrile;

cis-3-(cyanomethyl)-3-(4-{7-[1-(2-hydroxyethyl)-1H-pyrazol-4-yl]-1,6-naphthyridin-5-yl}-1H-pyrazol-1-yl)cyclobutanecarbonitrile;

cis-3-(cyanomethyl)-3-{3-[7-(1H-pyrazol-4-yl)-1,6-naphthyridin-5-yl]-1H-pyrazol-1-yl}cyclobutanecarbonitrile;

[3-{4-[7-(1H-pyrazol-4-yl)-1,6-naphthyridin-5-yl]-1H-pyrazol-1-yl}-1-(2,2,2-trifluoroethyl)azetidin-3-yl]acetonitrile;

2,2'-(cis-1-{4-[7-(1H-pyrazol-4-yl)-1,6-naphthyridin-5-yl]-1H-pyrazol-1-yl}cyclobutane-1,3-diyl)diacetonitrile;

trans-3-{3-[7-(5-amino-1H-pyrazol-4-yl)-1,6-naphthyridin-5-yl]-5-methyl-1H-pyrazol-1-yl}-3-(cyanomethyl)cyclobutanecarbonitrile;

cis-3-{3-[7-(2-aminopyridin-4-yl)-1,6-naphthyridin-5-yl]-1H-pyrazol-1-yl}-3-(cyanomethyl)cyclobutanecarbonitrile;

cis-3-(cyanomethyl)-3-(3-{7-[5-(hydroxymethyl)-1H-pyrazol-3-yl]-1,6-naphthyridin-5-yl}-1H-pyrazol-1-yl)cyclobutanecarbonitrile;

cis-3-(cyanomethyl)-3-{3-[7-(1-ethyl-1H-pyrazol-4-yl)-1,6-naphthyridin-5-yl]-1H-pyrazol-1-yl}cyclobutanecarbonitrile;

cis-3-{3-[7-(3-amino-1-methyl-1H-pyrazol-4-yl)-1,6-naphthyridin-5-yl]-1H-pyrazol-1-yl}-3-(cyanomethyl)cyclobutanecarbonitrile;

cis-3-{4-[7-(5-amino-1H-pyrazol-3-yl)quinolin-5-yl]-2H-1,2,3-triazol-2-yl}-3-(cyanomethyl)cyclobutanecarbonitrile;

cis-3-{3-[7-(6-aminopyridin-3-yl)-1,6-naphthyridin-5-yl]-1H-pyrazol-1-yl}-3-(cyanomethyl)cyclobutanecarbonitrile;

cis-3-{3-[7-(5-amino-1-methyl-1H-pyrazol-4-yl)-1,6-naphthyridin-5-yl]-1H-pyrazol-1-yl}-3-(cyanomethyl)cyclobutanecarbonitrile;

N-[6-(5-{2-[cis-3-cyano-1-(cyanomethyl)cyclobutyl]-2H-1,2,3-triazol-4-yl}quinolin-7-yl)pyridin-3-yl]methanesulfonamide;

cis-3-(cyanomethyl)-3-{3-[7-(1-methyl-1H-pyrazol-4-yl)-1,6-naphthyridin-5-yl]-1H-pyrazol-1-yl}cyclobutanecarbonitrile;

cis-3-{4-[7-(5-amino-6-methoxypyridin-2-yl)quinolin-5-yl]-2H-1,2,3-triazol-2-yl}-3-(cyanomethyl)cyclobutanecarbonitrile;

cis-3-(cyanomethyl)-3-{5-methyl-3-[7-(1H-pyrazol-4-yl)-1,6-naphthyridin-5-yl]-1H-pyrazol-1-yl}cyclobutanecarbonitrile;

cis-3-(cyanomethyl)-3-(3-{7-[5-(hydroxymethyl)-1H-pyrazol-4-yl]-1,6-naphthyridin-5-yl}-1H-pyrazol-1-yl)cyclobutanecarbonitrile;

cis-3-(cyanomethyl)-3-(3-{7-[1-(2-hydroxyethyl)-1H-pyrazol-4-yl]-1,6-naphthyridin-5-yl}-1H-pyrazol-1-yl)cyclobutanecarbonitrile;

cis-3-(cyanomethyl)-3-{3-[7-(5-methyl-1H-pyrazol-3-yl)-1,6-naphthyridin-5-yl]-1H-pyrazol-1-yl}cyclobutanecarbonitrile;

[3-(4-{7-[1-(tetrahydro-2H-pyran-4-yl)-1H-pyrazol-4-yl]-1,6-naphthyridin-5-yl}-1H-pyrazol-1-yl)-1-(2,2,2-trifluoroethyl)azetidin-3-yl]acetonitrile;

cis-3-(cyanomethyl)-3-{3-[7-(1H-pyrazol-5-yl)-1,6-naphthyridin-5-yl]-1H-pyrazol-1-yl}cyclobutanecarbonitrile;

trans-3-{3-[7-(3-amino-1H-pyrazol-4-yl)-1,6-naphthyridin-5-yl]-1H-pyrazol-1-yl}-3-(cyanomethyl)cyclobutanecarbonitrile;

N-[6-(5-{2-[cis-3-cyano-1-(cyanomethyl)cyclobutyl]-2H-1,2,3-triazol-4-yl}quinolin-7-yl)pyridin-2-yl]acetamide;

cis-3-(cyanomethyl)-3-{4-[7-(1H-pyrazol-3-yl)quinolin-5-yl]-2H-1,2,3-triazol-2-yl}cyclobutanecarbonitrile;

cis-3-(cyanomethyl)-3-{5-methyl-3-[7-(1H-pyrazol-3-yl)-1,6-naphthyridin-5-yl]-1H-pyrazol-1-yl}cyclobutanecarbonitrile;

2,2'-(trans-1-{4-[7-(1H-pyrazol-4-yl)-1,6-naphthyridin-5-yl]-1H-pyrazol-1-yl}cyclobutane-1,3-diyl)diacetonitrile;

cis-3-(cyanomethyl)-3-(3-{7-[2-(hydroxymethyl)pyridin-4-yl]-1,6-naphthyridin-5-yl}-1H-pyrazol-1-yl)cyclobutanecarbonitrile;

6-(5-{2-[cis-3-cyano-1-(cyanomethyl)cyclobutyl]-2H-1,2,3-triazol-4-yl}quinolin-7-yl)pyridine-2-carboxamide;

[3-{4-[7-(1-methyl-1H-pyrazol-4-yl)-1,6-naphthyridin-5-yl]-1H-pyrazol-1-yl}-1-(2,2,2-trifluoroethyl)azetidin-3-yl]acetonitrile;

N-[4-(5-{1-[trans-3-cyano-1-(cyanomethyl)cyclobutyl]-1H-pyrazol-3-yl}-1,6-naphthyridin-7-yl)phenyl]methanesulfonamide;

[3-(4-{7-[1-(oxetan-3-yl)-1H-pyrazol-4-yl]-1,6-naphthyridin-5-yl}-1H-pyrazol-1-yl)-1-(2,2,2-trifluoroethyl)azetidin-3-yl]acetonitrile;

[1-(methylsulfonyl)-3-{3-[7-(1H-pyrrolo[2,3-b]pyridin-3-yl)-1,6-naphthyridin-5-yl]-1H-pyrazol-1-yl}azetidin-3-yl]acetonitrile;

N-[5-(5-{1-[3-(cyanomethyl)-1-(methylsulfonyl)azetidin-3-yl]-1H-pyrazol-3-yl}-1,6-naphthyridin-7-yl)pyridin-2-yl]methanesulfonamide;

[3-{3-[7-(3-amino-1H-pyrazol-4-yl)-1,6-naphthyridin-5-yl]-1H-pyrazol-1-yl}-1-(methylsulfonyl)azetidin-3-yl]acetonitrile;

cis-3-(cyanomethyl)-3-{4-[7-(1H-pyrazol-4-yl)quinolin-5-yl]-2H-1,2,3-triazol-2-yl}cyclobutanecarbonitrile;

2,2'-(3-{4-[7-(1-methyl-1H-pyrazol-4-yl)pyrido[3,4-b]pyrazin-5-yl]-1H-pyrazol-1-yl}azetidine-1,3-diyl)diacetonitrile;

cis-3-{3-[7-(5-amino-1-methyl-1H-pyrazol-3-yl)-1,6-naphthyridin-5-yl]-1H-pyrazol-1-yl}-3-(cyanomethyl)cyclobutanecarbonitrile;

[cis-3-(1H-pyrazol-5-yl)-1-{3-[7-(1H-pyrazol-4-yl)-1,6-naphthyridin-5-yl]-1H-pyrazol-1-yl}cyclobutyl]acetonitrile;

[3-{4-[7-(1-methyl-1H-pyrazol-4-yl)pyrido[3,4-b]pyrazin-5-yl]-1H-pyrazol-1-yl}-1-(2,2,2-trifluoroethyl)azetidin-3-yl]acetonitrile;

2,2'-(cis-1-{3-[7-(1H-pyrazol-4-yl)-1,6-naphthyridin-5-yl]-1H-pyrazol-1-yl}cyclobutane-1,3-diyl)diacetonitrile;

[1-(oxetan-3-ylsulfonyl)-3-{3-[7-(1H-pyrazol-5-yl)-1,6-naphthyridin-5-yl]-1H-pyrazol-1-yl}azetidin-3-yl]acetonitrile;

[3-{4-[7-(1-methyl-1H-pyrazol-4-yl)-1,6-naphthyridin-5-yl]-1H-1,2,3-triazol-1-yl}-1-(2,2,2-trifluoroethyl)azetidin-3-yl]acetonitrile;

[1-(methylsulfonyl)-3-{4-[7-(1H-pyrazol-3-yl)-1,6-naphthyridin-5-yl]-2H-1,2,3-triazol-2-yl}azetidin-3-yl]acetonitrile;

cis-3-(cyanomethyl)-3-(4-{7-[4-(1H-tetrazol-5-yl)phenyl]quinolin-5-yl}-2H-1,2,3-triazol-2-yl)cyclobutanecarbonitrile;

5-(5-{1-[cis-3-cyano-1-(cyanomethyl)cyclobutyl]-1H-pyrazol-3-yl}-1,6-naphthyridin-7-yl)pyridine-2-sulfonamide;

trans-3-(cyanomethyl)-3-(4-{7-[1-(2-hydroxyethyl)-1H-pyrazol-4-yl]-1,6-naphthyridin-5-yl}-1H-pyrazol-1-yl)cyclobutanecarbonitrile;

[3-{3-[7-(3-fluoro-4-hydroxyphenyl)-1,6-naphthyridin-5-yl]-1H-pyrazol-1-yl}-1-(methylsulfonyl)azetidin-3-yl]acetonitrile;

4-(5-{2-[cis-3-cyano-1-(cyanomethyl)cyclobutyl]-2H-1,2,3-triazol-4-yl}quinolin-7-yl)benzoic acid;

3-amino-6-(5-{1-[trans-3-cyano-1-(cyanomethyl)cyclobutyl]-1H-pyrazol-3-yl}-1,6-naphthyridin-7-yl)pyridine-2-carboxamide;

[3-{3-[7-(1H-pyrazol-4-yl)-1,6-naphthyridin-5-yl]-1H-pyrazol-1-yl}-1-(2,2,2-trifluoroethyl)azetidin-3-yl]acetonitrile;

2,2'-(3-{5-[7-(1-methyl-1H-pyrazol-4-yl)-1,6-naphthyridin-5-yl]-1,2-oxazol-3-yl}azetidine-1,3-diyh)diacetonitrile;

[1-(methylsulfonyl)-3-{3-[7-(6-oxo-1,6-dihydropyridin-3-yl)-1,6-naphthyridin-5-yl]-1H-pyrazol-1-yl}azetidin-3-yl]acetonitrile;

cis-3-{3-[7-(2-amino-6-methylpyridin-4-yl)-1,6-naphthyridin-5-yl]-1H-pyrazol-1-yl}-3-(cyanomethyl)cyclobutanecarbonitrile;

[3-(3-{7-[1-(1-chloro-3-hydroxypropan-2-yl)-1H-pyrazol-4-yl]-1,6-naphthyridin-5-yl}-1H-pyrazol-1-yl)-1-(methylsulfonyl)azetidin-3-yl]acetonitrile;

[3-{3-[7-(4-hydroxyphenyl)-1,6-naphthyridin-5-yl]-1H-pyrazol-1-yl}-1-(methylsulfonyl)azetidin-3-yl]acetonitrile;

cis-3-(cyanomethyl)-1-methyl-3-{3-[7-(1H-pyrazol-4-yl)-1,6-naphthyridin-5-yl]-1H-pyrazol-1-yl}cyclobutanecarbonitrile;

trans-3-{3-[7-(3-amino-1-methyl-1H-pyrazol-4-yl)-1,6-naphthyridin-5-yl]-1H-pyrazol-1-yl}-3-(cyanomethyl)cyclobutanecarbonitrile;

trans-3-{4-[7-(5-amino-1H-pyrazol-3-yl)quinolin-5-yl]-2H-1,2,3-triazol-2-yl}-3-(cyanomethyl)cyclobutanecarbonitrile;

cis-3-{4-[7-(5-amino-1H-pyrazol-4-yl)quinolin-5-yl]-2H-1,2,3-triazol-2-yl}-3-(cyanomethyl)cyclobutanecarbonitrile;

cis-3-(cyanomethyl)-3-(4-{7-[1-(2-hydroxyethyl)-1H-pyrazol-4-yl]quinolin-5-yl}-2H-1,2,3-triazol-2-yl)cyclobutanecarbonitrile;

[3-(3-{7-[6-(dimethylamino)pyridin-3-yl]-1,6-naphthyridin-5-yl}-1H-pyrazol-1-yl)-1-(methylsulfonyl)azetidin-3-yl]acetonitrile;

[trans-1-(4-{7-[3-(hydroxymethyl)-1H-pyrazol-5-yl]-1,6-naphthyridin-5-yl}-1H-pyrazol-1-yl)-3-methoxycyclobutyl]acetonitrile;

cis-3-(cyanomethyl)-3-{3-[7-(3-methyl-1H-pyrazol-4-yl)-1,6-naphthyridin-5-yl]-1H-pyrazol-1-yl}cyclobutanecarbonitrile;

[1-(cyclopropylsulfonyl)-3-{4-[7-(1H-pyrazol-3-yl)quinolin-5-yl]-2H-1,2,3-triazol-2-yl}azetidin-3-yl]acetonitrile;

cis-3-(cyanomethyl)-3-(3-{7-[6-(methylsulfonyl)pyridin-3-yl]-1,6-naphthyridin-5-yl}-1H-pyrazol-1-yl)cyclobutanecarbonitrile;

3-(cyanomethyl)-3-{4-[7-(1H-pyrazol-3-yl)quinolin-5-yl]-2H-1,2,3-triazol-2-yl}azetidine-1-sulfonamide;

trans-3-(cyanomethyl)-3-(3-{7-[5-(hydroxymethyl)-1H-pyrazol-3-yl]-1,6-naphthyridin-5-yl}-1H-pyrazol-1-yl)cyclobutanecarbonitrile;

trans-3-(cyanomethyl)-3-{3-[7-(1H-pyrazol-4-yl)-1,6-naphthyridin-5-yl]-1H-pyrazol-1-yl}cyclobutanecarbonitrile;

cis-3-{3-[7-(2-aminopyridin-4-yl)-1,6-naphthyridin-5-yl]-1H-pyrazol-1-yl}-3-(cyanomethyl)-1-methylcyclobutanecarbonitrile;

3-(cyanomethyl)-3-{3-[7-(1-methyl-1H-pyrazol-4-yl)-1,6-naphthyridin-5-yl]-1H-pyrazol-1-yl}azetidine-1-sulfonamide;

cis-3-(cyanomethyl)-3-{4-[7-(1-methyl-1H-pyrazol-4-yl)quinolin-5-yl]-2H-1,2,3-triazol-2-yl}cyclobutanecarbonitrile;

cis-3-{4-[7-(5-aminopyridin-2-yl)quinolin-5-yl]-2H-1,2,3-triazol-2-yl}-3-(cyanomethyl)cyclobutanecarbonitrile;

2,2'-(cis-1-{3-[7-(1H-pyrazol-5-yl)-1,6-naphthyridin-5-yl]-1H-pyrazol-1-yl}cyclobutane-1,3-diyl)diacetonitrile;

cis-3-(cyanomethyl)-3-{4-[7-(2-methyl-1H-imidazol-4-yl)quinolin-5-yl]-2H-1,2,3-triazol-2-yl}cyclobutanecarbonitrile;

trans-3-(cyanomethyl)-3-(4-{7-[1-(2-hydroxyethyl)-1H-pyrazol-4-yl]quinolin-5-yl}-2H-1,2,3-triazol-2-yl)cyclobutanecarbonitrile;

trans-3-{3-[7-(2-aminopyridin-4-yl)-1,6-naphthyridin-5-yl]-1H-pyrazol-1-yl}-3-(cyanomethyl)cyclobutanecarbonitrile;

[1-(oxetan-3-ylsulfonyl)-3-{4-[7-(1H-pyrazol-5-yl)quinolin-5-yl]-2H-1,2,3-triazol-2-yl}azetidin-3-yl]acetonitrile;

4-(5-{2-[cis-3-cyano-1-(cyanomethyl)cyclobutyl]-2H-1,2,3-triazol-4-yl}quinolin-7-yl)benzamide;

trans-3-{3-[7-(5-amino-1-methyl-1H-pyrazol-4-yl)-1,6-naphthyridin-5-yl]-1H-pyrazol-1-yl}-3-(cyanomethyl)cyclobutanecarbonitrile;

cis-3-{3-[7-(5-amino-6-methoxypyridin-2-yl)-1,6-naphthyridin-5-yl]-1H-pyrazol-1-yl}-3-(cyanomethyl)cyclobutanecarbonitrile;

(cis-1-{3-[7-(5-amino-1H-pyrazol-3-yl)-1,6-naphthyridin-5-yl]-1H-pyrazol-1-yl}-3-methoxycyclobutyl)acetonitrile;

trans-3-(cyanomethyl)-3-{3-[7-(1H-pyrazol-5-yl)-1,6-naphthyridin-5-yl]-1H-pyrazol-1-yl}cyclobutanecarbonitrile;

[3-{3-[7-(3-amino-1-methyl-1H-pyrazol-4-yl)-1,6-naphthyridin-5-yl]-1H-pyrazol-1-yl}-1-(methylsulfonyl)azetidin-3-yl]acetonitrile;

[3-{3-[7-(6-hydroxypyridin-3-yl)-1,6-naphthyridin-5-yl]-1H-pyrazol-1-yl}-1-(2,2,2-trifluoroethyl)azetidin-3-yl]acetonitrile;

cis-3-(cyanomethyl)-3-(3-{7-[3-(hydroxymethyl)-1,2-oxazol-5-yl]-1,6-naphthyridin-5-yl}-1H-pyrazol-1-yl)cyclobutanecarbonitrile;

cis-3-{4-[7-(6-aminopyridin-2-yl)quinolin-5-yl]-2H-1,2,3-triazol-2-yl}-3-(cyanomethyl)cyclobutanecarbonitrile;

[1-(methylsulfonyl)-3-{3-[7-(pyrazolo[1,5-a]pyridin-3-yl)-1,6-naphthyridin-5-yl]-1H-pyrazol-1-yl}azetidin-3-yl]acetonitrile;

cis-3-(cyanomethyl)-3-[3-(7-{1-[2-(dimethylamino)ethyl]-1H-pyrazol-4-yl}-1,6-naphthyridin-5-yl)-1H-pyrazol-1-yl]cyclobutanecarbonitrile;

[cis-1-(4-{7-[3-(hydroxymethyl)-1H-pyrazol-5-yl]-1,6-naphthyridin-5-yl}-1H-pyrazol-1-yl)-3-methoxycyclobutyl]acetonitrile;

trans-3-(cyanomethyl)-3-{3-[7-(1-ethyl-1H-pyrazol-4-yl)-1,6-naphthyridin-5-yl]-1H-pyrazol-1-yl}cyclobutanecarbonitrile;

cis-3-{3-[7-(5-amino-1-methyl-1H-pyrazol-3-yl)-1,6-naphthyridin-5-yl]-5-methyl-1H-pyrazol-1-yl}-3-(cyanomethyl)cyclobutanecarbonitrile;

cis-3-(cyanomethyl)-3-(4-{7-[4-(hydroxymethyl)-1,3-thiazol-2-yl]quinolin-5-yl}-2H-1,2,3-triazol-2-yl)cyclobutanecarbonitrile;

cis-3-(cyanomethyl)-3-{4-[7-(5-hydroxy-6-methylpyridin-2-yl)quinolin-5-yl]-2H-1,2,3-triazol-2-yl}cyclobutanecarbonitrile;

trans-3-(cyanomethyl)-3-{4-[7-(1H-pyrazol-3-yl)quinolin-5-yl]-2H-1,2,3-triazol-2-yl}cyclobutanecarbonitrile;

2,2'-(3-{3-[7-(1-methyl-1H-pyrazol-4-yl)-1,6-naphthyridin-5-yl]-1H-pyrazol-1-yl}azetidine-1,3-diyhdiacetonitrile;

[1-(cyclopropylsulfonyl)-3-{3-[7-(1H-pyrazol-5-yl)-1,6-naphthyridin-5-yl]-1H-pyrazol-1-yl}azetidin-3-yl]acetonitrile;

N-[6-(5-{2-[trans-3-cyano-1-(cyanomethyl)cyclobutyl]-2H-1,2,3-triazol-4-yl}quinolin-7-yl)pyridin-3-yl]methanesulfonamide;

[3-{3-[7-(1-ethyl-1H-pyrazol-4-yl)-1,6-naphthyridin-5-yl]-1H-pyrazol-1-yl}-1-(2,2,2-trifluoroethyl)azetidin-3-yl]acetonitrile;

4-(5-{1-[cis-3-cyano-1-(cyanomethyl)cyclobutyl]-1H-pyrazol-3-yl}-1,6-naphthyridin-7-yl)pyridine-2-carboxamide;

[3-{3-[7-(1H-pyrazol-3-yl)-1,6-naphthyridin-5-yl]-1H-pyrazol-1-yl}-1-(2,2,2-trifluoroethyl)azetidin-3-yl]acetonitrile;

cis-3-(cyanomethyl)-3-{4-[7-(1-methyl-1H-pyrazol-3-yl)quinolin-5-yl]-2H-1,2,3-triazol-2-yl}cyclobutanecarbonitrile;

trans-3-{3-[7-(6-aminopyridin-3-yl)-1,6-naphthyridin-5-yl]-1H-pyrazol-1-yl}-3-(cyanomethyl)cyclobutanecarbonitrile;

trans-3-(cyanomethyl)-3-(3-{7-[3-(hydroxymethyl)-1-methyl-1H-pyrazol-4-yl]-1,6-naphthyridin-5-yl}-1H-pyrazol-1-yl)cyclobutanecarbonitrile;

trans-3-(cyanomethyl)-3-{3-[7-(5-methyl-1H-pyrazol-3-yl)-1,6-naphthyridin-5-yl]-1H-pyrazol-1-yl}cyclobutanecarbonitrile;

[trans-1-(4-{7-[1-(2-hydroxyethyl)-1H-pyrazol-4-yl]-1,6-naphthyridin-5-yl}-1H-pyrazol-1-yl)-3-methoxycyclobutyl]acetonitrile;

cis-3-{4-[7-(6-aminopyridin-3-yl)quinolin-5-yl]-2H-1,2,3-triazol-2-yl}-3-(cyanomethyl)cyclobutanecarbonitrile;

2,2'-[3-(3-{7-[1-(oxetan-3-yl)-1H-pyrazol-4-yl]-1,6-naphthyridin-5-yl}-1H-pyrazol-1-yl)azetidine-1,3-diyl]diacetonitrile;

cis-3-(cyanomethyl)-3-(3-{7-[3-(hydroxymethyl)-1-methyl-1H-pyrazol-5-yl]-1,6-naphthyridin-5-yl}-1H-pyrazol-1-yl)cyclobutanecarbonitrile;

trans-3-(cyanomethyl)-3-{4-[7-(1H-pyrazol-4-yl)quinolin-5-yl]-2H-1,2,3-triazol-2-yl}cyclobutanecarbonitrile;

cis-3-(cyanomethyl)-3-(4-{7-[5-(methylsulfonyl)pyridin-2-yl]quinolin-5-yl}-2H-1,2,3-triazol-2-yl)cyclobutanecarbonitrile;

[3-{4-[7-(1H-pyrazol-3-yl)quinolin-5-yl]-2H-1,2,3-triazol-2-yl}-1-(2,2,2-trifluoroethyl)azetidin-3-yl]acetonitrile;

cis-3-(cyanomethyl)-3-(4-{7-[3-(hydroxymethyl)-1H-pyrazol-4-yl]quinolin-5-yl}-2H-1,2,3-triazol-2-yl)cyclobutanecarbonitrile;

[3-{3-[7-(1-ethyl-6-oxo-1,6-dihydropyridin-3-yl)-1,6-naphthyridin-5-yl]-1H-pyrazol-1-yl}-1-(methylsulfonyl)azetidin-3-yl]acetonitrile;

[1-(cyclopropylsulfonyl)-3-{3-[7-(6-oxo-1,6-dihydropyridin-3-yl)-1,6-naphthyridin-5-yl]-1H-pyrazol-1-yl}azetidin-3-yl]acetonitrile;

trans-3-(cyanomethyl)-3-(3-{7-[5-(hydroxymethyl)-1H-pyrazol-4-yl]-1,6-naphthyridin-5-yl}-1H-pyrazol-1-yl)cyclobutanecarbonitrile;

[3-{3-[7-(1-methyl-1H-pyrazol-4-yl)-1,6-naphthyridin-5-yl]-1H-pyrazol-1-yl}-1-(2,2,2-trifluoroethyl)azetidin-3-yl]acetonitrile;

cis-3-(cyanomethyl)-1-methyl-3-{3-[7-(1H-pyrazol-3-yl)-1,6-naphthyridin-5-yl]-1H-pyrazol-1-yl}cyclobutanecarbonitrile;

3-(5-{2-[cis-3-cyano-1-(cyanomethyl)cyclobutyl]-2H-1,2,3-triazol-4-yl}quinolin-7-yl)benzamide;

cis-3-(cyanomethyl)-3-(4-{7-[5-(2-hydroxyethyl)-6-methylpyridin-2-yl]quinolin-5-yl}-2H-1,2,3-triazol-2-yl)cyclobutanecarbonitrile;

trans-3-(cyanomethyl)-3-(3-{7-[1-(2-hydroxyethyl)-1H-pyrazol-4-yl]-1,6-naphthyridin-5-yl}-1H-pyrazol-1-yl)cyclobutanecarbonitrile;

[3-{3-[7-(5-amino-1-methyl-1H-pyrazol-4-yl)-1,6-naphthyridin-5-yl]-1H-pyrazol-1-yl}-1-(methylsulfonyl)azetidin-3-yl]acetonitrile;

trans-3-(cyanomethyl)-3-{3-[7-(1-methyl-1H-pyrazol-4-yl)-1,6-naphthyridin-5-yl]-1H-pyrazol-1-yl}cyclobutanecarbonitrile;

N-[6-(5-{2-[trans-3-cyano-1-(cyanomethyl)cyclobutyl]-2H-1,2,3-triazol-4-yl}quinolin-7-yl)pyridin-2-yl]acetamide;

[1-(methylsulfonyl)-3-{4-[7-(1H-pyrazol-3-yl)quinolin-5-yl]-2H-1,2,3-triazol-2-yl}azetidin-3-yl]acetonitrile;

N-[6-(5-{2-[cis-3-cyano-1-(cyanomethyl)cyclobutyl]-2H-1,2,3-triazol-4-yl}quinolin-7-yl)pyridin-2-yl]methanesulfonamide;

cis-3-(cyanomethyl)-3-{4-[7-(4-methyl-3-oxo-3,4-dihydro-2H-pyrido[3,2-b][1,4]oxazin-6-yl)quinolin-5-yl]-2H-1,2,3-triazol-2-yl}cyclobutanecarbonitrile;

[3-{3-[7-(pyridin-4-yl)-1,6-naphthyridin-5-yl]-1H-pyrazol-1-yl}-1-(2,2,2-trifluoroethyl)azetidin-3-yl]acetonitrile;

trans-3-(cyanomethyl)-3-(3-{7-[5-(hydroxymethyl)-1-methyl-1H-pyrazol-4-yl]-1,6-naphthyridin-5-yl}-1H-pyrazol-1-yl)cyclobutanecarbonitrile;

[1-(methylsulfonyl)-3-(3-{7-[1-(oxetan-3-ylmethyl)-1H-pyrazol-4-yl]-1,6-naphthyridin-5-yl}-1H-pyrazol-1-yl)azetidin-3-yl]acetonitrile;

6-(5-{1-[cis-3-cyano-1-(cyanomethyl)cyclobutyl]-1H-pyrazol-4-yl}imidazo[1,2-a]pyridin-7-yl)pyridine-2-carboxamide;

cis-3-{4-[7-(5-amino-6-methoxypyridin-2-yl)imidazo[1,2-a]pyridin-5-yl]-1H-pyrazol-1-yl}-3-(cyanomethyl)cyclobutanecarbonitrile;

2,2'-(3-{4-[7-(1-methyl-1H-pyrazo-4-yl)quinolin-5-yl]-1H-pyrazol-1-yl}azetidine-1,3-diyhdiacetonitrile;

(trans-1-{3-[7-(5-amino-1H-pyrazol-3-yl)-1,6-naphthyridin-5-yl]-1H-pyrazol-1-yl}-3-methoxycyclobutyl)acetonitrile;

[3-{3-[7-(2-aminopyridin-4-yl)-1,6-naphthyridin-5-yl]-1H-pyrazol-1-yl}-1-(2,2,2-trifluoroethyl)azetidin-3-yl]acetonitrile;

[cis-1-(4-{7-[1-(2-hydroxyethyl)-1H-pyrazol-4-yl]-1,6-naphthyridin-5-yl}-1H-pyrazol-1-yl)-3-methoxycyclobutyl]acetonitrile;

[3-{3-[7-(2-hydroxyphenyl)-1,6-naphthyridin-5-yl]-1H-pyrazol-1-yl}-1-(methylsulfonyl)azetidin-3-yl]acetonitrile;

cis-3-(cyanomethyl)-3-(3-{7-[5-(hydroxymethyl)-1-methyl-1H-pyrazol-3-yl]-1,6-naphthyridin-5-yl}-1H-pyrazol-1-yl)cyclobutanecarbonitrile;

cis-3-(cyanomethyl)-3-{3-[7-(4,5,6,7-tetrahydropyrazolo[1,5-a]pyrazin-2-yl)-1,6-naphthyridin-5-yl]-1H-pyrazol-1-yl}cyclobutanecarbonitrile;

[1-(methylsulfonyl)-3-{3-[7-(1H-pyrazol-4-yl)-1,6-naphthyridin-5-yl]-1H-pyrazol-1-yl}azetidin-3-yl]acetonitrile;

[3-{3-[7-(1-methyl-1H-pyrazol-4-yl)[1,2,4]triazolo[1,5-a]pyridin-5-yl]-1H-pyrazol-1-yl}-1-(2,2,2-trifluoroethyl)azetidin-3-yl]acetonitrile;

{1-(methylsulfonyl)-3-[3-(7-{1-[(3R)-tetrahydrofuran-3-yl]-1H-pyrazol-4-yl}-1,6-naphthyridin-5-yl)-1H-pyrazol-1-yl]azetidin-3-yl}acetonitrile;

trans-3-(cyanomethyl)-3-(4-{7-[5-(hydroxymethyl)-1H-pyrazol-3-yl]quinolin-5-yl}-2H-1,2,3-triazol-2-yl)cyclobutanecarbonitrile;

cis-3-(cyanomethyl)-3-{4-[7-(2-methyl-3H-imidazo[4,5-b]pyridin-5-yl)quinolin-5-yl]-2H-1,2,3-triazol-2-yl}cyclobutanecarbonitrile;

6-(5-{2-[trans-3-cyano-1-(cyanomethyl)cyclobutyl]-2H-1,2,3-triazol-4-yl}quinolin-7-yl)pyridine-2-carboxamide;

cis-3-(cyanomethyl)-1-methyl-3-{3-[7-(5-methyl-1H-pyrazol-3-yl)-1,6-naphthyridin-5-yl]-1H-pyrazol-1-yl}cyclobutanecarbonitrile;

cis-3-(cyanomethyl)-3-{4-[7-(pyrazolo[1,5-a]pyrimidin-3-yl)quinolin-5-yl]-2H-1,2,3-triazol-2-yl}cyclobutanecarbonitrile;

{1-(methylsulfonyl)-3-[3-(7-{1-[(3S)-tetrahydrofuran-3-yl]-1H-pyrazol-4-yl}-1,6-naphthyridin-5-yl)-1H-pyrazol-1-yl]azetidin-3-yl}acetonitrile;

cis-3-{4-[7-(6-aminopyridazin-3-yl)quinolin-5-yl]-2H-1,2,3-triazol-2-yl}-3-(cyanomethyl)cyclobutanecarbonitrile;

trans-3-{4-[7-(5-amino-6-methoxypyridin-2-yl)quinolin-5-yl]-2H-1,2,3-triazol-2-yl}-3-(cyanomethyl)cyclobutanecarbonitrile;

[3-{3-[7-(2-methylpyridin-4-yl)-1,6-naphthyridin-5-yl]-1H-pyrazol-1-yl}-1-(methylsulfonyl)azetidin-3-yl]acetonitrile;

trans-3-(cyanomethyl)-3-{5-methyl-3-[7-(1H-pyrazol-4-yl)-1,6-naphthyridin-5-yl]-1H-pyrazol-1-yl}cyclobutanecarbonitrile;

[3-{3-[7-(3-hydroxyphenyl)-1,6-naphthyridin-5-yl]-1H-pyrazol-1-yl}-1-(methylsulfonyl)azetidin-3-yl]acetonitrile;

[3-{3-[7-(imidazo[1,2-a]pyridin-6-yl)-1,6-naphthyridin-5-yl]-1H-pyrazol-1-yl}-1-(methylsulfonyl)azetidin-3-yl]acetonitrile;

(cis-1-{3-[7-(3-amino-1H-pyrazol-4-yl)-1,6-naphthyridin-5-yl]-1H-pyrazol-1-yl}-3-methoxycyclobutyl)acetonitrile;

[1-(methylsulfonyl)-3-{4-[7-(1H-pyrazol-3-yl)quinolin-5-yl]-1H-pyrazol-1-yl}azetidin-3-yl]acetonitrile;

6-(5-{2-[cis-3-cyano-1-(cyanomethyl)cyclobutyl]-2H-1,2,3-triazol-4-yl}quinolin-7-yl)pyridine-3-carboxamide;

2,2'-(trans-1-{3-[7-(1H-pyrazol-5-yl)-1,6-naphthyridin-5-yl]-1H-pyrazol-1-yl}cyclobutane-1,3-diyhdiacetonitrile;

[3-{3-[7-(6-aminopyridin-3-yl)-1,6-naphthyridin-5-yl]-1H-pyrazol-1-yl}-1-(methylsulfonyl)azetidin-3-yl]acetonitrile;

cis-3-(cyanomethyl)-3-{3-[7-(6-hydroxypyridin-2-yl)-1,6-naphthyridin-5-yl]-1H-pyrazol-1-yl}cyclobutanecarbonitrile;

cis-3-(cyanomethyl)-3-{4-[7-(5-methyl-1H-pyrazol-3-yl)imidazo[1,2-a]pyridin-5-yl]-1H-pyrazol-1-yl}cyclobutanecarbonitrile;

cis-3-(cyanomethyl)-3-{3-[7-(1,5-dimethyl-1H-pyrazol-3-yl)-1,6-naphthyridin-5-yl]-1H-pyrazol-1-yl}cyclobutanecarbonitrile;

cis-3-(cyanomethyl)-3-{4-[7-(1H-pyrazol-3-yl)imidazo[1,2-a]pyridin-5-yl]-1H-pyrazol-1-yl}cyclobutanecarbonitrile;

[3-{3-[7-(6-aminopyridin-3-yl)-1,6-naphthyridin-5-yl]-1H-pyrazol-1-yl}-1-(2,2,2-trifluoroethyl)azetidin-3-yl]acetonitrile;

[3-(3-{7-[1-(2-hydroxyethyl)-1H-pyrazol-4-yl]-1,6-naphthyridin-5-yl}-1H-pyrazol-1-yl)-1-(methylsulfonyl)azetidin-3-yl]acetonitrile;

[3-{3-[7-(2-methylpyridin-4-yl)-1,6-naphthyridin-5-yl]-1H-pyrazol-1-yl}-1-(2,2,2-trifluoroethyl)azetidin-3-yl]acetonitrile;

[3-(3-{7-[1-(oxetan-3-yl)-1H-pyrazol-4-yl]-1,6-naphthyridin-5-yl}-1H-pyrazol-1-yl)-1-(2,2,2-trifluoroethyl)azetidin-3-yl]acetonitrile;

[3-{3-[7-(1-methyl-6-oxo-1,6-dihydropyridin-3-yl)-1,6-naphthyridin-5-yl]-1H-pyrazol-1-yl}-1-(methylsulfonyl)azetidin-3-yl]acetonitrile;

trans-3-(cyanomethyl)-3-{4-[7-(4-methyl-3-oxo-3,4-dihydro-2H-pyrido[3,2-b][1,4]oxazin-6-yl)quinolin-5-yl]-2H-1,2,3-triazol-2-yl}cyclobutanecarbonitrile;

(trans-1-{3-[7-(3-amino-1H-pyrazol-4-yl)-1,6-naphthyridin-5-yl]-1H-pyrazol-1-yl}-3-methoxycyclobutyl)acetonitrile;

[1-(cyclopropylsulfonyl)-3-{3-[7-(1-methyl-1H-pyrazol-4-yl)-1,6-naphthyridin-5-yl]-1H-pyrazol-1-yl}azetidin-3-yl]acetonitrile;

[1-(methylsulfonyl)-3-{3-[7-(1H-pyrazol-5-yl)-1,6-naphthyridin-5-yl]-1H-pyrazol-1-yl}azetidin-3-yl]acetonitrile;

[3-(3-{7-[1-(piperidin-4-yl)-1H-pyrazol-4-yl]-1,6-naphthyridin-5-yl}-1H-pyrazol-1-yl)-1-(2,2,2-trifluoroethyl)azetidin-3-yl]acetonitrile;

2,2'-(trans-1-{3-[7-(1H-pyrazol-4-yl)-1,6-naphthyridin-5-yl]-1H-pyrazol-1-yl}cyclobutane-1,3-diyhdiacetonitrile;

[3-(3-{7-[1-(1-methylpiperidin-4-yl)-1H-pyrazol-4-yl]-1,6-naphthyridin-5-yl}-1H-pyrazol-1-yl)-1-(2,2,2-trifluoroethyl)azetidin-3-yl]acetonitrile;

(cis-3-methoxy-1-{3-[7-(1H-pyrazol-4-yl)-1,6-naphthyridin-5-yl]-1H-pyrazol-1-yl}cyclobutyl)acetonitrile;

[3-{3-[7-(1-methyl-6-oxo-1,6-dihydropyridin-3-yl)-1,6-naphthyridin-5-yl]-1H-pyrazol-1-yl}-1-(2,2,2-trifluoroethyl)azetidin-3-yl]acetonitrile;

cis-3-(cyanomethyl)-3-{4-[7-(pyridin-2-yl)quinolin-5-yl]-2H-1,2,3-triazol-2-yl}cyclobutanecarbonitrile;

[3-{3-[7-(2,6-diaminopyridin-3-yl)-1,6-naphthyridin-5-yl]-1H-pyrazol-1-yl}-1-(methylsulfonyl)azetidin-3-yl]acetonitrile;

[1-(methylsulfonyl)-3-{4-[7-(1H-pyrazol-4-yl)quinolin-5-yl]-2H-1,2,3-triazol-2-yl}azetidin-3-yl]acetonitrile;

cis-3-(cyanomethyl)-3-{4-[7-(5-fluoropyriclin-2-yl)quinolin-5-yl]-2H-1,2,3-triazol-2-yl}cyclobutanecarbonitrile;

cis-3-{4-[7-(5-amino-6-methontpyrazin-2-yl)quinolin-5-yl]-2H-1,2,3-triazol-2-yl}-3-(cyanomethyl)cyclobutanecarbonitrile;

[3-{4-[7-(4-hydroxyphenyl)quinolin-5-yl]-2H-1,2,3-triazol-2-yl}-1-(methylsulfonyl)azetidin-3-yl]acetonitrile;

[3-{4-[7-(3-fluoro-4-hydrontphenyl)quinolin-5-yl]-2H-1,2,3-triazol-2-yl}-1-(methylsulfonyl)azetidin-3-yl]acetonitrile;

trans-3-{4-[7-(5-amino-1H-pyrazol-4-yl)quinolin-5-yl]-2H-1,2,3-triazol-2-yl}-3-(cyanomethyl)cyclobutanecarbonitrile;

[3-{3-[7-(5-methyl-6-oxo-1,6-dihydropyridin-3-yl)-1,6-naphthyridin-5-yl]-1H-pyrazol-1-yl}-1-(2,2,2-trifluoroethyl)azetidin-3-yl]acetonitrile;

cis-3-{3-[7-(6-aminopyridazin-4-yl)-1,6-naphthyridin-5-yl]-1H-pyrazol-1-yl}-3-(cyanomethyl)cyclobutanecarbonitrile;

cis-3-(cyanomethyl)-3-{4-[7-(1H-pyrazol-4-yl)imidazo[1,2-a]pyridin-5-yl]-1H-pyrazol-1-yl}cyclobutanecarbonitrile;

cis-3-{3-[7-(5-aminopyridin-2-yl)-1,6-naphthyridin-5-yl]-1H-pyrazol-1-yl}-3-(cyanomethyl)cyclobutanecarbonitrile;

trans-3-(cyanomethyl)-3-{3-[7-(3-methyl-1H-pyrazol-4-yl)-1,6-naphthyridin-5-yl]-1H-pyrazol-1-yl}cyclobutanecarbonitrile;

(cis-3-methoxy-1-{3-[7-(6-oxo-1,6-dihydropyridin-3-yl)-1,6-naphthyridin-5-yl]-1H-pyrazol-1-yl}cyclobutyl)acetonitrile;

[3-{4-[7-(1-methyl-1H-pyrazol-4-yl)quinolin-5-yl]-1H-1,2,3-triazol-1-yl}-1-(methylsulfonyl)azetidin-3-yl]acetonitrile;

[1-(ethylsulfonyl)-3-{3-[7-(1-methyl-1H-pyrazol-4-yl)-1,6-naphthyridin-5-yl]-1H-pyrazol-1-yl}azetidin-3-yl]acetonitrile;

[3-{3-[7-(1-methyl-1H-pyrazol-4-yl)-1,6-naphthyridin-5-yl]-1H-pyrazol-1-yl}-1-(methylsulfonyl)azetidin-3-yl]acetonitrile;

trans-3-(cyanomethyl)-3-{5-methyl-3-[7-(1H-pyrazol-3-yl)-1,6-naphthyridin-5-yl]-1H-pyrazol-1-yl}cyclobutanecarbonitrile;

trans-3-(cyanomethyl)-3-{4-[7-(1-methyl-1H-pyrazol-4-yl)quinolin-5-yl]-2H-1,2,3-triazol-2-yl}cyclobutanecarbonitrile;

[1-(methylsulfonyl)-3-{3-[7-(1,2,3,4-tetrahydropyrido[2,3-b]pyrazin-7-yl)-1,6-naphthyridin-5-yl]-1H-pyrazol-1-yl}azetidin-3-yl]acetonitrile;

4-(5-{2-[trans-3-cyano-1-(cyanomethyl)cyclobutyl]-2H-1,2,3-triazol-4-yl}quinolin-7-yl)benzoic acid;

5-(5-{1-[trans-3-cyano-1-(cyanomethyl)cyclobutyl]-1H-pyrazol-3-yl}-1,6-naphthyridin-7-yl)pyridine-2-sulfonamide;

[1-(methylsulfonyl)-3-{4-[7-(1H-pyrazol-4-yl)quinolin-5-yl]-1H-pyrazol-1-yl}azetidin-3-yl]acetonitrile;

cis-3-(cyanomethyl)-3-{4-[7-(4-hydroxyphenyl)imidazo[1,2-a]pyridin-5-yl]-1H-pyrazol-1-yl}cyclobutanecarbonitrile;

cis-3-(cyanomethyl)-3-{4-[7-(imidazo[1,2-b]pyridazin-3-yl)quinolin-5-yl]-2H-1,2,3-triazol-2-yl}cyclobutanecarbonitrile;

trans-3-(cyanomethyl)-3-{4-[7-(3-methyl-1H-pyrazol-5-yl)imidazo[1,2-a]pyridin-5-yl]-1H-pyrazol-1-yl}cyclobutanecarbonitrile;

trans-3-{3-[7-(5-amino-1-methyl-1H-pyrazol-3-yl)-1,6-naphthyridin-5-yl]-1H-pyrazol-1-yl}-3-(cyanomethyl)cyclobutanecarbonitrile;

cis-3-(cyanomethyl)-3-(4-{7-[4-(hydroxymethyl)-1,3-thiazol-2-yl]imidazo[1,2-a]pyridin-5-yl}-1H-pyrazol-1-yl)cyclobutanecarbonitrile;

[3-{3-[7-(5-methyl-1H-pyrazol-3-yl)-1,6-naphthyridin-5-yl]-1H-pyrazol-1-yl}-1-(2,2,2-trifluoroethyl)azetidin-3-yl]acetonitrile;

[3-{3-[7-(3-methyl-1H-pyrazol-4-yl)-1,6-naphthyridin-5-yl]-1H-pyrazol-1-yl}-1-(methylsulfonyl)azetidin-3-yl]acetonitrile;

[3-(3-{7-[1-(3-hydroxyprop-1-en-2-yl)-1H-pyrazol-4-yl]-1,6-naphthyridin-5-yl}-1H-pyrazol-1-yl)-1-(methylsulfonyl)azetidin-3-yl]acetonitrile;

trans-3-(cyanomethyl)-3-{4-[7-(1-methyl-1H-pyrazol-3-yl)quinolin-5-yl]-2H-1,2,3-triazol-2-yl}cyclobutanecarbonitrile;

{3-[3-(7-{1-[(3-hydroxyoxetan-3-yl)methyl]-1H-pyrazol-4-yl}-1,6-naphthyridin-5-yl)-1H-pyrazol-1-yl]-1-(methylsulfonyl)azetidin-3-yl}acetonitrile;

cis-3-(cyanomethyl)-3-{4-[7-(1-methyl-1H-pyrazol-4-yl)imidazo[1,2-a]pyridin-5-yl]-1H-pyrazol-1-yl}cyclobutanecarbonitrile;

[1-(methylsulfonyl)-3-{3-[7-(7H-pyrrolo[2,3-b]pyridin-5-yl)-1,6-naphthyridin-5-yl]-1H-pyrazol-1-yl}azetidin-3-yl]acetonitrile;

cis-3-{4-[7-(3-amino-1-methyl-1H-pyrazol-4-yl)quinolin-5-yl]-2H-1,2,3-triazol-2-yl}-3-(cyanomethyl)cyclobutanecarbonitrile;

N-[cis-3-(cyanomethyl)-3-{3-[7-(1H-pyrazol-3-yl)-1,6-naphthyridin-5-yl]-1H-pyrazol-1-yl}cyclobutyl]-N-methylacetamide;

trans-3-{4-[7-(5-aminopyridin-2-yl)quinolin-5-yl]-2H-1,2,3-triazol-2-yl}-3-(cyanomethyl)cyclobutanecarbonitrile;

[1-(methylsulfonyl)-3-(3-{7-[1-(oxetan-3-yl)-1H-pyrazol-4-yl]-1,6-naphthyridin-5-yl}-1H-pyrazol-1-yl)azetidin-3-yl]acetonitrile;

(cis-3-methoxy-1-{3-[7-(1H-pyrazol-5-yl)-1,6-naphthyridin-5-yl]-1H-pyrazol-1-yl}cyclobutyl)acetonitrile;

trans-3-(cyanomethyl)-3-(4-{7-[5-(hydroxymethyl)-1-methyl-1H-pyrazol-3-yl]quinolin-5-yl}-2H-1,2,3-triazol-2-yl)cyclobutanecarbonitrile;

cis-3-{4-[7-(5-aminopyrazin-2-yl)quinolin-5-yl]-2H-1,2,3-triazol-2-yl}-3-(cyanomethyl)cyclobutanecarbonitrile;

[cis-1-(3-{7-[3-(hydroxymethyl)-1H-pyrazol-5-yl]-1,6-naphthyridin-5-yl}-1H-pyrazol-1-yl)-3-methoxycyclobutyl]acetonitrile;

3-amino-6-(5-{1-[cis-3-cyano-1-(cyanomethyl)cyclobutyl]-1H-pyrazol-3-yl}-1,6-naphthyridin-7-yl)pyridine-2-carboxamide;

5-(5-{1-[3-(cyanomethyl)-1-(methylsulfonyl)azetidin-3-yl]-1H-pyrazol-3-yl}-1,6-naphthyridin-7-yl)pyridine-2-sulfonamide;

(trans-3-methoxy-1-{3-[7-(1H-pyrazol-5-yl)-1,6-naphthyridin-5-yl]-1H-pyrazol-1-yl}cyclobutyl)acetonitrile;

[1-(cyclopropylmethyl)-3-{3-[7-(1-methyl-1H-pyrazol-4-yl)-1,6-naphthyridin-5-yl]-1H-pyrazol-1-yl}azetidin-3-yl]acetonitrile;

[3-{3-[7-(1H-pyrrolo[3,2-b]pyridin-6-yl)-1,6-naphthyridin-5-yl]-1H-pyrazol-1-yl}-1-(2,2,2-trifluoroethyl)azetidin-3-yl]acetonitrile;

6-(5-{1-[cis-3-cyano-1-(cyanomethyl)cyclobutyl]-1H-pyrazol-3-yl}-1,6-naphthyridin-7-yl) pyridine-2-carboxamide;

trans-3-(cyanomethyl)-3-{3-[7-(6-hydroxypyridin-2-yl)-1,6-naphthyridin-5-yl]-1H-pyrazol-1-yl}cyclobutanecarbonitrile;

[1-(3,3-difluorocyclobutyl)-3-{3-[7-(6-hydroxypyridin-3-yl)-1,6-naphthyridin-5-yl]-1H-pyrazol-1-yl}azetidin-3-yl]acetonitrile;

cis-3-(cyanomethyl)-3-(3-{7-[4-(hydroxymethyl)-1,3-thiazol-2-yl]-1,6-naphthyridin-5-yl}-1H-pyrazol-1-yl)cyclobutanecarbonitrile;

(3-{3-[7-(3-amino-1H-pyrazol-4-yl)-1,6-naphthyridin-5-yl]-1H-pyrazol-1-yl}-1-ethylazetidin-3-yl)acetonitrile;

trans-3-{3-[7-(2-amino-6-methylpyridin-4-yl)-1,6-naphthyridin-5-yl]-1H-pyrazol-1-yl}-3-(cyanomethyl)cyclobutanecarbonitrile;

cis-3-{3-[7-(5-amino-1-methyl-1H-pyrazol-3-yl)-1,6-naphthyridin-5-yl]-1H-pyrazol-1-yl}-3-(cyanomethyl)-1-methylcyclobutanecarbonitrile;

4-(5-{1-[trans-3-cyano-1-(cyanomethyl)cyclobutyl]-1H-pyrazol-3-yl}-1,6-naphthyridin-7-yl)pyrimidine-2-carboxamide;

trans-3-(cyanomethyl)-1-methyl-3-{3-[7-(1H-pyrazol-4-yl)-1,6-naphthyridin-5-yl]-1H-pyrazol-1-yl}cyclobutanecarbonitrile;

cis-3-{4-[7-(8-aminoimidazo[1,2-a]pyrazin-6-yl)quinolin-5-yl]-2H-1,2,3-triazol-2-yl}-3-(cyanomethyl)cyclobutanecarbonitrile;

[3-{4-[7-(1-methyl-1H-pyrazol-3-yl)quinolin-5-yl]-2H-1,2,3-triazol-2-yl}-1-(methylsulfonyl)azetidin-3-yl]acetonitrile;

6-(5-{2-[cis-3-cyano-1-(cyanomethyl)cyclobutyl]-2H-1,2,3-triazol-4-yl}quinolin-7-yl)pyridine-2-carboxylic acid;

[3-{3-[7-(1-methyl-1H-pyrazol-5-yl)-1,6-naphthyridin-5-yl]-1H-pyrazol-1-yl}-1-(2,2,2-trifluoroethyl)azetidin-3-yl]acetonitrile;

(cis-3-methoxy-1-{4-[7-(1H-pyrazol-3-yl)quinolin-5-yl]-2H-1,2,3-triazol-2-yl}cyclobutyl)acetonitrile;

cis-3-(cyanomethyl)-3-{4-[7-(2-oxo-1,2-dihydropyridin-4-yl)quinolin-5-yl]-2H-1,2,3-triazol-2-yl}cyclobutanecarbonitrile;

3-(cyanomethyl)-N-methyl-3-{3-[7-(1-methyl-1H-pyrazol-4-yl)-1,6-naphthyridin-5-yl]-1H-pyrazol-1-yl}azetidine-1-sulfonamide;

cis-3-{4-[7-(6-aminopyridin-3-yl)imidazo[1,2-a]pyridin-5-yl]-1H-pyrazol-1-yl}-3-(cyanomethyl)cyclobutanecarbonitrile;

[cis-3-(1-methyl-1H-pyrazol-5-yl)-1-{3-[7-(1H-pyrazol-4-yl)-1,6-naphthyridin-5-yl]-1H-pyrazol-1-yl}cyclobutyl]acetonitrile;

[3-{3-[7-(5,6-diaminopyridin-3-yl)-1,6-naphthyridin-5-yl]-1H-pyrazol-1-yl}-1-(methylsulfonyl)azetidin-3-yl]acetonitrile;

4-(5-{2-[trans-3-cyano-1-(cyanomethyl)cyclobutyl]-2H-1,2,3-triazol-4-yl}quinolin-7-yl)benzamide;

[1-(methylsulfonyl)-3-(3-{7-[6-(methylsulfonyl)pyridin-3-yl]-1,6-naphthyridin-5-yl}-1H-pyrazol-1-yl)azetidin-3-yl]acetonitrile;

(trans-3-methoxy-1-{4-[7-(1H-pyrazol-3-yl)quinolin-5-yl]-2H-1,2,3-triazol-2-yl}cyclobutyl)acetonitrile;

[trans-3-(hydroxymethyl)-1-{3-[7-(1H-pyrazol-5-yl)-1,6-naphthyridin-5-yl]-1H-pyrazol-1-yl}cyclobutyl]acetonitrile;

trans-3-(cyanomethyl)-3-(4-{7-[2-(hydroxymethyl)-1,3-thiazol-5-yl]quinolin-5-yl}-2H-1,2,3-triazol-2-yl)cyclobutanecarbonitrile;

trans-3-{4-[7-(6-aminopyridin-2-yl)quinolin-5-yl]-2H-1,2,3-triazol-2-yl}-3-(cyanomethyl)cyclobutanecarbonitrile;

trans-3-(cyanomethyl)-3-(3-{7-[6-(methylsulfonyl)pyridin-3-yl]-1,6-naphthyridin-5-yl}-1H-pyrazol-1-yl)cyclobutanecarbonitrile;

cis-3-{4-[7-(5-amino-1H-pyrazol-4-yl)quinolin-5-yl]-2H-1,2,3-triazol-2-yl}-3-(cyanomethyl)-1-methylcyclobutanecarbonitrile;

[3-{3-[7-(6-methylpyridin-3-yl)-1,6-naphthyridin-5-yl]-1H-pyrazol-1-yl}-1-(2,2,2-trifluoroethyl)azetidin-3-yl]acetonitrile;

[1-(methylsulfonyl)-3-{4-[7-(6-oxo-1,6-dihydropyridin-3-yl)quinolin-5-yl]-2H-1,2,3-triazol-2-yl}azetidin-3-yl]acetonitrile;

trans-3-{4-[7-(6-aminopyridin-3-yl)quinolin-5-yl]-2H-1,2,3-triazol-2-yl}-3-(cyanomethyl)cyclobutanecarbonitrile;

[3-{3-[7-(2-amino-6-methylpyridin-3-yl)-1,6-naphthyridin-5-yl]-1H-pyrazol-1-yl}-1-(methylsulfonyl)azetidin-3-yl]acetonitrile;

cis-3-{4-[7-(3-amino-1H-pyrazol-4-yl)imidazo[1,2-a]pyridin-5-yl]-1H-pyrazol-1-yl}-3-(cyanomethyl)cyclobutanecarbonitrile;

[3-{3-[7-(6-methoxypyridin-3-yl)-1,6-naphthyridin-5-yl]-1H-pyrazol-1-yl}-1-(2,2,2-trifluoroethyl)azetidin-3-yl]acetonitrile;

[3-{3-[7-([1,2,4]triazolo[4,3-a]pyridin-6-yl)-1,6-naphthyridin-5-yl]-1H-pyrazol-1-yl}-1-(2,2,2-trifluoroethyl)azetidin-3-yl]acetonitrile;

[3-{3-[7-(pyridin-3-yl)-1,6-naphthyridin-5-yl]-1H-pyrazol-1-yl}-1-(2,2,2-trifluoroethyl)azetidin-3-yl]acetonitrile;

[trans-1-(3-{7-[3-(hydroxymethyl)-1H-pyrazol-5-yl]-1,6-naphthyridin-5-yl}-1H-pyrazol-1-yl)-3-methoxycyclobutyl]acetonitrile;

[trans-3-(2-hydroxypropan-2-yl)-1-{3-[7-(1H-pyrazol-3-yl)-1,6-naphthyridin-5-yl]-1H-pyrazol-1-yl}cyclobutyl]acetonitrile;

trans-3-{4-[7-(2-aminopyridin-4-yl)quinolin-5-yl]-2H-1,2,3-triazol-2-yl}-3-(cyanomethyl)cyclobutanecarbonitrile;

2-[3-{4-[7-(1-methyl-1H-pyrazol-4-yl)-1,6-naphthyridin-5-yl]-1H-pyrazol-1-yl}-1-(2,2,2-trifluoroethyl)azetidin-3-yl]acetamide;

trans-3-(cyanomethyl)-3-(4-{7-[3-(hydroxymethyl)-1H-pyrazol-4-yl]quinolin-5-yl}-2H-1,2,3-triazol-2-yl)cyclobutanecarbonitrile;

[3-{4-[7-(1-methyl-1H-pyrazol-4-yl)quinolin-5-yl]-2H-1,2,3-triazol-2-yl}-1-(methylsulfonyl)azetidin-3-yl]acetonitrile;

trans-3-(cyanomethyl)-3-{4-[7-(2-methyl-1H-imidazol-4-yl)quinolin-5-yl]-2H-1,2,3-triazol-2-yl}cyclobutanecarbonitrile;

[3-{5-methyl-3-[7-(1H-pyrazol-5-yl)-1,6-naphthyridin-5-yl]-1H-pyrazol-1-yl}-1-(methylsulfonyl)azetidin-3-yl]acetonitrile;

cis-3-(cyanomethyl)-3-(3-{7-[6-(hydroxymethyl)pyridin-2-yl]-1,6-naphthyridin-5-yl}-1H-pyrazol-1-yl)cyclobutanecarbonitrile;

[3-{4-[7-(6-aminopyridin-3-yl)quinolin-5-yl]-2H-1,2,3-triazol-2-yl}-1-(methylsulfonyl)azetidin-3-yl]acetonitrile;

trans-3-{4-[7-(5-amino-1H-pyrazol-4-yl)quinolin-5-yl]-1H-pyrazol-1-yl}-3-(cyanomethyl)cyclobutanecarbonitrile;

trans-3-(cyanomethyl)-3-{4-[7-(5-hydroxy-6-methylpyridin-2-yl)quinolin-5-yl]-2H-1,2,3-triazol-2-yl}cyclobutanecarbonitrile;

[3-{4-[7-(1-methyl-6-oxo-1,6-dihydropyridin-3-yl)quinolin-5-yl]-2H-1,2,3-triazol-2-yl}-1-(methylsulfonyl)azetidin-3-yl]acetonitrile;

(trans-3-methoxy-1-{3-[7-(1H-pyrazol-4-yl)-1,6-naphthyridin-5-yl]-1H-pyrazol-1-yl}cyclobutyl)acetonitrile;

3-(5-{2-[3-(cyanomethyl)-1-(methylsulfonyl)azetidin-3-yl]-2H-1,2,3-triazol-4-yl}quinolin-7-yl)benzamide;

cis-3-(cyanomethyl)-3-{4-[7-(5H-pyrrolo[2,3-b]pyrazin-2-yl)quinolin-5-yl]-2H-1,2,3-triazol-2-yl}cyclobutanecarbonitrile;

trans-3-{3-[7-(2-aminopyridin-4-yl)-1,6-naphthyridin-5-yl]-1H-pyrazol-1-yl}-3-(cyanomethyl)-1-methylcyclobutanecarbonitrile;

trans-3-(cyanomethyl)-3-(4-{7-[4-(hydroxymethyl)-1,3-thiazol-2-yl]quinolin-5-yl}-2H-1,2,3-triazol-2-yl)cyclobutanecarbonitrile;

[1-(methylsulfonyl)-3-{3-[7-(1,3-oxazol-5-yl)-1,6-naphthyridin-5-yl]-1H-pyrazol-1-yl}azetidin-3-yl]acetonitrile;

6-(5-{1-[trans-3-cyano-1-(cyanomethyl)cyclobutyl]-1H-pyrazol-3-yl}-1,6-naphthyridin-7-yl)-3-hydroxpyridine-2-carboxamide;

cis-3-{4-[7-(6-aminopyrazin-2-yl)quinolin-5-yl]-2H-1,2,3-triazol-2-yl}-3-(cyanomethyl)cyclobutanecarbonitrile;

trans-3-(cyanomethyl)-3-(4-{7-[5-(hydroxymethyl)-1,3-thiazol-2-yl]quinolin-5-yl}-2H-1,2,3-triazol-2-yl)cyclobutanecarbonitrile;

cis-3-(cyanomethyl)-3-(3-{7-[1-methyl-5-(methylamino)-1H-pyrazol-3-yl]-1,6-naphthyridin-5-yl}-1H-pyrazol-1-yl)cyclobutanecarbonitrile;

trans-3-{3-[7-(5-amino-1H-pyrazol-4-yl)-1,6-naphthyridin-5-yl]-4-methyl-1H-pyrazol-1-yl}-3-(cyanomethyl)cyclobutanecarbonitrile;

trans-3-(cyanomethyl)-3-(4-{7-[5-(methylsulfonyl)pyridin-2-yl]quinolin-5-yl}-2H-1,2,3-triazol-2-yl)cyclobutanecarbonitrile;

[cis-1-(3-{7-[1-(2-hydroxyethyl)-1H-pyrazol-4-yl]-1,6-naphthyridin-5-yl}-1H-pyrazol-1-yl)-3-methoxycyclobutyl]acetonitrile;

[cis-3-(2-hydroxpropan-2-yl)-1-{3-[7-(1H-pyrazol-4-yl)-1,6-naphthyridin-5-yl]-1H-pyrazol-1-yl}cyclobutyl]acetonitrile;

cis-3-(cyanomethyl)-3-{3-[7-(1H-pyrazol-3-yl)-1,6-naphthyridin-5-yl]-1H-pyrazol-1-yl}cyclobutanecarboxamide;

trans-3-{4-[7-(6-aminopyridazin-3-yl)quinolin-5-yl]-2H-1,2,3-triazol-2-yl}-3-(cyanomethyl)cyclobutanecarbonitrile;

cis-3-{4-[7-(5-amino-1-methyl-1H-pyrazol-4-yl)quinolin-5-yl]-2H-1,2,3-triazol-2-yl}-3-(cyanomethyl)cyclobutanecarbonitrile;

trans-3-(3-{7-[5-(aminomethyl)-1-methyl-1H-pyrazol-3-yl]-1,6-naphthyridin-5-yl}-1H-pyrazol-1-yl)-3-(cyanomethyl)cyclobutanecarbonitrile;

trans-3-{3-[7-(6-aminopyridazin-4-yl)-1,6-naphthyridin-5-yl]-1H-pyrazol-1-yl}-3-(cyanomethyl)cyclobutanecarbonitrile;

[3-{3-[7-(6-hydroxypyridin-2-yl)-1,6-naphthyridin-5-yl]-1H-pyrazol-1-yl}-1-(methylsulfonyl)azetidin-3-yl]acetonitrile;

[3-{5-methyl-3-[7-(1H-pyrazol-4-yl)-1,6-naphthyridin-5-yl]-1H-pyrazol-1-yl}-1-(methylsulfonyl)azetidin-3-yl]acetonitrile;

[cis-3-(hydroxymethyl)-1-{3-[7-(1H-pyrazol-5-yl)-1,6-naphthyridin-5-yl]-1H-pyrazol-1-yl}cyclobutyl]acetonitrile;

trans-3-(cyanomethyl)-3-(4-{7-[3-(hydroxymethyl)-1,2-thiazol-5-yl]quinolin-5-yl}-2H-1,2,3-triazol-2-yl)cyclobutanecarbonitrile;

trans-3-(cyanomethyl)-3-(3-{7-[3-(hydroxymethyl)-1-methyl-1H-pyrazol-5-yl]-1,6-naphthyridin-5-yl}-1H-pyrazol-1-yl)cyclobutanecarbonitrile;

3-(5-{2-[trans-3-cyano-1-(cyanomethyl)cyclobutyl]-2H-1,2,3-triazol-4-yl}quinolin-7-yl)benzamide;

[3-(4-{7-[3-(hydroxymethyl)phenyl]quinolin-5-yl}-2H-1,2,3-triazol-2-yl)-1-(methylsulfonyl)azetidin-3-yl]acetonitrile;

[3-{4-[7-(1-ethyl-6-oxo-1,6-dihydropyridin-3-yl)quinolin-5-yl]-2H-1,2,3-triazol-2-yl}-1-(methylsulfonyl)azetidin-3-yl]acetonitrile;

(1-ethyl-3-{3-[7-(6-hydroxpyridin-3-yl)-1,6-naphthyridin-5-yl]-1H-pyrazol-1-yl}azetidin-3-yl)acetonitrile;

[3-{3-[7-(imidazo[1,2-a]pyridin-7-yl)-1,6-naphthyridin-5-yl]-1H-pyrazol-1-yl}-1-(methylsulfonyl)azetidin-3-yl]acetonitrile;

N-[6-(5-{2-[trans-3-cyano-1-(cyanomethyl)cyclobutyl]-2H-1,2,3-triazol-4-yl}quinolin-7-yl)pyridin-2-yl]methanesulfonamide;

(cis-3-methoxy-1-{3-[7-(1-methyl-1H-pyrazol-4-yl)-1,6-naphthyridin-5-yl]-1H-pyrazol-1-yl}cyclobutyl)acetonitrile;

(6-{3-[7-(1H-pyrazol-3-yl)-1,6-naphthyridin-5-yl]-1H-pyrazol-1-yl}-2-oxaspiro[3.3]hept-6-yl)acetonitrile;

N-[5-(5-{1-[3-(cyanomethyl)-1-(methylsulfonyl)azetidin-3-yl]-1H-pyrazol-3-yl}-1,6-naphthyridin-7-yl)-2-methylpyridin-3-yl]acetamide;

trans-3-(cyanomethyl)-3-(4-{7-[5-(2-hydroxyethyl)-6-methylpyridin-2-yl]quinolin-5-yl}-2H-1,2,3-triazol-2-yl)cyclobutanecarbonitrile;

(1-[(1-fluorocyclopropyhmethyl]-3-{4-[7-(1H-pyrazol-3-yl)quinolin-5-yl]-2H-1,2,3-triazol-2-yl}azetidin-3-yl)acetonitrile;

trans-3-(cyanomethyl)-3-{3-[7-(4,5,6,7-tetrahydropyrazolo[1,5-a]pyrazin-2-yl)-1,6-naphthyridin-5-yl]-1H-pyrazol-1-yl}cyclobutanecarbonitrile;

[3-(4-{7-[4-fluoro-3-(hydroxymethyl)phenyl]quinolin-5-yl}-2H-1,2,3-triazol-2-yl)-1-(methylsulfonyl)azetidin-3-yl]acetonitrile;

[3-{3-[7-(2-hydroxypyridin-4-yl)-1,6-naphthyridin-5-yl]-1H-pyrazol-1-yl}-1-(methylsulfonyl)azetidin-3-yl]acetonitrile;

[3-{3-[7-(2-aminopyridin-3-yl)-1,6-naphthyridin-5-yl]-1H-pyrazol-1-yl}-1-(methylsulfonyl)azetidin-3-yl]acetonitrile;

cis-3-{4-[7-(8-aminoimidazo[1,2-a]pyrazin-3-yl)quinolin-5-yl]-2H-1,2,3-triazol-2-yl}-3-(cyanomethyl)cyclobutanecarbonitrile;

[3-{3-[7-(1-methyl-1H-pyrazol-4-yl)-1,6-naphthyridin-5-yl]-1H-pyrazol-1-yl}-1-(propylsulfonyl)azetidin-3-yl]acetonitrile;

[3-{3-[7-(5-aminopyridin-3-yl)-1,6-naphthyridin-5-yl]-1H-pyrazol-1-yl}-1-(methylsulfonyl)azetidin-3-yl]acetonitrile;

[3-{4-[7-(3-hydroxyphenyl)quinolin-5-yl]-2H-1,2,3-triazol-2-yl}-1-(methylsulfonyl)azetidin-3-yl]acetonitrile;

[1-(methylsulfonyl)-3-{3-[7-(1H-pyrazol-3-yl)quinolin-5-yl]-1H-pyrazol-1-yl}azetidin-3-yl]acetonitrile;

N-[trans-3-(cyanomethyl)-3-{3-[7-(1H-pyrazol-3-yl)-1,6-naphthyridin-5-yl]-1H-pyrazol-1-yl}cyclobutyl]-N-methylacetamide;

[3-{3-[7-(6-methylpyridin-3-yl)-1,6-naphthyridin-5-yl]-1H-pyrazol-1-yl}-1-(methylsulfonyl)azetidin-3-yl]acetonitrile;

N,N'-[5-(5-{1-[3-(cyanomethyl)-1-(methylsulfonyl)azetidin-3-yl]-1H-pyrazol-3-yl}-1,6-naphthyridin-7-yl)pyridine-2,3-diyl]diacetamide;

N-[trans-3-(cyanomethyl)-3-{3-[7-(1H-pyrazol-3-yl)-1,6-naphthyridin-5-yl]-1H-pyrazol-1-yl}cyclobutyl]acetamide;

[3-{3-[7-(2H-1,2,3-triazol-4-yl)-1,6-naphthyridin-5-yl]-1H-pyrazol-1-yl}-1-(2,2,2-trifluoroethyl)azetidin-3-yl]acetonitrile;

trans-3-{4-[7-(3-amino-1-methyl-1H-pyrazol-4-yl)quinolin-5-yl]-2H-1,2,3-triazol-2-yl}-3-(cyanomethyl)cyclobutanecarbonitrile;

[trans-1-(3-{7-[1-(2-hydroxyethyl)-1H-pyrazol-4-yl]-1,6-naphthyridin-5-yl}-1H-pyrazol-1-yl)-3-methoxycyclobutyl]acetonitrile;

cis-3-(cyanomethyl)-3-{4-[7-(2-methyl-1H-imidazol-5-yl)imidazo[1,2-a]pyridin-5-yl]-1H-pyrazol-1-yl}cyclobutanecarbonitrile;

4-(5-{1-[3-(cyanomethyl)-1-(2,2,2-trifluoroethyl)azetidin-3-yl]-1H-pyrazol-3-yl}-1,6-naphthyridin-7-yl)pyridine-2-carboxamide;

cis-3-(cyanomethyl)-N-methyl-3-{3-[7-(1H-pyrazol-3-yl)-1,6-naphthyridin-5-yl]-1H-pyrazol-1-yl}cyclobutanecarboxamide;

2-(5-{2-[cis-3-cyano-1-(cyanomethyl)cyclobutyl]-2H-1,2,3-triazol-4-yl}quinolin-7-yl)-5-fluoropyridine-4-carboxamide;

[3-{1-[7-(1-methyl-1H-pyrazol-4-yl)-1,6-naphthyridin-5-yl]-1H-pyrazol-3-yl}-1-(2,2,2-trifluoroethyl)azetidin-3-yl]acetonitrile;

cis-3-{4-[7-(6-aminopyrimidin-4-yl)quinolin-5-yl]-2H-1,2,3-triazol-2-yl}-3-(cyanomethyl)cyclobutanecarbonitrile;

[3-{3-[7-(6-amino-5-methylpyridin-3-yl)-1,6-naphthyridin-5-yl]-1H-pyrazol-1-yl}-1-(methylsulfonyl)azetidin-3-yl]acetonitrile;

trans-3-(4-{7-[4-(2-aminoethoxy)phenyl]quinolin-5-yl}-2H-1,2,3-triazol-2-yl)-3-(cyanomethyl)cyclobutanecarbonitrile;

[3-(3-{7-[2-(tetrahydro-2H-pyran-2-yl)-2H-1,2,3-triazol-4-yl]-1,6-naphthyridin-5-yl}-1H-pyrazol-1-yl)-1-(2,2,2-trifluoroethyl)azetidin-3-yl]acetonitrile;

cis-3-(cyanomethyl)-3-{4-[7-(1-methyl-1H-pyrazol-4-yl)imidazo[1,2-a]pyridin-5-yl]-2H-1,2,3-triazol-2-yl}cyclobutanecarbonitrile;

[3-{3-[7-(3-methyl-3H-imidazo[4,5-b]pyridin-6-yl)-1,6-naphthyridin-5-yl]-1H-pyrazol-1-yl}-1-(methylsulfonyl)azetidin-3-yl]acetonitrile;

[cis-3-methoxy-1-(3-{7-[1-(oxetan-3-yl)-1H-pyrazol-4-yl]-1,6-naphthyridin-5-yl}-1H-pyrazol-1-yl)cyclobutyl]acetonitrile;

[3-{4-[7-(1-methyl-1H-pyrazol-4-yl)[1,2,4]triazolo[1,5-a]pyridin-5-yl]-1H-pyrazol-1-yl}-1-(2,2,2-trifluoroethyl)azetidin-3-yl]acetonitrile;

[1-(methylsulfonyl)-3-{3-[7-(1H-pyrazol-4-yl)quinolin-5-yl]-1H-pyrazol-1-yl}azetidin-3-yl]acetonitrile;

trans-3-{3-[7-(5-amino-1-methyl-1H-pyrazol-3-yl)-1,6-naphthyridin-5-yl]-5-methyl-1H-pyrazol-1-yl}-3-(cyanomethyl)cyclobutanecarbonitrile;

trans-3-(cyanomethyl)-3-(4-{7-[3-(hydroxymethyl)-1-methyl-1H-pyrazol-4-yl]quinolin-5-yl}-2H-1,2,3-triazol-2-yl)cyclobutanecarbonitrile;

[3-(3-{7-[1-(azetidin-3-yl)-1H-pyrazol-4-yl]-1,6-naphthyridin-5-yl}-1H-pyrazol-1-yl)-1-(2,2,2-trifluoroethyl)azetidin-3-yl]acetonitrile;

trans-3-(cyanomethyl)-1-methyl-3-{3-[7-(1H-pyrazol-3-yl)-1,6-naphthyridin-5-yl]-1H-pyrazol-1-yl}cyclobutanecarbonitrile;

cis-3-(cyanomethyl)-3-{4-[7-(pyrazin-2-yl)quinolin-5-yl]-2H-1,2,3-triazol-2-yl}cyclobutanecarbonitrile;

[1-(methylsulfonyl)-3-{3-[7-(1H-pyrazol-5-yl)quinolin-5-yl]-1H-1,2,4-triazol-1-yl}azetidin-3-yl]acetonitrile;

[cis-3-(2-hydrontpropan-2-yl)-1-{3-[7-(1H-pyrazol-3-yl)-1,6-naphthyridin-5-yl]-1H-pyrazol-1-yl}cyclobutyl]acetonitrile;

[1-(methylsulfonyl)-3-{3-[7-(1H-pyrazolo[4,3-b]pyridin-6-yl)-1,6-naphthyridin-5-yl]-1H-pyrazol-1-yl}azetidin-3-yl]acetonitrile;

trans-3-(cyanomethyl)-3-{3-[7-(1,5-dimethyl-1H-pyrazol-3-yl)-1,6-naphthyridin-5-yl]-1H-pyrazol-1-yl}cyclobutanecarbonitrile;

cis-3-(cyanomethyl)-3-{4-[7-(imidazo[1,2-a]pyrimidin-3-yl)quinolin-5-yl]-2H-1,2,3-triazol-2-yl}cyclobutanecarbonitrile;

trans-3-{4-[7-(5-amino-1-methyl-1H-pyrazol-4-yl)quinolin-5-yl]-2H-1,2,3-triazol-2-yl}-3-(cyanomethyl)cyclobutanecarbonitrile;

[1-(methylsulfonyl)-3-{4-[7-(6-oxo-1,6-dihydropyridin-3-yl)quinolin-5-yl]-1H-1,2,3-triazol-1-yl}azetidin-3-yl]acetonitrile;

[1-ethyl-3-(3-{7-[5-(hydroxymethyl)-1H-pyrazol-3-yl]-1,6-naphthyridin-5-yl}-1H-pyrazol-1-yl)azetidin-3-yl]acetonitrile;

[3-{5-methyl-3-[7-(1H-pyrazol-3-yl)quinolin-5-yl]-1H-pyrazol-1-yl}-1-(methylsulfonyl)azetidin-3-yl]acetonitrile;

[1-(methylsulfonyl)-3-{3-[7-(1H-pyrazol-4-yl)quinolin-5-yl]-1H-1,2,4-triazol-1-yl}azetidin-3-yl]acetonitrile;

[3-{3-[7-(2-methontpyridin-4-yl)-1,6-naphthyridin-5-yl]-1H-pyrazol-1-yl}-1-(methylsulfonyl)azetidin-3-yl]acetonitrile;

trans-3-(cyanomethyl)-3-{4-[7-(1-methyl-1H-1,2,3-triazol-4-yl)quinolin-5-yl]-2H-1,2,3-triazol-2-yl}cyclobutanecarbonitrile;

cis-3-{4-[7-(2-aminopyrimidin-5-yl)quinolin-5-yl]-2H-1,2,3-triazol-2-yl}-3-(cyanomethyl)cyclobutanecarbonitrile;

[3-{3-[7-(1H-imidazol-2-yl)-1,6-naphthyridin-5-yl]-1H-pyrazol-1-yl}-1-(2,2,2-trifluoroethyl)azetidin-3-yl]acetonitrile;

[1-(methylsulfonyl)-3-{3-[7-(pyrazolo[1,5-a]pyrimidin-3-yl)-1,6-naphthyridin-5-yl]-1H-pyrazol-1-yl}azetidin-3-yl]acetonitrile;

(trans-1-{4-[7-(3-amino-1H-pyrazol-4-yl)quinolin-5-yl]-1H-pyrazol-1-yl}-3-methoxycyclobutyl)acetonitrile;

[3-{3-[7-(1-methyl-1H-pyrazol-3-yl)-1,6-naphthyridin-5-yl]-1H-pyrazol-1-yl}-1-(2,2,2-trifluoroethyl)azetidin-3-yl]acetonitrile;

{3-[3-(7-chloro-1,6-naphthyridin-5-yl)-1H-pyrazol-1-yl]-1-(2,2,2-trifluoroethyl)azetidin-3-yl}acetonitrile;

[1-(methylsulfonyl)-3-(3-{7-[1-(trifluoromethyl)-1H-pyrazol-4-yl]-1,6-naphthyridin-5-yl}-1H-pyrazol-1-yl)azetidin-3-yl]acetonitrile;

6-(5-{2-[trans-3-cyano-1-(cyanomethyl)cyclobutyl]-2H-1,2,3-triazol-4-yl}quinolin-7-yl)pyridine-2-carboxylic acid;

[3-(4-{7-[4-(aminomethyl)phenyl]quinolin-5-yl}-2H-1,2,3-triazol-2-yl)-1-(methylsulfonyl)azetidin-3-yl]acetonitrile;

[3-{3-[7-(5-amino-6-methylpyridin-3-yl)-1,6-naphthyridin-5-yl]-1H-pyrazol-1-yl}-1-(methylsulfonyl)azetidin-3-yl]acetonitrile;

cis-3-(cyanomethyl)-3-{4-[7-(2,3-dihydro-1H-pyrrolo[3,2-c]pyridin-6-yl)quinolin-5-yl]-2H-1,2,3-triazol-2-yl}cyclobutanecarbonitrile;

[3-{3-[7-(pyridazin-4-yl)-1,6-naphthyridin-5-yl]-1H-pyrazol-1-yl}-1-(2,2,2-trifluoroethyl)azetidin-3-yl]acetonitrile;

2-(5-{2-[cis-3-cyano-1-(cyanomethyl)cyclobutyl]-2H-1,2,3-triazol-4-yl}quinolin-7-yl)pyridine-4-carboxamide;

trans-3-(cyanomethyl)-1-methyl-3-{3-[7-(5-methyl-1H-pyrazol-3-yl)-1,6-naphthyridin-5-yl]-1H-pyrazol-1-yl}cyclobutanecarbonitrile;

[3-{3-[7-(2-methyl-1H-imidazol-4-yl)-1,6-naphthyridin-5-yl]-1H-pyrazol-1-yl}-1-(2,2,2-trifluoroethyl)azetidin-3-yl]acetonitrile;

[3-{4-[7-(1-methyl-1H-pyrazol-4-yl)imidazo[1,2-a]pyridin-5-yl]-1H-pyrazol-1-yl}-1-(2,2,2-trifluoroethyl)azetidin-3-yl]acetonitrile;

[3-{3-[7-(1-methyl-1H-pyrazol-4-yl)imidazo[1,2-a]pyridin-5-yl]-1H-pyrazol-1-yl}-1-(2,2,2-trifluoroethyl)azetidin-3-yl]acetonitrile;

[3-{3-[7-(3-methyl-1H-pyrazol-1-yl)-1,6-naphthyridin-5-yl]-1H-pyrazol-1-yl}-1-(2,2,2-trifluoroethyl)azetidin-3-yl]acetonitrile;

[3-{3-[7-(2-methoxypyrimidin-5-yl)-1,6-naphthyridin-5-yl]-1H-pyrazol-1-yl}-1-(2,2,2-trifluoroethyl)azetidin-3-yl]acetonitrile;

[3-{3-[7-(5-methylpyridin-3-yl)-1,6-naphthyridin-5-yl]-1H-pyrazol-1-yl}-1-(2,2,2-trifluoroethyl)azetidin-3-yl]acetonitrile;

[3-{3-[7-(3-fluoropyridin-4-yl)-1,6-naphthyridin-5-yl]-1H-pyrazol-1-yl}-1-(2,2,2-trifluoroethyl)azetidin-3-yl]acetonitrile;

[3-{3-[7-(pyrimidin-5-yl)-1,6-naphthyridin-5-yl]-1H-pyrazol-1-yl}-1-(2,2,2-trifluoroethyl)azetidin-3-yl]acetonitrile;

[3-{3-[7-(5-fluoropyridin-3-yl)-1,6-naphthyridin-5-yl]-1H-pyrazol-1-yl}-1-(2,2,2-trifluoroethyl)azetidin-3-yl]acetonitrile;

2,2'-(3-{4-[6-(1-methyl-1H-pyrazol-4-yl)[1,2,4]triazolo[1,5-a]pyrazin-8-yl]-1H-pyrazol-1-yl}azetidine-1,3-diyhdiacetonitrile;

[3-{4-[6-(1-methyl-1H-pyrazol-4-yl)[1,2,4]triazolo[1,5-a]pyrazin-8-yl]-1H-pyrazol-1-yl}-1-(methylsulfonyl)azetidin-3-yl]acetonitrile;

2,2'-(3-{3-[7-(1-methyl-1H-pyrazol-4-yl)pyrido[3,4-b]pyrazin-5-yl]-1H-pyrazol-1-yl}azetidine-1,3-diyhdiacetonitrile;

[3-{3-[7-(1-methyl-1H-pyrazol-4-yl)pyrido[3,4-b]pyrazin-5-yl]-1H-pyrazol-1-yl}-1-(2,2,2-trifluoroethyl)azetidin-3-yl]acetonitrile;

[1-(methylsulfonyl)-3-(3-{7-[1-(oxetan-3-yl)-1H-pyrazol-3-yl]-1,6-naphthyridin-5-yl}-1H-pyrazol-1-yl)azetidin-3-yl]acetonitrile;

[3-{3-[7-(imidazo[1,2-a]pyrimidin-6-yl)-1,6-naphthyridin-5-yl]-1H-pyrazol-1-yl}-1-(methylsulfonyl)azetidin-3-yl]acetonitrile;

[trans-3-(1-methyl-1H-pyrazol-5-yl)-1-{3-[7-(1H-pyrazol-4-yl)-1,6-naphthyridin-5-yl]-1H-pyrazol-1-yl}cyclobutyl]acetonitrile;

{3-[3-(1,6-naphthyridin-5-yl)-1H-pyrazol-1-yl]-1-(2,2,2-trifluoroethyl)azetidin-3-yl}acetonitrile;

[3-{3-[7-(2-methyl-2H-1,2,3-triazol-4-yl)-1,6-naphthyridin-5-yl]-1H-pyrazol-1-yl}-1-(2,2,2-trifluoroethyl)azetidin-3-yl]acetonitrile;

[3-{3-[7-(1,2-dimethyl-1H-imidazol-4-yl)-1,6-naphthyridin-5-yl]-1H-pyrazol-1-yl}-1-(2,2,2-trifluoroethyl)azetidin-3-yl]acetonitrile;

[3-(3-{7-[1-(oxetan-3-yl)-1H-imidazol-4-yl]-1,6-naphthyridin-5-yl}-1H-pyrazol-1-yl)-1-(2,2,2-trifluoroethyl)azetidin-3-yl]acetonitrile;

[3-{3-[7-(1-methyl-1H-imidazol-4-yl)-1,6-naphthyridin-5-yl]-1H-pyrazol-1-yl}-1-(2,2,2-trifluoroethyl)azetidin-3-yl]acetonitrile;

[3-{3-[7-(1-methyl-1H-pyrazol-4-yl)quinolin-5-yl]-1H-pyrazol-1-yl}-1-(2,2,2-trifluoroethyl)azetidin-3-yl]acetonitrile;

[3-{3-[7-(1,2-dimethyl-1H-imidazol-5-yl)-1,6-naphthyridin-5-yl]-1H-pyrazol-1-yl}-1-(2,2,2-trifluoroethyl)azetidin-3-yl]acetonitrile;

[3-(3-{7-[1-(oxetan-3-yl)-1H-pyrazol-3-yl]-1,6-naphthyridin-5-yl}-1H-pyrazol-1-yl)-1-(2,2,2-trifluoroethyl)azetidin-3-yl]acetonitrile;

[3-{3-[7-(1-methyl-1H-pyrazol-4-yl)quinolin-5-yl]-1H-pyrazol-1-yl}-1-(methylsulfonyl)azetidin-3-yl]acetonitrile;

[3-{3-[7-(6,7-dihydro-5H-cyclopenta[b]pyridin-3-yl)-1,6-naphthyridin-5-yl]-1H-pyrazol-1-yl}-1-(2,2,2-trifluoroethyl)azetidin-3-yl]acetonitrile;

[1-(methylsulfonyl)-3-{3-[7-(6-oxo-1,6-dihydropyridin-3-yl)quinolin-5-yl]-1H-pyrazol-1-yl}azetidin-3-yl]acetonitrile;

[1-(methylsulfonyl)-3-{3-[7-(6-oxo-1,6-dihydropyridin-3-yl)quinolin-5-yl]-1H-1,2,4-triazol-1-yl}azetidin-3-yl]acetonitrile;

[3-{3-[7-(2-methoxypyridin-3-yl)-1,6-naphthyridin-5-yl]-1H-pyrazol-1-yl}-1-(methylsulfonyl)azetidin-3-yl]acetonitrile;

trans-3-(cyanomethyl)-3-{3-[7-(1H-pyrazol-5-yl)-1,6-naphthyridin-5-yl]-1H-pyrazol-1-yl}cyclobutanecarboxamide;

trans-3-(cyanomethyl)-N-methyl-3-{3-[7-(1H-pyrazol-5-yl)-1,6-naphthyridin-5-yl]-1H-pyrazol-1-yl}cyclobutanecarboxamide;

{3-{3-[7-(2-fluorophenyl)-1,6-naphthyridin-5-yl]-1H-pyrazol-1-yl}-1-(methylsulfonyl)azetidin-3-yl]acetonitrile;

[3-(3-{7-[2-(hydroxymethyl)phenyl]-1,6-naphthyridin-5-yl}-1H-pyrazol-1-yl)-1-(methylsulfonyl)azetidin-3-yl]acetonitrile;

[3-{3-[7-(2-aminopyrimidin-5-yl)-1,6-naphthyridin-5-yl]-1H-pyrazol-1-yl}-1-(methylsulfonyl)azetidin-3-yl]acetonitrile;

[3-{3-[7-(4-fluoro-2-hydroxyphenyl)-1,6-naphthyridin-5-yl]-1H-pyrazol-1-yl}-1-(methylsulfonyl)azetidin-3-yl]acetonitrile;

[1-(methylsulfonyl)-3-{3-[7-(pyrimidin-5-yl)-1,6-naphthyridin-5-yl]-1H-pyrazol-1-yl}azetidin-3-yl]acetonitrile;

[3-{3-[7-(2-methoxypyrimidin-5-yl)-1,6-naphthyridin-5-yl]-1H-pyrazol-1-yl}-1-(methylsulfonyl)azetidin-3-yl]acetonitrile;

[3-{3-[7-(3-fluoro-5-hydroxyphenyl)-1,6-naphthyridin-5-yl]-1H-pyrazol-1-yl}-1-(methylsulfonyl)azetidin-3-yl]acetonitrile;

[3-{3-[7-(5-fluoro-2-hydroxyphenyl)-1,6-naphthyridin-5-yl]-1H-pyrazol-1-yl}-1-(methylsulfonyl)azetidin-3-yl]acetonitrile;

[3-{3-[7-(3-amino-5-methyl-1,2-oxazol-4-yl)-1,6-naphthyridin-5-yl]-1H-pyrazol-1-yl}-1-(methylsulfonyl)azetidin-3-yl]acetonitrile;

4-(5-{1-[3-(cyanomethyl)-1-(methylsulfonyl)azetidin-3-yl]-1H-pyrazol-3-yl}-1,6-naphthyridin-7-yl)-1-methyl-1H-pyrazole-5-carboxamide;

[1-(methylsulfonyl)-3-{3-[7-(1H-pyrrolo[3,2-b]pyridin-3-yl)-1,6-naphthyridin-5-yl]-1H-pyrazol-1-yl}azetidin-3-yl]acetonitrile;

[1-(methylsulfonyl)-3-{3-[7-(2-oxo-2,3-dihydro-1H-imidazo[4,5-b]pyridin-6-yl)-1,6-naphthyridin-5-yl]-1H-pyrazol-1-yl}azetidin-3-yl]acetonitrile;

N-[5-(5-{1-[3-(cyanomethyl)-1-(methylsulfonyl)azetidin-3-yl]-1H-pyrazol-3-yl}-1,6-naphthyridin-7-yl)pyridin-3-yl]methanesulfonamide;

[3-{3-[7-(5-hydroxy-6-methylpyridin-3-yl)-1,6-naphthyridin-5-yl]-1H-pyrazol-1-yl}-1-(methylsulfonyl)azetidin-3-yl]acetonitrile;

ethyl [5-(5-{1-[3-(cyanomethyl)-1-(methylsulfonyl)azetidin-3-yl]-1H-pyrazol-3-yl}-1,6-naphthyridin-7-yl)pyridin-3-yl]carbamate;

[3-{4-[7-(6-methylpyridin-3-yl)quinolin-5-yl]-2H-1,2,3-triazol-2-yl}-1-(methylsulfonyl)azetidin-3-yl]acetonitrile;

[3-{4-[7-(2-aminopyrimidin-5-yl)quinolin-5-yl]-2H-1,2,3-triazol-2-yl}-1-(methylsulfonyl)azetidin-3-yl]acetonitrile;

[3-{4-[7-(2-methoxypyrimidin-5-yl)quinolin-5-yl]-2H-1,2,3-triazol-2-yl}-1-(methylsulfonyl)azetidin-3-yl]acetonitrile;

[1-(methylsulfonyl)-3-{4-[7-(pyrimidin-5-yl)quinolin-5-yl]-2H-1,2,3-triazol-2-yl}azetidin-3-yl]acetonitrile;

[3-{4-[7-(2-methylpyridin-4-yl)quinolin-5-yl]-2H-1,2,3-triazol-2-yl}-1-(methylsulfonyl)azetidin-3-yl]acetonitrile;

[3-{4-[7-(6-amino-5-methylpyridin-3-yl)quinolin-5-yl]-2H-1,2,3-triazol-2-yl}-1-(methylsulfonyl)azetidin-3-yl]acetonitrile;

[3-{4-[7-(2-aminopyridin-3-yl)quinolin-5-yl]-2H-1,2,3-triazol-2-yl}-1-(methylsulfonyl)azetidin-3-yl]acetonitrile;

[3-{4-[7-(2-hydroxyphenyl)quinolin-5-yl]-2H-1,2,3-triazol-2-yl}-1-(methylsulfonyl)azetidin-3-yl]acetonitrile;

[3-(4-{7-[2-fluoro-3-(hydroxymethyl)phenyl]quinolin-5-yl}-2H-1,2,3-triazol-2-yl)-1-(methylsulfonyl)azetidin-3-yl]acetonitrile;

[3-{4-[7-(1-methyl-1H-pyrazol-5-yl)quinolin-5-yl]-2H-1,2,3-triazol-2-yl}-1-(methylsulfonyl)azetidin-3-yl]acetonitrile;

[1-(methylsulfonyl)-3-{4-[7-(3-oxo-2,3-dihydro-1H-isoindol-5-yl)quinolin-5-yl]-2H-1,2,3-triazol-2-yl}azetidin-3-yl]acetonitrile;

[1-(methylsulfonyl)-3-{4-[7-(7H-pyrrolo[2,3-b]pyridin-5-yl)quinolin-5-yl]-2H-1,2,3-triazol-2-yl}azetidin-3-yl]acetonitrile;

[3-(4-{7-[3-(aminomethyl)phenyl]quinolin-5-yl}-2H-1,2,3-triazol-2-yl)-1-(methylsulfonyl)azetidin-3-yl]acetonitrile;

[3-{4-[7-(2,4-dioxo-1,2,3,4-tetrahydropyrimidin-5-yl)quinolin-5-yl]-2H-1,2,3-triazol-2-yl}-1-(methylsulfonyl)azetidin-3-yl]acetonitrile;

[3-{4-[7-(5-fluoro-2-hydroxphenyl)quinolin-5-yl]-2H-1,2,3-triazol-2-yl}-1-(methylsulfonyl)azetidin-3-yl]acetonitrile;

[3-{4-[7-(3-fluoro-5-hydroxphenyl)quinolin-5-yl]-2H-1,2,3-triazol-2-yl}-1-(methylsulfonyl)azetidin-3-yl]acetonitrile;

[3-{4-[7-(4-fluoro-2-hydroxyphenyl)quinolin-5-yl]-2H-1,2,3-triazol-2-yl}-1-(methylsulfonyl)azetidin-3-yl]acetonitrile;

(2-acetyl-6-{3-[7-(1H-pyrazol-3-yl)-1,6-naphthyridin-5-yl]-1H-pyrazol-1-yl}-2-azaspiro[3.3]hept-6-yl)acetonitrile;

trans-3-(3-{7-[(6-aminopyridin-2-yl)oxy]-1,6-naphthyridin-5-yl}-1H-pyrazol-1-yl)-3-(cyanomethyl)cyclobutanecarbonitrile;

trans-3-{3-[7-(5-amino-1-methyl-1H-pyrazol-3-yl)-1,6-naphthyridin-5-yl]-1H-pyrazol-1-yl}-3-(cyanomethyl)-1-methylcyclobutanecarbonitrile;

trans-3-(cyanomethyl)-3-(3-{7-[1-methyl-5-(methylamino)-1H-pyrazol-3-yl]-1,6-naphthyridin-5-yl}-1H-pyrazol-1-yl)cyclobutanecarbonitrile;

cis-3-(cyanomethyl)-3-{4-[7-(2-oxo-2,3-dihydro-1H-indol-7-yl)quinolin-5-yl]-2H-1,2,3-triazol-2-yl}cyclobutanecarbonitrile;

cis-3-{4-[7-(2-aminopyridin-3-yl)quinolin-5-yl]-2H-1,2,3-triazol-2-yl}-3-(cyanomethyl)cyclobutanecarbonitrile;

cis-3-(cyanomethyl)-3-{4-[7-(5-fluoro-2-hydroxpyridin-4-yl)quinolin-5-yl]-2H-1,2,3-triazol-2-yl}cyclobutanecarbonitrile;

cis-3-(cyanomethyl)-3-(4-{7-[5-(2-hydroxyethoxy)pyrimidin-2-yl]quinolin-5-yl}-2H-1,2,3-triazol-2-yl)cyclobutanecarbonitrile;

cis-3-(cyanomethyl)-3-{4-[7-(1-methyl-1H-1,2,3-triazol-5-yl)quinolin-5-yl]-2H-1,2,3-triazol-2-yl}cyclobutanecarbonitrile;

4-(5-{2-[cis-3-cyano-1-(cyanomethyl)cyclobutyl]-2H-1,2,3-triazol-4-yl}quinolin-7-yl)-1-methyl-1H-pyrazole-5-carboxamide;

cis-3-(cyanomethyl)-3-{4-[7-(pyrimidin-5-yl)quinolin-5-yl]-2H-1,2,3-triazol-2-yl}cyclobutanecarbonitrile;

cis-3-(cyanomethyl)-3-{4-[7-(6-methylpyrazin-2-yl)quinolin-5-yl]-2H-1,2,3-triazol-2-yl}cyclobutanecarbonitrile;

cis-3-{4-[7-(6-amino-3-methylpyrazin-2-yl)quinolin-5-yl]-2H-1,2,3-triazol-2-yl}-3-(cyanomethyl)cyclobutanecarbonitrile;

trans-3-(cyanomethyl)-3-{4-[7-(5-fluoropyridin-2-yl)quinolin-5-yl]-2H-1,2,3-triazol-2-yl}cyclobutanecarbonitrile;

2-(5-{2-[trans-3-cyano-1-(cyanomethyl)cyclobutyl]-2H-1,2,3-triazol-4-yl}quinolin-7-yl)-5-fluoropyridine-4-carboxamide;

trans-3-(cyanomethyl)-3-{4-[7-(2-oxo-1,2-dihydropyridin-4-yl)quinolin-5-yl]-2H-1,2,3-triazol-2-yl}cyclobutanecarbonitrile;

trans-3-{4-[7-(5-amino-6-methoxypyrazin-2-yl)quinolin-5-yl]-2H-1,2,3-triazol-2-yl}-3-(cyanomethyl)cyclobutanecarbonitrile;

trans-3-{4-[7-(2-aminopyridin-3-yl)quinolin-5-yl]-2H-1,2,3-triazol-2-yl}-3-(cyanomethyl)cyclobutanecarbonitrile;

trans-3-{4-[7-(5-aminopyrazin-2-yl)quinolin-5-yl]-2H-1,2,3-triazol-2-yl}-3-(cyanomethyl)cyclobutanecarbonitrile;

trans-3-(cyanomethyl)-3-{4-[7-(pyrazolo[1,5-a]pyrimidin-3-yl)quinolin-5-yl]-2H-1,2,3-triazol-2-yl}cyclobutanecarbonitrile;

trans-3-(cyanomethyl)-3-{4-[7-(pyrimidin-2-yl)quinolin-5-yl]-2H-1,2,3-triazol-2-yl}cyclobutanecarbonitrile;

6-(5-{2-[trans-3-cyano-1-(cyanomethyl)cyclobutyl]-2H-1,2,3-triazol-4-yl}quinolin-7-yl)pyridine-3-carboxamide;

4-(5-{2-[trans-3-cyano-1-(cyanomethyl)cyclobutyl]-2H-1,2,3-triazol-4-yl}quinolin-7-yl)-1-methyl-1H-pyrazole-5-carboxamide;

trans-3-{4-[7-(6-aminopyrazin-2-yl)quinolin-5-yl]-2H-1,2,3-triazol-2-yl}-3-(cyanomethyl)cyclobutanecarbonitrile;

trans-3-(cyanomethyl)-3-{4-[7-(imidazo[1,2-a]pyrimidin-3-yl)quinolin-5-yl]-2H-1,2,3-triazol-2-yl}cyclobutanecarbonitrile;

trans-3-(cyanomethyl)-3-{4-[7-(2-oxo-2,3-dihydro-1H-indol-7-yl)quinolin-5-yl]-2H-1,2,3-triazol-2-yl}cyclobutanecarbonitrile;

2-(5-{2-[trans-3-cyano-1-(cyanomethyl)cyclobutyl]-2H-1,2,3-triazol-4-yl}quinolin-7-yl)pyridine-4-carboxamide;

trans-3-(cyanomethyl)-3-{4-[7-(6-methylpyrazin-2-yl)quinolin-5-yl]-2H-1,2,3-triazol-2-yl}cyclobutanecarbonitrile;

cis-3-{3-[7-(5-amino-1-methyl-1H-pyrazol-3-yl)-1,6-naphthyridin-5-yl]-4-methyl-1H-pyrazol-1-yl}-3-(cyanomethyl)cyclobutanecarbonitrile;

trans-3-{3-[7-(5-amino-1-methyl-1H-pyrazol-3-yl)-1,6-naphthyridin-5-yl]-4-methyl-1H-pyrazol-1-yl}-3-(cyanomethyl)cyclobutanecarbonitrile;

trans-3-(cyanomethyl)-3-{4-[7-(1-methyl-1H-pyrazol-4-yl)imidazo[1,2-a]pyridin-5-yl]-1H-pyrazol-1-yl}cyclobutanecarbonitrile;

trans-3-{3-[7-(5-aminopyridazin-3-yl)-1,6-naphthyridin-5-yl]-1H-pyrazol-1-yl}-3-(cyanomethyl)cyclobutanecarbonitrile;

cis-3-{3-[7-(5-aminopyridazin-3-yl)-1,6-naphthyridin-5-yl]-1H-pyrazol-1-yl}-3-(cyanomethyl)cyclobutanecarbonitrile;

trans-3-(cyanomethyl)-3-{4-[7-(1-methyl-1H-pyrazol-4-yl)imidazo[1,2-a]pyridin-5-yl]-2H-1,2,3-triazol-2-yl}cyclobutanecarbonitrile;

trans-3-(cyanomethyl)-3-(3-{7-[5-(hydroxymethyl)-1-methyl-1H-pyrazol-3-yl]-1,6-naphthyridin-5-yl}-1H-pyrazol-1-yl)cyclobutanecarbonitrile;

trans-3-(cyanomethyl)-3-(4-{7-[4-(hydroxymethyl)-1,3-thiazol-5-yl]quinolin-5-yl}-2H-1,2,3-triazol-2-yl)cyclobutanecarbonitrile;

trans-3-(cyanomethyl)-3-(4-{7-[5-(hydroxymethyl)-1-methyl-1H-pyrazol-4-yl]quinolin-5-yl}-2H-1,2,3-triazol-2-yl)cyclobutanecarbonitrile;

(cis-3-methoxy-1-{4-[7-(1-methyl-1H-pyrazol-4-yl)imidazo[1,2-a]pyridin-5-yl]-1H-pyrazol-1-yl}cyclobutyl)acetonitrile;

trans-3-(cyanomethyl)-3-{4-[7-(1H-pyrazol-3-yl)imidazol[1,2-a]pyridin-5-yl]-1H-pyrazol-1-yl}cyclobutanecarbonitrile;

4-(5-{1-[cis-3-cyano-1-(cyanomethyl)cyclobutyl]-1H-pyrazol-3-yl}-1,6-naphthyridin-7-yl)pyrimidine-2-carboxamide;

[cis-1-(4-{7-[3-(hydroxymethyl)-1H-pyrazol-4-yl]imidazo[1,2-a]pyridin-5-yl}-1H-pyrazol-1-yl)-3-methoxycyclobutyl]acetonitrile;

[trans-1-(4-{7-[3-(hydroxymethyl)-1H-pyrazol-4-yl]imidazo[1,2-a]pyridin-5-yl}-1H-pyrazol-1-yl)-3-methoxycyclobutyl]acetonitrile;

6-(5-{1-[cis-3-cyano-1-(cyanomethyl)cyclobutyl]-1H-pyrazol-3-yl}-1,6-naphthyridin-7-yl)-3-hydroxypyridine-2-carboxamide;

(3-{3-[7-(5-amino-1-methyl-1H-pyrazol-3-yl)-1,6-naphthyridin-5-yl]-1H-pyrazol-1-yl}-1-ethylazetidin-3-yl)acetonitrile;

trans-3-{4-[7-(3-amino-1H-pyrazol-4-yl)quinolin-5-yl]-2H-1,2,3-triazol-2-yl}-3-(cyanomethyl)-1-methylcyclobutanecarbonitrile;

(3-{3-[7-(3,6-dihydro-2H-pyran-4-yl)-1,6-naphthyridin-5-yl]-1H-pyrazol-1-yl}-1-ethylazetidin-3-yl)acetonitrile;

trans-3-(cyanomethyl)-3-(3-(7-(1-methyl-1H-pyrazol-4-yl)-1,6-naphthyridin-5-yl-2-d)-1H-pyrazol-1-yl)cyclobutane-1-carbonitrile;

(1-ethyl-3-{3-[7-(morpholin-4-yl)-1,6-naphthyridin-5-yl]-1H-pyrazol-1-yl}azetidin-3-yl)acetonitrile; and, (1-ethyl-3-{3-[7-(pyrrolidin-1-yl)-1,6-naphthyridin-5-yl]-1H-pyrazol-1-yl}azetidin-3-yl)acetonitrile; or, a pharmaceutically acceptable salt thereof.

The invention further provides a pharmaceutical composition comprising a compound having any of the above structures, or a pharmaceutically acceptable salt thereof, or a pharmaceutically acceptable solvate of said compound or salt, and a pharmaceutically acceptable excipient.

The invention also provides a method of treating a disease or condition for which a Tyk2 inhibitor is indicated, in a subject in need of such treatment, comprising administering to the subject a therapeutically effective amount of a compound having any of the above structures, or a pharmaceutically acceptable salt thereof, or a pharmaceutically acceptable solvate of said compound or salt.

The invention also provides a method of treating a disease or condition selected from inflammation, autoimmune disease, systemic lupus erythematous, lupus nephritis, discoid lupus, cutaneous lupus, central nervous system lupus, rheumatoid arthritis, psoriatic arthritis, inflammatory bowel disease, Crohn's disease, ulcerative colitis, asthma, allergic asthma, Type I diabetes, polymyositis, dermatomyositis, type I interferonopathies including Aicardi-Goutières syndrome and other mendelian diseases of overexpression of type I interferon, multiple sclerosis, primary progressive multiple sclerosis, relapsing remitting multiple sclerosis, primary biliary cirrhosis also known as primary biliary cholangitis, primary sclerosing cholangitis, autoimmune hepatitis, non-alcoholic fatty liver disease, non-alcoholic steatohepatitis, psoriasis, dermatomyositis, scleroderma, atopic dermatitis, vitiligo, alopecia areata, spondylopathy, ankylosing spondylitis, Alzheimer's disease, neuro-inflammation comprising administering to a subject suffering from said disease condition a therapeutically effective amount of a compound having any of the above structures, or a pharmaceutically acceptable salt thereof, or a pharmaceutically acceptable solvate of said compound or salt.

The invention further provides a method of treating an inflammatory or autoimmune condition comprising administering to a subject suffering therefrom a therapeutically effective amount of a compound having any of the above structures, or a pharmaceutically acceptable salt thereof, or a pharmaceutically acceptable solvate of said compound or salt.

In certain embodiments, the therapeutically effective amount used in accord with the method is from 0.01 mg/kg of body weight/day to 100 mg/kg of body weight/day. In certain other embodiments, the therapeutically effective amount used in accord with the method is wherein the therapeutically effective amount is from 0.1 mg/kg of body weight/day to 10 mg/kg of body weight/day.

Compounds of the invention that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of structure I or II can exist as cis- and trans-achiral diastereomers.

Included within the scope of the described compounds are all isomers (e.g., cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of structure I or II itself. Enantiomers may be separated through the formation of diastereomeric salts, for example by salt formation with an enantiomer-pure chiral acid, or by means of chromatography, for example by HPLC, using chromatographic substrates with chiral ligands. The present invention includes all pharmaceutically acceptable isotopically-labelled compounds of structure I or II wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of structure I or II, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances. Substitution with positron emitting isotopes, such as 11C, 18F, $^{15}$O and $^{13}$N, can be useful in Positron Emission Topography (PET) studies for examining substrate receptor occupancy. Isotopically-labeled compounds of structure I or II can generally be prepared by conventional techniques known to those skilled in the art or by processes analogous to those described in the accompanying Examples and Preparations using an appropriate isotopically-labeled reagent in place of the non-labeled reagent previously employed.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compounds of structure I or II include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see *Handbook of Pharmaceutical Salts: Properties, Selection*, and Use by Stahl and Wermuth (Wiley-VCH, 2002).

Pharmaceutically acceptable salts of compounds of structure I or II may be prepared, respectively, by one or more of three methods: (i) by reacting the compound of structure I or II with the desired acid or base; (ii) by removing an acid- or base-labile protecting group from a suitable precursor of the compound of structure I or II or by ring-opening a suitable cyclic precursor, for example, a lactone or lactam, using the desired acid or base; or (iii) by converting one salt of the compound of structure I or II to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in *Remington's Pharmaceutical Sciences*, Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

The present invention also provides any of the uses, methods or compositions as defined above wherein the compound of structure I or II, or a pharmaceutically acceptable salt thereof, or pharmaceutically acceptable solvate of said compound or salt, is used in combination with another pharmacologically active compound, particularly one of the functionally-defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of structure I or II, or a pharmaceutically acceptable salt thereof, or pharmaceutically acceptable solvate of said compound or salt, sulfasalazine, mesalazine, prednisone, azathioprine, infliximab, adalimumab, belimumab, becertolizumab, natalizumab, vedolizumab, hydrocortisone, budesonide, cyclosporin, tacrolimus, fexofenadine, 6-mercaptopurine, methotrexate, ursodeoxycholic acid, obeticholic acid, anti-histamines, rifampin, prednisone, methotrexate, azathioprine, cyclophosphamide, hydroxychloroquine, mofetil, sodium mycophenolate, tacrolimus, leflunomide, chloroquine and quinacrine, thalidomide, rituxan, NSAIDs, solumedrol, depomedrol and dexamethasone.

Other suitable agents for use in combination therapy with a compound of structure I or II, or a pharmaceutically acceptable salt thereof, or pharmaceutically acceptable solvate of said compound or salt, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an α1-adrenoceptor agonist or an a2-adrenoceptor agonist, e.g., phenylephrine, methoxamine, oxymetazoline or methylnorephrine; a muscarinic M3 receptor antagonist, e.g. tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast;

sodium cromoglycate or sodium nedocromil; a cyclooxygenase (COX) inhibitor, such as a non-selective inhibitor (e.g., aspirin or ibuprofen) or a selective inhibitor (e.g. celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an intigrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{2b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds and the pharmaceutically acceptable solvates of said specifically named compounds and salts.

Accordingly, the invention provides methods of treating or preventing a disease, condition or disorder associated with JAK in a subject, such as a human or non-human mammal, comprising administering an effective amount of one or more compounds described herein to the subject. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Conditions in which selective targeting of the JAK pathway or modulation of the JAK kinases, particularly Tyk2, are contemplated to be therapeutically useful include, inter alia, arthritis, asthma, autoimmune diseases, cancers or tumors, diabetes, certain eye diseases, disorders or conditions, inflammation, intestinal inflammations, allergies or conditions, neurodegenerative diseases, psoriasis, and transplant rejection. Conditions which can benefit from selective inhibition of Tyk2 are discussed in greater detail below.

Accordingly, the compound of structure I or II, or its pharmaceutically acceptable salts and solvates, and pharmaceutical compositions thereof, can be used to treat a variety of conditions or diseases such as the following:

Arthritis, including rheumatoid arthritis, juvenile arthritis, and psoriatic arthritis;

Autoimmune or inflammatory diseases or disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, autoimmune hepatitis, primary sclerosing cholangitis, chronic aggressive hepatitis, non-alcoholic fatty liver disease, non-alcoholic steatohepatitis ulcerative colitis and membranous glomerulopathy, systemic lupus erythematosis, rheumatoid arthritis, psoriatic arthritis, Sjogren's syndrome, Reiter's syndrome, polymyositis, dermatomyositis, type I interferonopathies including Aicardi-Goutières syndrome and other mendelian diseases of overexpression of type I interferon systemic sclerosis, polyarteritis nodosa, multiple sclerosis, relapsing remitting multiple sclerosis, primary progressive multiple sclerosis, secondary progressive multiple sclerosis, and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, including Crohn's disease, ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, or platelet aggregation;

Skin diseases, conditions or disorders including atopic dermatitis, eczema, psoriasis, scleroderma, pruritus or other pruritic conditions, vitiligo, alopecia;

Allergic reactions including allergic dermatitis in mammal (including horse allergic diseases such as bite hypersensitivity), summer eczema, sweet itch in horses, heaves, inflammatory airway disease, recurrent airway obstruction, airway hyper-responsiveness, or chronic obstruction pulmonary disease;

Asthma and other obstructive airways diseases, including chronic or inveterate asthma, late asthma, bronchitis, bronchial asthma, allergic asthma, intrinsic asthma, extrinsic asthma, or dust asthma;

Transplant rejection, including pancreas islet transplant rejection, bone marrow transplant rejection, graft-versushost disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation.

Chemical Synthesis

The skilled person will appreciate that the experimental conditions set forth in the schemes that follow are illustrative of suitable conditions for effecting the transformations shown, and that it may be necessary or desirable to vary the precise conditions employed for the preparation of compounds of structure I or II. It will be further appreciated that it may be necessary or desirable to carry out the transformations in a different order from that described in the schemes, or to modify one or more of the transformations, to provide the desired compound of the invention.

All of the derivatives of structure I or II can be prepared by the procedures described in the general methods presented below or by routine modifications thereof. The present invention also encompasses any one or more of these processes for preparing the derivatives of structure I or II in addition to any novel intermediates used therein.

The routes below, including those mentioned in the Examples and Preparations, illustrate methods of synthesising compounds of structure I or II. The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis-The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino, carboxylic acid or hydroxyl groups. The protecting groups used in the preparation of the compounds of the invention may be used in a conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the general synthetic methods below, unless otherwise specified, the substituents are as defined above with reference to the compounds of structure I or II above.

Where ratios of solvents are given, the ratios are by volume.

The compounds of the invention may be prepared by any method known in the art for the preparation of compounds of analogous structure. In particular, the compounds of the invention can be prepared by the procedures described by reference to the Schemes that follow or by similar processes.

The skilled person will appreciate that the experimental conditions set forth in the schemes that follow are illustrative of suitable conditions for effecting the transformations shown, and that it may be necessary or desirable to vary the precise conditions employed for the preparation of compounds of structure I or II. The person skilled in the art will appreciate that the following reactions may be heated thermally or under microwave irradiation.

The schemes are representative of methods useful in synthesizing the compounds of the present invention. They are not to constrain the scope of the invention in any way.

According to a first process, compounds of Formula (I)(B), where W is a C linked heterocycle, may be prepared from compounds of Formulae (IV), (V), (I)(A) and (VI) as illustrated by Scheme 1.

Scheme 1

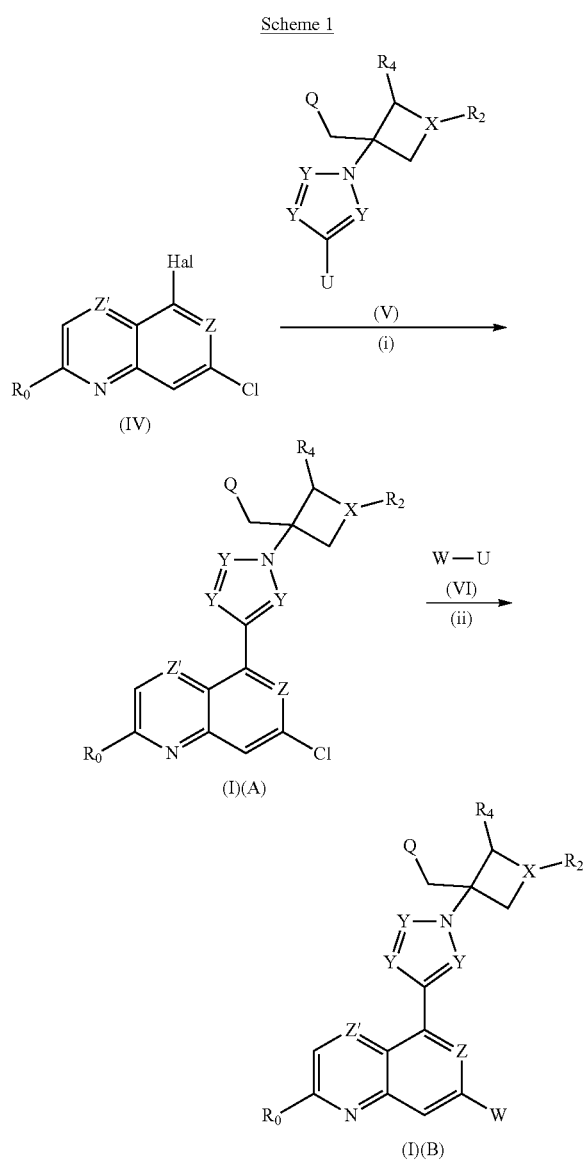

Hal is halo, preferably Cl or Br
U represents Hal (i), B(Pin) (ii), or B(OH)$_2$ (iii)

In Scheme 1, compounds of Formula (IV) are commercially available. Compounds of Formula (V)(ii) and (V)(iii) are commercially available or compounds of Formula (V)(ii) may be prepared from the compound of Formula (V)(i) by treatment with a suitable boronate such as B$_2$(Pin)$_2$, in the presence of a suitable base, such as K$_2$CO$_3$ or KOAc, and a suitable catalyst, such as Pd(dppf)Cl$_2$ or XPhos Pd G2, in a suitable solvent, such as dioxane. A skilled person also knows that alternative organometallic coupling strategies can be used involving alternative coupling partners, metals and solvent combinations.

A compound of the Formula (V)(ii) is prepared and isolated as described above or prepared in situ without isolation in a sequential cross-coupling strategy that is well understood by a skilled person. Thus, a compound of Formula (I)(A) may be prepared from compounds of Formulae (IV) and (V)(ii) or (iii) using a suitable organometallic cross-coupling reaction such as a Suzuki cross-coupling reaction according to process step (i). Typical Suzuki cross-coupling conditions, comprise a palladium catalyst containing suitable phosphine ligands, in the presence of an inorganic base, in aqueous solvent, at elevated temperatures either thermally or under microwave irradiation. Typical conditions comprise Pd(OAc)$_2$, Pd(dppf)Cl$_2$ or Pd(PPh$_3$)$_4$, XPhos, XPhos Pd G2, or cataCXium® with a suitable base such as K$_2$CO$_3$ or K$_3$PO$_4$, optionally with the addition of KF, in a suitable solvent such as aqueous dioxane or MeCN, optionally with toluene as co-solvent, or toluene, at from room temperature to reflux temperature.

The resulting compound of Formula (I)(A) is cross-coupled with a compound of the Formula (VI) (ii) or (iii) which are commercially available or the compound of Formula (VI)(ii) may be prepared from the compound of Formula (VI)(i) as described above for the preparation of compounds of Formula (V) (ii).

A compound of Formula (I)(B) may be prepared from compounds of Formulae (VI)(ii) or (iii) and (I)(A) according to process step (ii), a suitable organometallic cross-coupling reaction such as a Suzuki cross-coupling reaction, as described previously for process step (i). Alternatively, compounds of the Formula (I)(B) may be prepared by alternative cross-coupling strategies such as the Migita-Kosugi-Stille coupling using a compound of Formula (VI) (where U=SnBu$_3$) preceded if necessary by an arylstannane formation reaction.

According to a second process compounds of Formula (I)(B), where W is a C-linked heterocycle, may be prepared from compounds of Formulae (I)(A) as illustrated by Scheme 2.

Scheme 2

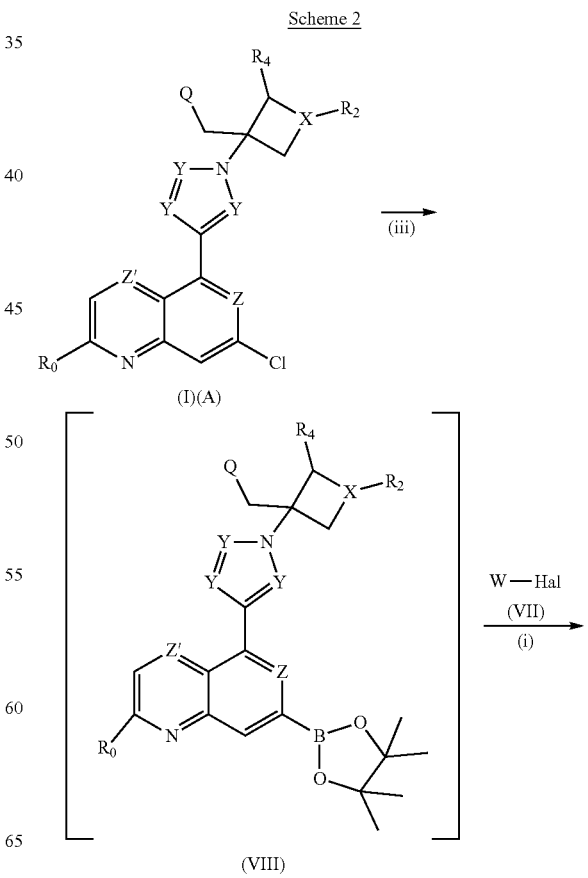

-continued

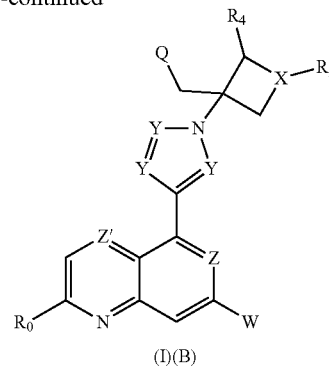

(I)(B)

Hal is halo, preferably Br or Cl

In scheme 2, the compound of Formula (VIII) may be prepared from the compound of Formula (I)(A) by process step (iii) a boronate ester formation, treatment with a suitable boronate such as $B_2(Pin)_2$, in the presence of a suitable base, such as $K_2CO_3$ or KOAc, and a suitable catalyst, such as $Pd(dppf)Cl_2$ or XPhos Pd G2, in a suitable solvent, such as dioxane at elevated temperature. A compound of the Formula (VIII) may be prepared and isolated or prepared in situ without isolation in a sequential cross-coupling strategy that is well understood by a skilled person. Compounds of Formula (I)(B) may be prepared from compounds of Formulae (VIII) and (VII) using a suitable organometallic cross-coupling reaction such as Suzuki cross-coupling reaction, as described previously for process step (i) in Scheme 1.

According to a third process, the compound of Formula (I)(A) may be prepared from the compounds (IV), (IX), (X), (XI) and (XII) as shown in Scheme 3.

Scheme 3

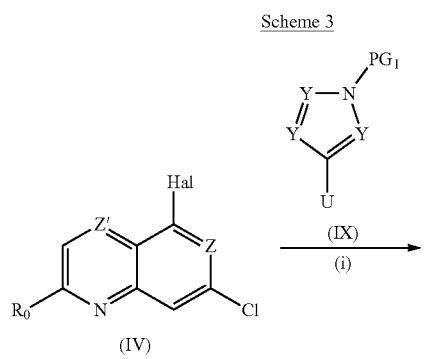

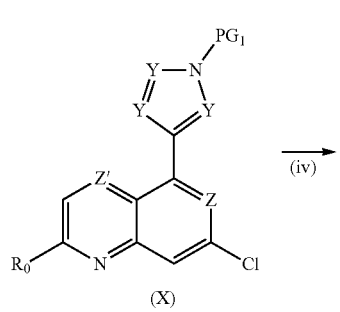

-continued

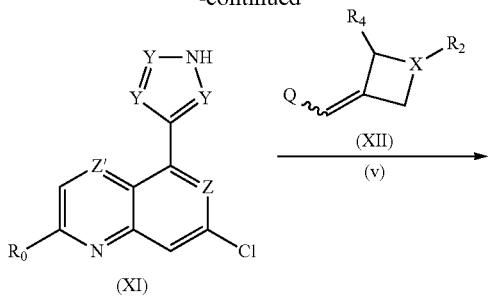

(XI)

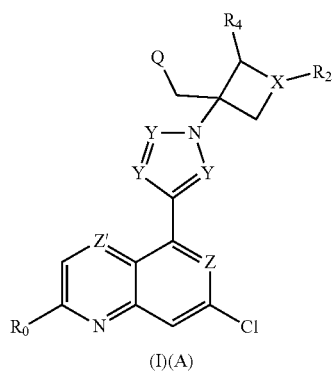

(I)(A)

$PG_1$ is a N-protecting group, preferably THP

Hal is halo, preferably Cl or Br; U represents Hal (i), B(Pin) (ii), or $B(OH)_2$ (iii)

In Scheme 3, compounds of Formula (IX)(ii) and (IX)(iii) are commercially available or compounds of Formula (IX) (ii) may be prepared from the compound of Formula (IX)(i) by treatment with a suitable boronate such as $B_2(Pin)_2$, in the presence of a suitable base, such as $K_2CO_3$ or KOAc, and a suitable catalyst, such as $Pd(dppf)Cl_2$ or XPhos Pd G2, in a suitable solvent, such as dioxane. A skilled person also knows that alternative organometallic coupling strategies can be used involving alternative coupling partners, metals and solvent combinations.

Compounds of Formula (X) may be prepared from compounds of Formulae (IV) and (IX) using a suitable organometallic cross-coupling reaction such as Suzuki cross-coupling reaction, as described previously for process step (i). Compounds of Formula (XI) may be prepared by deprotection of compounds of Formula (X) according to process step (iv). Typical conditions comprise treatment of compounds of Formula (X) with p-toluenesulfonic acid in a suitable solvent such as aqueous MeCN or MeOH at between room temperature and reflux temperature.

A compound of Formula (I)(A) may be prepared from compounds of Formulae (XII) and (XI) by process step (v), a Michael addition reaction, in the presence of a suitable base such as DBU in a suitable solvent, such as MeCN or benzene at between room temperature and reflux temperature. Compounds of Formula (XII) are commercially available, or may be prepared from the corresponding ketone by a Horner-Wadsworth-Emmons reaction with a suitable reagent such as diethyl(cyanomethyl)phosphonate under standard conditions.

According to a fourth process, compounds of Formula (I)(C), wherein the (YYNYC) heterocycle is a 1,2,3-triazole, may be prepared from the compounds (IV), (XIII), (XIV), and (XV) as shown in Scheme 4.

Scheme 4

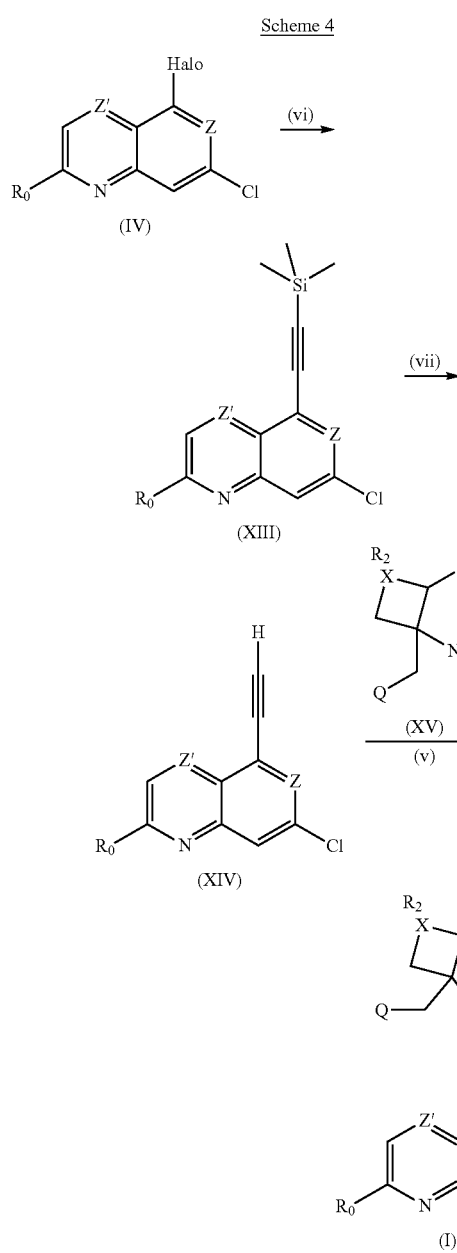

According to a fifth process, wherein, W represents a heterocyclic group linked through a nitrogen atom, compounds of Formula (I)(D) may be prepared from compounds of Formula (XI) (XVII), (XII) and (XVI) as shown in Scheme 5.

Scheme 5

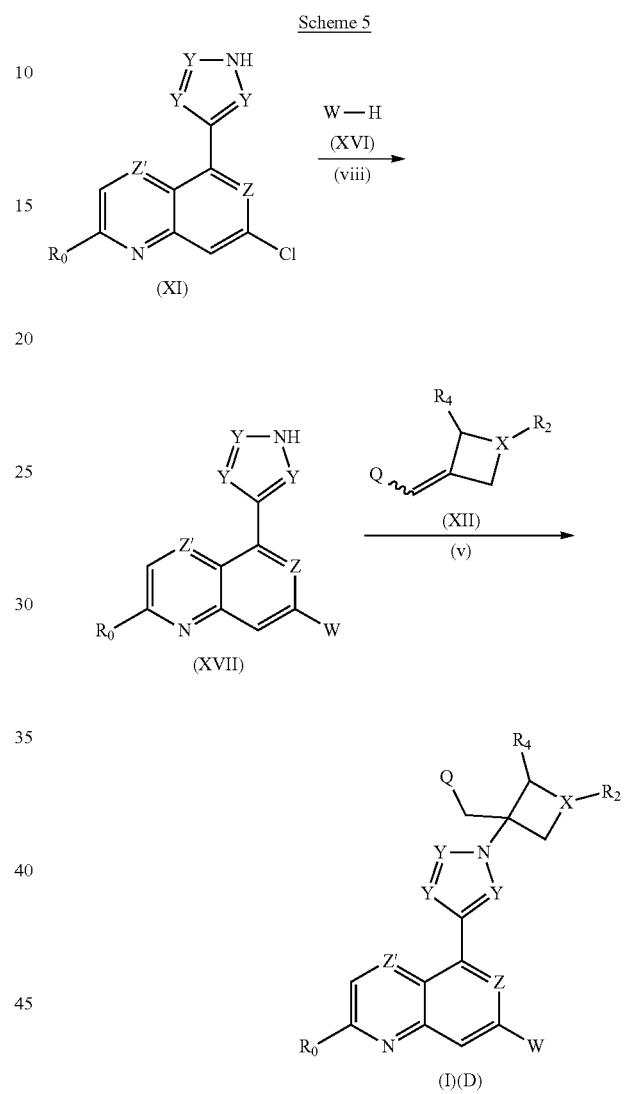

Compounds of Formula (XIII) may be prepared from compounds of Formula (IV) by process step (vi), treatment with (trimethylsilyl)acetylene in the presence of a suitable Pd catalyst, preferably $PdCl_2(PPh_3)_2$ and a catalytic amount of CuI, in the presence of a suitable base such as $Et_3N$ in a solvent such as dioxane, typically at elevated temperatures. Deprotection of compounds of Formula (XIII) by process step (vii), using standard conditions, typically by treatment with TBAF in aqueous solvent such as THF or DCM at ambient temperatures provides compounds of Formula (XIV). Compounds of Formula (I)(C) may be prepared by the cyclo-addition of compounds of Formula (XIV) with the azide of Formula (XV) in the presence of catalytic quantities of $CuSO_4$ and sodium ascorbate, in suitable solvents such as aqueous THF at ambient temperature. Optionally, the preparation of compounds of Formula (I)(C) from compounds of Formula (XIII) may be performed in one step, i.e., compounds of Formula (XIV) are prepared in situ.

Compounds of Formula (XVII) may be prepared from compounds of Formula (XI) according to process step (viii). This reaction may be achieved by reaction of the compound of Formula (XI) with an excess of amine WH (XVI), in the presence of an organic base such as DIPEA in a suitable solvent such as n-BuOH at between room temperature and reflux temperature. Alternatively, the compound of Formula (XVII) may be prepared by reaction with amine W—H (XVI), by a Buchwald-Hartwig amination reaction as described in the literature. Compounds of Formula (I)(D) may be prepared from compounds of Formula (XII) and (XVII) according to process step (v), a Michael addition as previously described in Scheme 3.

According to a sixth process, wherein, W represents a group linked through an oxygen atom, compounds of Formula (I)(E) may be prepared from compounds of Formula (I)(A) and (VIII) and W as shown in scheme 6.

Scheme 6

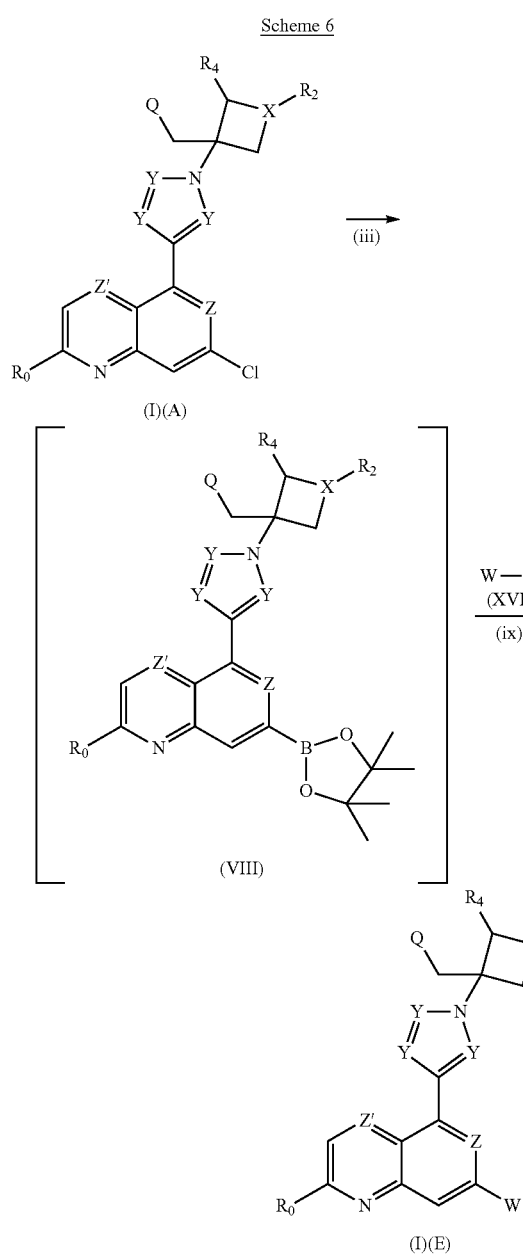

In Scheme 6, the compound of Formula (VIII) may be prepared from the compound of Formula (I)(A) by process step (iii), treatment with a suitable boronate such as $B_2(Pin)_2$, in the presence of a suitable base, such as $K_2CO_3$ or KOAc, and a suitable catalyst, such as Pd(dppf)Cl$_2$ or XPhos Pd G2, in a suitable solvent, such as dioxane at elevated temperature. A compound of the Formula (VIII) may prepared and isolated, or prepared in situ without isolation, in a sequential cross-coupling strategy that is well understood by a skilled person. A compound of Formula (I)(E) may be prepared from compounds of Formulae (VIII) and WH using a suitable organometallic cross-coupling reaction according to process step (ix). Typical conditions comprise a palladium catalyst containing suitable phosphine ligands such as XPhos in the presence of an inorganic base such as $K_3PO_4$, at elevated temperatures in a suitable solvent such as dioxane.

According to a seventh process, compounds of Formula (II)(B), where Y" is N and W is a heterocycle linked through a carbon atom, may be prepared from the compounds of Formulae (IV), (XVIII), (IVA) and (VI) as shown in Scheme 7.

Scheme 7

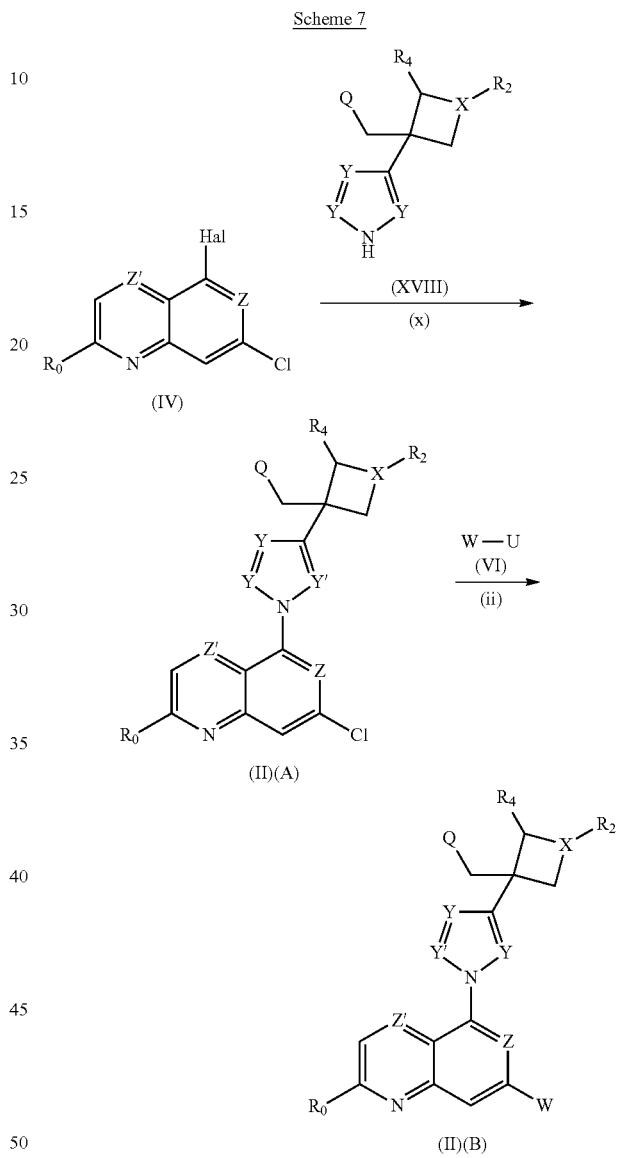

Hal is halo, preferably Cl or Br
U represents Hal (i), B(Pin) (ii), or B(OH)$_2$ (iii)

Compounds of Formula (II)(A) may be prepared by the reaction of compounds of Formula (IV) with the compound of Formula (XVIII) according to process step (x), in the presence of a suitable strong base, such as NaH in a suitable solvent such as DMF at low temperatures, typically between 0° C. and 20° C. Compounds of Formula (II)(B) may be prepared from compounds of Formulae (II)(A) and (VI) by a suitable organometallic cross-coupling reaction such as a Suzuki cross-coupling reaction, as described previously for process step (ii).

According to an eighth process, the compound of Formula (II)(D), where Y' is O and Y" is C and W is a heterocycle, may be prepared from the compounds (XIV), (XIX), (II)(C) and (VI) as shown in Scheme 8.

Scheme 8

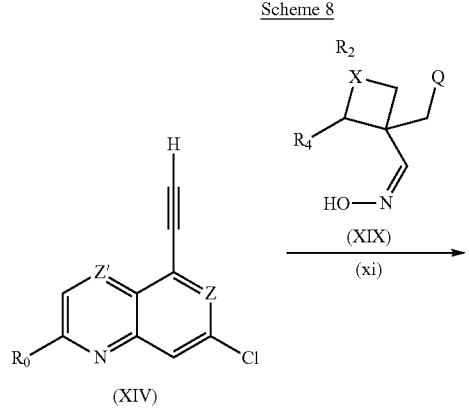

Scheme 9

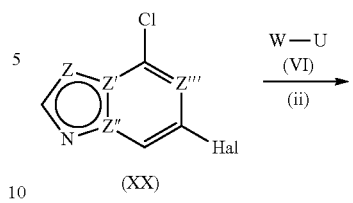

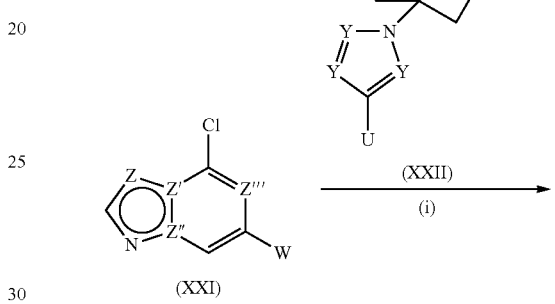

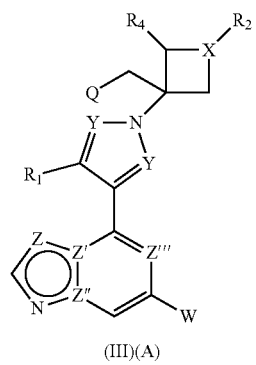

Compounds of Formula (II)(C) may be prepared by the addition of compounds of Formula (XIV) with the oxime of Formula (XIX), according to process step (xi), in the presence of NaOCl and a suitable base, typically Et$_3$N, in suitable solvents such as aqueous THF or DCM at temperatures between 0° and 20° C. Compounds of Formula (II)(D), where W is a heterocycle linked through a carbon atom, may be prepared from compounds of Formulae (II)(C) and (VI) by a suitable organometallic cross-coupling reaction such as a Suzuki cross-coupling reaction, as described previously for process step (ii).

According to a ninth process, the compound of Formula (III)(A), where W is a heterocycle linked through a carbon atom, may be prepared from the compounds (XX), (XXI), (VI) and (XXII) as shown in Scheme 9.

Hal is halo, preferably Cl or Br; U represents Hal (i), B(Pin) (ii), or B(OH)$_2$ (iii)

Compounds of Formula (XXI) may be prepared from compounds of Formulae (XX) and (VI) according to process step (ii) as previously described in Scheme 1. Compounds of Formula (II)(A) may be prepared from compounds of Formulae (XXI) and (XXII) according to process step (ii) an organometallic catalysed cross coupling reaction as described in Scheme 1. Compounds of Formula (XX) are commercially available or may be prepared by analogy with methods described in the literature, for example as in WO2016/148306 (Intermediate 2).

According to a tenth process, the compound of Formula (III)(B) may be prepared from the compounds (XXI), (XXIII), (XXIV), (XXV) and (XII) as shown in scheme 10.

Scheme 10

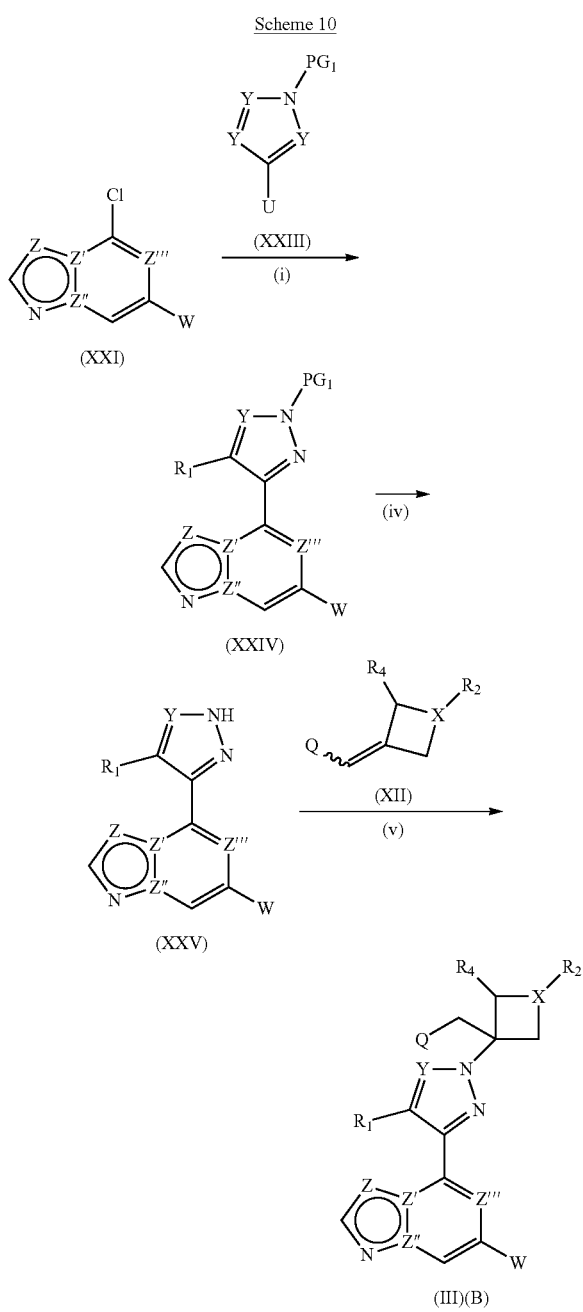

PG$_1$ is a N-protecting group, preferably THP
U represents Hal (i), B(Pin) (ii), or B(OH)$_2$ (iii)

In scheme 10, compounds of Formula (XXIII)(ii) and (XXIII)(iii) are commercially available or compounds of Formula (XXIII)(ii) may be prepared from the compound of Formula (XXIII)(i) by treatment with a suitable boronate such as B$_2$(Pin)$_2$, in the presence of a suitable base, such as K$_2$CO$_3$ or KOAc, and a suitable catalyst, such as Pd(dppf)Cl$_2$ or XPhos Pd G2, in a suitable solvent, such as dioxane. A skilled person also knows that alternative organometallic coupling strategies can be used involving alternative coupling partners, metals and solvent combinations.

A compound of Formula (XXIV) may be prepared from compounds of Formulae (XXI) and (XXIII) using a suitable organometallic cross-coupling reaction such as Suzuki cross-coupling reaction, as described previously for process step (i). Compounds of Formula (XXV) may be prepared by deprotection of compounds of Formula (XXIV) according to process step (iv). Typical conditions comprise treatment of compounds of Formula (XVIV) with p-toluenesulfonic acid in a suitable solvent such as aqueous MeCN or MeOH at between room temperature and reflux temperature A compound of Formula (II)(B) may be prepared from compounds of Formulae (XII) and (XXV) by process step (v), a Michael addition reaction, in the presence of a suitable base such as DBU in a suitable solvent, such as MeCN or benzene at between room temperature and reflux temperature. Compounds of Formula (XII) are commercially available, or may be prepared from the corresponding ketone by a Horner-Wadsworth-Emmons reaction with a suitable reagent such as diethyl(cycanomethyl)phosphonate under standard conditions.

Compounds of Formula (I), (II), and (IV) may be prepared from alternative compounds of Formula (I), (II), and (IV) respectively where X is N, R$_2$ is H, or W contains a reactive nitrogen atom, by derivitization through alkylation, reductive amination, acylation, sulfonylation, et cetera, of such alternative compounds of Formula (I), (II), and (IV) using methodology known to those skilled in the art.

Alternatively, compounds of Formula (I) (II), and (IV) may be prepared by conducting functional group interconversions of alternative compounds of Formula (I) (II), and (IV), using methodology known to those skilled in the art, such as hydrolysis of a nitrile group to an amide.

The following schemes and written descriptions provide general details regarding the preparation of the compounds of the invention. The skilled person will appreciate that the experimental conditions set forth in the schemes that follow are illustrative of suitable conditions for effecting the transformations shown, and that it may be necessary or desirable to vary the precise conditions employed for the preparation of compounds of Formula (I) and (II).

In executing the synthesis of the compounds of the invention, one skilled in the art will recognize the need to sample and assay reaction mixtures prior to work up in order to monitor the progress of reactions and decide whether the reaction should be continued or whether it is ready to be worked up to obtain the desired product. Common methods for assaying reaction mixtures include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation enantiomers is supercritical fluid chromatography employing a chiral stationary phase.

Experimental Section

Except where otherwise noted, reactions were run under an atmosphere of nitrogen. Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

The nomenclature in this patent is written as described by IUPAC (International Union of Pure and Applied Chemistry) using ChemBioDraw Ultra 13.0 software (supplied by Perkin Elmer) to generate the chemical names.

The following non-limiting Preparations and Examples illustrate the preparation of compounds and salts of the present invention. In the Examples and Preparations that are set out below, and in the aforementioned Schemes, the following abbreviations, definitions and analytical procedures may be referred to.

Other abbreviations common in the art may also be used. Standard IUPAC nomenclature has been used.

AcOH is acetic acid;
aq. is aqueous;
$B_2(Pin)_2$ is bis(pinacolato)diboron;
Boc is tert-butoxycarbonyl;
br is broad;
brine is a saturated solution of sodium chloride in water;
t-Bu is tert-butyl;
n-BuLi is n-butyllithium;
° C. is degrees celcius;
Cbz is carbobenzyloxy;
$CDCl_3$ is deutero-chloroform;
CDI is 1,1'-carbonyldiimidazole;
conc. is concentrated (in reference to reagents);
$Cs_2CO_3$ is cesium carbonate;
δ is chemical shift;
d is doublet;
DBU is 1,8-diazabicyclo[5.4.0]undec-7-ene;
DCM is dichloromethane;
DHP is 3,4-dihydro-2H-pyran;
DIPEA is N,N-diisopropylethylamine;
DMAP is 4-dimethylaminopyridine;
DMF is N,N-dimethylformamide;
DMSO is dimethyl sulfoxide;
$Et_2O$ is diethyl ether;
EtOAc is ethyl acetate;
EtOH is ethanol;
$(EtO)_2P(O)CH2CN$ is diethyl (cyanomethyl)phosphonate;
g is gram;
GCMS is gas chromatography mass spectrometry
HCl is hydrochloric acid;
$HCO_2H$ is formic acid;
HPLC is high performance liquid chromatography;
hrs is hours;
$H_2SO_4$ is sulfuric acid;
$K_2CO_3$ is potassium carbonate;
$KH_2PO_4$ is potassium dihydrogen phosphate
$K_2HPO_4$ is potassium monohydrogen phosphate;
$K_3PO_4$ is potassium phosphate (tribasic);
KOAc is potassium acetate
L is liter;
LCMS is liquid chromatography mass spectrometry;
LiBr is lithium bromide;
LiOH is lithium hydroxide;
m is multiplet;
M is molar;
MeCN is acetonitrile;
MeOH is methanol;
mg is milligram;
$MgSO_4$ is magnesium sulfate;
MHz is megaHertz;
min is minutes;

mL is milliliter;
mmol is millimole;
mol is mole;
MS m/z is mass spectrum ion peak;
MTBE is methyl t-butyl ether
$NaBH(OAc)_3$ is sodium triacetoxyborohydride;
$Na_2CO_3$ is sodium carbonate;
$NaHCO_3$ is sodium hydrogen carbonate;
$NaH_2PO_4$ is sodium dihydrogen phosphate;
$Na_2HPO_4$ is sodium monohydrogen phosphate;
NaI is sodium iodide;
$NaIO_4$ is sodium periodate;
NaOAc is sodium acetate;
NaOCl is sodium hypochlorite;
NaOH is sodium hydroxide;
$NH_3$ is ammonia;
$NH_4Cl$ ammonium chloride;
$NH_4OH$ is ammonium hydroxide;
$NH_4OAc$ is ammonium acetate;
NMR is nuclear magnetic resonance;
$OsO_4$ is osmium tetroxide;
Pd/C is palladium on carbon;
$Pd(dppf)Cl_2$ is 1,1-bis(diphenylphosphino)ferrocene palladium(II)dichloride;
$Pd(dppf)Cl_2$ DCM is 1,1-bis(diphenylphosphino)ferrocene palladium(II)dichloride; complex with dichloromethane (CAS: 95464-05-4);
$Pd(OAc)_2$ is palladium acetate;
$Pd(PPh_3)_4$ is tetrakis(triphenylphosphine)palladium;
PMB-Cl is (4-methoxy)benzyl chloride;
$POCl_3$ is phosphorus(V) oxychloride;
ppm is parts per million;
psi is pounds per square inch;
PTSA is para-toluenesulfonic acid
$PyHBr_3$ is pyridine hydrobromide perbromide
PyHCl is pyridine hydrochloride
q is quartet;
Rt is retention time;
$Rh_2(OAc)_4$ is rhodium (II) acetate dimer;
$RuCl_3$ hydrate is ruthenium(II) chloride hydrate;
s is singlet;
$SOCl_2$ is thionyl chloride;
t is triplet;
TBAB is tetrabutylammonium bromide
TEA is triethylamine;
TFA is trifluoroacetic acid;
THF is tetrahydrofuran;
TMSCl is chorotrimethylsilane;
μL is microliter;
μmol is micromole
XPhos Pd G2 is chloro(2-dicyclohexylphosphino-2',4',6'-triisopropyl-1,1'-biphenyl)[2-(2'-amino-1,1'-biphenyl)]palladium(II); CAS 1310584-14-5.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common NMR solvents: $CD_3CN$, deuteroacetonitrile; $CDCl_3$, deuterochloroform; $DMSO-d_6$, deuterodimethylsulfoxide; and $CD_3OD$, deuteromethanol. Where appropriate, tautomers may be recorded within the NMR data; and some exchangeable protons may not be visible.

Mass spectra were recorded using electron impact ionization (EI), electrospray ionisation (ESI) or atmospheric pressure chemical ionisation (APCI). The observed ions are reported as MS m/z and may be positive ions of the compound [M]$^+$, compound plus a proton [MH]$^+$, or compound plus a sodium ion [MNa]$^+$. In some cases the only observed ions may be fragment ions reported as [MH-(fragment lost)]$^+$. Where relevant, the reported ions are assigned for isotopes of chlorine ($^{35}$Cl and/or $^{37}$Cl), bromine ($^{79}$Br and/or $^{81}$Br) and tin ($^{129}$Sn). Wherein TLC, chromatography, or HPLC has been used to purify compounds, one skilled in the art may choose any appropriate solvent or combination of solvents to purify the desired compound. Chromatographic separations (excluding HPLC) were carried out using silica gel adsorbent unless otherwise noted.

All reactions were carried out using continuous stirring under an atmosphere of nitrogen or argon gas unless otherwise noted. In some cases, reactions were purged with nitrogen or argon gas prior to the start of the reaction. In these cases, the nitrogen or argon gas was bubbled through the liquid phase of the mixture for the approximate specified time. Solvents used were commercial anhydrous grades. All starting materials were commercially available products. In some cases, the Chemical Abstracts Service (CAS) identification number is provided to assist with clarity. In some cases, starting materials were prepared according to reported literature procedures as indicated by an asterisk (*). It will be apparent to one skilled in the art that the word "concentrated" as used herein generally refers to the practice of evaporation of solvent under reduced pressure, typically accomplished by the use of a rotary evaporator.

GCMS Conditions

Column: 12m×0.2mm, HP-1 Methyl Siloxane, 0.33 μm film, 1.0 ml/min column flow.

Methods: 7.6 min: Initial Oven Temp 105° C.; 0.1 min hold; 30° C./min ramp to 300° C. endpoint at 7.6 min; or 7.6 min: Initial Oven Temp 60° C.; 0.1 min hold; 40° C./min ramp to 320° C. endpoint at 7.6 min; or 5.1 min: Initial Oven Temp 40° C.; 0.1 min hold; 30° C./min ramp to 150° C. endpoint at 5.1min.

GC Inlet Parameters: Front Inlet, Split 30:1, He, 8 psi pressure, 250° C. Injector, 33.9 ml/min total flow.

MSD Tune: 230° C. Source Temp, 150° C. Quad Temp, 280° C. Aux2 Temp Injection Volume: 1.0 μL System Components: Agilent 5890 GC Oven with Agilent 5973 Mass Selective Detector LCMS Conditions Acid: Waters Acquity HSS T3, 2.1 mm×50 mm, C18, 1.7 μm; Column Temperature 60° C.

Base: Waters Acquity UPLC BEH, 2.1 mm×50 mm, C18, 1.8 μm; Column Temperature 60° C.

Mobile Phase: A: 0.1% formic acid in water (v/v); Mobile phase B: 0.1% formic acid in acetonitrile (v/v).

Mobile Phase A: 0.1% ammonia in water (v/v); Mobile phase B: 0.1% ammonia in acetonitrile (v/v)

Gradient Profiles: 1.5 min Run: Initial conditions: A-95%: B-5%; hold at initial from 0.0-0.1min; Linear Ramp to A-5%:B-95% over 0.1-1.0min; hold at A-5%:B-95% from 1.0-1.1min; return to initial conditions 1.1-1.5min Purification Methods (PM)

The compounds of the Examples were purified according to one of the Purification Methods (PM) referred to below unless otherwise described:

Purification Method A: Preparative HPLC using [Agella venusil ASB C18 150×21.2 mm×5 μm, from 16% MeCN in water (0.225% formic acid) to 36% MeCN in water (0.225% formic acid)]

Purification Method B: Preparative HPLC using [Phenomenex Gemini C18 250×21.2 mm×8 μm or 150 mm×25 mm×5 μm; from 16-55% MeCN in water (0.1% ammonia) to 36-60% MeCN in water (0.1% ammonia)]

Purification Method C: [YMC-Actus Triart C18 150×30 μm, from 24% MeCN in water (0.1% ammonia) to 44% MeCN in water (0.1% ammonia)]

Purification Method D: Preparative HPLC using [Phenomenex Gemini C18 250×21.2 mm×8 μm, from 25% MeCN in water (ammonia pH=10) to 45% MeCN in water (ammonia pH=10)] followed by chiral chromatography using AS 250×25 mm I.D. 20 μM column, with supercritical $CO_2$: EtOH or IPA (0.05% aqueous ammonia) 70:30 at from 50-80 mL/min Purification Method E: Preparative HPLC using [Phenomenex Gemini C18 250×21.2 mm×8 μm, from 25% MeCN in water (0.225% ammonia) to 45% MeCN in water (0.225% ammonia) followed by chiral chromatography using AD 250 mm×30 mm×20 μm column with mobile phase A: supercritical $CO_2$ and mobile phase B MeOH with 0.1% ammonia A:B 50:50 at 180 mL/min Purification Method F: Silica gel column chromatography eluting with 100% DCM to 12% MeOH with 1% $NH_4OH$.

Purification Method G: Silica gel column chromatography eluting with 97:2:1 DCM:MeOH:$NH_3$ followed by preparative HPLC.

Purification Method H: Preparative HPLC using Column: Waters XBridge C18 19 mm×100 mm, 5 μ; Mobile phase A: 0.03% ammonium hydroxide in water (v/v); Mobile phase B: 0.03% ammonium hydroxide in acetonitrile (v/v); from 5-20% B to 40-100% B at 25 mL/min flow rate.

Purification Method I: Preparative HPLC using Column: Waters Sunfire C18 19 mm×100 mm, 5μ; Mobile phase A: 0.05% TFA in water (v/v); Mobile phase B: 0.05% TFA in acetonitrile (v/v); from 20% B to 40% B at 6.75 minutes, then to 100% B at 7 minutes at 30 mL/min flow rate.

Specific Rotation

Specific rotations based on the equation [α]=(100·α)/(l·c) and are reported as unitless numbers where the concentration c is in g/100 mL and the path length l is in decimeters. The units of the specific rotation, (degmL)/(gdm), are implicit and are not included with the reported value.

| Ex. | Name | Data |
| --- | --- | --- |
| 1 | [3-{4-[7-(1H-pyrazol-4-yl)-1,6-naphthyridin-5-yl]-1H-pyrazol-1-yl}-1-(2,2,2-trifluoroethyl)azetidin-3-yl]acetonitrile | LCMS m/z = 439 |
| 2 | 2,2'-(trans-1-{4-[7-(1H-pyrazol-4-yl)-1,6-naphthyridin-5-yl]-1H-pyrazol-1-yl}cyclobutane-1,3-diyl)diacetonitrile | LCMS m/z = 395 [M + H]$^+$ |
| 3 | 2,2'-(cis-1-{4-[7-(1H-pyrazol-4-yl)-1,6-naphthyridin-5-yl]-1H-pyrazol-1-yl}cyclobutane-1,3-diyl)diacetonitrile | LCMS m/z = 395 [M + H]$^+$ |
| 4 | [3-{4-[7-(1-methyl-1H-pyrazol-4-yl)-1,6-naphthyridin-5-yl]-1H-pyrazol-1-yl}-1-(2,2,2-trifluoroethyl)azetidin-3-yl]acetonitrile | LCMS m/z = 453 |

-continued

| Ex. | Name | Data |
|---|---|---|
| 5 | 2-[3-{4-[7-(1-methyl-1H-pyrazol-4-yl)-1,6-naphthyridin-5-yl]-1H-pyrazol-1-yl}-1-(2,2,2-trifluoroethyl)azetidin-3- | LCMS m/z = 472 |
| 6 | cis-3-(cyanomethyl)-3-(4-{7-[1-(2-hydroxyethyl)-1H-pyrazol-4-yl]-1,6-naphthyridin-5-yl}-1H-pyrazol-1-yl)cyclobutanecarbonitrile | LCMS m/z = 425 [M + H]+ |
| 7 | trans-3-(cyanomethyl)-3-(4-{7-[1-(2-hydroxyethyl)-1H-pyrazol-4-yl]-1,6-naphthyridin-5-yl}-1H-pyrazol-1-yl)cyclobutanecarbonitrile | LCMS m/z = 425 [M + H]+ |
| 8 | [cis-1-(4-{7-[1-(2-hydroxyethyl)-1H-pyrazol-4-yl]-1,6-naphthyridin-5-yl}-1H-pyrazol-1-yl)-3-methoxycyclobutyl]acetonitrile | LCMS m/z = 430 [M + H]+ |
| 9 | [trans-1-(4-{7-[1-(2-hydroxyethyl)-1H-pyrazol-4-yl]-1,6-naphthyridin-5-yl}-1H-pyrazol-1-yl)-3-methoxycyclobutyl]acetonitrile | LCMS m/z = 430 [M + H]+ |
| 10 | [3-(4-{7-[1-(oxetan-3-yl)-1H-pyrazol-4-yl]-1,6-naphthyridin-5-yl}-1H-pyrazol-1-yl)-1-(2,2,2-trifluoroethyl)azetidin-3- | LCMS m/z = 495 |
| 11 | [3-(4-{7-[1-(tetrahydro-2H-pyran-4-yl)-1H-pyrazol-4-yl]-1,6-naphthyridin-5-yl}-1H-pyrazol-1-yl)-1-(2,2,2-trifluoroethyl)azetidin-3-yl]acetonitrile | LCMS m/z = 523 [M + H]+ |
| 12 | [cis-1-(4-{7-[3-(hydroxymethyl)-1H-pyrazol-5-yl]-1,6-naphthyridin-5-yl}-1H-pyrazol-1-yl)-3-methoxycyclobutyl]acetonitrile | LCMS m/z = 416 [M + H]+ |
| 13 | [trans-1-(4-{7-[3-(hydroxymethyl)-1H-pyrazol-5-yl]-1,6-naphthyridin-5-yl}-1H-pyrazol-1-yl)-3-methoxycyclobutyl]acetonitrile | LCMS m/z = 416 [M + H]+ |
| 14 | {3-[3-(7-chloro-1,6-naphthyridin-5-yl)-1H-pyrazol-1-yl]-1-(2,2,2-trifluoroethyl)azetidin-3-yl}acetonitrile | LCMS m/z = 407 [M + H]+ |
| 15 | {3-[3-(1,6-naphthyridin-5-yl)-1H-pyrazol-1-yl]-1-(2,2,2-trifluoroethyl)azetidin-3-yl}acetonitrile | LCMS m/z = 480 [M + H]+ |
| 16 | [3-{3-[7-(1H-pyrazol-3-yl)-1,6-naphthyridin-5-yl]-1H-pyrazol-1-yl}-1-(2,2,2-trifluoroethyl)azetidin-3-yl]acetonitrile | LCMS m/z = 439 [M + H]+ |
| 17 | [1-(methylsulfonyl)-3-{3-[7-(1H-pyrazol-5-yl)-1,6-naphthyridin-5-yl]-1H-pyrazol-1-yl}azetidin-3-yl]acetonitrile | LCMS m/z = 435 [M + H]+ |
| 18 | [1-(cyclopropylsulfonyl)-3-{3-[7-(1H-pyrazol-5-yl)-1,6-naphthyridin-5-yl]-1H-pyrazol-1-yl}azetidin-3-yl]acetonitrile | LCMS m/z = 461 [M + H]+ |
| 19 | [1-(oxetan-3-ylsulfonyl)-3-{3-[7-(1H-pyrazol-5-yl)-1,6-naphthyridin-5-yl]-1H-pyrazol-1-yl}azetidin-3-yl]acetonitrile | LCMS m/z = 477 [M + H]+ |
| 20 | trans-3-(cyanomethyl)-3-{3-[7-(1H-pyrazol-5-yl)-1,6-naphthyridin-5-yl]-1H-pyrazol-1-yl}cyclobutanecarbonitrile | LCMS m/z = 381 [M + H]+ |
| 21 | cis-3-(cyanomethyl)-3-{3-[7-(1H-pyrazol-5-yl)-1,6-naphthyridin-5-yl]-1H-pyrazol-1-yl}cyclobutanecarbonitrile | LCMS m/z = 381 [M + H]+ |
| 22 | 2,2'-(trans-1-{3-[7-(1H-pyrazol-5-yl)-1,6-naphthyridin-5-yl]-1H-pyrazol-1-yl}cyclobutane-1,3-diyl)diacetonitrile | LCMS m/z = 395 [M + H]+ |
| 23 | 2,2'-(cis-1-{3-[7-(1H-pyrazol-5-yl)-1,6-naphthyridin-5-yl]-1H-pyrazol-1-yl}cyclobutane-1,3-diyl)diacetonitrile | LCMS m/z = 395 [M + H]+ |
| 24 | cis-3-(cyanomethyl)-3-{3-[7-(1H-pyrazol-5-yl)-1,6-naphthyridin-5-yl]-1H-pyrazol-1-yl}cyclobutanecarboxamide | LCMS m/z = 399 [M + H]+ |
| 25 | trans-3-(cyanomethyl)-3-{3-[7-(1H-pyrazol-5-yl)-1,6-naphthyridin-5-yl]-1H-pyrazol-1-yl}cyclobutanecarboxamide | LCMS m/z = 399 [M + H]+ |
| 26 | cis-3-(cyanomethyl)-N-methyl-3-{3-[7-(1H-pyrazol-3-yl)-1,6-naphthyridin-5-yl]-1H-pyrazol-1-yl}cyclobutanecarboxamide | LCMS m/z = 413 [M + H]+ |
| 27 | trans-3-(cyanomethyl)-N-methyl-3-{3-[7-(1H-pyrazol-5-yl)-1,6-naphthyridin-5-yl]-1H-pyrazol-1-yl}cyclobutanecarboxamide | LCMS m/z = 413 [M + H]+ |
| 28 | [trans-3-(hydroxymethyl)-1-{3-[7-(1H-pyrazol-5-yl)-1,6-naphthyridin-5-yl]-pyrazol-1-yl}cyclobutyl]acetonitrile | LCMS m/z = 386 [M + H]+ |
| 29 | [cis-3-(hydroxymethyl)-1-{3-[7-(1H-pyrazol-5-yl)-1,6-naphthyridin-5-yl]-1H-pyrazol-1-yl}cyclobutyl]acetonitrile | LCMS m/z = 386 [M + H]+ |
| 30 | (trans-3-methoxy-1-{3-[7-(1H-pyrazol-5-yl)-1,6-naphthyridin-5-yl]-1H-pyrazol-1-yl}cyclobutyl)acetonitrile | LCMS m/z = 386 [M + H]+ |
| 31 | (cis-3-methoxy-1-{3-[7-(1H-pyrazol-5-yl)-1,6-naphthyridin-5-yl]-1H-pyrazol-1-yl}cyclobutyl)acetonitrile | LCMS m/z = 386 [M + H]+ |
| 32 | N-[trans-3-(cyanomethyl)-3-{3-[7-(1H-pyrazol-3-yl)-1,6-naphthyridin-5-yl]-pyrazol-1-yl}cyclobutyl]acetamide | LCMS m/z = 435 [M + H]+ |
| 33 | N-[trans-3-(cyanomethyl)-3-{3-[7-(1H-pyrazol-3-yl)-1,6-naphthyridin-5-yl]-pyrazol-1-yl}cyclobutyl]-N-methylacetamide | LCMS m/z = 427 [M + H]+ |
| 34 | N-[cis-3-(cyanomethyl)-3-{3-[7-(1H-pyrazol-3-yl)-1,6-naphthyridin-5-yl]-pyrazol-1-yl}cyclobutyl]-N-methylacetamide | LCMS m/z = 427 [M + H]+ |
| 35 | cis-3-(cyanomethyl)-1-methyl-3-{3-[7-(1H-pyrazol-3-yl)-1,6-naphthyridin-5-yl]-1H-pyrazol-1-yl}cyclobutanecarbonitrile | LCMS m/z = 395 [M + H]+ |
| 36 | trans-3-(cyanomethyl)-1-methyl-3-{3-[7-(1H-pyrazol-3-yl)-1,6-naphthyridin-5-yl]-1H-pyrazol-1-yl}cyclobutanecarbonitrile | LCMS m/z = 395 [M + H]+ |
| 37 | (6-{3-[7-(1H-pyrazol-3-yl)-1,6-naphthyridin-5-yl]-1H-pyrazol-1-yl}-2-oxaspiro[3.3]hept-6-yl)acetonitrile | LCMS m/z = 398 [M + H]+ |
| 38 | (2-acetyl-6-{3-[7-(1H-pyrazol-3-yl)-1,6-naphthyridin-5-yl]-1H-pyrazol-1-yl}-2-azaspiro[3.3]hept-6-yl)acetonitrile | LCMS m/z = 439 [M + H]+ |
| 39 | [trans-3-(2-hydroxypropan-2-yl)-1-{3-[7-(1H-pyrazol-3-yl)-1,6-naphthyridin-5-yl]-1H-pyrazol-1-yl}cyclobutyl]acetonitrile | LCMS m/z = 436 [M + H]+ |

| Ex. | Name | Data |
|---|---|---|
| 40 | [cis-3-(2-hydroxypropan-2-yl)-1-{3-[7-(1H-pyrazol-3-yl)-1,6-naphthyridin-5-yl]-1H-pyrazol-1-yl}cyclobutyl]acetonitrile | LCMS m/z = 436 [M + H]$^+$ |
| 41 | trans-3-{3-[7-(5-amino-1H-pyrazol-3-yl)-1,6-naphthyridin-5-yl]-1H-pyrazol-1-yl}-3-(cyanomethyl)cyclobutanecarbonitrile | LCMS m/z = 396 [M + H]$^+$ |
| 42 | [3-{3-[7-(5-methyl-1H-pyrazol-3-yl)-1,6-naphthyridin-5-yl]-1H-pyrazol-1-yl}-1-(2,2,2-trifluoroethyl)azetidin-3-yl]acetonitrile | LCMS m/z = 453 [M + H]$^+$ |
| 43 | trans-3-(cyanomethyl)-3-{3-[7-(5-methyl-1H-pyrazol-3-yl)-1,6-naphthyridin-5-yl]-1H-pyrazol-1-yl}cyclobutanecarbonitrile | LCMS m/z = 395 [M + H]$^+$ |
| 44 | cis-3-(cyanomethyl)-3-{3-[7-(5-methyl-1H-pyrazol-3-yl)-1,6-naphthyridin-5-yl]-1H-pyrazol-1-yl}cyclobutanecarbonitrile | LCMS m/z = 395 [M + H]$^+$ |
| 45 | cis-3-(cyanomethyl)-1-methyl-3-{3-[7-(5-methyl-1H-pyrazol-3-yl)-1,6-naphthyridin-5-yl]-1H-pyrazol-1-yl}cyclobutanecarbonitrile | LCMS m/z = 409 [M + H]$^+$ |
| 46 | trans-3-(cyanomethyl)-1-methyl-3-{3-[7-(5-methyl-1H-pyrazol-3-yl)-1,6-naphthyridin-5-yl]-1H-pyrazol-1-yl}cyclobutanecarbonitrile | LCMS m/z = 431 [M + H]$^+$ |
| 47 | [1-ethyl-3-(3-{7-[5-(hydroxymethyl)-1H-pyrazol-3-yl]-1,6-naphthyridin-5-yl}-1H-pyrazol-1-yl)azetidin-3-yl]acetonitrile | LCMS m/z = 437 [M + H]$^+$ |
| 48 | trans-3-(cyanomethyl)-3-(3-{7-[5-(hydroxymethyl)-1H-pyrazol-3-yl]-1,6-naphthyridin-5-yl}-1H-pyrazol-1-yl)cyclobutanecarbonitrile | LCMS m/z = 411 [M + H]$^+$ |
| 49 | cis-3-(cyanomethyl)-3-(3-{7-[5-(hydroxymethyl)-1H-pyrazol-3-yl]-1,6-naphthyridin-5-yl}-1H-pyrazol-1-yl)cyclobutanecarbonitrile | LCMS m/z = 411 [M + H]$^+$ |
| 50 | [trans-1-(3-{7-[3-(hydroxymethyl)-1H-pyrazol-5-yl]-1,6-naphthyridin-5-yl}-1H-pyrazol-1-yl)-3-methoxycyclobutyl]acetonitrile | LCMS m/z = 416 [M + H]$^+$ |
| 51 | [cis-1-(3-{7-[3-(hydroxymethyl)-1H-pyrazol-5-yl]-1,6-naphthyridin-5-yl}-1H-pyrazol-1-yl)-3-methoxycyclobutyl]acetonitrile | LCMS m/z = 416 [M + H]$^+$ |
| 52 | (cis-1-{3-[7-(5-amino-1H-pyrazol-3-yl)-1,6-naphthyridin-5-yl]-1H-pyrazol-1-yl}-3-methoxycyclobutyl)acetonitrile | LCMS m/z = 401 [M + H]$^+$ |
| 53 | (trans-1-{3-[7-(5-amino-1H-pyrazol-3-yl)-1,6-naphthyridin-5-yl]-1H-pyrazol-1-yl}-3-methoxycyclobutyl)acetonitrile | LCMS m/z = 401 [M + H]$^+$ |
| 54 | [3-{3-[7-(1-methyl-1H-pyrazol-5-yl)-1,6-naphthyridin-5-yl]-1H-pyrazol-1-yl}-1-(2,2,2-trifluoroethyl)azetidin-3-yl]acetonitrile | LCMS m/z = 475 [M + H]$^+$ |
| 55 | [3-{3-[7-(1-methyl-1H-pyrazol-3-yl)-1,6-naphthyridin-5-yl]-1H-pyrazol-1-yl}-1-(2,2,2-trifluoroethyl)azetidin-3-yl]acetonitrile | LCMS m/z = 453 [M + H]$^+$ |
| 56 | [1-(methylsulfonyl)-3-(3-{7-[1-(oxetan-3-yl)-1H-pyrazol-3-yl]-1,6-naphthyridin-5-yl}-1H-pyrazol-1-yl)azetidin-3-yl]acetonitrile | LCMS m/z = 491 [M + H]$^+$ |
| 57 | [3-(3-{7-[1-(oxetan-3-yl)-1H-pyrazol-3-yl]-1,6-naphthyridin-5-yl}-1H-pyrazol-1-yl)-1-(2,2,2-trifluoroethyl)azetidin-3-yl]acetonitrile | LCMS m/z = 495 [M + H]$^+$ |
| 58 | trans-3-(cyanomethyl)-3-{3-[7-(1,5-dimethyl-1H-pyrazol-3-yl)-1,6-naphthyridin-5-yl]-1H-pyrazol-1-yl}cyclobutanecarbonitrile | LCMS m/z = 409 [M + H]$^+$ |
| 59 | cis-3-(cyanomethyl)-3-{3-[7-(1,5-dimethyl-1H-pyrazol-3-yl)-1,6-naphthyridin-5-yl]-1H-pyrazol-1-yl}cyclobutanecarbonitrile | LCMS m/z = 409 [M + H]$^+$ |
| 60 | trans-3-(cyanomethyl)-3-(3-{7-[3-(hydroxymethyl)-1-methyl-1H-pyrazol-5-yl]-1,6-naphthyridin-5-yl}-1H-pyrazol-1-yl)cyclobutanecarbonitrile | LCMS m/z = 425 [M + H]$^+$ |
| 61 | cis-3-(cyanomethyl)-3-(3-{7-[3-(hydroxymethyl)-1-methyl-1H-pyrazol-5-yl]-1,6-naphthyridin-5-yl}-1H-pyrazol-1-yl)cyclobutanecarbonitrile | LCMS m/z = 425 [M + H]$^+$ |
| 62 | trans-3-(cyanomethyl)-3-(3-{7-[5-(hydroxymethyl)-1-methyl-1H-pyrazol-3-yl]-1,6-naphthyridin-5-yl}-1H-pyrazol-1-yl)cyclobutanecarbonitrile | LCMS m/z = 425 [M + H]$^+$ |
| 63 | cis-3-(cyanomethyl)-3-(3-{7-[5-(hydroxymethyl)-1-methyl-1H-pyrazol-3-yl]-1,6-naphthyridin-5-yl}-1H-pyrazol-1-yl)cyclobutanecarbonitrile | LCMS m/z = 425 [M + H]$^+$ |
| 64 | (3-{3-[7-(5-amino-1-methyl-1H-pyrazol-3-yl)-1,6-naphthyridin-5-yl]-1H-pyrazol-1-yl}-1-ethylazetidin-3-yl)acetonitrile | LCMS m/z = 414 [M + H]$^+$ |
| 65 | trans-3-{3-[7-(5-amino-1-methyl-1H-pyrazol-3-yl)-1,6-naphthyridin-5-yl]-1H-pyrazol-1-yl}-3-(cyanomethyl)cyclobutanecarbonitrile | LCMS m/z = 410 [M + H]$^+$ |
| 66 | cis-3-{3-[7-(5-amino-1-methyl-1H-pyrazol-3-yl)-1,6-naphthyridin-5-yl]-1H-pyrazol-1-yl}-3-(cyanomethyl)cyclobutanecarbonitrile | LCMS m/z = 410 [M + H]$^+$ |
| 67 | cis-3-{3-[7-(5-amino-1-methyl-1H-pyrazol-3-yl)-1,6-naphthyridin-5-yl]-1H-pyrazol-1-yl}-3-(cyanomethyl)-1-methylcyclobutanecarbonitrile | LCMS m/z = 424 [M + H]$^+$ |
| 68 | trans-3-{3-[7-(5-amino-1-methyl-1H-pyrazol-3-yl)-1,6-naphthyridin-5-yl]-1H-pyrazol-1-yl}-3-(cyanomethyl)-1-methylcyclobutanecarbonitrile | LCMS m/z = 424 [M + H]$^+$ |
| 69 | cis-3-(cyanomethyl)-3-(3-{7-[1-methyl-5-(methylamino)-1H-pyrazol-3-yl]-,6-naphthyridin-5-yl}-1H-pyrazol-1-yl)cyclobutanecarbonitrile | LCMS m/z = 424 [M + H]$^+$ |
| 70 | trans-3-(cyanomethyl)-3-(3-{7-[1-methyl-5-(methylamino)-1H-pyrazol-3-yl]-1,6-naphthyridin-5-yl}-1H-pyrazol-1-yl)cyclobutanecarbonitrile | LCMS m/z = 446 [M + Na]$^+$ |
| 71 | trans-3-(3-{7-[5-(aminomethyl)-1-methyl-1H-pyrazol-3-yl]-1,6-naphthyridin-5-yl}-1H-pyrazol-1-yl)-3-(cyanomethyl)cyclobutanecarbonitrile | LCMS m/z = 446 [M + Na]$^+$ |
| 72 | cis-3-(cyanomethyl)-3-{3-[7-(4,5,6,7-tetrahydropyrazolo[1,5-a]pyrazin-2-yl)-1,6-naphthyridin-5-yl]-1H-pyrazol-1-yl}cyclobutanecarbonitrile | LCMS m/z = 436 [M + H]$^+$ |
| 73 | trans-3-(cyanomethyl)-3-{3-[7-(4,5,6,7-tetrahydropyrazolo[1,5-a]pyrazin-2-yl)-1,6-naphthyridin-5-yl]-1H-pyrazol-1-yl}cyclobutanecarbonitrile | LCMS m/z = 436 [M + H]$^+$ |
| 74 | [3-{3-[7-(1H-pyrazol-4-yl)-1,6-naphthyridin-5-yl]-1H-pyrazol-1-yl}-1-(2,2,2-trifluoroethyl)azetidin-3-yl]acetonitrile | LCMS m/z = 439 [M + H]$^+$ |
| 75 | [1-(methylsulfonyl)-3-{3-[7-(1H-pyrazol-4-yl)-1,6-naphthyridin-5-yl]-1H-pyrazol-1-yl}azetidin-3-yl]acetonitrile | LCMS m/z = 435 [M + H]$^+$ |
| 76 | cis-3-(cyanomethyl)-3-{3-[7-(1H-pyrazol-4-yl)-1,6-naphthyridin-5-yl]-1H-pyrazol-1-yl}cyclobutanecarbonitrile | LCMS m/z = 381 [M + H]$^+$ |

| Ex. | Name | Data |
|---|---|---|
| 77 | trans-3-(cyanomethyl)-3-{3-[7-(1H-pyrazol-4-yl)-1,6-naphthyridin-5-yl]-1H-pyrazol-1-yl}cyclobutanecarbonitrile | LCMS m/z = 381 [M + H]+ |
| 78 | 2,2'-(cis-1-{3-[7-(1H-pyrazol-4-yl)-1,6-naphthyridin-5-yl]-1H-pyrazol-1-yl}cyclobutane-1,3-diyl)diacetonitrile | LCMS m/z = 395 [M + H]+ |
| 79 | 2,2'-(trans-1-{3-[7-(1H-pyrazol-4-yl)-1,6-naphthyridin-5-yl]-1H-pyrazol-1-yl}cyclobutane-1,3-diyl)diacetonitrile | LCMS m/z = 395 [M + H]+ |
| 80 | (cis-3-methoxy-1-{3-[7-(1H-pyrazol-4-yl)-1,6-naphthyridin-5-yl]-1H-pyrazol-1-yl}cyclobutyl)acetonitrile | LCMS m/z = 386 [M + H]+ |
| 81 | (trans-3-methoxy-1-{3-[7-(1H-pyrazol-4-yl)-1,6-naphthyridin-5-yl]-1H-pyrazol-1-yl}cyclobutyl)acetonitrile | LCMS m/z = 386 [M + H]+ |
| 82 | [cis-3-(2-hydroxpropan-2-yl)-1-{3-[7-(1H-pyrazol-4-yl)-1,6-naphthyridin-5-yl]-1H-pyrazol-1-yl}cyclobutyl]acetonitrile | LCMS m/z = 414 [M + H]+ |
| 83 | trans-3-(cyanomethyl)-1-methyl-3-{3-[7-(1H-pyrazol-4-yl)-1,6-naphthyridin-5-yl]-1H-pyrazol-1-yl}cyclobutanecarbonitrile | LCMS m/z = 395 [M + H]+ |
| 84 | cis-3-(cyanomethyl)-1-methyl-3-{3-[7-(1H-pyrazol-4-yl)-1,6-naphthyridin-5-yl]-1H-pyrazol-1-yl}cyclobutanecarbonitrile | LCMS m/z = 395 [M + H]+ |
| 85 | [cis-3-(1H-pyrazol-5-yl)-1-{3-[7-(1H-pyrazol-4-yl)-1,6-naphthyridin-5-yl]-1H-pyrazol-1-yl}cyclobutyl]acetonitrile | LCMS m/z = 422 [M + H]+ |
| 86 | [cis-3-(1-methyl-1H-pyrazol-5-yl)-1-{3-[7-(1H-pyrazol-4-yl)-1,6-naphthyridin-5-yl]-1H-pyrazol-1-yl}cyclobutyl]acetonitrile | LCMS m/z = 436 [M + H]+ |
| 87 | [trans-3-(1-methyl-1H-pyrazol3-[7-(1H-pyrazol-4-yl)-1,6-naphthyridin-5-yl]-1H-pyrazol-1-yl}cyclobutyl]acetonitrile | LCMS m/z = 436 [M + H]+ |
| 88 | [3-{3-[7-(3-methyl-1H-pyrazol-4-yl)-1,6-naphthyridin-5-yl]-1H-pyrazol-1-yl}-1-(methylsulfonyl)azetidin-3-yl]acetonitrile | LCMS m/z = 449 [M + H]+ |
| 89 | trans-3-(cyanomethyl)-3-{3-[7-(3-methyl-1H-pyrazol-4-yl)-1,6-naphthyridin-5-yl]-1H-pyrazol-1-yl}cyclobutanecarbonitrile | LCMS m/z = 395 [M + H]+ |
| 90 | cis-3-(cyanomethyl)-3-{3-[7-(3-methyl-1H-pyrazol-4-yl)-1,6-naphthyridin-5-yl]-1H-pyrazol-1-yl}cyclobutanecarbonitrile | LCMS m/z = 395 [M + H]+ |
| 91 | trans-3-(cyanomethyl)-3-(3-{7-[5-(hydroxymethyl)-1H-pyrazol-4-yl]-1,6-naphthyridin-5-yl}-1H-pyrazol-1-yl)cyclobutanecarbonitrile | LCMS m/z = 411 [M + H]+ |
| 92 | cis-3-(cyanomethyl)-3-(3-{7-[5-(hydroxymethyl)-1H-pyrazol-4-yl]-1,6-naphthyridin-5-yl}-1H-pyrazol-1-yl)cyclobutanecarbonitrile | LCMS m/z = 411 [M + H]+ |
| 93 | [3-{3-[7-(3-amino-1H-pyrazol-4-yl)-1,6-naphthyridin-5-yl]-1H-pyrazol-1-yl}-1-(methylsulfonyl)azetidin-3-yl]acetonitrile | LCMS m/z = 450 [M + H]+ |
| 94 | (3-{3-[7-(3-amino-1H-pyrazol-4-yl)-1,6-naphthyridin-5-yl]-1H-pyrazol-1-yl}-1-ethylazetidin-3-yl)acetonitrile | LCMS m/z = 400 [M + H]+ |
| 95 | (trans-1-{3-[7-(3-amino-1H-pyrazol-4-yl)-1,6-naphthyridin-5-yl]-1H-pyrazol-1-yl}-3-methoxycyclobutyl)acetonitrile | LCMS m/z = 401 [M + H]+ |
| 96 | (cis-1-{3-[7-(3-amino-1H-pyrazol-4-yl)-1,6-naphthyridin-5-yl]-1H-pyrazol-1-yl}-3-methoxycyclobutyl)acetonitrile | LCMS m/z = 401 [M + H]+ |
| 97 | cis-3-{3-[7-(3-amino-1H-pyrazol-4-yl)-1,6-naphthyridin-5-yl]-1H-pyrazol-1-yl}-3-(cyanomethyl)cyclobutanecarbonitrile | LCMS m/z = 396 [M + H]+ |
| 98 | trans-3-{3-[7-(3-amino-1H-pyrazol-4-yl)-1,6-naphthyridin-5-yl]-1H-pyrazol-1-yl}-3-(cyanomethyl)cyclobutanecarbonitrile | LCMS m/z = 396 [M + H]+ |
| 99 | [3-{3-[7-(1-methyl-1H-pyrazol-4-yl)-1,6-naphthyridin-5-yl]-1H-pyrazol-1-yl}-1-(2,2,2-trifluoroethyl)azetidin-3-yl]acetonitrile | LCMS m/z = 454 [M + H]+ |
| 100 | 2,2'-(3-{3-[7-(1-methyl-1H-pyrazol-4-yl)-1,6-naphthyridin-5-yl]-1H-pyrazol-1-yl}azetidine-1,3-diyl)diacetonitrile | LCMS m/z = 410 [M + H]+ |
| 101 | [1-(cyclopropylmethyl)-3-{3-[7-(1-methyl-1H-pyrazol-4-yl)-1,6-naphthyridin-5-yl]-1H-pyrazol-1-yl}azetidin-3-yl]acetonitrile | LCMS m/z = 425 [M + H]+ |
| 102 | trans-3-(cyanomethyl)-3-{3-[7-(1-methyl-1H-pyrazol-4-yl)-1,6-naphthyridin-5-yl]-1H-pyrazol-1-yl}cyclobutanecarbonitrile | LCMS m/z = 395 [M + H]+ |
| 103 | cis-3-(cyanomethyl)-3-{3-[7-(1-methyl-1H-pyrazol-4-yl)-1,6-naphthyridin-5-yl]-1H-pyrazol-1-yl}cyclobutanecarbonitrile | LCMS m/z = 395 [M + H]+ |
| 104 | [3-{3-[7-(1-methyl-1H-pyrazol-4-yl)-1,6-naphthyridin-5-yl]-1H-pyrazol-1-yl}-1-(methylsulfonyl)azetidin-3-yl]acetonitrile | LCMS m/z = 449 [M + H]+ |
| 105 | [1-(ethylsulfonyl)-3-{3-[7-(1-methyl-1H-pyrazol-4-yl)-1,6-naphthyridin-5-yl]-1H-pyrazol-1-yl}azetidin-3-yl]acetonitrile | LCMS m/z = 463 [M + H]+ |
| 106 | [3-{3-[7-(1-methyl-1H-pyrazol-4-yl)-1,6-naphthyridin-5-yl]-1H-pyrazol-1-yl}-1-(propylsulfonyl)azetidin-3-yl]acetonitrile | LCMS m/z = 477 [M + H]+ |
| 107 | [1-(cyclopropylsulfonyl)-3-{3-[7-(1-methyl-1H-pyrazol-4-yl)-1,6-naphthyridin-5-yl]-1H-pyrazol-1-yl}azetidin-3-yl]acetonitrile | LCMS m/z = 475 [M + H]+ |
| 108 | 3-(cyanomethyl)-3-{3-[7-(1-methyl-1H-pyrazol-4-yl)-1,6-naphthyridin-5-yl]-1H-pyrazol-1-yl}azetidine-1-sulfonamide | LCMS m/z = 450 [M + H]+ |
| 109 | 3-(cyanomethyl)-N-methyl-3-{3-[7-(1-methyl-1H-pyrazol-4-yl)-1,6-naphthyridin-5-yl]-1H-pyrazol-1-yl}azetidine-1-sulfonamide | LCMS m/z = 464 [M + H]+ |
| 110 | (cis-3-methoxy-1-{3-[7-(1-methyl-1H-pyrazol-4-yl)-1,6-naphthyridin-5-yl]-1H-pyrazol-1-yl}cyclobutyl)acetonitrile | LCMS m/z = 400 [M + H]+ |
| 111 | [3-{3-[7-(1-ethyl-1H-pyrazol-4-yl)-1,6-naphthyridin-5-yl]-1H-pyrazol-1-yl}-1-(2,2,2-trifluoroethyl)azetidin-3-yl]acetonitrile | LCMS m/z = 489 [M + Na]+ |
| 112 | cis-3-(cyanomethyl)-3-{3-[7-(1-ethyl-1H-pyrazol-4-yl)-1,6-naphthyridin-5-yl]-1H-pyrazol-1-yl}cyclobutanecarbonitrile | LCMS m/z = 409 [M + H]+ |
| 113 | trans-3-(cyanomethyl)-3-{3-[7-(1-ethyl-1H-pyrazol-4-yl)-1,6-naphthyridin-5-yl]-1H-pyrazol-1-yl}cyclobutanecarbonitrile | LCMS m/z = 409 [M + H]+ |
| 114 | cis-3-(cyanomethyl)-3-[3-(7-{1-[2-(dimethylamino)ethyl]-1H-pyrazol-4-yl}-1,6-naphthyridin-5-yl)-1H-pyrazol-1-yl]cyclobutanecarbonitrile | LCMS m/z = 474 [M + Na]+ |

| Ex. | Name | Data |
|---|---|---|
| 115 | [3-(3-{7-[1-(azetidin-3-yl)-1H-pyrazol-4-yl]-1,6-naphthyridin-5-yl}-1H-pyrazol-1-yl)-1-(2,2,2-trifluoroethyl)azetidin-3-yl]acetonitrile | LCMS m/z = 494 [M + H]+ |
| 116 | [3-(3-{7-[1-(piperidin-4-yl)-1H-pyrazol-4-yl]-1,6-naphthyridin-5-yl}-1H-pyrazol-1-yl)-1-(2,2,2-trifluoroethyl)azetidin-3-yl]acetonitrile | LCMS m/z = 522 [M + H]+ |
| 117 | [3-(3-{7-[1-(1-methylpiperidin-4-yl)-1H-pyrazol-4-yl]-1,6-naphthyridin-5-yl}-1H-pyrazol-1-yl)-1-(2,2,2-trifluoroethyl)azetidin-3-yl]acetonitrile | LCMS m/z = 536 [M + H]+ |
| 118 | [1-(methylsulfonyl)-3-(3-{7-[1-(trifluoromethyl)-1H-pyrazol-4-yl]-1,6-naphthyridin-5-yl}-1H-pyrazol-1-yl)azetidin-3-yl]acetonitrile | LCMS m/z = 503 [M + H]+ |
| 119 | [3-(3-{7-[1-(oxetan-3-yl)-1H-pyrazol-4-yl]-1,6-naphthyridin-5-yl}-1H-pyrazol-1-yl)-1-(2,2,2-trifluoroethyl)azetidin-3-yl]acetonitrile | LCMS m/z = 495 [M + H]+ |
| 120 | 2,2'-[3-(3-{7-[1-(oxetan-3-yl)-1H-pyrazol-4-yl]-1,6-naphthyridin-5-yl}-1H-pyrazol-1-yl)azetidine-1,3-diyl]diacetonitrile | LCMS m/z = 452 [M + H]+ |
| 121 | [1-(methylsulfonyl)-3-(3-{7-[1-(oxetan-3-yl)-1H-pyrazol-4-yl]-1,6-naphthyridin-5-yl}-1H-pyrazol-1-yl)azetidin-3-yl]acetonitrile | LCMS m/z = 491 [M + H]+ |
| 122 | [cis-3-methoxy-1-(3-{7-[1-(oxetan-3-yl)-1H-pyrazol-4-yl]-1,6-naphthyridin-5-yl}-1H-pyrazol-1-yl)cyclobutyl]acetonitrile | LCMS m/z = 442 [M + H]+ |
| 123 | {1-(methylsulfonyl)-3-[3-(7-{1-[(3S)-tetrahydrofuran-3-yl]-1H-pyrazol-4-yl}-1,6-naphthyridin-5-yl)-1H-pyrazol-1-yl]azetidin-3-yl}acetonitrile | LCMS m/z = 505 [M + H]+ |
| 124 | {1-(methylsulfonyl)-3-[3-(7-{1-[(3R)-tetrahydrofuran-3-yl]-1H-pyrazol-4-yl}-1,6-naphthyridin-5-yl)-1H-pyrazol-1-yl]azetidin-3-yl}acetonitrile | LCMS m/z = 505 [M + H]+ |
| 125 | [3-(3-{7-[1-(2-hydroxyethyl)-1H-pyrazol-4-yl]-1,6-naphthyridin-5-yl}-1H-pyrazol-1-yl)-1-(methylsulfonyl)azetidin-3-yl]acetonitrile | LCMS m/z = 479 [M + H]+ |
| 126 | trans-3-(cyanomethyl)-3-(3-{7-[1-(2-hydroxyethyl)-1H-pyrazol-4-yl]-1,6-naphthyridin-5-yl}-1H-pyrazol-1-yl)cyclobutanecarbonitrile | LCMS m/z = 425 [M + H]+ |
| 127 | cis-3-(cyanomethyl)-3-(3-{7-[1-(2-hydroxyethyl)-1H-pyrazol-4-yl]-1,6-naphthyridin-5-yl}-1H-pyrazol-1-yl)cyclobutanecarbonitrile | LCMS m/z = 425 [M + H]+ |
| 128 | [cis-1-(3-{7-[1-(2-hydroxyethyl)-1H-pyrazol-4-yl]-1,6-naphthyridin-5-yl}-1H-pyrazol-1-yl)-3-methoxycyclobutyl]acetonitrile | LCMS m/z = 430 [M + H]+ |
| 129 | [trans-1-(3-{7-[1-(2-hydroxyethyl)-1H-pyrazol-4-yl]-1,6-naphthyridin-5-yl}-1H-pyrazol-1-yl)-3-methoxycyclobutyl]acetonitrile | LCMS m/z = 430 [M + H]+ |
| 130 | [3-(3-{7-[1-(1-chloro-3-hydroxypropan-2-yl)-1H-pyrazol-4-yl]-1,6-naphthyridin-5-yl}-1H-pyrazol-1-yl)-1-(methylsulfonyl)azetidin-3-yl]acetonitrile | LCMS m/z = 527 [M + H]+ |
| 131 | [3-(3-{7-[1-(3-hydroxyprop-1-en-2-yl)-1H-pyrazol-4-yl]-1,6-naphthyridin-5-yl}-1H-pyrazol-1-yl)-1-(methylsulfonyl)azetidin-3-yl]acetonitrile | LCMS m/z = 491 [M + H]+ |
| 132 | [1-(methylsulfonyl)-3-(3-{7-[1-(oxetan-3-ylmethyl)-1H-pyrazol-4-yl]-1,6-naphthyridin-5-yl}-1H-pyrazol-1-yl)azetidin-3-yl]acetonitrile | LCMS m/z = 505 [M + H]+ |
| 133 | {3-[3-(7-{1-[(3-hydroxyoxetan-3-yl)methyl]-1H-pyrazol-4-yl}-1,6-naphthyridin-5-yl)-1H-pyrazol-1-yl]-1-(methylsulfonyl)azetidin-3-yl}acetonitrile | LCMS m/z = 521 [M + H]+ |
| 134 | 4-(5-{1-[3-(cyanomethyl)-1-(methylsulfonyl)azetidin-3-yl]-1H-pyrazol-3-yl}-1,6-naphthyridin-7-yl)-1-methyl-1H-pyrazole-5-carboxamide | LCMS m/z = 492 [M + H]+ |
| 135 | trans-3-(cyanomethyl)-3-(3-{7-[3-(hydroxymethyl)-1-methyl-1H-pyrazol-4-yl]-1,6-naphthyridin-5-yl}-1H-pyrazol-1-yl)cyclobutanecarbonitrile | LCMS m/z = 447 [M + Na]+ |
| 136 | trans-3-(cyanomethyl)-3-(3-{7-[5-(hydroxymethyl)-1-methyl-1H-pyrazol-4-yl]-1,6-naphthyridin-5-yl}-1H-pyrazol-1-yl)cyclobutanecarbonitrile | LCMS m/z = 425 [M + H]+ |
| 137 | [3-{3-[7-(5-amino-1-methyl-1H-pyrazol-4-yl)-1,6-naphthyridin-5-yl]-1H-pyrazol-1-yl}-1-(methylsulfonyl)azetidin-3-yl]acetonitrile | LCMS m/z = 464 [M + H]+ |
| 138 | [3-{3-[7-(3-amino-1-methyl-1H-pyrazol-4-yl)-1,6-naphthyridin-5-yl]-1H-pyrazol-1-yl}-1-(methylsulfonyl)azetidin-3-yl]acetonitrile | LCMS m/z = 464 [M + H]+ |
| 139 | trans-3-{3-[7-(3-amino-1-methyl-1H-pyrazol-4-yl)-1,6-naphthyridin-5-yl]-1H-pyrazol-1-yl}-3-(cyanomethyl)cyclobutanecarbonitrile | LCMS m/z = 410 [M + H]+ |
| 140 | cis-3-{3-[7-(3-amino-1-methyl-1H-pyrazol-4-yl)-1,6-naphthyridin-5-yl]-1H-pyrazol-1-yl}-3-(cyanomethyl)cyclobutanecarbonitrile | LCMS m/z = 410 [M + H]+ |
| 141 | trans-3-{3-[7-(5-amino-1-methyl-1H-pyrazol-4-yl)-1,6-naphthyridin-5-yl]-1H-pyrazol-1-yl}-3-(cyanomethyl)cyclobutanecarbonitrile | LCMS m/z = 410 [M + H]+ |
| 142 | cis-3-{3-[7-(5-amino-1-methyl-1H-pyrazol-4-yl)-1,6-naphthyridin-5-yl]-1H-pyrazol-1-yl}-3-(cyanomethyl)cyclobutanecarbonitrile | LCMS m/z = 410 [M + H]+ |
| 143 | [3-{3-[7-(3-methyl-1H-pyrazol-1-yl)-1,6-naphthyridin-5-yl]-1H-pyrazol-1-yl}-1-(2,2,2-trifluoroethyl)azetidin-3-yl]acetonitrile | LCMS m/z = 453 [M + H]+ |
| 144 | [3-(3-{7-[1-(oxetan-3-yl)-1H-imidazol-4-yl]-1,6-naphthyridin-5-yl}-1H-pyrazol-1-yl)-1-(2,2,2-trifluoroethyl)azetidin-3-yl]acetonitrile | LCMS m/z = 495 [M + H]+ |
| 145 | [1-(methylsulfonyl)-3-{3-[7-(1,3-oxazol-5-yl)-1,6-naphthyridin-5-yl]-1H-pyrazol-1-yl}azetidin-3-yl]acetonitrile | LCMS m/z = 436 [M + H]+ |
| 146 | cis-3-(cyanomethyl)-3-(3-{7-[3-(hydroxymethyl)-1,2-oxazol-5-yl]-1,6-naphthyridin-5-yl}-1H-pyrazol-1-yl)cyclobutanecarbonitrile | LCMS m/z = 434 [M + Na]+ |
| 147 | [3-{3-[7-(3-amino-5-methyl-1,2-oxazol-4-yl)-1,6-naphthyridin-5-yl]-1H-pyrazol-1-yl}-1-(methylsulfonyl)azetidin-3-yl]acetonitrile | LCMS m/z = 465 [M + H]+ |
| 148 | [3-{3-[7-(1H-imidazol-2-yl)-1,6-naphthyridin-5-yl]-1H-pyrazol-1-yl}-1-(2,2,2-trifluoroethyl)azetidin-3-yl]acetonitrile | LCMS m/z = 440 [M + H]+ |
| 149 | [3-{3-[7-(1-methyl-1H-imidazol-4-yl)-1,6-naphthyridin-5-yl]-1H-pyrazol-1-yl}-1-(2,2,2-trifluoroethyl)azetidin-3-yl]acetonitrile | LCMS m/z = 453 [M + H]+ |
| 150 | [3-{3-[7-(2-methyl-1H-imidazol-4-yl)-1,6-naphthyridin-5-yl]-1H-pyrazol-1-yl}-1-(2,2,2-trifluoroethyl)azetidin-3-yl]acetonitrile | LCMS m/z = 453 [M + H]+ |
| 151 | [3-{3-[7-(1,2-dimethyl-1H-imidazol-4-yl)-1,6-naphthyridin-5-yl]-1H-pyrazol-1-yl}-1-(2,2,2-trifluoroethyl)azetidin-3-yl]acetonitrile | LCMS m/z = 467 [M + H]+ |
| 152 | [3-{3-[7-(1,2-dimethyl-1H-imidazol-5-yl)-1,6-naphthyridin-5-yl]-1H-pyrazol-1-yl}-1-(2,2,2-trifluoroethyl)azetidin-3-yl]acetonitrile | LCMS m/z = 467 [M + H]+ |

| Ex. | Name | Data |
|---|---|---|
| 153 | [3-{3-[7-(2H-1,2,3-triazol-4-yl)-1,6-naphthyridin-5-yl]-1H-pyrazol-1-yl}-1-(2,2,2-trifluoroethyl)azetidin-3-yl]acetonitrile | LCMS m/z = 440 [M + H]⁺ |
| 154 | [3-{3-[7-(2-methyl-2H-1,2,3-triazol-4-yl)-1,6-naphthyridin-5-yl]-1H-pyrazol-1-yl}-1-(2,2,2-trifluoroethyl)azetidin-3-yl]acetonitrile | LCMS m/z = 454 [M + H]⁺ |
| 155 | [3-(3-{7-[2-(tetrahydro-2H-pyran-2-yl)-2H-1,2,3-triazol-4-yl]-1,6-naphthyridin-5-yl}-1H-pyrazol-1-yl)-1-(2,2,2-trifluoroethyl)azetidin-3-yl]acetonitrile | LCMS m/z = 525 [M + H]⁺ |
| 156 | cis-3-(cyanomethyl)-3-(3-{7-[4-(hydroxymethyl)-1,3-thiazol-2-yl]-1,6-naphthyridin-5-yl}-1H-pyrazol-1-yl)cyclobutanecarbonitrile | LCMS m/z = 428 [M + H]⁺ |
| 157 | [1-(methylsulfonyl)-3-{3-[7-(7H-pyrrolo[2,3-b]pyridin-5-yl)-1,6-naphthyridin-5-yl]-1H-pyrazol-1-yl}azetidin-3-yl]acetonitrile | LCMS m/z = 485 [M + H]⁺ |
| 158 | [3-{3-[7-(1H-pyrrolo[3,2-b]pyridin-6-yl)-1,6-naphthyridin-5-yl]-1H-pyrazol-1-yl}-1-(2,2,2-trifluoroethyl)azetidin-3-yl]acetonitrile | LCMS m/z = 489 [M + H]⁺ |
| 159 | [1-(methylsulfonyl)-3-{3-[7-(1H-pyrrolo[2,3-b]pyridin-3-yl)-1,6-naphthyridin-5-yl]-1H-pyrazol-1-yl}azetidin-3-yl]acetonitrile | LCMS m/z = 485 [M + H]⁺ |
| 160 | [1-(methylsulfonyl)-3-{3-[7-(1H-pyrrolo[3,2-b]pyridin-3-yl)-1,6-naphthyridin-5-yl]-1H-pyrazol-1-yl}azetidin-3-yl]acetonitrile | LCMS m/z = 485 [M + H]⁺ |
| 161 | [1-(methylsulfonyl)-3-{3-[7-(pyrazolo[1,5-a]pyridin-3-yl)-1,6-naphthyridin-5-yl]-1H-pyrazol-1-yl}azetidin-3-yl]acetonitrile | LCMS m/z = 485 [M + H]⁺ |
| 162 | [3-{3-[7-(imidazo[1,2-a]pyridin-6-yl)-1,6-naphthyridin-5-yl]-1H-pyrazol-1-yl}-1-(methylsulfonyl)azetidin-3-yl]acetonitrile | LCMS m/z = 485 [M + H]⁺ |
| 163 | [3-{3-[7-(imidazo[1,2-a]pyridin-7-yl)-1,6-naphthyridin-5-yl]-1H-pyrazol-1-yl}-1-(methylsulfonyl)azetidin-3-yl]acetonitrile | LCMS m/z = 485 [M + H]⁺ |
| 164 | [3-{3-[7-(3-methyl-3H-imidazo[4,5-b]pyridin-6-yl)-1,6-naphthyridin-5-yl]-1H-pyrazol-1-yl}-1-(methylsulfonyl)azetidin-3-yl]acetonitrile | LCMS m/z = 500 [M + H]⁺ |
| 165 | [3-{3-[7-(imidazo[1,2-a]pyrimidin-6-yl)-1,6-naphthyridin-5-yl]-1H-pyrazol-1-yl}-1-(methylsulfonyl)azetidin-3-yl]acetonitrile | LCMS m/z = 486 [M + H]⁺ |
| 166 | [1-(methylsulfonyl)-3-{3-[7-(1H-pyrazolo[4,3-b]pyridin-6-yl)-1,6-naphthyridin-5-yl]-1H-pyrazol-1-yl}azetidin-3-yl]acetonitrile | LCMS m/z = 486 [M + H]⁺ |
| 167 | [3-{3-[7-([1,2,4]triazolo[4,3-a]pyridin-6-yl)-1,6-naphthyridin-5-yl]-1H-pyrazol-1-yl}-1-(2,2,2-trifluoroethyl)azetidin-3-yl]acetonitrile | LCMS m/z = 490 [M + H]⁺ |
| 168 | [1-(methylsulfonyl)-3-{3-[7-(pyrazolo[1,5-a]pyrimidin-3-yl)-1,6-naphthyridin-5-yl]-1H-pyrazol-1-yl}azetidin-3-yl]acetonitrile | LCMS m/z = 486 [M + H]⁺ |
| 169 | [1-(methylsulfonyl)-3-{3-[7-(2-oxo-2,3-dihydro-1H-imidazo[4,5-b]pyridin-6-yl)-1,6-naphthyridin-5-yl]-1H-pyrazol-1-yl}azetidin-3-yl]acetonitrile | LCMS m/z = 502 [M + H]⁺ |
| 170 | [1-(methylsulfonyl)-3-{3-[7-(1,2,3,4-tetrahydropyrido[2,3-b]pyrazin-7-yl)-1,6-naphthyridin-5-yl]-1H-pyrazol-1-yl}azetidin-3-yl]acetonitrile | LCMS m/z = 502 [M + H]⁺ |
| 171 | [3-{3-[7-(pyridin-3-yl)-1,6-naphthyridin-5-yl]-1H-pyrazol-1-yl}-1-(2,2,2-trifluoroethyl)azetidin-3-yl]acetonitrile | LCMS m/z = 450 [M + H]⁺ |
| 172 | [3-{3-[7-(pyridin-4-yl)-1,6-naphthyridin-5-yl]-1H-pyrazol-1-yl}-1-(2,2,2-trifluoroethyl)azetidin-3-yl]acetonitrile | LCMS m/z = 450 [M + H]⁺ |
| 173 | [3-{3-[7-(5-methylpyridin-3-yl)-1,6-naphthyridin-5-yl]-1H-pyrazol-1-yl}-1-(2,2,2-trifluoroethyl)azetidin-3-yl]acetonitrile | LCMS m/z = 486 [M + Na]⁺ |
| 174 | [3-{3-[7-(2-methylpyridin-4-yl)-1,6-naphthyridin-5-yl]-1H-pyrazol-1-yl}-1-(methylsulfonyl)azetidin-3-yl]acetonitrile | LCMS m/z = 460 [M + H]⁺ |
| 175 | [3-{3-[7-(6-methylpyridin-3-yl)-1,6-naphthyridin-5-yl]-1H-pyrazol-1-yl}-1-(methylsulfonyl)azetidin-3-yl]acetonitrile | LCMS m/z = 460 [M + H]⁺ |
| 176 | [3-{3-[7-(2-methylpyridin-4-yl)-1,6-naphthyridin-5-yl]-1H-pyrazol-1-yl}-1-(2,2,2-trifluoroethyl)azetidin-3-yl]acetonitrile | LCMS m/z = 464 [M + H]⁺ |
| 177 | [3-{3-[7-(6-methylpyridin-3-yl)-1,6-naphthyridin-5-yl]-1H-pyrazol-1-yl}-1-(2,2,2-trifluoroethyl)azetidin-3-yl]acetonitrile | LCMS m/z = 486 [M + Na]⁺ |
| 178 | [3-{3-[7-(5-fluoropyridin-3-yl)-1,6-naphthyridin-5-yl]-1H-pyrazol-1-yl}-1-(2,2,2-trifluoroethyl)azetidin-3-yl]acetonitrile | LCMS m/z = 490 [M + Na]⁺ |
| 179 | [3-{3-[7-(3-fluoropyridin-4-yl)-1,6-naphthyridin-5-yl]-1H-pyrazol-1-yl}-1-(2,2,2-trifluoroethyl)azetidin-3-yl]acetonitrile | LCMS m/z = 490 [M + Na]⁺ |
| 180 | [3-{3-[7-(6-hydroxypyridin-2-yl)-1,6-naphthyridin-5-yl]-1H-pyrazol-1-yl}-1-(methylsulfonyl)azetidin-3-yl]acetonitrile | LCMS m/z = 462 [M + H]+ |
| 181 | cis-3-(cyanomethyl)-3-{3-[7-(6-hydroxypyridin-2-yl)-1,6-naphthyridin-5-yl]-1H-pyrazol-1-yl}cyclobutanecarbonitrile | LCMS m/z = 430 M + Na]⁺ |
| 182 | trans-3-(cyanomethyl)-3-{3-[7-(6-hydroxypyridin-2-yl)-1,6-naphthyridin-5-yl]-1H-pyrazol-1-yl}cyclobutanecarbonitrile | LCMS m/z = 430 M + Na]⁺ |
| 183 | [3-{3-[7-(6-hydroxypyridin-3-yl)-1,6-naphthyridin-5-yl]-1H-pyrazol-1-yl}-1-(2,2,2-trifluoroethyl)azetidin-3-yl]acetonitrile | LCMS m/z = 466 [M + H]⁺ |
| 184 | (1-ethyl-3-{3-[7-(6-hydroxypyridin-3-yl)-1,6-naphthyridin-5-yl]-1H-pyrazol-1-yl}azetidin-3-yl)acetonitrile | LCMS m/z = 412 [M + H]⁺ |
| 185 | [1-(3,3-difluorocyclobutyl)-3-{3-[7-(6-hydroxypyridin-3-yl)-1,6-naphthyridin-5-yl]-1H-pyrazol-1-yl}azetidin-3-yl]acetonitrile | LCMS m/z = 474 [M + H]⁺ |
| 186 | [3-{3-[7-(2-hydroxypyridin-4-yl)-1,6-naphthyridin-5-yl]-1H-pyrazol-1-yl}-1-(methylsulfonyl)azetidin-3-yl]acetonitrile | LCMS m/z = 462 [M + H]⁺ |
| 187 | [3-{3-[7-(2-methoxypyridin-3-yl)-1,6-naphthyridin-5-yl]-1H-pyrazol-1-yl}-1-(methylsulfonyl)azetidin-3-yl]acetonitrile | LCMS m/z = 476 [M + H]⁺ |
| 188 | [3-{3-[7-(6-methoxypyridin-3-yl)-1,6-naphthyridin-5-yl]-1H-pyrazol-1-yl}-1-(2,2,2-trifluoroethyl)azetidin-3-yl]acetonitrile | LCMS m/z = 480 [M + H]⁺ |
| 189 | [3-{3-[7-(2-methoxypyridin-4-yl)1,6-naphthyridin-5-yl]-1H-pyrazol-1-yl}-1-(methylsulfonyl)azetidin-3-yl]acetonitrile | LCMS m/z = 476 [M + H]⁺ |
| 190 | cis-3-{3-[7-(5-aminopyridin-2-yl)-1,6-naphthyridin-5-yl]-1H-pyrazol-1-yl}-3-(cyanomethyl)cyclobutanecarbonitrile | LCMS m/z = 407 [M + H]⁺ |

| Ex. | Name | Data |
|---|---|---|
| 191 | [3-{3-[7-(2-aminopyridin-3-yl)1,6-naphthyridin-5-yl]-1H-pyrazol-1-yl}-1-(methylsulfonyl)azetidin-3-yl]acetonitrile | LCMS m/z = 483 [M + Na]$^+$ |
| 192 | [3-{3-[7-(6-aminopyridin-3-yl)1,6-naphthyridin-5-yl]-1H-pyrazol-1-yl}-1-(2,2,2-trifluoroethyl)azetidin-3-yl]acetonitrile | LCMS m/z = 487 [M + Na]$^+$ |
| 193 | [3-{3-[7-(5-aminopyridin-3-yl)1,6-naphthyridin-5-yl]-1H-pyrazol-1-yl}-1-(methylsulfonyl)azetidin-3-yl]acetonitrile | LCMS m/z = 461 [M + H]$^+$ |
| 194 | [3-{3-[7-(6-aminopyridin-3-yl)1,6-naphthyridin-5-yl]-1H-pyrazol-1-yl}-1-(methylsulfonyl)azetidin-3-yl]acetonitrile | LCMS m/z = 461 [M + H]$^+$ |
| 195 | cis-3-{3-[7-(6-aminopyridin-3-yl)-1,6-naphthyridin-5-yl]-1H-pyrazol-1-yl}-3-(cyanomethyl)cyclobutanecarbonitrile | LCMS m/z = 407 [M + H]$^+$ |
| 196 | trans-3-{3-[7-(6-aminopyridin-3-yl)-1,6-naphthyridin-5-yl]-1H-pyrazol-1-yl}-3-(cyanomethyl)cyclobutanecarbonitrile | LCMS m/z = 407 [M + H]$^+$ |
| 197 | [3-{3-[7-(2-aminopyridin-4-yl)1,6-naphthyridin-5-yl]-1H-pyrazol-1-yl}-1-(2,2,2-trifluoroethyl)azetidin-3-yl]acetonitrile | LCMS m/z = 465 [M + H]$^+$ |
| 198 | cis-3-{3-[7-(2-aminopyridin-4-yl)-1,6-naphthyridin-5-yl]-1H-pyrazol-1-yl}-3-(cyanomethyl)cyclobutanecarbonitrile | LCMS m/z = 407 [M + H]$^+$ |
| 199 | trans-3-{3-[7-(2-aminopyridin-4-yl)-1,6-naphthyridin-5-yl]-1H-pyrazol-1-yl}-3-(cyanomethyl)cyclobutanecarbonitrile | LCMS m/z = 407 [M + H]$^+$ |
| 200 | trans-3-{3-[7-(2-aminopyridin-4-yl)-1,6-naphthyridin-5-yl]-1H-pyrazol-1-yl}-3-(cyanomethyl)-1-methylcyclobutanecarbonitrile | LCMS m/z = 421 [M + H]$^+$ |
| 201 | cis-3-{3-[7-(2-aminopyridin-4-yl)-1,6-naphthyridin-5-yl]-1H-pyrazol-1-yl}-3-(cyanomethyl)-1-methylcyclobutanecarbonitrile | LCMS m/z = 421 [M + H]$^+$ |
| 202 | ethyl [5-(5-{1-[3-(cyanomethyl)-1-(methylsulfonyl)azetidin-3-yl]-1H-pyrazol-3-yl}-1,6-naphthyridin-7-yl)pyridin-2-yl]carbamate | LCMS m/z = 533 [M + H]$^+$ |
| 203 | [3-(3-{7-[6-(dimethylamino)pyridin-3-yl]-1,6-naphthyridin-5-yl}-1H-pyrazol-1-yl)1-(methylsulfonyl)azetidin-3-yl]acetonitrile | LCMS m/z = 489 [M + H]$^+$ |
| 204 | N-[5-(5-{1-[3-(cyanomethyl)-1-(methylsulfonyl)azetidin-3-yl]-1H-pyrazol-3-yl}-1,6-naphthyridin-7-yl)pyridin-3-yl]methanesulfonamide | LCMS m/z = 539 [M + H]$^+$ |
| 205 | N-[5-(5-{1-[3-(cyanomethyl)-1-(methylsulfonyl)azetidin-3-yl]-1H-pyrazol-3-yl}-1,6-naphthyridin-7-yl)pyridin-2-yl]methanesulfonamide | LCMS m/z = 539 [M + H]$^+$ |
| 206 | [1-(methylsulfonyl)-3-(3-{7-[6-(methylsulfonyl)pyridin-3-yl]-1,6-naphthyridin-5-yl}-1H-pyrazol-1-yl)azetidin-3-yl]acetonitrile | LCMS m/z = 524 [M + H]$^+$ |
| 207 | cis-3-(cyanomethyl)-3-(3-{7-[6-(methylsulfonyl)pyridin-3-yl]-1,6-naphthyridin-5-yl}-1H-pyrazol-1-yl)cyclobutanecarbonitrile | LCMS m/z = 492+M + Na |
| 208 | trans-3-(cyanomethyl)-3-(3-{7-[6-(methylsulfonyl)pyridin-3-yl]-1,6-naphthyridin-5-yl}-1H-pyrazol-1-yl)cyclobutanecarbonitrile | LCMS m/z = 492+M + Na |
| 209 | 5-(5-{1-[3-(cyanomethyl)-1-(methylsulfonyl)azetidin-3-yl]-1H-pyrazol-3-yl}-1,6-naphthyridin-7-yl)pyridine-2-sulfonamide | LCMS m/z = 525 [M + H]$^+$ |
| 210 | 5-(5-{1-[trans-3-cyano-1-(cyanomethyl)cyclobutyl]-1H-pyrazol-3-yl}-1,6-naphthyridin-7-yl)pyridine-2-sulfonamide | LCMS m/z = 471 [M + H]$^+$ |
| 211 | 5-(5-{1-[cis-3-cyano-1-(cyanomethyl)cyclobutyl]-1H-pyrazol-3-yl}-1,6-naphthyridin-7-yl)pyridine-2-sulfonamide | LCMS m/z = 471 [M + H]$^+$ |
| 212 | cis-3-(cyanomethyl)-3-(3-{7-[6-(hydroxymethyl)pyridin-2-yl]-1,6-naphthyridin-5-yl}-1H-pyrazol-1-yl)cyclobutanecarbonitrile | LCMS m/z = 444 [M + Na]$^+$ |
| 213 | cis-3-(cyanomethyl)-3-(3-{7-[2-(hydroxymethyl)pyridin-4-yl]-1,6-naphthyridin-5-yl}-1H-pyrazol-1-yl)cyclobutanecarbonitrile | LCMS m/z = 444 [M + Na]$^+$ |
| 214 | 6-(5-{1-[cis-3-cyano-1-(cyanomethyl)cyclobutyl]-1H-pyrazol-3-yl}-1,6-naphthyridin-7-yl)pyridine-2-carboxamide | LCMS m/z = 435 [M + H]$^+$ |
| 215 | 4-(5-{1-[3-(cyanomethyl)-1-(2,2,2-trifluoroethyl)azetidin-3-yl]-1H-pyrazol-3-yl}-1,6-naphthyridin-7-yl)pyridine-2-carboxamide | LCMS m/z = 493 [M + H]$^+$ |
| 216 | 4-(5-{1-[cis-3-cyano-1-(cyanomethyl)cyclobutyl]-1H-pyrazol-3-yl}-1,6-naphthyridin-7-yl)pyridine-2-carboxamide | LCMS m/z = 435 [M + H]$^+$ |
| 217 | [3-{3-[7-(5-amino-6-methylpyridin-3-yl)-1,6-naphthyridin-5-yl]-1H-pyrazol-1-yl}-1-(methylsulfonyl)azetidin-3-yl]acetonitrile | LCMS m/z = 475 [M + H]$^+$ |
| 218 | [3-{3-[7-(2-amino-6-methylpyridin-3-yl)-1,6-naphthyridin-5-yl]-1H-pyrazol-1-yl}-1-(methylsulfonyl)azetidin-3-yl]acetonitrile | LCMS m/z = 475 [M + H]$^+$ |
| 219 | [3-{3-[7-(6-amino-5-methylpyridin-3-yl)-1,6-naphthyridin-5-yl]-1H-pyrazol-1-yl}-1-(methylsulfonyl)azetidin-3-yl]acetonitrile | LCMS m/z = 475 [M + H]$^+$ |
| 220 | trans-3-{3-[7-(2-amino-6-methylpyridin-4-yl)-1,6-naphthyridin-5-yl]-1H-pyrazol-1-yl}-3-(cyanomethyl)cyclobutanecarbonitrile | LCMS m/z = 421 [M + H]$^+$ |
| 221 | cis-3-{3-[7-(2-amino-6-methylpyridin-4-yl)-1,6-naphthyridin-5-yl]-1H-pyrazol-1-yl}-3-(cyanomethyl)cyclobutanecarbonitrile | LCMS m/z = 421 [M + H]$^+$ |
| 222 | [3-{3-[7-(5-hydroxy-6-methylpyridin-3-yl)-1,6-naphthyridin-5-yl]-1H-pyrazol-1-yl}-1-(methylsulfonyl)azetidin-3-yl]acetonitrile | LCMS m/z = 476 [M + H]$^+$ |
| 223 | cis-3-{3-[7-(5-amino-6-methoxypyridin-2-yl)-1,6-naphthyridin-5-yl]-1H-pyrazol-1-yl}-3-(cyanomethyl)cyclobutanecarbonitrile | LCMS m/z = 437 [M + H]$^+$ |
| 224 | 3-amino-6-(5-{1-[cis-3-cyano-1-(cyanomethyl)cyclobutyl]-1H-pyrazol-3-yl}-1,6-naphthyridin-7-yl)pyridine-2-carboxamide | LCMS m/z = 472 [M + Na]$^+$ |
| 225 | 3-amino-6-(5-{1-[trans-3-cyano-1-(cyanomethyl)cyclobutyl]-1H-pyrazol-3-yl}-1,6-naphthyridin-7-yl)pyridine-2-carboxamide | LCMS m/z = 472 [M + Na]$^+$ |
| 226 | 6-(5-{1-[trans-3-cyano-1-(cyanomethyl)cyclobutyl]-1H-pyrazol-3-yl}-1,6-naphthyridin-7-yl)-3-hydroxypyridine-2-carboxamide | LCMS m/z = 473 [M + Na]$^+$ |
| 227 | 6-(5-{1-[cis-3-cyano-1-(cyanomethyl)cyclobutyl]-1H-pyrazol-3-yl}-1,6-naphthyridin-7-yl)-3-hydroxypyridine-2-carboxamide | LCMS m/z = 473 [M + Na]$^+$ |
| 228 | N-[5-(5-{1-[3-(cyanomethyl)-1-(methylsulfonyl)azetidin-3-yl]-1H-pyrazol-3-yl}-1,6-naphthyridin-7-yl)-2-methylpyridin-3-yl]acetamide | LCMS m/z = 517 [M + H]$^+$ |

| Ex. | Name | Data |
|---|---|---|
| 229 | [3-{3-[7-(5,6-diaminopyridin-3-yl)-1,6-naphthyridin-5-yl]-1H-pyrazol-1-yl}-1-(methylsulfonyl)azetidin-3-yl]acetonitrile | LCMS m/z = 476 [M + H]+ |
| 230 | [3-{3-[7-(2,6-diaminopyridin-3-yl)-1,6-naphthyridin-5-yl]-1H-pyrazol-1-yl}-1-(methylsulfonyl)azetidin-3-yl]acetonitrile | LCMS m/z = 476 [M + H]+ |
| 231 | N,N'-[5-(5-{1-[3-(cyanomethyl)-1-(methylsulfonyl)azetidin-3-yl]-1H-pyrazol-3-yl}-1,6-naphthyridin-7-yl)pyridine-2,3-diyl]diacetamide | LCMS m/z = 560 [M + H]+ |
| 232 | [3-{3-[7-(6,7-dihydro-5H-cyclopenta[b]pyridin-3-yl)-1,6-naphthyridin-5-yl]-1H-pyrazol-1-yl}-1-(2,2,2-trifluoroethyl)azetidin-3-yl]acetonitrile | LCMS m/z = 490 [M + H]+ |
| 233 | [3-{3-[7-(pyridazin-4-yl)-1,6-naphthyridin-5-yl]-1H-pyrazol-1-yl}-1-(2,2,2-trifluoroethyl)azetidin-3-yl]acetonitrile | LCMS m/z = 451 [M + H]+ |
| 234 | [3-{3-[7-(pyrimidin-5-yl)-1,6-naphthyridin-5-yl]-1H-pyrazol-1-yl}-1-(2,2,2-trifluoroethyl)azetidin-3-yl]acetonitrile | LCMS m/z = 473 [M + Na]+ |
| 235 | [1-(methylsulfonyl)-3-{3-[7-(pyrimidin-5-yl)-1,6-naphthyridin-5-yl]-1H-pyrazol-1-yl}azetidin-3-yl]acetonitrile | LCMS m/z = 447 [M + H]+ |
| 236 | [3-{3-[7-(2-methoxypyrimidin-5-yl)-1,6-naphthyridin-5-yl]-1H-pyrazol-1-yl}-1-(2,2,2-trifluoroethyl)azetidin-3-yl]acetonitrile | LCMS m/z = 481 [M + H]+ |
| 237 | [3-{3-[7-(2-methoxypyrimidin-5-yl)-1,6-naphthyridin-5-yl]-1H-pyrazol-1-yl}-1-(methylsulfonyl)azetidin-3-yl]acetonitrile | LCMS m/z = 477 [M + H]+ |
| 238 | [3-{3-[7-(2-aminopyrimidin-5-yl)-1,6-naphthyridin-5-yl]-1H-pyrazol-1-yl}-1-(methylsulfonyl)azetidin-3-yl]acetonitrile | LCMS m/z = 462 [M + H]+ |
| 239 | trans-3-{3-[7-(6-aminopyridazin-4-yl)-1,6-naphthyridin-5-yl]-1H-pyrazol-1-yl}-3-(cyanomethyl)cyclobutanecarbonitrile | LCMS m/z = 408 [M + H]+ |
| 240 | cis-3-{3-[7-(6-aminopyridazin-4-yl)-1,6-naphthyridin-5-yl]-1H-pyrazol-1-yl}-3-(cyanomethyl)cyclobutanecarbonitrile | LCMS m/z = 408 [M + H]+ |
| 241 | trans-3-{3-[7-(5-aminopyridazin-3-yl)-1,6-naphthyridin-5-yl]-1H-pyrazol-1-yl}-3-(cyanomethyl)cyclobutanecarbonitrile | LCMS m/z = 408 [M + H]+ |
| 242 | cis-3-{3-[7-(5-aminopyridazin-3-yl)-1,6-naphthyridin-5-yl]-1H-pyrazol-1-yl}-3-(cyanomethyl)cyclobutanecarbonitrile | LCMS m/z = 408 [M + H]+ |
| 243 | 4-(5-{1-[trans-3-cyano-1-(cyanomethyl)cyclobutyl]-1H-pyrazol-3-yl}-1,6-naphthyridin-7-yl)pyrimidine-2-carboxamide | LCMS m/z = 436 [M + H]+ |
| 244 | 4-(5-{1-[cis-3-cyano-1-(cyanomethyl)cyclobutyl]-1H-pyrazol-3-yl}-1,6-naphthyridin-7-yl)pyrimidine-2-carboxamide | LCMS m/z = 436 [M + H]+ |
| 245 | [1-(methylsulfonyl)-3-{3-[7-(6-oxo-1,6-dihydropyridin-3-yl)-1,6-naphthyridin-5-yl]-1H-pyrazol-1-yl}azetidin-3-yl]acetonitrile | LCMS m/z = 462 [M + H]+ |
| 246 | [1-(cyclopropylsulfonyl)-3-{3-[7-(6-oxo-1,6-dihydropyridin-3-yl)-1,6-naphthyridin-5-yl]-1H-pyrazol-1-yl}azetidin-3-yl]acetonitrile | LCMS m/z = 488 [M + H]+ |
| 247 | (cis-3-methoxy-1-{3-[7-(6-oxo-1,6-dihydropyridin-3-yl)-1,6-naphthyridin-5-yl]-1H-pyrazol-1-yl}cyclobutyl)acetonitrile | LCMS m/z = 413 [M + H]+ |
| 248 | [3-{3-[7-(1-methyl-6-oxo-1,6-dihydropyridin-3-yl)-1,6-naphthyridin-5-yl]-1H-pyrazol-1-yl}-1-(methylsulfonyl)azetidin-3-yl]acetonitrile | LCMS m/z = 476 [M + H]+ |
| 249 | [3-{3-[7-(1-methyl-6-oxo-1,6-dihydropyridin-3-yl)-1,6-naphthyridin-5-yl]-1H-pyrazol-1-yl}-1-(2,2,2-trifluoroethyl)azetidin-3-yl]acetonitrile | LCMS m/z = 480 [M + H]+ |
| 250 | [3-{3-[7-(5-methyl-6-oxo-1,6-dihydropyridin-3-yl)-1,6-naphthyridin-5-yl]-1H-pyrazol-1-yl}-1-(2,2,2-trifluoroethyl)azetidin-3-yl]acetonitrile | LCMS m/z = 480 [M + H]+ |
| 251 | [3-{3-[7-(1-ethyl-6-oxo-1,6-dihydropyridin-3-yl)-1,6-naphthyridin-5-yl]-1H-pyrazol-1-yl}-1-(methylsulfonyl)azetidin-3-yl]acetonitrile | LCMS m/z = 490 [M + H]+ |
| 252 | [3-{3-[7-(2-hydroxyphenyl)-1,6-naphthyridin-5-yl]-1H-pyrazol-1-yl}-1-(methylsulfonyl)azetidin-3-yl]acetonitrile | LCMS m/z = 461 [M + H]+ |
| 253 | [3-{3-[7-(3-hydroxyphenyl)-1,6-naphthyridin-5-yl]-1H-pyrazol-1-yl}-1-(methylsulfonyl)azetidin-3-yl]acetonitrile | LCMS m/z = 461 [M + H]+ |
| 254 | [3-{3-[7-(4-hydroxyphenyl)-1,6-naphthyridin-5-yl]-1H-pyrazol-1-yl}-1-(methylsulfonyl)azetidin-3-yl]acetonitrile | LCMS m/z = 461 [M + H]+ |
| 255 | [3-(3-{7-[2-(hydroxymethyl)phenyl]-1,6-naphthyridin-5-yl}-1H-pyrazol-1-yl)-1-(methylsulfonyl)azetidin-3-yl]acetonitrile | LCMS m/z = 475 [M + H]+ |
| 256 | N-[4-(5-{1-[cis-3-cyano-1-(cyanomethyl)cyclobutyl]-1H-pyrazol-3-yl}-1,6-naphthyridin-7-yl)phenyl]methanesulfonamide | LCMS m/z = 484 [M + H]+ |
| 257 | N-[4-(5-{1-[trans-3-cyano-1-(cyanomethyl)cyclobutyl]-1H-pyrazol-3-yl}-1,6-naphthyridin-7-yl)phenyl]methanesulfonamide | LCMS m/z = 484 [M + H]+ |
| 258 | [3-{3-[7-(2-fluorophenyl)-1,6-naphthyridin-5-yl]-1H-pyrazol-1-yl}-1-(methylsulfonyl)azetidin-3-yl]acetonitrile | LCMS m/z = 463 [M + H]+ |
| 259 | [3-{3-[7-(4-fluoro-2-hydroxyphenyl)-1,6-naphthyridin-5-yl]-1H-pyrazol-1-yl}-1-(methylsulfonyl)azetidin-3-yl]acetonitrile | LCMS m/z = 479 [M + H]+ |
| 260 | [3-{3-[7-(3-fluoro-4-hydroxyphenyl)-1,6-naphthyridin-5-yl]-1H-pyrazol-1-yl}-1-(methylsulfonyl)azetidin-3-yl]acetonitrile | LCMS m/z = 479 [M + H]+ |
| 261 | [3-{3-[7-(3-fluoro-5-hydroxyphenyl)-1,6-naphthyridin-5-yl]-1H-pyrazol-1-yl}-1-(methylsulfonyl)azetidin-3-yl]acetonitrile | LCMS m/z = 479 [M + H]+ |
| 262 | [3-{3-[7-(5-fluoro-2-hydroxyphenyl)-1,6-naphthyridin-5-yl]-1H-pyrazol-1-yl}-1-(methylsulfonyl)azetidin-3-yl]acetonitrile | LCMS m/z = 479 [M + H]+ |
| 263 | (3-{3-[7-(3,6-dihydro-2H-pyran-4-yl)-1,6-naphthyridin-5-yl]-1H-pyrazol-1-yl}-1-ethylazetidin-3-yl)acetonitrile | LCMS m/z = 401 [M + H]+ |
| 264 | (1-ethyl-3-{3-[7-(morpholin-4-yl)-1,6-naphthyridin-5-yl]-1H-pyrazol-1-yl}azetidin-3-yl)acetonitrile | LCMS m/z = 404 [M + H]+ |
| 265 | (1-ethyl-3-{3-[7-(pyrrolidin-1-yl)-1,6-naphthyridin-5-yl]-1H-pyrazol-1-yl}azetidin-3-yl)acetonitrile | LCMS m/z = 388 [M + H]+ |
| 266 | trans-3-(3-{7-[(6-aminopyridin-2-yl)oxy]-1,6-naphthyridin-5-yl}-1H-pyrazol-1-yl)-3-(cyanomethyl)cyclobutanecarbonitrile | LCMS m/z = 432 [M + H]+ |

-continued

| Ex. | Name | Data |
|---|---|---|
| 267 | [3-{5-methyl-3-[7-(1H-pyrazol-5-yl)-1,6-naphthyridin-5-yl]-1H-pyrazol-1-yl}-1-(methylsulfonyl)azetidin-3-yl]acetonitrile | LCMS m/z = 449 [M + H]⁺ |
| 268 | cis-3-(cyanomethyl)-3-{5-methyl-3-[7-(1H-pyrazol-3-yl)-1,6-naphthyridin-5-yl]-1H-pyrazol-1-yl}cyclobutanecarbonitrile | LCMS m/z = 395 [M + H]⁺ |
| 269 | trans-3-(cyanomethyl)-3-{5-methyl-3-[7-(1H-pyrazol-3-yl)-1,6-naphthyridin-5-yl]-1H-pyrazol-1-yl}cyclobutanecarbonitrile | LCMS m/z = 395 [M + H]⁺ |
| 270 | trans-3-{3-[7-(5-amino-1-methyl-1H-pyrazol-3-yl)-1,6-naphthyridin-5-yl]-5-methyl-1H-pyrazol-1-yl}-3-(cyanomethyl)cyclobutanecarbonitrile | LCMS m/z = 424 [M + H]⁺ |
| 271 | cis-3-{3-[7-(5-amino-1-methyl-1H-pyrazol-3-yl)-1,6-naphthyridin-5-yl]-5-methyl-1H-pyrazol-1-yl}-3-(cyanomethyl)cyclobutanecarbonitrile | LCMS m/z = 424 [M + H]⁺ |
| 272 | [3-{5-methyl-3-[7-(1H-pyrazol-4-yl)-1,6-naphthyridin-5-yl]-1H-pyrazol-1-yl}-1-(methylsulfonyl)azetidin-3-yl]acetonitrile | LCMS m/z = 449 [M + H]⁺ |
| 273 | trans-3-(cyanomethyl)-3-{5-methyl-3-[7-(1H-pyrazol-4-yl)-1,6-naphthyridin-5-yl]-1H-pyrazol-1-yl}cyclobutanecarbonitrile | LCMS m/z = 395 [M + H]⁺ |
| 274 | cis-3-(cyanomethyl)-3-{5-methyl-3-[7-(1H-pyrazol-4-yl)-1,6-naphthyridin-5-yl]-1H-pyrazol-1-yl}cyclobutanecarbonitrile | LCMS m/z = 395 [M + H]⁺ |
| 275 | trans-3-{3-[7-(5-amino-1H-pyrazol-4-yl)-1,6-naphthyridin-5-yl]-5-methyl-1H-pyrazol-1-yl}-3-(cyanomethyl)cyclobutanecarbonitrile | LCMS m/z = 432 [M + Na]⁺ |
| 276 | trans-3-{3-[7-(5-amino-1H-pyrazol-4-yl)-1,6-naphthyridin-5-yl]-4-methyl-1H-pyrazol-1-yl}-3-(cyanomethyl)cyclobutanecarbonitrile | LCMS m/z = 410 [M + H]⁺ |
| 277 | cis-3-{3-[7-(5-amino-1-methyl-1H-pyrazol-3-yl)-1,6-naphthyridin-5-yl]-4-methyl-1H-pyrazol-1-yl}-3-(cyanomethyl)cyclobutanecarbonitrile | LCMS m/z = 424 [M + H]⁺ |
| 278 | trans-3-{3-[7-(5-amino-1-methyl-1H-pyrazol-3-yl)-1,6-naphthyridin-5-yl]-4-methyl-1H-pyrazol-1-yl}-3-(cyanomethyl)cyclobutanecarbonitrile | LCMS m/z = 424 [M + H]⁺ |
| 279 | [3-{1-[7-(1-methyl-1H-pyrazol-4-yl)-1,6-naphthyridin-5-yl]-1H-pyrazol-3-yl}-1-(2,2,2-trifluoroethyl)azetidin-3-yl]acetonitrile | LCMS m/z = 453 [M + H]⁺ |
| 280 | [3-{4-[7-(1-methyl-1H-pyrazol-4-yl)-1,6-naphthyridin-5-yl]-1H-1,2,3-triazol-1-yl}-1-(2,2,2-trifluoroethyl)azetidin-3-yl]acetonitrile | LCMS m/z = 454.2 [M + H]⁺ |
| 281 | [1-(methylsulfonyl)-3-{4-[7-(1H-pyrazol-3-yl)-1,6-naphthyridin-5-yl]-2H-1,2,3-triazol-2-yl}azetidin-3-yl]acetonitrile | LCMS m/z = 436 [M + H]⁺ |
| 282 | 2,2'-(3-{5-[7-(1-methyl-1H-pyrazol-4-yl)-1,6-naphthyridin-5-yl]-1,2-oxazol-3-yl}azetidine-1,3-diyl)diacetonitrile | LCMS m/z = 411 [M + H]⁺ |
| 283 | [1-(methylsulfonyl)-3-{3-[7-(1H-pyrazol-3-yl)quinolin-5-yl]-1H-pyrazol-1-yl}azetidin-3-yl]acetonitrile | LCMS m/z = 434 [M + H]⁺ |
| 284 | [1-(methylsulfonyl)-3-{3-[7-(1H-pyrazol-4-yl)quinolin-5-yl]-1H-pyrazol-1-yl}azetidin-3-yl]acetonitrile | LCMS m/z = 434 [M + H]⁺ |
| 285 | [3-{3-[7-(1-methyl-1H-pyrazol-4-yl)quinolin-5-yl]-1H-pyrazol-1-yl}-1-(2,2,2-trifluoroethyl)azetidin-3-yl]acetonitrile | LCMS m/z= 452 [M + H]⁺ |
| 286 | [3-{3-[7-(1-methyl-1H-pyrazol-4-yl)quinolin-5-yl]-1H-pyrazol-1-yl}-1-(methylsulfonyl)azetidin-3-yl]acetonitrile | LCMS m/z = 448 [M + H]⁺ |
| 287 | [1-(methylsulfonyl)-3-{3-[7-(6-oxo-1,6-dihydropyridin-3-yl)quinolin-5-yl]-1H-pyrazol-1-yl}azetidin-3-yl]acetonitrile | LCMS m/z = 461 [M + H]⁺ |
| 288 | [1-(methylsulfonyl)-3-{4-[7-(1H-pyrazol-3-yl)quinolin-5-yl]-1H-pyrazol-1-yl}azetidin-3-yl]acetonitrile | LCMS m/z = 434 [M + H]⁺ |
| 289 | [1-(methylsulfonyl)-3-{4-[7-(1H-pyrazol-4-yl)quinolin-5-yl]-1H-pyrazol-1-yl}azetidin-3-yl]acetonitrile | LCMS m/z = 434 [M + H]⁺ |
| 290 | trans-3-{4-[7-(5-amino-1H-pyrazol-4-yl)quinolin-5-yl]-1H-pyrazol-1-yl}-3-(cyanomethyl)cyclobutanecarbonitrile | LCMS m/z = 395 [M + H]⁺ |
| 291 | (trans-1-{4-[7-(3-amino-1H-pyrazol-4-yl)quinolin-5-yl]-1H-pyrazol-1-yl}-3-methoxycyclobutyl)acetonitrile | LCMS m/z = 400 [M + H]⁺ |
| 292 | 2,2'-(3-{4-[7-(1-methyl-1H-pyrazol-4-yl)quinolin-5-yl]-1H-pyrazol-1-yl}azetidine-1,3-diyl)diacetonitrile | LCMS m/z = 409 [M + H]⁺ |
| 293 | [3-{5-methyl-3-[7-(1H-pyrazol-3-yl)quinolin-5-yl]-1H-pyrazol-1-yl}-1-(methylsulfonyl)azetidin-3-yl]acetonitrile | LCMS m/z = 448 [M + H]⁺ |
| 294 | [3-{4-[7-(1-methyl-1H-pyrazol-4-yl)quinolin-5-yl]-1H-1,2,3-triazol-1-yl}-1-(methylsulfonyl)azetidin-3-yl]acetonitrile | LCMS m/z = 449 [M + H]⁺ |
| 295 | [1-(methylsulfonyl)-3-{4-[7-(6-oxo-1,6-dihydropyridin-3-yl)quinolin-5-yl]-1H-1,2,3-triazol-1-yl}azetidin-3-yl]acetonitrile | LCMS m/z = 462 [M + H]⁺ |
| 296 | [3-{4-[7-(1H-pyrazol-3-yl)quinolin-5-yl]-2H-1,2,3-triazol-2-yl}-1-(2,2,2-trifluoroethyl)azetidin-3-yl]acetonitrile | LCMS m/z = 439 [M + H]⁺ |
| 297 | (1-[(1-fluorocyclopropyl)methyl]-3-{4-[7-(1H-pyrazol-3-yl)quinolin-5-yl]-2H-1,2,3-triazol-2-yl}azetidin-3-yl)acetonitrile | LCMS m/z = 429 [M + H]⁺ |
| 298 | [1-(methylsulfonyl)-3-{4-[7-(1H-pyrazol-3-yl)quinolin-5-yl]-2H-1,2,3-triazol-2-yl}azetidin-3-yl]acetonitrile | LCMS m/z = 435 [M + H]⁺ |
| 299 | [1-(cyclopropylsulfonyl)-3-{4-[7-(1H-pyrazol-3-yl)quinolin-5-yl]-2H-1,2,3-triazol-2-yl}azetidin-3-yl]acetonitrile | LCMS m/z = 461 [M + H]⁺ |
| 300 | 3-(cyanomethyl)-3-{4-[7-(1H-pyrazol-3-yl)quinolin-5-yl]-2H-1,2,3-triazol-2-yl}azetidine-1-sulfonamide | LCMS m/z = 436 [M + H]⁺ |
| 301 | [1-(oxetan-3-ylsulfonyl)-3-{4-[7-(1H-pyrazol-5-yl)quinolin-5-yl]-2H-1,2,3-triazol-2-yl}azetidin-3-yl]acetonitrile | LCMS m/z = 477 [M + Na]⁺ |
| 302 | trans-3-(cyanomethyl)-3-{4-[7-(1H-pyrazol-3-yl)quinolin-5-yl]-2H-1,2,3-triazol-2-yl}cyclobutanecarbonitrile | LCMS m/z = 381 [M + H]⁺ |
| 303 | cis-3-(cyanomethyl)-3-{4-[7-(1H-pyrazol-3-yl)quinolin-5-yl]-2H-1,2,3-triazol-2-yl}cyclobutanecarbonitrile | LCMS m/z = 381 [M + H]⁺ |
| 304 | (cis-3-methoxy-1-{4-[7-(1H-pyrazol-3-yl)quinolin-5-yl]-2H-1,2,3-triazol-2-yl}cyclobutyl)acetonitrile | LCMS m/z = 386 [M + H]⁺ |

| Ex. | Name | Data |
|---|---|---|
| 305 | (trans-3-methoxy-1-{4-[7-(1H-pyrazol-3-yl)quinolin-5-yl]-2H-1,2,3-triazol-2-yl}cyclobutyl)acetonitrile | LCMS m/z = 386 [M + H]+ |
| 306 | trans-3-{4-[7-(5-amino-1H-pyrazol-3-yl)quinolin-5-yl]-2H-1,2,3-triazol-2-yl}-3-(cyanomethyl)cyclobutanecarbonitrile | LCMS m/z = 396 [M + H]+ |
| 307 | cis-3-{4-[7-(5-amino-1H-pyrazol-3-yl)quinolin-5-yl]-2H-1,2,3-triazol-2-yl}-3-(cyanomethyl)cyclobutanecarbonitrile | LCMS m/z = 396 [M + H]+ |
| 308 | trans-3-(cyanomethyl)-3-(4-{7-[5-(hydroxymethyl)-1H-pyrazol-3-yl]quinolin-5-yl}-2H-1,2,3-triazol-2-yl)cyclobutanecarbonitrile | LCMS m/z = 411 [M + H]+ |
| 309 | trans-3-(cyanomethyl)-3-(4-{7-[5-(hydroxymethyl)-1-methyl-1H-pyrazol-3-yl]quinolin-5-yl}-2H-1,2,3-triazol-2-yl)cyclobutanecarbonitrile | LCMS m/z = 425 [M + H]+ |
| 310 | [3-{4-[7-(1-methyl-1H-pyrazol-5-yl)quinolin-5-yl]-2H-1,2,3-triazol-2-yl}-1-(methylsulfonyl)azetidin-3-yl]acetonitrile | LCMS m/z = 449 [M + H]+ |
| 311 | [3-{4-[7-(1-methyl-1H-pyrazol-3-yl)quinolin-5-yl]-2H-1,2,3-triazol-2-yl}-1-(methylsulfonyl)azetidin-3-yl]acetonitrile | LCMS m/z = 449 [M + H]+ |
| 312 | trans-3-(cyanomethyl)-3-{4-[7-(1-methyl-1H-pyrazol-3-yl)quinolin-5-yl]-2H-1,2,3-triazol-2-yl}cyclobutanecarbonitrile | LCMS m/z = 395 [M + H]+ |
| 313 | cis-3-(cyanomethyl)-3-{4-[7-(1-methyl-1H-pyrazol-3-yl)quinolin-5-yl]-2H-1,2,3-triazol-2-yl}cyclobutanecarbonitrile | LCMS m/z = 395 [M + H]+ |
| 314 | [1-(methylsulfonyl)-3-{4-[7-(1H-pyrazol-4-yl)quinolin-5-yl]-2H-1,2,3-triazol-2-yl}azetidin-3-yl]acetonitrile | LCMS m/z = 435 [M + H]+ |
| 315 | trans-3-(cyanomethyl)-3-{4-[7-(1H-pyrazol-4-yl)quinolin-5-yl]-2H-1,2,3-triazol-2-yl}cyclobutanecarbonitrile | LCMS m/z = 381 [M + H]+ |
| 316 | cis-3-(cyanomethyl)-3-{4-[7-(1H-pyrazol-4-yl)quinolin-5-yl]-2H-1,2,3-triazol-2-yl}cyclobutanecarbonitrile | LCMS m/z = 381 [M + H]+ |
| 317 | trans-3-(cyanomethyl)-3-(4-{7-[3-(hydroxymethyl)-1H-pyrazol-4-yl]quinolin-5-yl}-2H-1,2,3-triazol-2-yl)cyclobutanecarbonitrile | LCMS m/z = 411 [M + H]+ |
| 318 | cis-3-(cyanomethyl)-3-(4-{7-[3-(hydroxymethyl)-1H-pyrazol-4-yl]quinolin-5-yl}-2H-1,2,3-triazol-2-yl)cyclobutanecarbonitrile | LCMS m/z = 411 [M + H]+ |
| 319 | trans-3-{4-[7-(5-amino-1H-pyrazol-4-yl)quinolin-5-yl]-2H-1,2,3-triazol-2-yl}-3-(cyanomethyl)cyclobutanecarbonitrile | LCMS m/z = 396 [M + H]+ |
| 320 | cis-3-{4-[7-(5-amino-1H-pyrazol-4-yl)quinolin-5-yl]-2H-1,2,3-triazol-2-yl}-3-(cyanomethyl)cyclobutanecarbonitrile | LCMS m/z = 396 [M + H]+ |
| 321 | trans-3-{4-[7-(3-amino-1H-pyrazol-4-yl)quinolin-5-yl]-2H-1,2,3-triazol-2-yl}-3-(cyanomethyl)-1-methylcyclobutanecarbonitrile | LCMS m/z = 410 [M + H]+ |
| 322 | cis-3-{4-[7-(5-amino-1H-pyrazol-4-yl)quinolin-5-yl]-2H-1,2,3-triazol-2-yl}-3-(cyanomethyl)-1-methylcyclobutanecarbonitrile | LCMS m/z = 410 [M + H]+ |
| 323 | [3-{4-[7-(1-methyl-1H-pyrazol-4-yl)quinolin-5-yl]-2H-1,2,3-triazol-2-yl}-1-(methylsulfonyl)azetidin-3-yl]acetonitrile | LCMS m/z = 449 [M + H]+ |
| 324 | trans-3-(cyanomethyl)-3-{4-[7-(1-methyl-1H-pyrazol-4-yl)quinolin-5-yl]-2H-1,2,3-triazol-2-yl}cyclobutanecarbonitrile | LCMS m/z = 395 [M + H]+ |
| 325 | cis-3-(cyanomethyl)-3-{4-[7-(1-methyl-1H-pyrazol-4-yl)quinolin-5-yl]-2H-1,2,3-triazol-2-yl}cyclobutanecarbonitrile | LCMS m/z = 395 [M + H]+ |
| 326 | trans-3-(cyanomethyl)-3-(4-{7-[1-(2-hydroxyethyl)-1H-pyrazol-4-yl]quinolin-5-yl}-2H-1,2,3-triazol-2-yl)cyclobutanecarbonitrile | LCMS m/z = 425 [M + H]+ |
| 327 | cis-3-(cyanomethyl)-3-(4-{7-[1-(2-hydroxyethyl)-1H-pyrazol-4-yl]quinolin-5-yl}-2H-1,2,3-triazol-2-yl)cyclobutanecarbonitrile | LCMS m/z = 425 [M + H]+ |
| 328 | trans-3-(cyanomethyl)-3-(4-{7-[5-(hydroxymethyl)-1-methyl-1H-pyrazol-4-yl]quinolin-5-yl}-2H-1,2,3-triazol-2-yl)cyclobutanecarbonitrile | LCMS m/z = 425 [M + H]+ |
| 329 | trans-3-(cyanomethyl)-3-(4-{7-[3-(hydroxymethyl)-1H-pyrazol-4-yl]quinolin-5-yl}-2H-1,2,3-triazol-2-yl)cyclobutanecarbonitrile | LCMS m/z = 425 [M + H]+ |
| 330 | trans-3-{4-[7-(5-amino-1-methyl-1H-pyrazol-4-yl)quinolin-5-yl]-2H-1,2,3-triazol-2-yl}-3-(cyanomethyl)cyclobutanecarbonitrile | LCMS m/z = 410 [M + H]+ |
| 331 | cis-3-{4-[7-(5-amino-1-methyl-1H-pyrazol-4-yl)quinolin-5-yl]-2H-1,2,3-triazol-2-yl}-3-(cyanomethyl)cyclobutanecarbonitrile | LCMS m/z = 410 [M + H]+ |
| 332 | cis-3-{4-[7-(3-amino-1-methyl-1H-pyrazol-4-yl)quinolin-5-yl]-2H-1,2,3-triazol-2-yl}-3-(cyanomethyl)cyclobutanecarbonitrile | LCMS m/z = 410 [M + H]+ |
| 333 | trans-3-{4-[7-(3-amino-1-methyl-1H-pyrazol-4-yl)quinolin-5-yl]-2H-1,2,3-triazol-2-yl}-3-(cyanomethyl)cyclobutanecarbonitrile | LCMS m/z = 410 [M + H]+ |
| 334 | 4-(5-{2-[cis-3-cyano-1-(cyanomethyl)cyclobutyl]-2H-1,2,3-triazol-4-yl}quinolin-7-yl)-1-methyl-1H-pyrazole-5-carboxamide | LCMS m/z = 438 [M + H]+ |
| 335 | 4-(5-{2-[trans-3-cyano-1-(cyanomethyl)cyclobutyl]-2H-1,2,3-triazol-4-yl}quinolin-7-yl)-1-methyl-1H-pyrazole-5-carboxamide | LCMS m/z = 438 [M + H]+ |
| 336 | cis-3-(cyanomethyl)-3-{4-[7-(2-methyl-1H-imidazol-4-yl)quinolin-5-yl]-2H-1,2,3-triazol-2-yl}cyclobutanecarbonitrile | LCMS m/z = 395 [M + H]+ |
| 337 | trans-3-(cyanomethyl)-3-{4-[7-(2-methyl-1H-imidazol-4-yl)quinolin-5-yl]-2H-1,2,3-triazol-2-yl}cyclobutanecarbonitrile | LCMS m/z = 395 [M + H]+ |
| 338 | cis-3-(cyanomethyl)-3-{4-[7-(1-methyl-1H-1,2,3-triazol-5-yl)quinolin-5-yl]-2H-1,2,3-triazol-2-yl}cyclobutanecarbonitrile | LCMS m/z = 396 [M + H]+ |
| 339 | trans-3-(cyanomethyl)-3-{4-[7-(1-methyl-1H-1,2,3-triazol-4-yl)quinolin-5-yl]-2H-1,2,3-triazol-2-yl}cyclobutanecarbonitrile | LCMS m/z = 396 [M + H]+ |
| 340 | cis-3-(cyanomethyl)-3-(4-{7-[4-(hydroxymethyl)-1,3-thiazol-2-yl]quinolin-5-yl}-2H-1,2,3-triazol-2-yl)cyclobutanecarbonitrile | LCMS m/z = 428 [M + H]+ |
| 341 | trans-3-(cyanomethyl)-3-(4-{7-[4-(hydroxymethyl)-1,3-thiazol-2-yl]quinolin-5-yl}-2H-1,2,3-triazol-2-yl)cyclobutanecarbonitrile | LCMS m/z = 428 [M + H]+ |
| 342 | trans-3-(cyanomethyl)-3-(4-{7-[2-(hydroxymethyl)-1,3-thiazol-5-yl]quinolin-5-yl}-2H-1,2,3-triazol-2-yl)cyclobutanecarbonitrile | LCMS m/z = 428 [M + H]+ |

-continued

| Ex. | Name | Data |
|---|---|---|
| 343 | trans-3-(cyanomethyl)-3-(4-{7-[5-(hydroxymethyl)-1,3-thiazol-2-yl]quinolin-5-yl}-2H-1,2,3-triazol-2-yl)cyclobutanecarbonitrile | LCMS m/z = 428 [M + H]⁺ |
| 344 | trans-3-(cyanomethyl)-3-(4-{7-[4-(hydroxymethyl)-1,3-thiazol-5-yl]quinolin-5-yl}-2H-1,2,3-triazol-2-yl)cyclobutanecarbonitrile | LCMS m/z = 428 [M + H]⁺ |
| 345 | trans-3-(cyanomethyl)-3-(4-{7-[3-(hydroxymethyl)-1,2-thiazol-5-yl]quinolin-5-yl}-2H-1,2,3-triazol-2-yl)cyclobutanecarbonitrile | LCMS m/z = 428 [M + H]⁺ |
| 346 | cis-3-(cyanomethyl)-3-{4-[7-(pyridin-2-yl)quinolin-5-yl]-2H-1,2,3-triazol-2-yl}cyclobutanecarbonitrile | LCMS m/z = 392 [M + H]⁺ |
| 347 | cis-3-(cyanomethyl)-3-{4-[7-(5-fluoropyridin-2-yl)quinolin-5-yl]-2H-1,2,3-triazol-2-yl}cyclobutanecarbonitrile | LCMS m/z = 410 [M + H]⁺ |
| 348 | trans-3-(cyanomethyl)-3-{4-[7-(5-fluoropyridin-2-yl)quinolin-5-yl]-2H-1,2,3-triazol-2-yl}cyclobutanecarbonitrile | LCMS m/z = 410 [M + H]⁺ |
| 349 | 6-(5-{2-[trans-3-cyano-1-(cyanomethyl)cyclobutyl]-2H-1,2,3-triazol-4-yl}quinolin-7-yl)pyridine-2-carboxamide | LCMS m/z = 435 [M + H]⁺ |
| 350 | 6-(5-{2-[cis-3-cyano-1-(cyanomethyl)cyclobutyl]-2H-1,2,3-triazol-4-yl}quinolin-7-yl)pyridine-2-carboxamide | LCMS m/z = 435 [M + H]⁺ |
| 351 | 6-(5-{2-[trans-3-cyano-1-(cyanomethyl)cyclobutyl]-2H-1,2,3-triazol-4-yl}quinolin-7-yl)pyridine-3-carboxamide | LCMS m/z = 435 [M + H]⁺ |
| 352 | 6-(5-{2-[cis-3-cyano-1-(cyanomethyl)cyclobutyl]-2H-1,2,3-triazol-4-yl}quinolin-7-yl)pyridine-3-carboxamide | LCMS m/z = 435 [M + H]⁺ |
| 353 | 2-(5-{2-[cis-3-cyano-1-(cyanomethyl)cyclobutyl]-2H-1,2,3-triazol-4-yl}quinolin-7-yl)pyridine-4-carboxamide | LCMS m/z = 435 [M + H]⁺ |
| 354 | 2-(5-{2-[trans-3-cyano-1-(cyanomethyl)cyclobutyl]-2H-1,2,3-triazol-4-yl}quinolin-7-yl)pyridine-4-carboxamide | LCMS m/z = 435 [M + H]⁺ |
| 355 | [3-{4-[7-(6-methylpyridin-3-yl)quinolin-5-yl]-2H-1,2,3-triazol-2-yl}-1-(methylsulfonyl)azetidin-3-yl]acetonitrile | LCMS m/z = 460 [M + H]⁺ |
| 356 | [3-{4-[7-(2-methylpyridin-4-yl)quinolin-5-yl]-2H-1,2,3-triazol-2-yl}-1-(methylsulfonyl)azetidin-3-yl]acetonitrile | LCMS m/z = 460 [M + H]⁺ |
| 357 | trans-3-{4-[7-(6-aminopyridin-2-yl)quinolin-5-yl]-2H-1,2,3-triazol-2-yl}-3-(cyanomethyl)cyclobutanecarbonitrile | LCMS m/z = 407 [M + H]⁺ |
| 358 | cis-3-{4-[7-(6-aminopyridin-2-yl)quinolin-5-yl]-2H-1,2,3-triazol-2-yl}-3-(cyanomethyl)cyclobutanecarbonitrile | LCMS m/z = 407 [M + H]⁺ |
| 359 | cis-3-{4-[7-(5-aminopyridin-2-yl)quinolin-5-yl]-2H-1,2,3-triazol-2-yl}-3-(cyanomethyl)cyclobutanecarbonitrile | LCMS m/z = 407 [M + H]⁺ |
| 360 | trans-3-{4-[7-(5-aminopyridin-2-yl)quinolin-5-yl]-2H-1,2,3-triazol-2-yl}-3-(cyanomethyl)cyclobutanecarbonitrile | LCMS m/z = 407 [M + H]⁺ |
| 361 | [3-{4-[7-(2-aminopyridin-3-yl)quinolin-5-yl]-2H-1,2,3-triazol-2-yl}-1-(methylsulfonyl)azetidin-3-yl]acetonitrile | LCMS m/z = 461 [M + H]⁺ |
| 362 | cis-3-{4-[7-(2-aminopyridin-3-yl)quinolin-5-yl]-2H-1,2,3-triazol-2-yl}-3-(cyanomethyl)cyclobutanecarbonitrile | LCMS m/z = 407 [M + H]⁺ |
| 363 | trans-3-{4-[7-(2-aminopyridin-3-yl)quinolin-5-yl]-2H-1,2,3-triazol-2-yl}-3-(cyanomethyl)cyclobutanecarbonitrile | LCMS m/z = 407 [M + H]⁺ |
| 364 | [3-{4-[7-(6-aminopyridin-3-yl)quinolin-5-yl]-2H-1,2,3-triazol-2-yl}-1-(methylsulfonyl)azetidin-3-yl]acetonitrile | LCMS m/z = 461 [M + H]⁺ |
| 365 | trans-3-{4-[7-(6-aminopyridin-3-yl)quinolin-5-yl]-2H-1,2,3-triazol-2-yl}-3-(cyanomethyl)cyclobutanecarbonitrile | LCMS m/z = 407 [M + H]⁺ |
| 366 | cis-3-{4-[7-(6-aminopyridin-3-yl)quinolin-5-yl]-2H-1,2,3-triazol-2-yl}-3-(cyanomethyl)cyclobutanecarbonitrile | LCMS m/z = 407 [M + H]⁺ |
| 367 | trans-3-{4-[7-(2-aminopyridin-4-yl)quinolin-5-yl]-2H-1,2,3-triazol-2-yl}-3-(cyanomethyl)cyclobutanecarbonitrile | LCMS m/z = 407 [M + H]⁺ |
| 368 | cis-3-(cyanomethyl)-3-(4-{7-[5-(methylsulfonyl)pyridin-2-yl]quinolin-5-yl}-2H-1,2,3-triazol-2-yl)cyclobutanecarbonitrile | LCMS m/z = 470 [M + H]⁺ |
| 369 | trans-3-(cyanomethyl)-3-(4-{7-[5-(methylsulfonyl)pyridin-2-yl]quinolin-5-yl}-2H-1,2,3-triazol-2-yl)cyclobutanecarbonitrile | LCMS m/z = 470 [M + H]⁺ |
| 370 | 6-(5-{2-[cis-3-cyano-1-(cyanomethyl)cyclobutyl]-2H-1,2,3-triazol-4-yl}quinolin-7-yl)pyridine-2-carboxylic acid | LCMS m/z = 436 [M + H]⁺ |
| 371 | 6-(5-{2-[trans-3-cyano-1-(cyanomethyl)cyclobutyl]-2H-1,2,3-triazol-4-yl}quinolin-7-yl)pyridine-2-carboxylic acid | LCMS m/z = 436 [M + H]⁺ |
| 372 | N-[6-(5-{2-[cis-3-cyano-1-(cyanomethyl)cyclobutyl]-2H-1,2,3-triazol-4-yl}quinolin-7-yl)pyridin-2-yl]methanesulfonamide | LCMS m/z = 485 [M + H]⁺ |
| 373 | N-[6-(5-{2-[trans-3-cyano-1-(cyanomethyl)cyclobutyl]-2H-1,2,3-triazol-4-yl}quinolin-7-yl)pyridin-2-yl]methanesulfonamide | LCMS m/z = 485 [M + H]⁺ |
| 374 | N-[6-(5-{2-[cis-3-cyano-1-(cyanomethyl)cyclobutyl]-2H-1,2,3-triazol-4-yl}quinolin-7-yl)pyridin-3-yl]methanesulfonamide | LCMS m/z = 485 [M + H]+ |
| 375 | N-[6-(5-{2-[trans-3-cyano-1-(cyanomethyl)cyclobutyl]-2H-1,2,3-triazol-4-yl}quinolin-7-yl)pyridin-3-yl]methanesulfonamide | LCMS m/z = 485 [M + H]⁺ |
| 376 | N-[6-(5-{2-[trans-3-cyano-1-(cyanomethyl)cyclobutyl]-2H-1,2,3-triazol-4-yl}quinolin-7-yl)pyridin-2-yl]acetamide | LCMS m/z = 449 [M + H]⁺ |
| 377 | N-[6-(5-{2-[cis-3-cyano-1-(cyanomethyl)cyclobutyl]-2H-1,2,3-triazol-4-yl}quinolin-7-yl)pyridin-2-yl]acetamide | LCMS m/z = 449 [M + H]⁺ |
| 378 | cis-3-(cyanomethyl)-3-(4-{7-[5-(2-hydroxyethyl)-6-methylpyridin-2-yl]quinolin-5-yl}-2H-1,2,3-triazol-2-yl)cyclobutanecarbonitrile | LCMS m/z = 450 [M + H]⁺ |
| 379 | trans-3-(cyanomethyl)-3-(4-{7-[5-(2-hydroxyethyl)-6-methylpyridin-2-yl]quinolin-5-yl}-2H-1,2,3-triazol-2-yl)cyclobutanecarbonitrile | LCMS m/z = 450 [M + H]⁺ |
| 380 | cis-3-(cyanomethyl)-3-{4-[7-(2,3-dihydro-1H-pyrrolo[3,2-c]pyridin-6-yl)quinolin-5-yl]-2H-1,2,3-triazol-2-yl}cyclobutanecarbonitrile | LCMS m/z = 433 [M + H]⁺ |

| Ex. | Name | Data |
|---|---|---|
| 381 | cis-3-(cyanomethyl)-3-{4-[7-(5-hydroxy-6-methylpyridin-2-yl)quinolin-5-yl]-2H-1,2,3-triazol-2-yl}cyclobutanecarbonitrile | LCMS m/z = 422 [M + H]⁺ |
| 382 | trans-3-(cyanomethyl)-3-{4-[7-(5-hydroxy-6-methylpyridin-2-yl)quinolin-5-yl]-2H-1,2,3-triazol-2-yl}cyclobutanecarbonitrile | LCMS m/z = 422 [M + H]⁺ |
| 383 | cis-3-{4-[7-(5-amino-6-methoxypyridin-2-yl)quinolin-5-yl]-2H-1,2,3-triazol-2-yl}-3-(cyanomethyl)cyclobutanecarbonitrile | LCMS m/z = 437 [M + H]⁺ |
| 384 | trans-3-{4-[7-(5-amino-6-methontpyridin-2-yl)quinolin-5-yl]-2H-1,2,3-triazol-2-yl}-3-(cyanomethyl)cyclobutanecarbonitrile | LCMS m/z = 437 [M + H]⁺ |
| 385 | 2-(5-{2-[cis-3-cyano-1-(cyanomethyl)cyclobutyl]-2H-1,2,3-triazol-4-yl}quinolin-7-yl)5-fluoropyridine-4-carboxamide | LCMS m/z = 453 [M + H]⁺ |
| 386 | 2-(5-{2-[trans-3-cyano-1-(cyanomethyl)cyclobutyl]-2H-1,2,3-triazol-4-yl}quinolin-7-yl)-5-fluoropyridine-4-carboxamide | LCMS m/z = 453 [M + H]⁺ |
| 387 | cis-3-(cyanomethyl)-3-{4-[7-(5-fluoro-2-hydroxypyridin-4-yl)quinolin-5-yl]-2H-1,2,3-triazol-2-yl}cyclobutanecarbonitrile | LCMS m/z = 426 [M + H]⁺ |
| 388 | [3-{4-[7-(6-amino-5-methylpyridin-3-yl)quinolin-5-yl]-2H-1,2,3-triazol-2-yl}-1-(methylsulfonyl)azetidin-3-yl]acetonitrile | LCMS m/z = 475 [M + H]⁺ |
| 389 | [1-(methylsulfonyl)-3-{4-[7-(pyrimidin-5-yl)quinolin-5-yl]-2H-1,2,3-triazol-2-yl}azetidin-3-yl]acetonitrile | LCMS m/z = 447 [M + H]⁺ |
| 390 | trans-3-(cyanomethyl)-3-{4-[7-(pyrimidin-2-yl)quinolin-5-yl]-2H-1,2,3-triazol-2-yl}cyclobutanecarbonitrile | LCMS m/z = 393 [M + H]⁺ |
| 391 | cis-3-(cyanomethyl)-3-{4-[7-(pyrimidin-5-yl)quinolin-5-yl]-2H-1,2,3-triazol-2-yl}cyclobutanecarbonitrile | LCMS m/z = 393 [M + H]⁺ |
| 392 | cis-3-(cyanomethyl)-3-{4-[7-(pyrazin-2-yl)quinolin-5-yl]-2H-1,2,3-triazol-2-yl}cyclobutanecarbonitrile | LCMS m/z = 393 [M + H]⁺ |
| 393 | [3-{4-[7-(2-aminopyrimidin-5-yl)quinolin-5-yl]-2H-1,2,3-triazol-2-yl}-1-(methylsulfonyl)azetidin-3-yl]acetonitrile | LCMS m/z = 462 [M + H]⁺ |
| 394 | cis-3-{4-[7-(2-aminopyrimidin-5-yl)quinolin-5-yl]-2H-1,2,3-triazol-2-yl}-3-(cyanomethyl)cyclobutanecarbonitrile | LCMS m/z = 408 [M + H]⁺ |
| 395 | cis-3-{4-[7-(6-aminopyrimidin-4-yl)quinolin-5-yl]-2H-1,2,3-triazol-2-yl}-3-(cyanomethyl)cyclobutanecarbonitrile | LCMS m/z = 408 [M + H]⁺ |
| 396 | cis-3-{4-[7-(6-aminopyrazin-2-yl)quinolin-5-yl]-2H-1,2,3-triazol-2-yl}-3-(cyanomethyl)cyclobutanecarbonitrile | LCMS m/z = 408 [M + H]⁺ |
| 397 | trans-3-{4-[7-(6-aminopyrazin-2-yl)quinolin-5-yl]-2H-1,2,3-triazol-2-yl}-3-(cyanomethyl)cyclobutanecarbonitrile | LCMS m/z = 408 [M + H]⁺ |
| 398 | cis-3-{4-[7-(5-aminopyrazin-2-yl)quinolin-5-yl]-2H-1,2,3-triazol-2-yl}-3-(cyanomethyl)cyclobutanecarbonitrile | LCMS m/z = 408 [M + H]⁺ |
| 399 | trans-3-{4-[7-(5-aminopyrazin-2-yl)quinolin-5-yl]-2H-1,2,3-triazol-2-yl}-3-(cyanomethyl)cyclobutanecarbonitrile | LCMS m/z = 408 [M + H]⁺ |
| 400 | cis-3-{4-[7-(6-aminopyridazin-3-yl)quinolin-5-yl]-2H-1,2,3-triazol-2-yl}-3-(cyanomethyl)cyclobutanecarbonitrile | LCMS m/z = 408 [M + H]⁺ |
| 401 | trans-3-{4-[7-(6-aminopyridazin-3-yl)quinolin-5-yl]-2H-1,2,3-triazol-2-yl}-3-(cyanomethyl)cyclobutanecarbonitrile | LCMS m/z = 408 [M + H]⁺ |
| 402 | cis-3-(cyanomethyl)-3-{4-[7-(6-methylpyrazin-2-yl)quinolin-5-yl]-2H-1,2,3-triazol-2-yl}cyclobutanecarbonitrile | LCMS m/z = 407 [M + H]⁺ |
| 403 | trans-3-(cyanomethyl)-3-{4-[7-(6-methylpyrazin-2-yl)quinolin-5-yl]-2H-1,2,3-triazol-2-yl}cyclobutanecarbonitrile | LCMS m/z = 407 [M + H]⁺ |
| 404 | cis-3-{4-[7-(6-amino-3-methylpyrazin-2-yl)quinolin-5-yl]-2H-1,2,3-triazol-2-yl}-3-(cyanomethyl)cyclobutanecarbonitrile | LCMS m/z = 422 [M + H]⁺ |
| 405 | [3-{4-[7-(2-methoxypyrimidin-5-yl)quinolin-5-yl]-2H-1,2,3-triazol-2-yl}-1-(methylsulfonyl)azetidin-3-yl]acetonitrile | LCMS m/z = 477 [M + H]⁺ |
| 406 | cis-3-(cyanomethyl)-3-(4-{7-[5-(2-hydroxyethoxy)pyrimidin-2-yl]quinolin-5-yl}-2H-1,2,3-triazol-2-yl)cyclobutanecarbonitrile | LCMS m/z = 422 [M + H]⁺ |
| 407 | cis-3-{4-[7-(5-amino-6-methoxypyrazin-2-yl)quinolin-5-yl]-2H-1,2,3-triazol-2-yl}-3-(cyanomethyl)cyclobutanecarbonitrile | LCMS m/z = 438 [M + H]⁺ |
| 408 | trans-3-{4-[7-(5-amino-6-methontpyrazin-2-yl)quinolin-5-yl]-2H-1,2,3-triazol-2-yl}-3-(cyanomethyl)cyclobutanecarbonitrile | LCMS m/z = 438 [M + H]⁺ |
| 409 | [1-(methylsulfonyl)-3-{4-[7-(6-oxo-1,6-dihydropyridin-3-yl)quinolin-5-yl]-2H-1,2,3-triazol-2-yl}azetidin-3-yl]acetonitrile | LCMS m/z = 462 [M + H]⁺ |
| 410 | cis-3-(cyanomethyl)-3-{4-[7-(2-oxo-1,2-dihydropyridin-4-yl)quinolin-5-yl]-2H-1,2,3-triazol-2-yl}cyclobutanecarbonitrile | LCMS m/z = 408 [M + H]⁺ |
| 411 | trans-3-(cyanomethyl)-3-{4-[7-(2-oxo-1,2-d i hyd ropyridin-4-yl)quinolin-5-yl]-2H-1,2,3-triazol-2-yl}cyclobutanecarbonitrile | LCMS m/z = 408 [M + H]⁺ |
| 412 | [3-{4-[7-(1-methyl-6-oxo-1,6-dihydropyridin-3-yl)quinolin-5-yl]-2H-1,2,3-triazol-2-yl}-1-(methylsulfonyl)azetidin-3-yl]acetonitrile | LCMS m/z = 476 [M + H]⁺ |
| 413 | [3-{4-[7-(1-ethyl-6-oxo-1,6-dihydropyridin-3-yl)quinolin-5-yl]-2H-1,2,3-triazol-2-yl}-1-(methylsulfonyl)azetidin-3-yl]acetonitrile | LCMS m/z = 490 [M + H]⁺ |
| 414 | [3-{4-[7-(2,4-dioxo-1,2,3,4-tetrahydropyrimidin-5-yl)quinolin-5-yl]-2H-1,2,3-triazol-2-yl}-1-(methylsulfonyl)azetidin-3-yl]acetonitrile | LCMS m/z = 479 [M + H]⁺ |
| 415 | [1-(methylsulfonyl)-3-{4-[7-(7H-pyrrolo[2,3-b]pyridin-5-yl)quinolin-5-yl]-2H-1,2,3-triazol-2-yl}azetidin-3-yl]acetonitrile | LCMS m/z = 485 [M + H]⁺ |
| 416 | cis-3-(cyanomethyl)-3-{4-[7-(5H-pyrrolo[2,3-b]pyrazin-2-yl)quinolin-5-yl]-2H-1,2,3-triazol-2-yl}cyclobutanecarbonitrile | LCMS m/z = 453 [M + H]⁺ |
| 417 | cis-3-(cyanomethyl)-3-{4-[7-(imidazo[1,2-a]pyrimidin-3-yl)quinolin-5-yl]-2H-1,2,3-triazol-2-yl}cyclobutanecarbonitrile | LCMS m/z = 432 [M + H]⁺ |
| 418 | trans-3-(cyanomethyl)-3-{4-[7-(imidazo[1,2-a]pyrimidin-3-yl)quinolin-5-yl]-2H-1,2,3-triazol-2-yl}cyclobutanecarbonitrile | LCMS m/z = 432 [M + H]⁺ |

-continued

| Ex. | Name | Data |
|---|---|---|
| 419 | cis-3-(cyanomethyl)-3-{4-[7-(pyrazolo[1,5-a]pyrimidin-3-yl)quinolin-5-yl]-2H-1,2,3-triazol-2-yl}cyclobutanecarbonitrile | LCMS m/z = 432 [M + H]+ |
| 420 | trans-3-(cyanomethyl)-3-{4-[7-(pyrazolo[1,5-a]pyrimidin-3-yl)quinolin-5-yl]-2H-1,2,3-triazol-2-yl}cyclobutanecarbonitrile | LCMS m/z = 432 [M + H]+ |
| 421 | cis-3-(cyanomethyl)-3-{4-[7-(imidazo[1,2-b]pyridazin-3-yl)quinolin-5-yl]-2H-1,2,3-triazol-2-yl}cyclobutanecarbonitrile | LCMS m/z = 432 [M + H]+ |
| 422 | cis-3-{4-[7-(8-aminoimidazo[1,2-a]pyrazin-3-yl)quinolin-5-yl]-2H-1,2,3-triazol-2-yl}-3-(cyanomethyl)cyclobutanecarbonitrile | LCMS m/z = 447 [M + H]+ |
| 423 | cis-3-{4-[7-(8-aminoimidazo[1,2-a]pyrazin-6-yl)quinolin-5-yl]-2H-1,2,3-triazol-2-yl}-3-(cyanomethyl)cyclobutanecarbonitrile | LCMS m/z = 447 [M + H]+ |
| 424 | cis-3-(cyanomethyl)-3-{4-[7-(2-methyl-3H-imidazo[4,5-b]pyridin-5-yl)quinolin-5-yl]-2H-1,2,3-triazol-2-yl}cyclobutanecarbonitrile | LCMS m/z = 446 [M + H]+ |
| 425 | cis-3-(cyanomethyl)-3-{4-[7-(4-methyl-3-oxo-3,4-dihydro-2H-pyrido[3,2-b][1,4]oxazin-6-yl)quinolin-5-yl]-2H-1,2,3-triazol-2-yl}cyclobutanecarbonitrile | LCMS m/z = 477 [M + H]+ |
| 426 | trans-3-(cyanomethyl)-3-{4-[7-(4-methyl-3-oxo-3,4-dihydro-2H-pyrido[3,2-b][1,4]oxazin-6-yl)quinolin-5-yl]-2H-1,2,3-triazol-2-yl}cyclobutanecarbonitrile | LCMS m/z = 477 [M + H]+ |
| 427 | [3-(4-{7-[3-(aminomethyl)phenyl]quinolin-5-yl}-2H-1,2,3-triazol-2-yl)-1-(methylsulfonyl)azetidin-3-yl]acetonitrile | LCMS m/z = 474 [M + H]+ |
| 428 | [3-(4-{7-[4-(aminomethyl)phenyl]quinolin-5-yl}-2H-1,2,3-triazol-2-yl)-1-(methylsulfonyl)azetidin-3-yl]acetonitrile | LCMS m/z = 474 [M + H]+ |
| 429 | [3-(4-{7-[3-(hydroxymethyl)phenyl]quinolin-5-yl}-2H-1,2,3-triazol-2-yl)-1-(methylsulfonyl)azetidin-3-yl]acetonitrile | LCMS m/z = 475 [M + H]+ |
| 430 | 3-(5-{2-[3-(cyanomethyl)-1-(methylsulfonyl)azetidin-3-yl]-2H-1,2,3-triazol-4-yl}quinolin-7-yl)benzamide | LCMS m/z = 488 [M + H]+ |
| 431 | 3-(5-{2-[cis-3-cyano-1-(cyanomethyl)cyclobutyl]-2H-1,2,3-triazol-4-yl}quinolin-7-yl)benzamide | LCMS m/z = 434 [M + H]+ |
| 432 | 3-(5-{2-[trans-3-cyano-1-(cyanomethyl)cyclobutyl]-2H-1,2,3-triazol-4-yl}quinolin-7-yl)benzamide | LCMS m/z = 434 [M + H]+ |
| 433 | 4-(5-{2-[cis-3-cyano-1-(cyanomethyl)cyclobutyl]-2H-1,2,3-triazol-4-yl}quinolin-7-yl)benzamide | LCMS m/z = 434 [M + H]+ |
| 434 | 4-(5-{2-[trans-3-cyano-1-(cyanomethyl)cyclobutyl]-2H-1,2,3-triazol-4-yl}quinolin-7-yl)benzamide | LCMS m/z = 434 [M + H]+ |
| 435 | 4-(5-{2-[cis-3-cyano-1-(cyanomethyl)cyclobutyl]-2H-1,2,3-triazol-4-yl}quinolin-7-yl)benzoic acid | LCMS m/z = 435 [M + H]+ |
| 436 | 4-(5-{2-[trans-3-cyano-1-(cyanomethyl)cyclobutyl]-2H-1,2,3-triazol-4-yl}quinolin-7-yl)benzoic acid | LCMS m/z = 435 [M + H]+ |
| 437 | [3-{4-[7-(2-hydroxyphenyl)quinolin-5-yl]-2H-1,2,3-triazol-2-yl}-1-(methylsulfonyl)azetidin-3-yl]acetonitrile | LCMS m/z = 461 [M + H]+ |
| 438 | [3-{4-[7-(3-hydroxyphenyl)quinolin-5-yl]-2H-1,2,3-triazol-2-yl}-1-(methylsulfonyl)azetidin-3-yl]acetonitrile | LCMS m/z = 461 [M + H]+ |
| 439 | [3-{4-[7-(4-hydroxyphenyl)quinolin-5-yl]-2H-1,2,3-triazol-2-yl}-1-(methylsulfonyl)azetidin-3-yl]acetonitrile | LCMS m/z = 461 [M + H]+ |
| 440 | trans-3-(4-{7-[4-(2-aminoethoxy)phenyl]quinolin-5-yl}-2H-1,2,3-triazol-2-yl)-3-(cyanomethyl)cyclobutanecarbonitrile | LCMS m/z = 450 [M + H]+ |
| 441 | [3-{4-[7-(4-fluoro-2-hydroxyphenyl)quinolin-5-yl]-2H-1,2,3-triazol-2-yl}-1-(methylsulfonyl)azetidin-3-yl]acetonitrile | LCMS m/z = 479 [M + H]+ |
| 442 | [3-{4-[7-(5-fluoro-2-hydroxyphenyl)quinolin-5-yl]-2H-1,2,3-triazol-2-yl}-1-(methylsulfonyl)azetidin-3-yl]acetonitrile | LCMS m/z = 479 [M + H]+ |
| 443 | [3-{4-[7-(3-fluoro-5-hydroxyphenyl)quinolin-5-yl]-2H-1,2,3-triazol-2-yl}-1-(methylsulfonyl)azetidin-3-yl]acetonitrile | LCMS m/z = 479 [M + H]+ |
| 444 | [3-{4-[7-(3-fluoro-4-hydroxyphenyl)quinolin-5-yl]-2H-1,2,3-triazol-2-yl}-1-(methylsulfonyl)azetidin-3-yl]acetonitrile | LCMS m/z = 479 [M + H]+ |
| 445 | [3-(4-{7-[2-fluoro-3-(hydroxymethyl)phenyl]quinolin-5-yl}-2H-1,2,3-triazol-2-yl)-1-(methylsulfonyl)azetidin-3-yl]acetonitrile | LCMS m/z = 493 [M + H]+ |
| 446 | [3-(4-{7-[4-fluoro-3-(hydroxymethyl)phenyl]quinolin-5-yl}-2H-1,2,3-triazol-2-yl)-1-(methylsulfonyl)azetidin-3-yl]acetonitrile | LCMS m/z = 493 [M + H]+ |
| 447 | cis-3-(cyanomethyl)-3-(4-{7-[4-(1H-tetrazol-5-yl)phenyl]quinolin-5-yl}-2H-1,2,3-triazol-2-yl)cyclobutanecarbonitrile | LCMS m/z = 459 [M + H]+ |
| 448 | [1-(methylsulfonyl)-3-{4-[7-(3-oxo-2,3-dihydro-1H-isoindol-5-yl)quinolin-5-yl]-2H-1,2,3-triazol-2-yl}azetidin-3-yl]acetonitrile | LCMS m/z = 500 [M + H]+ |
| 449 | cis-3-(cyanomethyl)-3-{4-[7-(2-oxo-2,3-dihydro-1H-indol-7-yl)quinolin-5-yl]-2H-1,2,3-triazol-2-yl}cyclobutanecarbonitrile | LCMS m/z = 446 [M + H]+ |
| 450 | trans-3-(cyanomethyl)-3-{4-[7-(2-oxo-2,3-dihydro-1H-indol-7-yl)quinolin-5-yl]-2H-1,2,3-triazol-2-yl}cyclobutanecarbonitrile | LCMS m/z = 446 [M + H]+ |
| 451 | [1-(methylsulfonyl)-3-{3-[7-(6-oxo-1,6-dihydropyridin-3-yl)quinolin-5-yl]-1H-1,2,4-triazol-1-yl}azetidin-3-yl]acetonitrile | LCMS m/z = 462 [M + H]+ |
| 452 | [1-(methylsulfonyl)-3-{3-[7-(1H-pyrazol-5-yl)quinolin-5-yl]-1H-1,2,4-triazol-1-yl}azetidin-3-yl]acetonitrile | LCMS m/z = 435 [M + H]+ |
| 453 | [1-(methylsulfonyl)-3-{3-[7-(1H-pyrazol-4-yl)quinolin-5-yl]-1H-1,2,4-triazol-1-yl}azetidin-3-yl]acetonitrile | LCMS m/z = 435 [M + H]+ |
| 454 | cis-3-(cyanomethyl)-3-{4-[7-(1H-pyrazol-3-yl)imidazo[1,2-a]pyridin-5-yl]-1H-pyrazol-1-yl}cyclobutanecarbonitrile | LCMS m/z = 369 [M + H]+ |
| 455 | trans-3-(cyanomethyl)-3-{4-[7-(1H-pyrazol-3-yl)imidazo[1,2-a]pyridin-5-yl]-1H-pyrazol-1-yl}cyclobutanecarbonitrile | LCMS m/z = 369 [M + H]+ |

| Ex. | Name | Data |
|---|---|---|
| 456 | cis-3-(cyanomethyl)-3-{4-[7-(1H-pyrazol-4-yl)imidazo[1,2-a]pyridin-5-yl]-1H-pyrazol-1-yl}cyclobutanecarbonitrile | LCMS m/z = 369 [M + H]+ |
| 457 | [3-{4-[7-(1-methyl-1H-pyrazol-4-yl)imidazo[1,2-a]pyridin-5-yl]-1H-pyrazol-1-yl}-1-(2,2,2-trifluoroethyl)azetidin-3-yl]acetonitrile | LCMS m/z = 441 [M + H]+ |
| 458 | cis-3-(cyanomethyl)-3-{4-[7-(1-methyl-1H-pyrazol-4-yl)imidazo[1,2-a]pyridin-5-yl]-1H-pyrazol-1-yl}cyclobutanecarbonitrile | LCMS m/z = 383 [M + H]+ |
| 459 | trans-3-(cyanomethyl)-3-{4-[7-(1-methyl-1H-pyrazol-4-yl)imidazo[1,2-a]pyridin-5-yl]-1H-pyrazol-1-yl}cyclobutanecarbonitrile | LCMS m/z = 383 [M + H]+ |
| 460 | (cis-3-methoxy-1-{4-[7-(1-methyl-1H-pyrazol-4-yl)imidazo[1,2-a]pyridin-5-yl]-1H-pyrazol-1-yl}cyclobutyl)acetonitrile | LCMS m/z = 388 [M + H]+ |
| 461 | trans-3-(cyanomethyl)-3-{4-[7-(3-methyl-1H-pyrazol-5-yl)imidazo[1,2-a]pyridin-5-yl]-1H-pyrazol-1-yl}cyclobutanecarbonitrile | LCMS m/z = 383 [M + H]+ |
| 462 | cis-3-(cyanomethyl)-3-{4-[7-(5-methyl-1H-pyrazol-3-yl)imidazo[1,2-a]pyridin-5-yl]-1H-pyrazol-1-yl}cyclobutanecarbonitrile | LCMS m/z = 383 [M + H]+ |
| 463 | [cis-1-(4-{7-[3-(hydroxymethyl)-1H-pyrazol-4-yl]imidazo[1,2-a]pyridin-5-yl}-1H-pyrazol-1-yl)-3-methoxycyclobutyl]acetonitrile | LCMS m/z = 404 [M + H]+ |
| 464 | [trans-1-(4-{7-[3-(hydroxymethyl)-1H-pyrazol-4-yl]imidazo[1,2-a]pyridin-5-yl}-1H-pyrazol-1-yl)-3-methoxycyclobutyl]acetonitrile | LCMS m/z = 404 [M + H]+ |
| 465 | cis-3-(cyanomethyl)-3-{4-[7-(2-methyl-1H-imidazol-5-yl)imidazo[1,2-a]pyridin-5-yl]-1H-pyrazol-1-yl}cyclobutanecarbonitrile | LCMS m/z = 383 [M + H]+ |
| 466 | cis-3-{4-[7-(3-amino-1H-pyrazol-4-yl)imidazo[1,2-a]pyridin-5-yl]-1H-pyrazol-1-yl}-3-(cyanomethyl)cyclobutanecarbonitrile | LCMS m/z = 384 [M + H]+ |
| 467 | cis-3-(cyanomethyl)-3-(4-{7-[4-(hydroxymethyl)-1,3-thiazol-2-yl]imidazo[1,2-a]pyridin-5-yl}-1H-pyrazol-1-yl)cyclobutanecarbonitrile | LCMS m/z = 416 [M + H]+ |
| 468 | cis-3-(cyanomethyl)-3-{4-[7-(4-hydroxyphenyl)imidazo[1,2-a]pyridin-5-yl]-1H-pyrazol-1-yl}cyclobutanecarbonitrile | LCMS m/z = 395 [M + H]+ |
| 469 | cis-3-{4-[7-(6-aminopyridin-3-yl)imidazo[1,2-a]pyridin-5-yl]-1H-pyrazol-1-yl}-3-(cyanomethyl)cyclobutanecarbonitrile | LCMS m/z = 395 [M + H]+ |
| 470 | 6-(5-{1-[cis-3-cyano-1-(cyanomethyl)cyclobutyl]-1H-pyrazol-4-yl}imidazo[1,2-a]pyridin-7-yl)pyridine-2-carboxamide | LCMS m/z = 423 [M + H]+ |
| 471 | cis-3-{4-[7-(5-amino-6-methoxypyridin-2-yl)imidazo[1,2-a]pyridin-5-yl]-1H-pyrazol-1-yl}-3-(cyanomethyl)cyclobutanecarbonitrile | LCMS m/z = 425 [M + H]+ |
| 472 | [3-{3-[7-(1-methyl-1H-pyrazol-4-yl)imidazo[1,2-a]pyridin-5-yl]-1H-pyrazol-1-yl}-1-(2,2,2-trifluoroethyl)azetidin-3-yl]acetonitrile | LCMS m/z = 441 [M + H]+ |
| 473 | cis-3-(cyanomethyl)-3-{4-[7-(1-methyl-1H-pyrazol-4-yl)imidazo[1,2-a]pyridin-5-yl]-2H-1,2,3-triazol-2-yl}cyclobutanecarbonitrile | LCMS m/z = 384 [M + H]+ |
| 474 | trans-3-(cyanomethyl)-3-{4-[7-(1-methyl-1H-pyrazol-4-yl)imidazo[1,2-a]pyridin-5-yl]-2H-1,2,3-triazol-2-yl}cyclobutanecarbonitrile | LCMS m/z = 384 [M + H]+ |
| 475 | [3-{4-[7-(1-methyl-1H-pyrazol-4-yl)[1,2,4]triazolo[1,5-a]pyridin-5-yl]-1H-pyrazol-1-yl}-1-(2,2,2-trifluoroethyl)azetidin-3-yl]acetonitrile | LCMS m/z = 442 [M + H]+ |
| 476 | [3-{3-[7-(1-methyl-1H-pyrazol-4-yl)[1,2,4]triazolo[1,5-a]pyridin-5-yl]-1H-pyrazol-1-yl}-1-(2,2,2-trifluoroethyl)azetidin-3-yl]acetonitrile | HRMS m/z = 442.17 [M + H]+ |
| 477 | 2,2'-(3-{4-[6-(1-methyl-1H-pyrazol-4-yl)[1,2,4]triazolo[1,5-a]pyrazin-8-yl]-1H-pyrazol-1-yl}azetidine-1,3-diyl)diacetonitrile | LCMS m/z = 405 [M + H]+ |
| 478 | [3-{4-[6-(1-methyl-1H-pyrazol-4-yl)[1,2,4,5-a]pyrazin-8-yl]-1H-pyrazol-1-yl}-1-(methylsulfonyl)azetidin-3-yl]acetonitrile | LCMS m/z = 439 [M + H]+ |
| 479 | [3-{4-[7-(1-methyl-1H-pyrazol-4-yl)pyrido[3,4-b]pyrazin-5-yl]-1H-pyrazol-1-yl}-1-(2,2,2-trifluoroethyl)azetidin-3-yl]acetonitrile | LCMS m/z = 476 [M + Na]+ |
| 480 | 2,2'-(3-{4-[7-(1-methyl-1H-pyrazol-4-yl)pyrido[3,4-b]pyrazin-5-yl]-1H-pyrazol-1-yl}azetidine-1,3-diyl)diacetonitrile | LCMS m/z = 433 [M + Na]+ |
| 481 | 2,2'-(3-{3-[7-(1-methyl-1H-pyrazol-4-yl)pyrido[3,4-b]pyrazin-5-yl]-1H-pyrazol-1-yl}azetidine-1,3-diyl)diacetonitrile | LCMS m/z = 411 [M + H]+ |
| 482 | [3-{3-[7-(1-methyl-1H-pyrazol-4-yl)pyrido[3,4-b]pyrazin-5-yl]-1H-pyrazol-1-yl}-1-(2,2,2-trifluoroethyl)azetidin-3-yl]acetonitrile | LCMS m/z = 454 [M + H]+ |
| 483 | trans-3-(cyanomethyl)-3-(3-(7-(1-methyl-1H-pyrazol-4-yl)-1,6-naphthyridin-5-yl-2-d)-1H-pyrazol-1-yl)cyclobutane-1-carbonitrile | LCMS m/z = 396 [M + H]+ |

Biological Evaluation

Compounds of the invention were evaluated by in vitro methods to determine their respective ability to inhibit the JAK kinases (TYK2, JAK1, JAK2, JAK3).

Assay Format

The human JAK inhibitory activity was determined by using a microfluidic assay to monitor phosphorylation of a synthetic peptide by the recombinant human kinase domain of each of the four members of the JAK family, JAK1, JAK2, JAK3 and TYK2. Reaction mixtures contained 1 µM of a fluorescently labeled synthetic peptide, a concentration less than the apparent $K_m$, and 1 mM ATP. Each assay condition was optimized for enzyme concentration and room temperature incubation time to obtain a conversion rate of 20% to 30% phosphorylated peptide product. Reactions were terminated by the addition of stop buffer containing EDTA. Utilizing the LabChip 3000 mobility shift technology (Caliper Life Science), each assay reaction was sampled to determine the level of phosphorylation. This technology is separation-based, allowing direct detection of fluorescently labeled substrates and products. Separations are controlled by a combination of vacuum pressure and electric field strength optimized for each peptide substrate.

Assay Protocol
JAK Caliper Enzyme Assay at 1mM ATP

Compounds were added to a 384-well plate. Reaction mixtures contained 10 mM HEPES, pH 7.4, 10 mM $MgCl_2$, 0.01% BSA, 0.0005% Tween 20, 1 mM ATP and 1 μM peptide substrate. The JAK1 and TYK2 assays contained 1 μM of the IRStide peptide (5FAM-KKSRGDYMTMQID) and the JAK2 and JAK3 assays contained 1 μM of the JAKtide peptide (FITC-KGGEEEEYFELVKK). The assays were initiated by the addition of 20 nM JAK1, 1 nM JAK2, 1 nM JAK or 1 nM TYK2 enzyme and were incubated at room temperature for three hours for JAK1, 60 minutes for JAK2, 75 minutes for JAK3 or 135 minutes for TYK2. Enzyme concentrations and incubation times were optimized for each new enzyme preps and were modified slightly over time to ensure 20% to 30% phosphorylation. The assays were stopped with 15 μL of 180 mM HEPES, pH 7.4, 20 mM EDTA, and 0.2% Coating Reagent 3. The assay plates were placed on a Caliper Life Science LC3000 instrument, and each well was sampled using appropriate separation conditions to measure the unphosphorylated and phosphorylated peptide.

Data Analysis

The data was collected using the HTS Well Analyzer software from Caliper Life Sciences. The data output for data analysis is the percent product converted calculated on peak height (Equation 1).

$$\% \text{ product converted} = 100 * ((\text{product})/(\text{product} + \text{substrate})) \quad \text{Equation 1:}$$

The percent effect at each compound concentration was calculated based on the positive and negative control well contained within each assay plate (Equation 2). The positive control wells contained a saturating concentration of a control compound that produced a level of phosphorylation comparable to background (i.e., completely inhibited JAK1, JAK2, JAK3 or TYK2). The negative control wells contained DMSO alone (at the same concentration as the compound wells) that was used to set the baseline activity in the assay (i.e., uninhibited JAK1, JAK2, JAK3 or TYK2).

$$\% \text{ effect} = 100 * ((\text{sample well negative control})/(\text{positive control} - \text{negative control})) \quad \text{Equation 2:}$$

The percent effect was plotted against the compound concentration compound.

An unconstrained sigmoid curve was fitted using a 4 parameter logistic model and the compound concentration required for 50% inhibition ($IC_{50}$) was determined (Equation 3).

$$y = ((\max - \min)/(1 + ((x/IC_{50})^s))) + \min \quad \text{Equation 3:}$$

where max is the maximum asymptote (complete inhibition), min is the minimum asymptote (no inhibition) and s is the slope factor. $IC_{50}$ values are reported in nM for each compound:

TABLE I

JAK Caliper Data

| Example No. | TYK2 IC50 (nM) | JAK1 IC50 (nM) | JAK2 IC50 (nM) | JAK3 IC50 (nM) |
|---|---|---|---|---|
| 1 | 15 | 35 | 39 | 7140 |
| 2 | 50 | 86 | 127 | >10000 |
| 3 | 14 | 37 | 26 | 5976 |
| 4 | 17 | 97 | 26 | 5169 |
| 5 | 1108 | 2825 | 2950 | >10000 |
| 6 | 15 | 21 | 10 | 1116 |
| 7 | 89 | 189 | 70 | >10000 |
| 8 | 130 | 661 | 126 | >10000 |
| 9 | 77 | 520 | 107 | >10000 |
| 10 | 20 | 86 | 10 | 1997 |
| 11 | 21 | 70 | 14 | 2618 |
| 12 | 63 | 407 | 101 | >10000 |
| 13 | 42 | 266 | 82 | >10000 |
| 14 | 1466 | 8958 | >10000 | >10000 |
| 15 | 7684 | >10000 | >10000 | >10000 |
| 16 | 23 | 475 | 431 | >10000 |
| 17 | 44 | 1018 | 464 | >10000 |
| 18 | 20 | 451 | 811 | >10000 |
| 19 | 26 | 175 | 188 | 9907 |
| 20 | 25 | 381 | 240 | >10000 |
| 21 | 9 | 71 | 50 | 6748 |
| 22 | 61 | 834 | 891 | >10000 |
| 23 | 15 | 324 | 216 | >10000 |
| 24 | 167 | 3671 | 1687 | >10000 |
| 25 | 1645 | >10000 | 8676 | >10000 |
| 26 | 1468 | 6074 | 3899 | >10000 |
| 27 | 7557 | >10000 | >10000 | >10000 |
| 28 | 207 | 2572 | 1790 | >10000 |
| 29 | 437 | 3799 | 2345 | >10000 |
| 30 | 75 | 1960 | 1767 | >10000 |
| 31 | 53 | 1804 | 955 | >10000 |
| 32 | 730 | 5827 | 3429 | >10000 |
| 33 | 850 | 5699 | 5196 | >10000 |
| 34 | 238 | 1699 | 1014 | >10000 |
| 35 | 44 | 569 | 339 | >10000 |
| 36 | 1055 | 7100 | 5740 | >10000 |
| 37 | 369 | 4282 | 2826 | >10000 |
| 38 | 4021 | >10000 | 5634 | >10000 |
| 39 | 205 | 2768 | 2080 | >10000 |
| 40 | 730 | 7298 | 4593 | >10000 |
| 41 | 8 | 14 | 21 | 1235 |
| 42 | 36 | 1606 | 456 | >10000 |
| 43 | 14 | 502 | 91 | >10000 |
| 44 | 7 | 66 | 18 | 2883 |
| 45 | 33 | 739 | 125 | >10000 |
| 46 | 867 | 9684 | 2774 | >10000 |
| 47 | 254 | 7722 | 1939 | >10000 |
| 48 | 15 | 292 | 73 | >10000 |
| 49 | 7 | 42 | 16 | 2316 |
| 50 | 59 | 2754 | 861 | >10000 |
| 51 | 45 | 1913 | 509 | >10000 |
| 52 | 19 | 379 | 235 | >10000 |
| 53 | 26 | 654 | 396 | >10000 |
| 54 | 214 | 2300 | 2097 | >10000 |
| 55 | 156 | 8867 | 2557 | >10000 |
| 56 | 225 | >10000 | 1483 | >10000 |
| 57 | 257 | >10000 | 2346 | >10000 |
| 58 | 34 | 7434 | 510 | >10000 |
| 59 | 16 | 880 | 92 | >10000 |
| 60 | 190 | 3849 | 915 | >10000 |
| 61 | 39 | 521 | 123 | >10000 |
| 62 | 153 | >10000 | 1032 | >10000 |
| 63 | 17 | 672 | 70 | 6554 |
| 64 | 440 | >10000 | 5903 | >10000 |
| 65 | 18 | 1591 | 172 | >10000 |
| 66 | 7 | 155 | 22 | 2503 |
| 67 | 39 | 2177 | 246 | >10000 |
| 68 | 1591 | >10000 | 4330 | >10000 |
| 69 | 158 | 3399 | 556 | >10000 |
| 70 | 661 | >10000 | 3501 | >10000 |
| 71 | 109 | 3716 | 205 | 7928 |
| 72 | 28 | 676 | 48 | 5102 |
| 73 | 33 | 4631 | 206 | >10000 |
| 74 | 13 | 217 | 267 | 9655 |
| 75 | 46 | 679 | 444 | >10000 |
| 76 | 7 | 35 | 33 | 1540 |
| 77 | 25 | 293 | 242 | >10000 |
| 78 | 14 | 172 | 104 | 8610 |
| 79 | 74 | 1049 | 774 | >10000 |

TABLE I-continued

JAK Caliper Data

| Example No. | TYK2 IC50 (nM) | JAK1 IC50 (nM) | JAK2 IC50 (nM) | JAK3 IC50 (nM) |
|---|---|---|---|---|
| 80 | 47 | 1060 | 927 | >10000 |
| 81 | 101 | 3094 | 2173 | >10000 |
| 82 | 418 | 3581 | 2388 | >10000 |
| 83 | 410 | 2241 | 2446 | >10000 |
| 84 | 22 | 240 | 174 | >10000 |
| 85 | 30 | 166 | 103 | 5244 |
| 86 | 430 | 2409 | 1432 | >10000 |
| 87 | 2320 | >10000 | >10000 | >10000 |
| 88 | 60 | 1623 | 875 | >10000 |
| 89 | 89 | 1315 | 770 | >10000 |
| 90 | 32 | 269 | 126 | >10000 |
| 91 | 34 | 562 | 160 | >10000 |
| 92 | 9 | 63 | 22 | 1849 |
| 93 | 7 | 121 | 46 | 5056 |
| 94 | 94 | 2097 | 940 | >10000 |
| 95 | 22 | 1008 | 354 | >10000 |
| 96 | 31 | 790 | 243 | >10000 |
| 97 | 5 | 12 | 6 | 735 |
| 98 | 8 | 73 | 33 | 5251 |
| 99 | 16 | 563 | 133 | >10000 |
| 100 | 14 | 425 | 71 | >10000 |
| 101 | 73 | 2038 | 430 | >10000 |
| 102 | 17 | 591 | 90 | 9608 |
| 103 | 7 | 55 | 13 | 873 |
| 104 | 19 | 1377 | 164 | >10000 |
| 105 | 39 | 1347 | 174 | 8089 |
| 106 | 138 | 5399 | 895 | >10000 |
| 107 | 24 | 1009 | 243 | >10000 |
| 108 | 16 | 311 | 50 | 1593 |
| 109 | 68 | 2369 | 378 | >10000 |
| 110 | 61 | 4113 | 558 | >10000 |
| 111 | 27 | 458 | 139 | 9055 |
| 112 | 12 | 43 | 15 | 634 |
| 113 | 22 | 409 | 67 | 8970 |
| 114 | 46 | 404 | 41 | 1172 |
| 115 | 120 | 7061 | 327 | >10000 |
| 116 | 41 | 1041 | 54 | 4420 |
| 117 | 88 | 1060 | 64 | 6964 |
| 118 | 843 | 9060 | 4165 | >10000 |
| 119 | 29 | 976 | 82 | 8384 |
| 120 | 15 | 521 | 28 | 8525 |
| 121 | 20 | 1754 | 101 | 9591 |
| 122 | 110 | 6655 | 391 | >10000 |
| 123 | 21 | 744 | 54 | 9661 |
| 124 | 27 | 715 | 68 | 9877 |
| 125 | 33 | 965 | 162 | >10000 |
| 126 | 41 | 583 | 119 | >10000 |
| 127 | 17 | 64 | 20 | 1046 |
| 128 | 115 | 3534 | 620 | >10000 |
| 129 | 133 | 5924 | 1233 | >10000 |
| 130 | 32 | 232 | 63 | 9523 |
| 131 | 251 | 1632 | 1273 | >10000 |
| 132 | 22 | 619 | 70 | 9123 |
| 133 | 76 | 1674 | 229 | >10000 |
| 134 | 685 | >10000 | >10000 | >10000 |
| 135 | 20 | 489 | 34 | 2023 |
| 136 | 44 | 618 | 260 | >10000 |
| 137 | 52 | 586 | 207 | >10000 |
| 138 | 8 | 382 | 21 | 3187 |
| 139 | 10 | 243 | 20 | 3721 |
| 140 | 8 | 48 | 10 | 474 |
| 141 | 49 | 355 | 127 | >10000 |
| 142 | 19 | 53 | 30 | 2158 |
| 143 | 767 | >10000 | 6673 | >10000 |
| 144 | 223 | >10000 | 1373 | >10000 |
| 145 | 172 | 3294 | 1789 | >10000 |
| 146 | 26 | 400 | 99 | >10000 |
| 147 | 7554 | >10000 | >10000 | >10000 |
| 148 | 235 | 8797 | 2553 | >10000 |
| 149 | 125 | >10000 | 1315 | >10000 |
| 150 | 290 | 9828 | 3420 | >10000 |
| 151 | 309 | >10000 | 1662 | >10000 |
| 152 | 4143 | >10000 | >10000 | >10000 |
| 153 | 239 | 5840 | 3348 | >10000 |
| 154 | 287 | >10000 | 3181 | >10000 |
| 155 | 312 | 6455 | 2774 | >10000 |
| 156 | 119 | 2053 | 815 | >10000 |
| 157 | 148 | 1684 | 856 | >10000 |
| 158 | 33 | 1974 | 666 | >10000 |
| 159 | 7 | 120 | 116 | >10000 |
| 160 | 795 | >10000 | 5569 | >10000 |
| 161 | 35 | 404 | 368 | >10000 |
| 162 | 68 | 788 | 546 | >10000 |
| 163 | 42 | 4065 | 294 | >10000 |
| 164 | 235 | 6567 | 4724 | >10000 |
| 165 | 1394 | >10000 | 9440 | >10000 |
| 166 | 44 | 7378 | 728 | >10000 |
| 167 | 129 | 2728 | 1290 | >10000 |
| 168 | 592 | 8819 | 6588 | >10000 |
| 169 | 22 | >10000 | 241 | >10000 |
| 170 | 56 | 1434 | 399 | >10000 |
| 171 | 66 | 2733 | 974 | >10000 |
| 172 | 27 | 608 | 388 | >10000 |
| 173 | 1880 | >10000 | 7885 | >10000 |
| 174 | 49 | 785 | 332 | >10000 |
| 175 | 135 | 5738 | 1179 | >10000 |
| 176 | 71 | 966 | 634 | >10000 |
| 177 | 58 | 2606 | 794 | >10000 |
| 178 | 1370 | >10000 | 6783 | >10000 |
| 179 | 285 | >10000 | 9669 | >10000 |
| 180 | 42 | 3740 | 369 | >10000 |
| 181 | 40 | 853 | 123 | >10000 |
| 182 | 53 | 2021 | 224 | >10000 |
| 183 | 21 | 384 | 397 | >10000 |
| 184 | 221 | 4030 | 4029 | >10000 |
| 185 | 88 | 2031 | 2073 | >10000 |
| 186 | 74 | 4855 | 612 | >10000 |
| 187 | 781 | >10000 | >10000 | >10000 |
| 188 | 80 | 2715 | 902 | >10000 |
| 189 | 84 | 8338 | 725 | >10000 |
| 190 | 55 | 1312 | 596 | >10000 |
| 191 | 75 | 5055 | 931 | >10000 |
| 192 | 68 | 951 | 841 | >10000 |
| 193 | 147 | 5567 | 1678 | >10000 |
| 194 | 45 | 843 | 436 | >10000 |
| 195 | 9 | 50 | 31 | 2056 |
| 196 | 45 | 488 | 233 | >10000 |
| 197 | 37 | 656 | 688 | >10000 |
| 198 | 7 | 39 | 32 | 1933 |
| 199 | 20 | 337 | 199 | >10000 |
| 200 | 573 | 3221 | 2969 | >10000 |
| 201 | 31 | 308 | 177 | >10000 |
| 202 | 135 | >10000 | >10000 | >10000 |
| 203 | 14 | 264 | 86 | >10000 |
| 204 | 799 | >10000 | 6689 | >10000 |
| 205 | 17 | 120 | 149 | >10000 |
| 206 | 50 | 2533 | 479 | >10000 |
| 207 | 24 | 285 | 56 | 9271 |
| 208 | 81 | 2583 | 362 | >10000 |
| 209 | 51 | 1942 | 433 | >10000 |
| 210 | 62 | 1526 | 300 | >10000 |
| 211 | 17 | 181 | 39 | 9816 |
| 212 | 198 | 2953 | 900 | >10000 |
| 213 | 19 | 87 | 46 | 4334 |
| 214 | 53 | 2017 | 471 | >10000 |
| 215 | 175 | 6012 | 2189 | >10000 |
| 216 | 36 | 464 | 117 | >10000 |
| 217 | 189 | 9345 | 1623 | >10000 |
| 218 | 38 | 2700 | 562 | >10000 |
| 219 | 488 | 6411 | 1749 | >10000 |
| 220 | 92 | 2138 | 768 | >10000 |
| 221 | 21 | 230 | 93 | 6647 |
| 222 | 57 | >10000 | 1297 | >10000 |
| 223 | 15 | 365 | 230 | >10000 |
| 224 | 45 | 1940 | 1051 | >10000 |
| 225 | 9 | 215 | 122 | >10000 |
| 226 | 112 | 3304 | 929 | >10000 |
| 227 | 1184 | >10000 | 9305 | >10000 |

TABLE I-continued

JAK Caliper Data

| Example No. | TYK2 IC50 (nM) | JAK1 IC50 (nM) | JAK2 IC50 (nM) | JAK3 IC50 (nM) |
|---|---|---|---|---|
| 228 | 704 | 4346 | 6626 | >10000 |
| 229 | 81 | 2459 | 1003 | >10000 |
| 230 | 33 | 1122 | 451 | >10000 |
| 231 | 948 | 5764 | 7898 | >10000 |
| 232 | 1514 | >10000 | 5816 | >10000 |
| 233 | 347 | 9577 | 6174 | >10000 |
| 234 | 2657 | >10000 | >10000 | >10000 |
| 235 | 5513 | >10000 | >10000 | >10000 |
| 236 | 2360 | >10000 | >10000 | >10000 |
| 237 | 2040 | >10000 | >10000 | >10000 |
| 238 | 1920 | >10000 | 8973 | >10000 |
| 239 | 96 | 3725 | 1115 | >10000 |
| 240 | 48 | 1276 | 448 | >10000 |
| 241 | 3393 | >10000 | >10000 | >10000 |
| 242 | 503 | >10000 | 3773 | >10000 |
| 243 | 48 | 2216 | 726 | >10000 |
| 244 | 424 | >10000 | >10000 | >10000 |
| 245 | 11 | 220 | 131 | >10000 |
| 246 | 32 | 554 | 971 | >10000 |
| 247 | 49 | 1341 | 778 | >10000 |
| 248 | 96 | 994 | 532 | >10000 |
| 249 | 178 | 1078 | 1151 | >10000 |
| 250 | 55 | 1257 | 821 | >10000 |
| 251 | 48 | 541 | 229 | >10000 |
| 252 | 15 | 663 | 118 | >10000 |
| 253 | | | | |
| 254 | 11 | 237 | 205 | >10000 |
| 255 | 3173 | >10000 | >10000 | >10000 |
| 256 | 11 | 12 | 15 | 454 |
| 257 | 20 | 110 | 59 | 6422 |
| 258 | 255 | >10000 | >10000 | >10000 |
| 259 | 19 | >10000 | 566 | >10000 |
| 260 | 27 | 198 | 325 | >10000 |
| 261 | 118 | >10000 | >10000 | >10000 |
| 262 | 242 | >10000 | >10000 | >10000 |
| 263 | 1389 | >10000 | 9573 | >10000 |
| 264 | 6986 | >10000 | >10000 | >10000 |
| 265 | 4819 | >10000 | >10000 | >10000 |
| 266 | 1909 | >10000 | 3316 | >10000 |
| 267 | 57 | 2950 | 843 | >10000 |
| 268 | 8 | 81 | 33 | 7785 |
| 269 | 27 | 1379 | 447 | >10000 |
| 270 | 46 | 6904 | 574 | >10000 |
| 271 | 16 | 429 | 46 | 7074 |
| 272 | 120 | 3790 | 1393 | >10000 |
| 273 | 49 | 786 | 311 | >10000 |
| 274 | 9 | 60 | 34 | 3362 |
| 275 | 13 | 38 | 20 | 2650 |
| 276 | 144 | 3476 | 947 | >10000 |
| 277 | 675 | >10000 | 2298 | >10000 |
| 278 | 1431 | >10000 | 9843 | >10000 |
| 279 | 194 | 6338 | 686 | >10000 |
| 280 | 9 | 182 | 28 | 3257 |
| 281 | 16 | 179 | 90 | >10000 |
| 282 | 60 | 219 | 45 | >10000 |
| 283 | 176 | 5667 | 1996 | >10000 |
| 284 | 171 | 6833 | 2501 | >10000 |
| 285 | 342 | >10000 | 2950 | >10000 |
| 286 | 212 | >10000 | 1811 | >10000 |
| 287 | 201 | >10000 | 5383 | >10000 |
| 288 | 112 | 796 | 336 | >10000 |
| 289 | 197 | 1527 | 525 | >10000 |
| 290 | 236 | 2963 | 1747 | >10000 |
| 291 | 343 | 8823 | 3735 | >10000 |
| 292 | 36 | 653 | 71 | >10000 |
| 293 | 81 | 8187 | 2985 | >10000 |
| 294 | 267 | 1342 | 151 | >10000 |
| 295 | 155 | 7716 | 2579 | >10000 |
| 296 | 41 | 534 | 598 | >10000 |
| 297 | 315 | 4589 | 2467 | >10000 |
| 298 | 23 | 594 | 239 | >10000 |
| 299 | 10 | 280 | 252 | >10000 |
| 300 | 16 | 291 | 123 | 3320 |
| 301 | 17 | 338 | 195 | >10000 |
| 302 | 20 | 436 | 173 | >10000 |
| 303 | 5 | 81 | 29 | 3098 |
| 304 | 36 | 2301 | 788 | >10000 |
| 305 | 35 | 2555 | 1050 | >10000 |
| 306 | 14 | 255 | 174 | 9159 |
| 307 | 7 | 49 | 30 | 1931 |
| 308 | 18 | 719 | 131 | >10000 |
| 309 | 29 | 1877 | 163 | >10000 |
| 310 | 725 | >10000 | >10000 | >10000 |
| 311 | 25 | 2257 | 287 | >10000 |
| 312 | 31 | 1635 | 246 | >10000 |
| 313 | 25 | 486 | 79 | 5474 |
| 314 | 32 | 1147 | 390 | >10000 |
| 315 | 19 | 524 | 215 | >10000 |
| 316 | 8 | 122 | 48 | 2727 |
| 317 | 57 | 2830 | 838 | >10000 |
| 318 | 17 | 540 | 137 | 9269 |
| 319 | 16 | 1254 | 530 | >10000 |
| 320 | 5 | 256 | 77 | 8033 |
| 321 | 844 | >10000 | 7687 | >10000 |
| 322 | 74 | 2594 | 959 | >10000 |
| 323 | 69 | 2838 | 244 | >10000 |
| 324 | 30 | 1422 | 144 | 9930 |
| 325 | 11 | 319 | 32 | 2150 |
| 326 | 9 | 332 | 45 | 4171 |
| 327 | 20 | 262 | 52 | 3293 |
| 328 | 1290 | >10000 | 8630 | >10000 |
| 329 | 71 | 6999 | 666 | >10000 |
| 330 | 143 | 7695 | 1617 | >10000 |
| 331 | 115 | 3701 | 740 | >10000 |
| 332 | 16 | 1688 | 105 | >10000 |
| 333 | 31 | 5871 | 380 | >10000 |
| 334 | 736 | >10000 | 4706 | >10000 |
| 335 | 5268 | >10000 | >10000 | >10000 |
| 336 | 8 | 326 | 32 | 3575 |
| 337 | 33 | 2909 | 243 | >10000 |
| 338 | 2465 | >10000 | >10000 | >10000 |
| 339 | 36 | 8368 | 146 | >10000 |
| 340 | 13 | 432 | 94 | 8906 |
| 341 | 57 | 3244 | 649 | >10000 |
| 342 | 135 | 2575 | 990 | >10000 |
| 343 | 65 | 3341 | 660 | >10000 |
| 344 | 776 | >10000 | >10000 | >10000 |
| 345 | 249 | 3814 | 1860 | >10000 |
| 346 | 23 | 1083 | 123 | >10000 |
| 347 | 26 | 1201 | 114 | >10000 |
| 348 | 143 | >10000 | 876 | >10000 |
| 349 | 17 | 738 | 100 | >10000 |
| 350 | 7 | 97 | 25 | 2470 |
| 351 | 131 | >10000 | 688 | >10000 |
| 352 | 27 | 825 | 106 | >10000 |
| 353 | 1570 | 9629 | >10000 | >10000 |
| 354 | 7245 | >10000 | >10000 | >10000 |
| 355 | 137 | >10000 | 1579 | >10000 |
| 356 | 130 | >10000 | 973 | >10000 |
| 357 | 99 | 2581 | 670 | >10000 |
| 358 | 20 | 404 | 92 | 3758 |
| 359 | 13 | 321 | 69 | 6699 |
| 360 | 40 | 1717 | 354 | >10000 |
| 361 | 3635 | >10000 | >10000 | >10000 |
| 362 | 1964 | >10000 | >10000 | >10000 |
| 363 | 6845 | >10000 | >10000 | >10000 |
| 364 | 67 | 2961 | 834 | >10000 |
| 365 | 103 | 2663 | 938 | >10000 |
| 366 | 26 | 520 | 167 | 8163 |
| 367 | 93 | 2804 | 1286 | >10000 |
| 368 | 15 | 525 | 42 | 7246 |
| 369 | 55 | 3509 | 281 | >10000 |
| 370 | 30 | 2289 | 345 | >10000 |
| 371 | 110 | 9283 | 1610 | >10000 |
| 372 | 21 | 600 | 80 | 5972 |
| 373 | 69 | 4073 | 411 | >10000 |
| 374 | 9 | 53 | 25 | 2892 |
| 375 | 30 | 452 | 148 | >10000 |

TABLE I-continued

JAK Caliper Data

| Example No. | TYK2 IC50 (nM) | JAK1 IC50 (nM) | JAK2 IC50 (nM) | JAK3 IC50 (nM) |
|---|---|---|---|---|
| 376 | 36 | 593 | 155 | 9482 |
| 377 | 14 | 73 | 33 | 1349 |
| 378 | 35 | 575 | 93 | 9501 |
| 379 | 123 | 4365 | 540 | >10000 |
| 380 | 194 | 9393 | 811 | >10000 |
| 381 | 30 | 432 | 138 | >10000 |
| 382 | 141 | 3059 | 1022 | >10000 |
| 383 | 7 | 59 | 35 | 4251 |
| 384 | 33 | 769 | 256 | >10000 |
| 385 | 984 | 6269 | 6785 | >10000 |
| 386 | 3764 | >10000 | >10000 | >10000 |
| 387 | 4838 | >10000 | >10000 | >10000 |
| 388 | 1780 | >10000 | 6881 | >10000 |
| 389 | 5036 | >10000 | >10000 | >10000 |
| 390 | 1281 | >10000 | >10000 | >10000 |
| 391 | 2844 | >10000 | 9840 | >10000 |
| 392 | 660 | 7111 | 3053 | >10000 |
| 393 | 3467 | >10000 | >10000 | >10000 |
| 394 | 1028 | 8565 | 5272 | >10000 |
| 395 | 78 | 6350 | 774 | >10000 |
| 396 | 506 | 3327 | 1480 | >10000 |
| 397 | 2325 | >10000 | 8951 | >10000 |
| 398 | 204 | 1895 | 1037 | >10000 |
| 399 | 2403 | >10000 | >10000 | >10000 |
| 400 | 16 | 748 | 67 | 9133 |
| 401 | 55 | 3700 | 369 | >10000 |
| 402 | 2528 | >10000 | 6291 | >10000 |
| 403 | 7189 | >10000 | >10000 | >10000 |
| 404 | 7399 | >10000 | >10000 | >10000 |
| 405 | 3064 | >10000 | >10000 | >10000 |
| 406 | 2150 | >10000 | >10000 | >10000 |
| 407 | 257 | 1201 | 1013 | >10000 |
| 408 | 2089 | >10000 | >10000 | >10000 |
| 409 | 53 | 2607 | 982 | >10000 |
| 410 | 39 | 2339 | 207 | >10000 |
| 411 | 257 | >10000 | 1687 | >10000 |
| 412 | 167 | 3078 | 1288 | >10000 |
| 413 | 90 | 4024 | 682 | >10000 |
| 414 | 276 | >10000 | 6168 | >10000 |
| 415 | 1090 | >10000 | 5529 | >10000 |
| 416 | 696 | 3200 | 2302 | >10000 |
| 417 | 110 | 7469 | 291 | >10000 |
| 418 | 1536 | >10000 | 8067 | >10000 |
| 419 | 105 | 739 | 200 | >10000 |
| 420 | 909 | >10000 | 1696 | >10000 |
| 421 | 113 | 1558 | 353 | >10000 |
| 422 | 292 | 5379 | 1465 | >10000 |
| 423 | 76 | 2249 | 183 | >10000 |
| 424 | 23 | 728 | 82 | 9362 |
| 425 | 12 | 608 | 29 | >10000 |
| 426 | 24 | 1000 | 50 | >10000 |
| 427 | 709 | >10000 | 3154 | >10000 |
| 428 | 128 | 9323 | 924 | >10000 |
| 429 | 112 | 4001 | 1120 | >10000 |
| 430 | 93 | 3144 | 909 | >10000 |
| 431 | 31 | 572 | 169 | >10000 |
| 432 | 172 | 3904 | 1044 | >10000 |
| 433 | 20 | 352 | 116 | 6700 |
| 434 | 99 | 2522 | 748 | >10000 |
| 435 | 17 | 208 | 179 | >10000 |
| 436 | 75 | 1493 | 1130 | >10000 |
| 437 | 1212 | >10000 | >10000 | >10000 |
| 438 | 107 | 5626 | 1962 | >10000 |
| 439 | 30 | 1208 | 609 | >10000 |
| 440 | 139 | 6431 | 805 | >10000 |
| 441 | 1105 | >10000 | >10000 | >10000 |
| 442 | 7539 | >10000 | >10000 | >10000 |
| 443 | 631 | >10000 | 6455 | >10000 |
| 444 | 77 | 1244 | 1178 | >10000 |
| 445 | 330 | >10000 | 5613 | >10000 |
| 446 | 101 | 4726 | 964 | >10000 |
| 447 | 17 | 180 | 160 | 9400 |
| 448 | 257 | >10000 | 2683 | >10000 |
| 449 | 368 | >10000 | 6502 | >10000 |
| 450 | 1425 | >10000 | >10000 | >10000 |
| 451 | 283 | >10000 | 7157 | >10000 |
| 452 | 322 | 7186 | 6806 | >10000 |
| 453 | 259 | 8303 | 3176 | >10000 |
| 454 | 36 | 912 | 468 | >10000 |
| 455 | 319 | >10000 | 5676 | >10000 |
| 456 | 126 | 1308 | 812 | >10000 |
| 457 | 252 | >10000 | 3944 | >10000 |
| 458 | 25 | 1681 | 204 | >10000 |
| 459 | 297 | >10000 | 3154 | >10000 |
| 460 | 395 | >10000 | 5363 | >10000 |
| 461 | 20 | 1563 | 389 | >10000 |
| 462 | 20 | 873 | 188 | >10000 |
| 463 | 2141 | >10000 | >10000 | >10000 |
| 464 | 4656 | >10000 | >10000 | >10000 |
| 465 | 54 | 5998 | 859 | >10000 |
| 466 | 73 | 2705 | 1261 | >10000 |
| 467 | 51 | 1597 | 518 | >10000 |
| 468 | 127 | 1530 | 1218 | >10000 |
| 469 | 102 | 2391 | 1037 | >10000 |
| 470 | 25 | 620 | 147 | >10000 |
| 471 | 33 | 631 | 349 | >10000 |
| 472 | 5673 | >10000 | 7204 | >10000 |
| 473 | 90 | 6471 | 1931 | >10000 |
| 474 | 1120 | >10000 | >10000 | >10000 |
| 475 | 462 | 6670 | 6848 | >10000 |
| 476 | 480 | 693 | 486 | 7284 |
| 477 | 261 | >10000 | 2634 | >10000 |
| 478 | 281 | >10000 | 2194 | >10000 |
| 479 | 11 | 169 | 24 | 3404 |
| 480 | 11 | 145 | 17 | 3751 |
| 481 | 1367 | >10000 | 3533 | >10000 |
| 482 | 3792 | >10000 | >10000 | >10000 |

Selected compounds were assessed for their ability to inhibit IL-12 signaling in a human whole blood flow cytometry assay. IL-12 signals through TYK2 and JAK2.

Human Whole Blood IL-12 Induced STAT4 Phosphorylation Assay

Test articles were prepared as 30 mM stocks in DMSO. An 11-point 2.5 dilution series was created in DMSO with a top concentration of 10 mM. Further dilution was done by adding 4 µL of the above test article solutions into 96 µL of PBS with a top concentration of 400 µM. Human whole blood was collected from healthy donors via vein puncture into Vacutainer collection tubes containing sodium heparin (Catalog No. 366480; Becton Dickinson, Franklin Lakes, N.J.). Blood was warmed to 37° C. prior to use. Human whole blood was aliquoted (90 mL/well) in 96-well, deep-well, V-bottom plates and treated with compounds at 11 different concentrations (0.2% DMSO final) at 37° C. for 60 minutes. This was followed by a challenge with IL-12 (5 mL/well; final, 5 ng/mL) for 15 minutes. Samples were treated with warm 1× Lyse/Fix buffer (700 mL/well) to terminate activation and further incubated at 37° C. for 20 minutes to lyse red blood cells. Plates were centrifuged at 300×g for 5 minutes, supernatant was aspirated, and cells were washed with 800 mL per well of staining buffer (PBS containing 0.5% fetal bovine serum and 0.01% sodium azide). The washed cell pellets were resuspended with 350 mL/well of pre-chilled 90% methanol, and incubated at 4° C. for 30 minutes. Plates were centrifuged at 300×g for 5 minutes, supernatant containing 90% methanol was aspirated, and cells were washed with 800 mL /well of staining buffer. Cell pellets were resuspended in staining buffer containing anti-pSTAT4-AlexaFluor647 (1 to 150 dilution, 150 mL/well), and incubated at room temperature in the dark overnight.

Samples were transferred to 96-well U-bottom plates and flow cytometric analysis was performed on a FACSCalibur or LSRFortessa equipped with a HTS plate loader (BD Biosciences). The lymphocyte population was gated for histogram analysis of pSTAT4. Background fluorescence was defined using unstimulated cells and a gate was placed at the foot of the peak to include ~0.5% gated population. The histogram statistical analysis was performed using CellQuestÓ Pro version 5.2.1 (BD Biosciences) or FACS-Diva version 6.2 (BD Biosciences) software. Relative fluorescence unit (RFU), which measures the level of phospho STAT4, was calculated by multiplying the percent positive population and its mean fluorescence. Data from 11 compound concentrations (singlicate at each concentration) was normalized as a percentage of control based on the formula:

% of Control=100'$(A-B)/(C-B)$ where A is the RFU from wells containing compound and IL-12, B is the RFU from wells without IL-12 and compound (minimum fluorescence) and C is the RFU from wells containing only IL-12 (maximum fluorescence). Inhibition curves and $IC_{50}$ values were determined using the Prism version 5 software (GraphPad, La Jolla, Calif.).

| Example No. | Human whole blood IL-12 (nM) |
|---|---|
| 41 | 76 |
| 78 | 76 |
| 103 | 40 |
| 120 | 44 |
| 315 | 123 |
| 458 | 177 |

What is claimed is:

1. A compound having the structure:

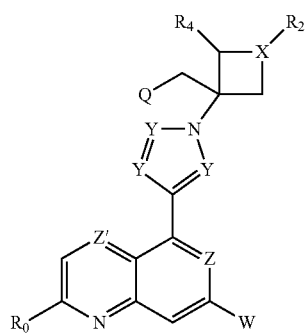

(I)

or a pharmaceutically acceptable salt thereof, or a pharmaceutically acceptable solvate of said compound or pharmaceutically acceptable salt, wherein:

W is H, halo, or is selected from the group consisting of:

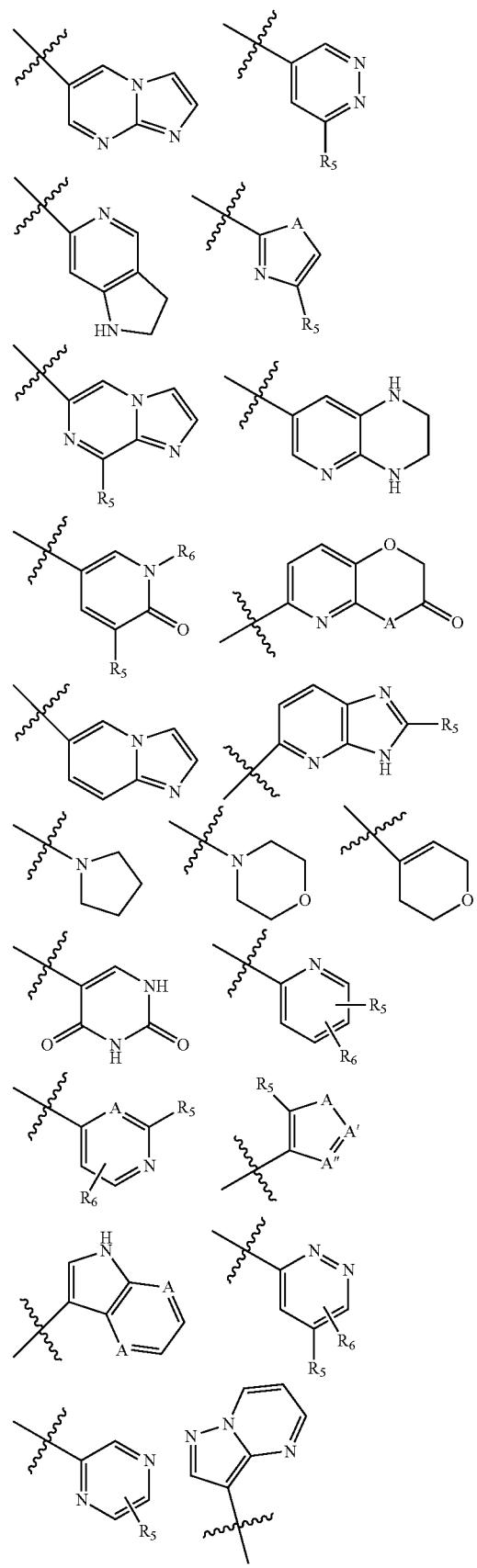

-continued

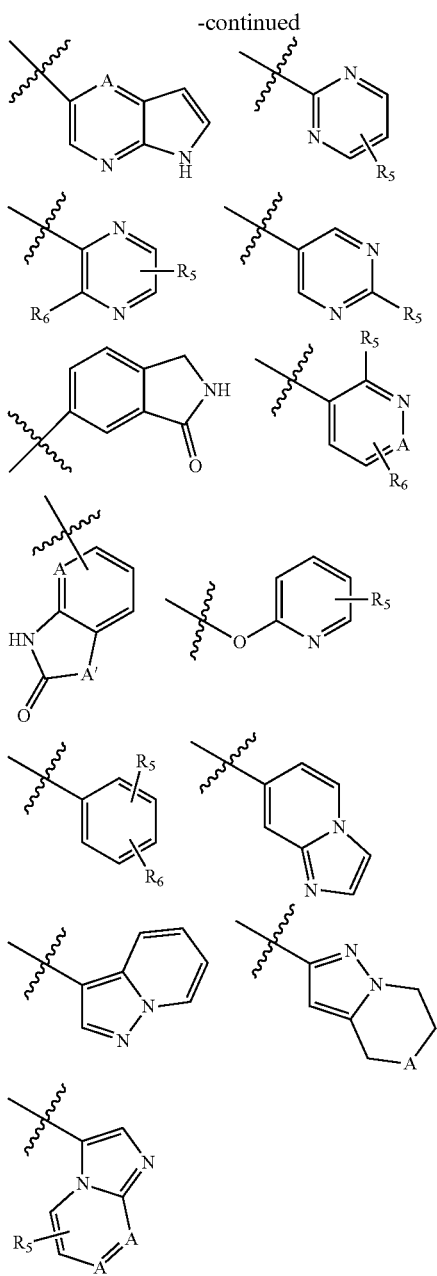

A, A' and A" are independently O, S, C═O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C═O; where C$_1$-C$_6$ alkyl is optionally substituted by OH, halo, N(C$_1$-C$_6$ alkyl) and heterocyclic;

R$_0$ is H, D or C$_1$-C$_6$ alkyl-;

Y, Z, and Z' are independently C—R$_1$, or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-;

Y' is O, C—R$_1$ or N, where R$_1$ is H, halo, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)- or hydroxy(C$_1$-C$_6$ alkyl)-;

Q is CN or CONH$_2$;

R$_2$ is selected from the group consisting of H, C$_1$-C$_6$ alkyl-, C$_1$-C$_6$ alkoxy-, hydroxy(C$_1$-C$_6$ alkyl)-, phenyl(C$_1$-C$_6$ alkyl)-, C$_3$-C$_8$ cycloalkyl, halo(C$_3$-C$_8$ cycloalkyl), spirocyclic, formyl, heteroaryl, heterocyclic, —COR, —OCOR, —COOR, —NR$_7$COR, CONR$_7$R$_8$, and —(CH$_2$)$_n$—W', where W' is cyano, hydroxy, C$_3$-C$_8$ cycloalkyl, —SO$_2$NR$_7$R$_8$, and —SO$_2$-R$_9$, where R$_9$ is C$_1$-C$_6$ alkyl, C$_3$-C$_8$ cycloalkyl, heteroaryl, or heterocyclic; wherein each of said alkyl, cycloalkyl, heterocyclic, or heteroaryl may be unsubstituted or substituted by halo, cyano, hydroxy, or C$_1$-C$_6$ alkyl; or, R$_2$ and R$_3$ when taken together forms a C$_3$-C$_8$ cycloalkyl group or C$_4$-C$_8$ heterocyclic group; wherein heterocyclic or heteroaryl group may be substituted by C$_1$-C$_6$ alkyl, halo or hydroxy;

X is C—R$_3$ or N, where R$_3$ may be H or C$_1$-C$_6$ alkyl;

R$_4$, R$_5$ and R$_6$ are independently H, halo, amino, —OH, —CO$_2$H, —CONH$_2$, C$_1$-C$_6$ alkyl, C$_1$-C$_6$ alkoxy-, —hydroxy(C$_1$-C$_6$ alkoxy)-, hydroxy(C$_1$-C$_6$ alkoxy)-, heteroaryl-, heterocyclic-, —SO$_2$NH$_2$, —NHSO$_2$(C$_1$-C$_6$ alkyl), —NHCO(C$_1$-C$_6$ alkyl), —NHCO$_2$(C$_1$-C$_6$ alkyl), —SO$_2$(C$_1$-C$_6$ alkyl), amino(C$_1$-C$_6$ alkoxy), amino(C$_1$-C$_6$ alkyl)- or hydroxy(C$_1$-C$_6$ alkyl)-;

R, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl; and, n is 0, 1, 2 or 3.

2. The compound of claim 1 wherein X is C.

3. The compound of claim 1 wherein R$_2$ is CN and R$_4$ is H.

4. The compound of claim 1 wherein Y is CH or N.

5. The compound of claim 1 wherein Z is N and Z' is CH.

6. The compound of claim 1 having the structure (Ia):

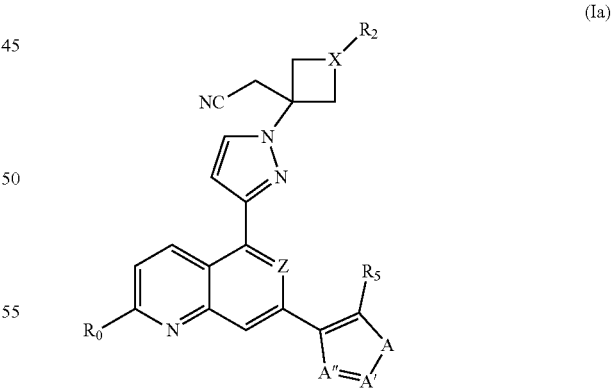

(Ia)

or a pharmaceutically acceptable salt thereof, or a pharmaceutically acceptable solvate of said compound or pharmaceutically acceptable salt, wherein:

A, A' and A" are independently O, S, C═O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy($C_1$-$C_6$ alkyl)-, or hydroxy(halo-$C_1$-$C_6$ alkyl)-, where each said moiety may be present or absent, and is present where the rules of valency permit, subject to the proviso that not more than one of A, A' and A" is O, S or C=O; where $C_1$-$C_6$ alkyl is optionally substituted by OH, halo, N($C_1$-$C_6$ alkyl) and heterocyclic;

$R_0$ is H, D or $C_1$-$C_6$ alkyl-;

Z is C—$R_1$ or N, where $R_1$ is H, halo, amino, —$NR_7COR_6$, $COR_6$, —$CONR_7R_8$, —$NHSO_2$($C_1$-$C_6$ alkyl), $C_1$-$C_6$ alkyl, halo, amino($C_1$-$C_6$ alkyl)- or hydroxy($C_1$-$C_6$ alkyl)-; Z" and Z''' are independently C—R' or N—R";

$R_5$ and $R_6$ are independently H, halo, amino, —OH, —$CO_2H$, —$CONH_2$, $C_1$-$C_6$ alkyl, $C_1$-$C_6$ alkoxy-, —hydroxy($C_1$-$C_6$ alkoxy)-, hydroxy($C_1$-$C_6$ alkoxy)-, heteroaryl-, heterocyclic-, —$SO_2NH_2$, —$NHSO_2$($C_1$-$C_6$ alkyl), —$NHCO$($C_1$-$C_6$ alkyl), —$NHCO_2$($C_1$-$C_6$ alkyl), —$SO_2$($C_1$-$C_6$ alkyl), amino($C_1$-$C_6$ alkoxy), amino($C_1$-$C_6$ alkyl)- or hydroxy($C_1$-$C_6$ alkyl)-; and, $R_7$ and $R_8$ are each independently H, $C_1$-$C_6$ alkyl, $C_1$-$C_4$ alkoxy($C_1$-$C_6$ alkyl) or $C_3$-$C_8$ cycloalkyl, said $C_1$-$C_6$ alkyl is optionally substituted by halo, CN or hydroxy; or, $R_7$ and $R_8$ together with the atom bonded thereto form a 5- or 6-membered ring, said ring being optionally substituted by halo, hydroxy, CN, or $C_1$-$C_6$ alkyl.

7. The compound of claim 1 having the structure (Ib):

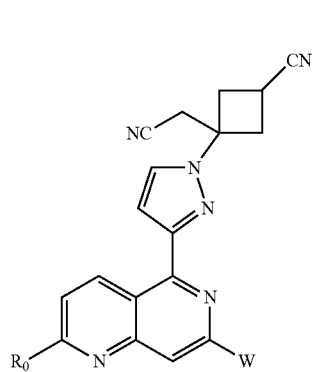

(Ib)

or a pharmaceutically acceptable salt thereof, or a pharmaceutically acceptable solvate of said compound or pharmaceutically acceptable salt, wherein:

W is H, halo, or is selected from the group consisting of:

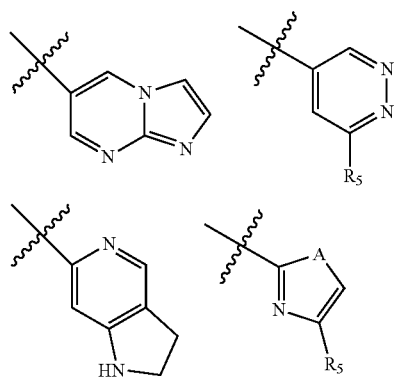

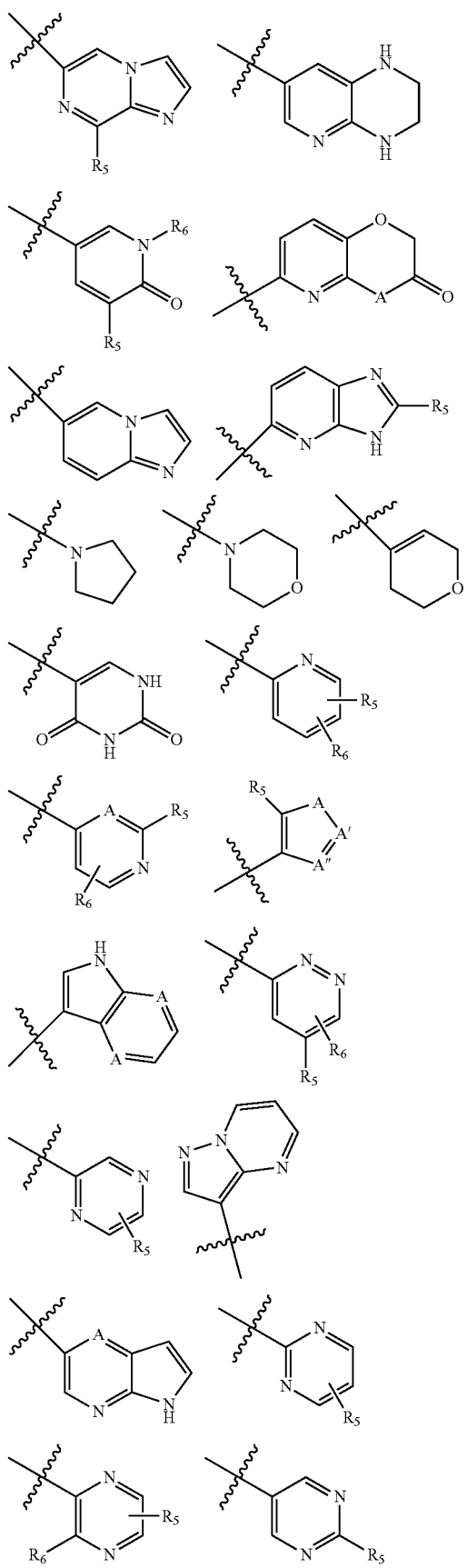

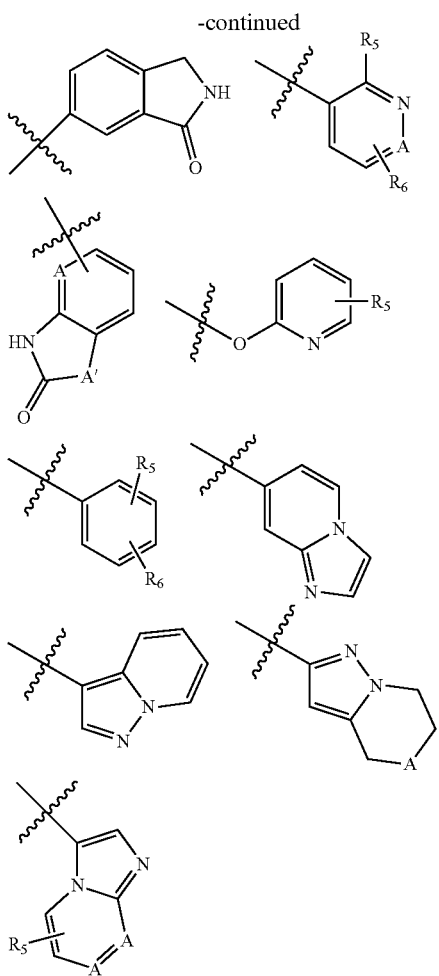

A, A' and A" are independently O, S, C=O, C—R', N or N—R", where R' and R" may independently be H, amino, —NR$_7$COR$_6$, COR$_6$, —CONR$_7$R$_8$, —NHSO$_2$(C$_1$-C$_6$ alkyl), C$_1$-C$_6$ alkyl, halo, amino(C$_1$-C$_6$ alkyl)-, C$_3$-C$_8$ cycloalkyl, heteroaryl, heterocyclic, heterocyclic(C$_1$-C$_6$ alk-yl)-, hydroxy(C$_1$-C$_6$ alkyl)-, or hydroxy(halo-C$_1$-C$_6$ alkyl)-, where each said moiety may be present or absent, and is present where the rules of valency permit, subject to the proviso that not more than one of A, A' and A" is O, S or C=O; where C$_1$-C$_6$ alkyl is optionally substituted by OH, halo, N(C$_1$-C$_6$ alkyl) and heterocyclic;

R$_0$ is H, D or C$_1$-C$_6$ alkyl-;

R$_5$ and R$_6$ are independently H, halo, amino, —OH, —CO$_2$H, —CONH$_2$, C$_1$-C$_6$ alkyl, C$_1$-C$_6$ alkoxy-, hydroxy(C$_1$-C$_6$ alkoxy)-, hydroxy(C$_1$-C$_6$ alkoxy)-, heteroaryl-, heterocyclic-, —SO$_2$NH$_2$, —NHSO$_2$(C$_1$-C$_6$ alkyl), —NHCO(C$_1$-C$_6$ alkyl), —NHCO$_2$(C$_1$-C$_6$ alkyl), —SO$_2$(C$_1$-C$_6$ alkyl), amino(C$_1$-C$_6$ alkoxy), amino(C$_1$-C$_6$ alkyl)- or hydroxy(C$_1$-C$_6$ alkyl)-; and, R$_7$ and R$_8$ are each independently H, C$_1$-C$_6$ alkyl, C$_1$-C$_4$ alkoxy(C$_1$-C$_6$ alkyl) or C$_3$-C$_8$ cycloalkyl, said C$_1$-C$_6$ alkyl is optionally substituted by halo, CN or hydroxy; or, R$_7$ and R$_8$ together with the atom bonded thereto form a 5- or 6-membered ring, said ring being optionally substituted by halo, hydroxy, CN, or C$_1$-C$_6$ alkyl.

8. The compound of claim 1 selected from the group consisting of:

[3-{4-[7-(1H-pyrazol-4-yl)-1,6-naphthyridin-5-yl]-1H-pyrazol-1-yl}-1-(2,2,2-trifluoroethyl)azetidin-3-yl]acetonitrile;

2,2'-(cis-1-{4-[7-(1H-pyrazol-4-yl)-1,6-naphthyridin-5-yl]-1H-pyrazol-1-yl}cyclobutane-1,3-diyl)diacetonitrile;

[3-{4-[7-(1-methyl-1H-pyrazol-4-yl)-1,6-naphthyridin-5-yl]-1H-pyrazol-1-yl}-1-(2,2,2-trifluoroethyl)azetidin-3-yl]acetonitrile;

cis-3-(cyanomethyl)-3-(4-{7-[1-(2-hydroxyethyl)-1H-pyrazol-4-yl]-1,6-naphthyridin-5-yl}-1H-pyrazol-1-yl)cyclobutanecarbonitrile;

[3-(4-{7-[1-(oxetan-3-yl)-1H-pyrazol-4-yl]-1,6-naphthyridin-5-yl}-1H-pyrazol-1-yl)-1-(2,2,2-trifluoroethyl)azetidin-3-yl]acetonitrile;

[3-(4-{7-[1-(tetrahydro-2H-pyran-4-yl)-1H-pyrazol-4-yl]-1,6-naphthyridin-5-yl}-1H-pyrazol-1-yl)-1-(2,2,2-trifluoroethyl)azetidin-3-yl]acetonitrile;

[trans-1-(4-{7-[3-(hydroxymethyl)-1H-pyrazol-5-yl]-1,6-naphthyridin-5-yl}-1H-pyrazol-1-yl)-3-methoxycyclobutyl]acetonitrile;

[3-{3-[7-(1H-pyrazol-3-yl)-1,6-naphthyridin-5-yl]-1H-pyrazol-1-yl}-1-(2,2,2-trifluoroethyl)azetidin-3-yl]acetonitrile;

[1-(methylsulfonyl)-3-{3-[7-(1H-pyrazol-5-yl)-1,6-naphthyridin-5-yl]-1H-pyrazol-1-yl}azetidin-3-yl]acetonitrile;

[1-(cyclopropylsulfonyl)-3-{3-[7-(1H-pyrazol-5-yl)-1,6-naphthyridin-5-yl]-1H-pyrazol-1-yl}azetidin-3-yl]acetonitrile;

[1-(oxetan-3-ylsulfonyl)-3-{3-[7-(1H-pyrazol-5-yl)-1,6-naphthyridin-5-yl]-1H-pyrazol-1-yl}azetidin-3-yl]acetonitrile;

trans-3-(cyanomethyl)-3-{3-[7-(1H-pyrazol-5-yl)-1,6-naphthyridin-5-yl]-1H-pyrazol-1-yl}cyclobutanecarbonitrile;

cis-3-(cyanomethyl)-3-{3-[7-(1H-pyrazol-5-yl)-1,6-naphthyridin-5-yl]-1H-pyrazol-1-yl}cyclobutanecarbonitrile;

2,2'-(cis-1-{3-[7-(1H-pyrazol-5-yl)-1,6-naphthyridin-5-yl]-1H-pyrazol-1-yl}cyclobutane-1,3-diyl)diacetonitrile;

cis-3-(cyanomethyl)-1-methyl-3-{3-[7-(1H-pyrazol-3-yl)-1,6-naphthyridin-5-yl]-1H-pyrazol-1-yl}cyclobutanecarbonitrile;

trans-3-{3-[7-(5-amino-1H-pyrazol-3-yl)-1,6-naphthyridin-5-yl]-1H-pyrazol-1-yl}-3-(cyanomethyl)cyclobutanecarbonitrile;

[3-{3-[7-(5-methyl-1H-pyrazol-3-yl)-1,6-naphthyridin-5-yl]-1H-pyrazol-1-yl}-1-(2,2,2-trifluoroethyl)azetidin-3-yl]acetonitrile;

trans-3-(cyanomethyl)-3-{3-[7-(5-methyl-1H-pyrazol-3-yl)-1,6-naphthyridin-5-yl]-1H-pyrazol-1-yl}cyclobutanecarbonitrile;

cis-3-(cyanomethyl)-3-{3-[7-(5-methyl-1H-pyrazol-3-yl)-1,6-naphthyridin-5-yl]-1H-pyrazol-1-yl}cyclobutanecarbonitrile;

cis-3-(cyanomethyl)-1-methyl-3-{3-[7-(5-methyl-1H-pyrazol-3-yl)-1,6-naphthyridin-5-yl]-1H-pyrazol-1-yl}cyclobutanecarbonitrile;

trans-3-(cyanomethyl)-3-(3-{7-[5-(hydroxymethyl)-1H-pyrazol-3-yl]-1,6-naphthyridin-5-yl}-1H-pyrazol-1-yl)cyclobutanecarbonitrile;

cis-3-(cyanomethyl)-3-(3-{7-[5-(hydroxymethyl)-1H-pyrazol-3-yl]-1,6-naphthyridin-5-yl}-1H-pyrazol-1-yl)cyclobutanecarbonitrile;

[cis-1-(3-{7-[3-(hydroxymethyl)-1H-pyrazol-5-yl]-1,6-naphthyridin-5-yl}-1H-pyrazol-1-yl)-3-methoxycyclobutyl]acetonitrile;

(cis-1-{3-[7-(5-amino-1H-pyrazol-3-yl)-1,6-naphthyridin-5-yl]-1H-pyrazol-1-yl}-3-methoxycyclobutyl)acetonitrile;

(trans-1-{3-[7-(5-amino-1H-pyrazol-3-yl)-1,6-naphthyridin-5-yl]-1H-pyrazol-1-yl}-3-methoxycyclobutyl)acetonitrile;

trans-3-(cyanomethyl)-3-{3-[7-(1,5-dimethyl-1H-pyrazol-3-yl)-1,6-naphthyridin-5-yl]-1H-pyrazol-1-yl}cyclobutanecarbonitrile;

cis-3-(cyanomethyl)-3-{3-[7-(1,5-dimethyl-1H-pyrazol-3-yl)-1,6-naphthyridin-5-yl]-1H-pyrazol-1-yl}cyclobutanecarbonitrile;

cis-3-(cyanomethyl)-3-(3-{7-[3-(hydroxymethyl)-1-methyl-1H-pyrazol-5-yl]-1,6-naphthyridin-5-yl}-1H-pyrazol-1-yl)cyclobutanecarbonitrile;

cis-3-(cyanomethyl)-3-(3-{7-[5-(hydroxymethyl)-1-methyl-1H-pyrazol-3-yl]-1,6-naphthyridin-5-yl}-1H-pyrazol-1-yl)cyclobutanecarbonitrile;

trans-3-{3-[7-(5-amino-1-methyl-1H-pyrazol-3-yl)-1,6-naphthyridin-5-yl]-1H-pyrazol-1-yl}-3-(cyanomethyl)cyclobutanecarbonitrile;

cis-3-{3-[7-(5-amino-1-methyl-1H-pyrazol-3-yl)-1,6-naphthyridin-5-yl]-1H-pyrazol-1-yl}-3-(cyanomethyl)cyclobutanecarbonitrile;

cis-3-{3-[7-(5-amino-1-methyl-1H-pyrazol-3-yl)-1,6-naphthyridin-5-yl]-1H-pyrazol-1-yl}-3-(cyanomethyl)-1-methylcyclobutanecarbonitrile;

cis-3-(cyanomethyl)-3-{3-[7-(4,5,6,7-tetrahydropyrazolo[1,5-a]pyrazin-2-yl)-1,6-naphthyridin-5-yl]-1H-pyrazol-1-yl}cyclobutanecarbonitrile;

trans-3-(cyanomethyl)-3-{3-[7-(4,5,6,7-tetrahydropyrazolo[1,5-a]pyrazin-2-yl)-1,6-naphthyridin-5-yl]-1H-pyrazol-1-yl}cyclobutanecarbonitrile;

[3-{3-[7-(1H-pyrazol-4-yl)-1,6-naphthyridin-5-yl]-1H-pyrazol-1-yl}-1-(2,2,2-trifluoroethyl)azetidin-3-yl]acetonitrile;

[1-(methylsulfonyl)-3-{3-[7-(1H-pyrazol-4-yl)-1,6-naphthyridin-5-yl]-1H-pyrazol-1-yl}azetidin-3-yl]acetonitrile;

cis-3-(cyanomethyl)-3-{3-[7-(1H-pyrazol-4-yl)-1,6-naphthyridin-5-yl]-1H-pyrazol-1-yl}cyclobutanecarbonitrile;

trans-3-(cyanomethyl)-3-{3-[7-(1H-pyrazol-4-yl)-1,6-naphthyridin-5-yl]-1H-pyrazol-1-yl}cyclobutanecarbonitrile;

2,2'-(cis-1-{3-[7-(1H-pyrazol-4-yl)-1,6-naphthyridin-5-yl]-1H-pyrazol-1-yl}cyclobutane-1,3-diyl)diacetonitrile;

(cis-3-methoxy-1-{3-[7-(1H-pyrazol-4-yl)-1,6-naphthyridin-5-yl]-1H-pyrazol-1-yl}cyclobutyl)acetonitrile;

cis-3-(cyanomethyl)-1-methyl-3-{3-[7-(1H-pyrazol-4-yl)-1,6-naphthyridin-5-yl]-1H-pyrazol-1-yl}cyclobutanecarbonitrile;

[cis-3-(1H-pyrazol-5-yl)-1-{3-[7-(1H-pyrazol-4-yl)-1,6-naphthyridin-5-yl]-1H-pyrazol-1-yl}cyclobutyl]acetonitrile;

cis-3-(cyanomethyl)-3-{3-[7-(3-methyl-1H-pyrazol-4-yl)-1,6-naphthyridin-5-yl]-1H-pyrazol-1-yl}cyclobutanecarbonitrile;

trans-3-(cyanomethyl)-3-(3-{7-[5-(hydroxymethyl)-1H-pyrazol-4-yl]-1,6-naphthyridin-5-yl}-1H-pyrazol-1-yl)cyclobutanecarbonitrile;

cis-3-(cyanomethyl)-3-(3-{7-[5-(hydroxymethyl)-1H-pyrazol-4-yl]-1,6-naphthyridin-5-yl}-1H-pyrazol-1-yl)cyclobutanecarbonitrile;

[3-{3-[7-(3-amino-1H-pyrazol-4-yl)-1,6-naphthyridin-5-yl]-1H-pyrazol-1-yl}-1-(methylsulfonyl)azetidin-3-yl]acetonitrile;

(trans-1-{3-[7-(3-amino-1H-pyrazol-4-yl)-1,6-naphthyridin-5-yl]-1H-pyrazol-1-yl}-3-methoxycyclobutyl)acetonitrile;

(cis-1-{3-[7-(3-amino-1H-pyrazol-4-yl)-1,6-naphthyridin-5-yl]-1H-pyrazol-1-yl}-3-methoxycyclobutyl)acetonitrile;

cis-3-{3-[7-(3-amino-1H-pyrazol-4-yl)-1,6-naphthyridin-5-yl]-1H-pyrazol-1-yl}-3-(cyanomethyl)cyclobutanecarbonitrile;

trans-3-{3-[7-(3-amino-1H-pyrazol-4-yl)-1,6-naphthyridin-5-yl]-1H-pyrazol-1-yl}-3-(cyanomethyl)cyclobutanecarbonitrile;

[3-{3-[7-(1-methyl-1H-pyrazol-4-yl)-1,6-naphthyridin-5-yl]-1H-pyrazol-1-yl}-1-(2,2,2-trifluoroethyl)azetidin-3-yl]acetonitrile;

2,2'-(3-{3-[7-(1-methyl-1H-pyrazol-4-yl)-1,6-naphthyridin-5-yl]-1H-pyrazol-1-yl}azetidine-1,3-diyl)diacetonitrile;

trans-3-(cyanomethyl)-3-{3-[7-(1-methyl-1H-pyrazol-4-yl)-1,6-naphthyridin-5-yl]-1H-pyrazol-1-yl}cyclobutanecarbonitrile;

cis-3-(cyanomethyl)-3-{3-[7-(1-methyl-1H-pyrazol-4-yl)-1,6-naphthyridin-5-yl]-1H-pyrazol-1-yl}cyclobutanecarbonitrile;

[3-{3-[7-(1-methyl-1H-pyrazol-4-yl)-1,6-naphthyridin-5-yl]-1H-pyrazol-1-yl}-1-(methylsulfonyl)azetidin-3-yl]acetonitrile;

[1-(ethylsulfonyl)-3-{3-[7-(1-methyl-1H-pyrazol-4-yl)-1,6-naphthyridin-5-yl]-1H-pyrazol-1-yl}azetidin-3-yl]acetonitrile;

[1-(cyclopropylsulfonyl)-3-{3-[7-(1-methyl-1H-pyrazol-4-yl)-1,6-naphthyridin-5-yl]-1H-pyrazol-1-yl}azetidin-3-yl]acetonitrile;

3-(cyanomethyl)-3-{3-[7-(1-methyl-1H-pyrazol-4-yl)-1,6-naphthyridin-5-yl]-1H-pyrazol-1-yl}azetidine-1-sulfonamide;

[3-{3-[7-(1-ethyl-1H-pyrazol-4-yl)-1,6-naphthyridin-5-yl]-1H-pyrazol-1-yl}-1-(2,2,2-trifluoroethyl)azetidin-3-yl]acetonitrile;

cis-3-(cyanomethyl)-3-{3-[7-(1-ethyl-1H-pyrazol-4-yl)-1,6-naphthyridin-5-yl]-1H-pyrazol-1-yl}cyclobutanecarbonitrile;

trans-3-(cyanomethyl)-3-{3-[7-(1-ethyl-1H-pyrazol-4-yl)-1,6-naphthyridin-5-yl]-1H-pyrazol-1-yl}cyclobutanecarbonitrile;

cis-3-(cyanomethyl)-3-[3-(7-{1-[2-(dimethylamino)ethyl]-1H-pyrazol-4-yl}-1,6-naphthyridin-5-yl)-1H-pyrazol-1-yl]cyclobutanecarbonitrile;

[3-(3-{7-[1-(piperidin-4-yl)-1H-pyrazol-4-yl]-1,6-naphthyridin-5-yl}-1H-pyrazol-1-yl)-1-(2,2,2-trifluoroethyl)azetidin-3-yl]acetonitrile;

[3-(3-{7-[1-(oxetan-3-yl)-1H-pyrazol-4-yl]-1,6-naphthyridin-5-yl}-1H-pyrazol-1-yl)-1-(2,2,2-trifluoroethyl)azetidin-3-yl]acetonitrile;

2,2'-[3-(3-{7-[1-(oxetan-3-yl)-1H-pyrazol-4-yl]-1,6-naphthyridin-5-yl}-1H-pyrazol-1-yl)azetidine-1,3-diyl]diacetonitrile;

[1-(methylsulfonyl)-3-(3-{7-[1-(oxetan-3-yl)-1H-pyrazol-4-yl]-1,6-naphthyridin-5-yl}-1H-pyrazol-1-yl)azetidin-3-yl]acetonitrile;

{1-(methylsulfonyl)-3-[3-(7-{1-[(3S)-tetrahydrofuran-3-yl]-1H-pyrazol-4-yl}-1,6-naphthyridin-5-yl)-1H-pyrazol-1-yl]azetidin-3-yl}acetonitrile;

{1-(methylsulfonyl)-3-[3-(7-{1-[(3R)-tetrahydrofuran-3-yl]-1H-pyrazol-4-yl}-1,6-naphthyridin-5-yl)-1H-pyrazol-1-yl]azetidin-3-yl}acetonitrile;

[3-(3-{7-[1-(2-hydroxyethyl)-1H-pyrazol-4-yl]-1,6-naphthyridin-5-yl}-1H-pyrazol-1-yl)-1-(methylsulfonyl)azetidin-3-yl]acetonitrile;

trans-3-(cyanomethyl)-3-(3-{7-[1-(2-hydroxyethyl)-1H-pyrazol-4-yl]-1,6-naphthyridin-5-yl}-1H-pyrazol-1-yl)cyclobutanecarbonitrile;

cis-3-(cyanomethyl)-3-(3-{7-[1-(2-hydroxyethyl)-1H-pyrazol-4-yl]-1,6-naphthyridin-5-yl}-1H-pyrazol-1-yl)cyclobutanecarbonitrile;

[3-(3-{7-[1-(1-chloro-3-hydroxypropan-2-yl)-1H-pyrazol-4-yl]-1,6-naphthyridin-5-yl}-1H-pyrazol-1-yl)-1-(methylsulfonyl)azetidin-3-yl]acetonitrile;

[1-(methylsulfonyl)-3-(3-{7-[1-(oxetan-3-ylmethyl)-1H-pyrazol-4-yl]-1,6-naphthyridin-5-yl}-1H-pyrazol-1-yl)azetidin-3-yl]acetonitrile;

trans-3-(cyanomethyl)-3-(3-{7-[3-(hydroxymethyl)-1-methyl-1H-pyrazol-4-yl]-1,6-naphthyridin-5-yl}-1H-pyrazol-1-yl)cyclobutanecarbonitrile;

trans-3-(cyanomethyl)-3-(3-{7-[5-(hydroxymethyl)-1-methyl-1H-pyrazol-4-yl]-1,6-naphthyridin-5-yl}-1H-pyrazol-1-yl)cyclobutanecarbonitrile;

[3-{3-[7-(3-amino-1-methyl-1H-pyrazol-4-yl)-1,6-naphthyridin-5-yl]-1H-pyrazol-1-yl}-1-(methylsulfonyl)azetidin-3-yl]acetonitrile;

trans-3-{3-[7-(3-amino-1-methyl-1H-pyrazol-4-yl)-1,6-naphthyridin-5-yl]-1H-pyrazol-1-yl}-3-(cyanomethyl)cyclobutanecarbonitrile;

cis-3-{3-[7-(3-amino-1-methyl-1H-pyrazol-4-yl)-1,6-naphthyridin-5-yl]-1H-pyrazol-1-yl}-3-(cyanomethyl)cyclobutanecarbonitrile;

trans-3-{3-[7-(5-amino-1-methyl-1H-pyrazol-4-yl)-1,6-naphthyridin-5-yl]-1H-pyrazol-1-yl}-3-(cyanomethyl)cyclobutanecarbonitrile;

cis-3-{3-[7-(5-amino-1-methyl-1H-pyrazol-4-yl)-1,6-naphthyridin-5-yl]-1H-pyrazol-1-yl}-3-(cyanomethyl)cyclobutanecarbonitrile;

cis-3-(cyanomethyl)-3-(3-{7-[3-(hydroxymethyl)-1,2-oxazol-5-yl]-1,6-naphthyridin-5-yl}-1H-pyrazol-1-yl)cyclobutanecarbonitrile;

[3-{3-[7-(1H-pyrrolo[3,2-b]pyridin-6-yl)-1,6-naphthyridin-5-yl]-1H-pyrazol-1-yl}-1-(2,2,2-trifluoroethyl)azetidin-3-yl]acetonitrile;

[1-(methylsulfonyl)-3-{3-[7-(1H-pyrrolo[2,3-b]pyridin-3-yl)-1,6-naphthyridin-5-yl]-1H-pyrazol-1-yl}azetidin-3-yl]acetonitrile;

[1-(methylsulfonyl)-3-{3-[7-(pyrazolo[1,5-a]pyridin-3-yl)-1,6-naphthyridin-5-yl]-1H-pyrazol-1-yl}azetidin-3-yl]acetonitrile;

[3-{3-[7-(imidazo[1,2-a]pyridin-7-yl)-1,6-naphthyridin-5-yl]-1H-pyrazol-1-yl}-1-(methylsulfonyl)azetidin-3-yl]acetonitrile;

[1-(methylsulfonyl)-3-{3-[7-(1H-pyrazolo[4,3-b]pyridin-6-yl)-1,6-naphthyridin-5-yl]-1H-pyrazol-1-yl}azetidin-3-yl]acetonitrile;

[1-(methylsulfonyl)-3-{3-[7-(2-oxo-2,3-dihydro-1H-imidazo[4,5-b]pyridin-6-yl)-1,6-naphthyridin-5-yl]-1H-pyrazol-1-yl}azetidin-3-yl]acetonitrile;

[3-{3-[7-(pyridin-4-yl)-1,6-naphthyridin-5-yl]-1H-pyrazol-1-yl}-1-(2,2,2-trifluoroethyl)azetidin-3-yl]acetonitrile;

[3-{3-[7-(2-methylpyridin-4-yl)-1,6-naphthyridin-5-yl]-1H-pyrazol-1-yl}-1-(methylsulfonyl)azetidin-3-yl]acetonitrile;

[3-{3-[7-(6-hydroxypyridin-2-yl)-1,6-naphthyridin-5-yl]-1H-pyrazol-1-yl}-1-(methylsulfonyl)azetidin-3-yl]acetonitrile;

cis-3-(cyanomethyl)-3-{3-[7-(6-hydroxypyridin-2-yl)-1,6-naphthyridin-5-yl]-1H-pyrazol-1-yl}cyclobutanecarbonitrile;

[3-{3-[7-(6-hydroxypyridin-3-yl)-1,6-naphthyridin-5-yl]-1H-pyrazol-1-yl}-1-(2,2,2-trifluoroethyl)azetidin-3-yl]acetonitrile;

[3-{3-[7-(6-aminopyridin-3-yl)-1,6-naphthyridin-5-yl]-1H-pyrazol-1-yl}-1-(methylsulfonyl)azetidin-3-yl]acetonitrile;

cis-3-{3-[7-(6-aminopyridin-3-yl)-1,6-naphthyridin-5-yl]-1H-pyrazol-1-yl}-3-(cyanomethyl)cyclobutanecarbonitrile;

trans-3-{3-[7-(6-aminopyridin-3-yl)-1,6-naphthyridin-5-yl]-1H-pyrazol-1-yl}-3-(cyanomethyl)cyclobutanecarbonitrile;

[3-{3-[7-(2-aminopyridin-4-yl)-1,6-naphthyridin-5-yl]-1H-pyrazol-1-yl}-1-(2,2,2-trifluoroethyl)azetidin-3-yl]acetonitrile;

cis-3-{3-[7-(2-aminopyridin-4-yl)-1,6-naphthyridin-5-yl]-1H-pyrazol-1-yl}-3-(cyanomethyl)cyclobutanecarbonitrile;

trans-3-{3-[7-(2-aminopyridin-4-yl)-1,6-naphthyridin-5-yl]-1H-pyrazol-1-yl}-3-(cyanomethyl)cyclobutanecarbonitrile;

cis-3-{3-[7-(2-aminopyridin-4-yl)-1,6-naphthyridin-5-yl]-1H-pyrazol-1-yl}-3-(cyanomethyl)-1-methylcyclobutanecarbonitrile;

[3-(3-{7-[6-(dimethylamino)pyridin-3-yl]-1,6-naphthyridin-5-yl}-1H-pyrazol-1-yl)-1-(methylsulfonyl)azetidin-3-yl]acetonitrile;

N-[5-(5-{1-[3-(cyanomethyl)-1-(methylsulfonyl)azetidin-3-yl]-1H-pyrazol-3-yl}-1,6-naphthyridin-7-yl)pyridin-2-yl]methanesulfonamide;

cis-3-(cyanomethyl)-3-(3-{7-[6-(methylsulfonyl)pyridin-3-yl]-1,6-naphthyridin-5-yl}-1H-pyrazol-1-yl)cyclobutanecarbonitrile;

5-(5-{1-[cis-3-cyano-1-(cyanomethyl)cyclobutyl]-1H-pyrazol-3-yl}-1,6-naphthyridin-7-yl)pyridine-2-sulfonamide;

cis-3-(cyanomethyl)-3-(3-{7-[2-(hydroxymethyl)pyridin-4-yl]-1,6-naphthyridin-5-yl}-1H-pyrazol-1-yl)cyclobutanecarbonitrile;

4-(5-{1-[cis-3-cyano-1-(cyanomethyl)cyclobutyl]-1H-pyrazol-3-yl}-1,6-naphthyridin-7-yl)pyridine-2-carboxamide;

[3-{3-[7-(2-amino-6-methylpyridin-3-yl)-1,6-naphthyridin-5-yl]-1H-pyrazol-1-yl}-1-(methylsulfonyl)azetidin-3-yl]acetonitrile;

cis-3-{3-[7-(2-amino-6-methylpyridin-4-yl)-1,6-naphthyridin-5-yl]-1H-pyrazol-1-yl}-3-(cyanomethyl)cyclobutanecarbonitrile;

cis-3-{3-[7-(5-amino-6-methoxypyridin-2-yl)-1,6-naphthyridin-5-yl]-1H-pyrazol-1-yl}-3-(cyanomethyl)cyclobutanecarbonitrile;

3-amino-6-(5-{1-[cis-3-cyano-1-(cyanomethyl)cyclobutyl]-1H-pyrazol-3-yl}-1,6-naphthyridin-7-yl)pyridine-2-carboxamide;

3-amino-6-(5-{1-[trans-3-cyano-1-(cyanomethyl)cyclobutyl]-1H-pyrazol-3-yl}-1,6-naphthyridin-7-yl)pyridine-2-carboxamide;

[3-{3-[7-(2,6-diaminopyridin-3-yl)-1,6-naphthyridin-5-yl]-1H-pyrazol-1-yl}-1-(methylsulfonyl)azetidin-3-yl]acetonitrile;

cis-3-{3-[7-(6-aminopyridazin-4-yl)-1,6-naphthyridin-5-yl]-1H-pyrazol-1-yl}-3-(cyanomethyl)cyclobutanecarbonitrile;

4-(5-{1-[trans-3-cyano-1-(cyanomethyl)cyclobutyl]-1H-pyrazol-3-yl}-1,6-naphthyridin-7-yl)pyrimidine-2-carboxamide;

[1-(methylsulfonyl)-3-{3-[7-(6-oxo-1,6-dihydropyridin-3-yl)-1,6-naphthyridin-5-yl]-1H-pyrazol-1-yl}azetidin-3-yl]acetonitrile;

[1-(cyclopropylsulfonyl)-3-{3-[7-(6-oxo-1,6-dihydropyridin-3-yl)-1,6-naphthyridin-5-yl]-1H-pyrazol-1-yl}azetidin-3-yl]acetonitrile;

(cis-3-methoxy-1-{3-[7-(6-oxo-1,6-dihydropyridin-3-yl)-1,6-naphthyridin-5-yl]-1H-pyrazol-1-yl}cyclobutyl)acetonitrile;

[3-{3-[7-(1-ethyl-6-oxo-1,6-dihydropyridin-3-yl)-1,6-naphthyridin-5-yl]-1H-pyrazol-1-yl}-1-(methylsulfonyl)azetidin-3-yl]acetonitrile;

[3-{3-[7-(2-hydroxyphenyl)-1,6-naphthyridin-5-yl]-1H-pyrazol-1-yl}-1-(methylsulfonyl)azetidin-3-yl]acetonitrile;

[3-{3-[7-(4-hydroxyphenyl)-1,6-naphthyridin-5-yl]-1H-pyrazol-1-yl}-1-(methylsulfonyl)azetidin-3-yl]acetonitrile;

N-[4-(5-{1-[cis-3-cyano-1-(cyanomethyl)cyclobutyl]-1H-pyrazol-3-yl}-1,6-naphthyridin-7-yl)phenyl]methanesulfonamide;

N-[4-(5-{1-[trans-3-cyano-1-(cyanomethyl)cyclobutyl]-1H-pyrazol-3-yl}-1,6-naphthyridin-7-yl)phenyl]methanesulfonamide;

[3-{3-[7-(4-fluoro-2-hydroxyphenyl)-1,6-naphthyridin-5-yl]-1H-pyrazol-1-yl}-1-(methylsulfonyl)azetidin-3-yl]acetonitrile;

[3-{3-[7-(3-fluoro-4-hydroxyphenyl)-1,6-naphthyridin-5-yl]-1H-pyrazol-1-yl}-1-(methylsulfonyl)azetidin-3-yl]acetonitrile;

cis-3-(cyanomethyl)-3-{5-methyl-3-[7-(1H-pyrazol-3-yl)-1,6-naphthyridin-5-yl]-1H-pyrazol-1-yl}cyclobutanecarbonitrile;

trans-3-(cyanomethyl)-3-{5-methyl-3-[7-(1H-pyrazol-3-yl)-1,6-naphthyridin-5-yl]-1H-pyrazol-1-yl}cyclobutanecarbonitrile;

trans-3-{3-[7-(5-amino-1-methyl-1H-pyrazol-3-yl)-1,6-naphthyridin-5-yl]-5-methyl-1H-pyrazol-1-yl}-3-(cyanomethyl)cyclobutanecarbonitrile;

cis-3-{3-[7-(5-amino-1-methyl-1H-pyrazol-3-yl)-1,6-naphthyridin-5-yl]-5-methyl-1H-pyrazol-1-yl}-3-(cyanomethyl)cyclobutanecarbonitrile;

trans-3-(cyanomethyl)-3-{5-methyl-3-[7-(1H-pyrazol-4-yl)-1,6-naphthyridin-5-yl]-1H-pyrazol-1-yl}cyclobutanecarbonitrile;

cis-3-(cyanomethyl)-3-{5-methyl-3-[7-(1H-pyrazol-4-yl)-1,6-naphthyridin-5-yl]-1H-pyrazol-1-yl}cyclobutanecarbonitrile;

trans-3-{3-[7-(5-amino-1H-pyrazol-4-yl)-1,6-naphthyridin-5-yl]-5-methyl-1H-pyrazol-1-yl}-3-(cyanomethyl)cyclobutanecarbonitrile;

[3-{4-[7-(1-methyl-1H-pyrazol-4-yl)-1,6-naphthyridin-5-yl]-1H-1,2,3-triazol-1-yl}-1-(2,2,2-trifluoroethyl)azetidin-3-yl]acetonitrile;

[1-(methylsulfonyl)-3-{4-[7-(1H-pyrazol-3-yl)-1,6-naphthyridin-5-yl]-2H-1,2,3-triazol-2-yl}azetidin-3-yl]acetonitrile;

2,2'-(3-{4-[7-(1-methyl-1H-pyrazol-4-yl)quinolin-5-yl]-1H-pyrazol-1-yl}azetidine-1,3-diyl)diacetonitrile;

[3-{4-[7-(1H-pyrazol-3-yl)quinolin-5-yl]-2H-1,2,3-triazol-2-yl}-1-(2,2,2-trifluoroethyl)azetidin-3-yl]acetonitrile;

[1-(methylsulfonyl)-3-{4-[7-(1H-pyrazol-3-yl)quinolin-5-yl]-2H-1,2,3-triazol-2-yl}azetidin-3-yl]acetonitrile;

[1-(cyclopropylsulfonyl)-3-{4-[7-(1H-pyrazol-3-yl)quinolin-5-yl]-2H-1,2,3-triazol-2-yl}azetidin-3-yl]acetonitrile;

3-(cyanomethyl)-3-{4-[7-(1H-pyrazol-3-yl)quinolin-5-yl]-2H-1,2,3-triazol-2-yl}azetidine-1-sulfonamide;

[1-(oxetan-3-ylsulfonyl)-3-{4-[7-(1H-pyrazol-5-yl)quinolin-5-yl]-2H-1,2,3-triazol-2-yl}azetidin-3-yl]acetonitrile;

trans-3-(cyanomethyl)-3-{4-[7-(1H-pyrazol-3-yl)quinolin-5-yl]-2H-1,2,3-triazol-2-yl}cyclobutanecarbonitrile;

cis-3-(cyanomethyl)-3-{4-[7-(1H-pyrazol-3-yl)quinolin-5-yl]-2H-1,2,3-triazol-2-yl}cyclobutanecarbonitrile;

(cis-3-methoxy-1-{4-[7-(1H-pyrazol-3-yl)quinolin-5-yl]-2H-1,2,3-triazol-2-yl}cyclobutyl)acetonitrile;

(trans-3-methoxy-1-{4-[7-(1H-pyrazol-3-yl)quinolin-5-yl]-2H-1,2,3-triazol-2-yl}cyclobutyl)acetonitrile;

trans-3-{4-[7-(5-amino-1H-pyrazol-3-yl)quinolin-5-yl]-2H-1,2,3-triazol-2-yl}-3-(cyanomethyl)cyclobutanecarbonitrile;

cis-3-{4-[7-(5-amino-1H-pyrazol-3-yl)quinolin-5-yl]-2H-1,2,3-triazol-2-yl}-3-(cyanomethyl)cyclobutanecarbonitrile;

trans-3-(cyanomethyl)-3-(4-{7-[5-(hydroxymethyl)-1H-pyrazol-3-yl]quinolin-5-yl}-2H-1,2,3-triazol-2-yl)cyclobutanecarbonitrile;

trans-3-(cyanomethyl)-3-(4-{7-[5-(hydroxymethyl)-1-methyl-1H-pyrazol-3-yl]quinolin-5-yl}-2H-1,2,3-triazol-2-yl)cyclobutanecarbonitrile;

[3-{4-[7-(1-methyl-1H-pyrazol-3-yl)quinolin-5-yl]-2H-1,2,3-triazol-2-yl}-1-(methylsulfonyl)azetidin-3-yl]acetonitrile;

trans-3-(cyanomethyl)-3-{4-[7-(1-methyl-1H-pyrazol-3-yl)quinolin-5-yl]-2H-1,2,3-triazol-2-yl}cyclobutanecarbonitrile;

cis-3-(cyanomethyl)-3-{4-[7-(1-methyl-1H-pyrazol-3-yl)quinolin-5-yl]-2H-1,2,3-triazol-2-yl}cyclobutanecarbonitrile;

[1-(methylsulfonyl)-3-{4-[7-(1H-pyrazol-4-yl)quinolin-5-yl]-2H-1,2,3-triazol-2-yl}azetidin-3-yl]acetonitrile;

trans-3-(cyanomethyl)-3-{4-[7-(1H-pyrazol-4-yl)quinolin-5-yl]-2H-1,2,3-triazol-2-yl}cyclobutanecarbonitrile;

cis-3-(cyanomethyl)-3-{4-[7-(1H-pyrazol-4-yl)quinolin-5-yl]-2H-1,2,3-triazol-2-yl}cyclobutanecarbonitrile;

cis-3-(cyanomethyl)-3-(4-{7-[3-(hydroxymethyl)-1H-pyrazol-4-yl]quinolin-5-yl}-2H-1,2,3-triazol-2-yl)cyclobutanecarbonitrile;

trans-3-{4-[7-(5-amino-1H-pyrazol-4-yl)quinolin-5-yl]-2H-1,2,3-triazol-2-yl}-3-(cyanomethyl)cyclobutanecarbonitrile;

cis-3-{4-[7-(5-amino-1H-pyrazol-4-yl)quinolin-5-yl]-2H-1,2,3-triazol-2-yl}-3-(cyanomethyl)cyclobutanecarbonitrile;

trans-3-(cyanomethyl)-3-{4-[7-(1-methyl-1H-pyrazol-4-yl)quinolin-5-yl]-2H-1,2,3-triazol-2-yl}cyclobutanecarbonitrile;

cis-3-(cyanomethyl)-3-{4-[7-(1-methyl-1H-pyrazol-4-yl)quinolin-5-yl]-2H-1,2,3-triazol-2-yl}cyclobutanecarbonitrile;

trans-3-(cyanomethyl)-3-(4-{7-[1-(2-hydroxyethyl)-1H-pyrazol-4-yl]quinolin-5-yl}-2H-1,2,3-triazol-2-yl)cyclobutanecarbonitrile;

cis-3-(cyanomethyl)-3-(4-{7-[1-(2-hydroxyethyl)-1H-pyrazol-4-yl]quinolin-5-yl}-2H-1,2,3-triazol-2-yl)cyclobutanecarbonitrile;

cis-3-{4-[7-(3-amino-1-methyl-1H-pyrazol-4-yl)quinolin-5-yl]-2H-1,2,3-triazol-2-yl}-3-(cyanomethyl)cyclobutanecarbonitrile;

trans-3-{4-[7-(3-amino-1-methyl-1H-pyrazol-4-yl)quinolin-5-yl]-2H-1,2,3-triazol-2-yl}-3-(cyanomethyl)cyclobutanecarbonitrile;

cis-3-(cyanomethyl)-3-{4-[7-(2-methyl-1H-imidazol-4-yl)quinolin-5-yl]-2H-1,2,3-triazol-2-yl}cyclobutanecarbonitrile;

trans-3-(cyanomethyl)-3-{4-[7-(2-methyl-1H-imidazol-4-yl)quinolin-5-yl]-2H-1,2,3-triazol-2-yl}cyclobutanecarbonitrile;

trans-3-(cyanomethyl)-3-{4-[7-(1-methyl-1H-1,2,3-triazol-4-yl)quinolin-5-yl]-2H-1,2,3-triazol-2-yl}cyclobutanecarbonitrile;

cis-3-(cyanomethyl)-3-(4-{7-[4-(hydroxymethyl)-1,3-thiazol-2-yl]quinolin-5-yl}-2H-1,2,3-triazol-2-yl)cyclobutanecarbonitrile;

cis-3-(cyanomethyl)-3-{4-[7-(pyridin-2-yl)quinolin-5-yl]-2H-1,2,3-triazol-2-yl}cyclobutanecarbonitrile;

cis-3-(cyanomethyl)-3-{4-[7-(5-fluoropyridin-2-yl)quinolin-5-yl]-2H-1,2,3-triazol-2-yl}cyclobutanecarbonitrile;

6-(5-{2-[trans-3-cyano-1-(cyanomethyl)cyclobutyl]-2H-1,2,3-triazol-4-yl}quinolin-7-yl)pyridine-2-carboxamide;

6-(5-{2-[cis-3-cyano-1-(cyanomethyl)cyclobutyl]-2H-1,2,3-triazol-4-yl}quinolin-7-yl)pyridine-2-carboxamide;

6-(5-{2-[cis-3-cyano-1-(cyanomethyl)cyclobutyl]-2H-1,2,3-triazol-4-yl}quinolin-7-yl)pyridine-3-carboxamide;

cis-3-{4-[7-(6-aminopyridin-2-yl)quinolin-5-yl]-2H-1,2,3-triazol-2-yl}-3-(cyanomethyl)cyclobutanecarbonitrile;

cis-3-{4-[7-(5-aminopyridin-2-yl)quinolin-5-yl]-2H-1,2,3-triazol-2-yl}-3-(cyanomethyl)cyclobutanecarbonitrile;

trans-3-{4-[7-(5-aminopyridin-2-yl)quinolin-5-yl]-2H-1,2,3-triazol-2-yl}-3-(cyanomethyl)cyclobutanecarbonitrile;

cis-3-{4-[7-(6-aminopyridin-3-yl)quinolin-5-yl]-2H-1,2,3-triazol-2-yl}-3-(cyanomethyl)cyclobutanecarbonitrile;

cis-3-(cyanomethyl)-3-(4-{7-[5-(methylsulfonyl)pyridin-2-yl]quinolin-5-yl}-2H-1,2,3-triazol-2-yl)cyclobutanecarbonitrile;

6-(5-{2-[cis-3-cyano-1-(cyanomethyl)cyclobutyl]-2H-1,2,3-triazol-4-yl}quinolin-7-yl)pyridine-2-carboxylic acid;

N-[6-(5-{2-[cis-3-cyano-1-(cyanomethyl)cyclobutyl]-2H-1,2,3-triazol-4-yl}quinolin-7-yl)pyridin-2-yl]methanesulfonamide;

N-[6-(5-{2-[cis-3-cyano-1-(cyanomethyl)cyclobutyl]-2H-1,2,3-triazol-4-yl}quinolin-7-yl)pyridin-3-yl]methanesulfonamide;

N-[6-(5-{2-[trans-3-cyano-1-(cyanomethyl)cyclobutyl]-2H-1,2,3-triazol-4-yl}quinolin-7-yl)pyridin-3-yl]methanesulfonamide;

N-[6-(5-{2-[trans-3-cyano-1-(cyanomethyl)cyclobutyl]-2H-1,2,3-triazol-4-yl}quinolin-7-yl)pyridin-2-yl]acetamide;

N-[6-(5-{2-[cis-3-cyano-1-(cyanomethyl)cyclobutyl]-2H-1,2,3-triazol-4-yl}quinolin-7-yl)pyridin-2-yl]acetamide;

cis-3-(cyanomethyl)-3-(4-{7-[5-(2-hydroxyethyl)-6-methylpyridin-2-yl]quinolin-5-yl}-2H-1,2,3-triazol-2-yl)cyclobutanecarbonitrile;

cis-3-(cyanomethyl)-3-{4-[7-(5-hydroxy-6-methylpyridin-2-yl)quinolin-5-yl]-2H-1,2,3-triazol-2-yl}cyclobutanecarbonitrile;

cis-3-{4-[7-(5-amino-6-methoxypyridin-2-yl)quinolin-5-yl]-2H-1,2,3-triazol-2-yl}-3-(cyanomethyl)cyclobutanecarbonitrile;

trans-3-{4-[7-(5-amino-6-methoxypyridin-2-yl)quinolin-5-yl]-2H-1,2,3-triazol-2-yl}-3-(cyanomethyl)cyclobutanecarbonitrile;

cis-3-{4-[7-(6-aminopyridazin-3-yl)quinolin-5-yl]-2H-1,2,3-triazol-2-yl}-3-(cyanomethyl)cyclobutanecarbonitrile;

cis-3-(cyanomethyl)-3-{4-[7-(2-oxo-1,2-dihydropyridin-4-yl)quinolin-5-yl]-2H-1,2,3-triazol-2-yl}cyclobutanecarbonitrile;

cis-3-(cyanomethyl)-3-{4-[7-(2-methyl-3H-imidazo[4,5-b]pyridin-5-yl)quinolin-5-yl]-2H-1,2,3-triazol-2-yl}cyclobutanecarbonitrile;

or, a pharmaceutically acceptable salt thereof.

9. A pharmaceutical composition comprising a compound of claim 1, or a pharmaceutically acceptable salt thereof, or a pharmaceutically acceptable solvate of said compound or salt, and a pharmaceutically acceptable excipient.

10. A method of treating a disease or condition selected from systemic lupus erythematous, lupus nephritis, discoid lupus, cutaneous lupus, central nervous system lupus, rheumatoid arthritis, psoriatic arthritis, inflammatory bowel disease, Crohn's disease, ulcerative colitis, asthma, allergic asthma, Type I diabetes, polymyositis, dermatomyositis, type I interferonopathies including Aicardi-Goutières syndrome and other mendelian diseases of overexpression of type I interferon, multiple sclerosis, primary progressive multiple sclerosis, relapsing remitting multiple sclerosis, primary biliary cirrhosis also known as primary biliary cholangitis, primary sclerosing cholangitis, autoimmune hepatitis, non-alcoholic fatty liver disease, non-alcoholic steatohepatitis, psoriasis, dermatomyositis, scleroderma, atopic dermatitis, vitiligo, alopecia areata, spondylopathy, ankylosing spondylitis, Alzheimer's disease, neuro-inflammation comprising administering to a subject suffering from said disease condition a therapeutically effective amount of a compound of claim 1, or a pharmaceutically acceptable salt thereof, or a pharmaceutically acceptable solvate of said compound or salt.

* * * * *